US009975907B2

(12) United States Patent
Li et al.

(10) Patent No.: US 9,975,907 B2
(45) Date of Patent: *May 22, 2018

(54) PYRIMIDINONES AS PI3K INHIBITORS

(71) Applicants: Incyte Corporation, Wilmington, DE (US); Incyte Holdings Corporation, Wilmington, DE (US)

(72) Inventors: Yun-Long Li, Chadds Ford, PA (US); Brian W. Metcalf, Moraga, CA (US); Andrew P. Combs, Kennett Square, PA (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/221,163

(22) Filed: Jul. 27, 2016

(65) Prior Publication Data

US 2017/0050987 A1     Feb. 23, 2017

Related U.S. Application Data

(63) Continuation of application No. 14/146,169, filed on Jan. 2, 2014, now Pat. No. 9,434,746, which is a continuation of application No. 12/824,924, filed on Jun. 28, 2010, now Pat. No. 8,940,752.

(60) Provisional application No. 61/259,765, filed on Nov. 10, 2009, provisional application No. 61/221,160, filed on Jun. 29, 2009.

(51) Int. Cl.
    C07D 519/00   (2006.01)
    C07D 471/04   (2006.01)
    C07D 487/04   (2006.01)
    C07D 513/04   (2006.01)

(52) U.S. Cl.
    CPC ......... C07D 519/00 (2013.01); C07D 471/04 (2013.01); C07D 487/04 (2013.01); C07D 513/04 (2013.01)

(58) Field of Classification Search
    CPC .................................................. C07D 471/04
    See application file for complete search history.

(56) References Cited

U.S. PATENT DOCUMENTS

| 3,037,980 | A | 6/1962 | Hitchings et al. |
| 3,169,967 | A | 2/1965 | Schittler |
| 3,506,643 | A | 4/1970 | Thiel et al. |
| 3,862,189 | A | 1/1975 | Schwender |
| 3,936,454 | A | 2/1976 | Schwender |
| 3,962,443 | A | 6/1976 | Minami et al. |
| 4,482,629 | A | 11/1984 | Nakagawa et al. |
| 4,840,951 | A | 6/1989 | Iwasaki et al. |
| 4,845,020 | A | 7/1989 | Itoh et al. |
| 4,861,701 | A | 8/1989 | Burns et al. |
| 5,124,331 | A | 6/1992 | Arita et al. |
| 5,208,250 | A | 5/1993 | Cetenko et al. |
| 5,252,580 | A | 10/1993 | Takahashi et al. |
| 5,294,620 | A | 3/1994 | Ratcliffe et al. |
| 5,314,883 | A | 5/1994 | Tanikawa et al. |
| 5,459,132 | A | 10/1995 | Bru-Magniez et al. |
| 5,521,184 | A | 5/1996 | Zimmerman |
| 5,646,153 | A | 7/1997 | Spada et al. |
| 5,811,439 | A | 9/1998 | Ogawa et al. |
| 5,866,702 | A | 2/1999 | Mackman et al. |
| 6,028,076 | A | 2/2000 | Hirota et al. |
| 6,342,501 | B1 | 1/2002 | Townsend et al. |
| 6,376,501 | B1 | 4/2002 | Isobe et al. |
| 6,392,047 | B1 | 5/2002 | Geissler et al. |
| 6,479,487 | B1 | 11/2002 | Dumont et al. |
| 6,630,496 | B1 | 10/2003 | Seehra et al. |
| 6,734,187 | B1 | 5/2004 | Tanaka et al. |
| 6,828,344 | B1 | 12/2004 | Seehra et al. |
| 7,129,264 | B2 | 10/2006 | Smallheer et al. |
| 7,494,987 | B2 | 2/2009 | Akada et al. |
| 7,495,002 | B2 | 2/2009 | Langkopt et al. |
| 7,528,143 | B2 | 5/2009 | Noronha et al. |
| 7,598,257 | B2 | 10/2009 | Rodgers et al. |
| 7,612,114 | B2 | 11/2009 | Hamaoka et al. |
| 8,680,108 | B2 | 3/2014 | Li et al. |
| 8,759,359 | B2 | 6/2014 | Combs et al. |
| 8,940,752 | B2 * | 1/2015 | Li .................. C07D 471/04 514/265.1 |
| 9,096,600 | B2 | 8/2015 | Li et al. |
| 9,199,982 | B2 | 12/2015 | Li et al. |
| 9,249,087 | B2 | 2/2016 | Kozikowski et al. |
| 9,309,251 | B2 | 4/2016 | Combs et al. |
| 9,434,746 | B2 * | 9/2016 | Li .................. C07D 471/04 |

(Continued)

FOREIGN PATENT DOCUMENTS

| AT | 388372 | 6/1989 |
| CA | 1066701 | 11/1979 |

(Continued)

OTHER PUBLICATIONS

"A to Z List of Cancers," National Cancer Institute (http://www.cancer.gov/) (Downloaded May 29, 2014), 22 pages.
"Angiogenesis" Merriam-Webster.com. Merriam-Webster, n.d. Web Jun. 16, 2014, www.merriam-webster.com/dictionary/angiogenesis, 3 pages.
"Arthritis: MedlinePlus Medical Encyclopedica," 2014, p. 1-5, accessed online Oct. 7, 2014; http://www.nlm.nih.gove/medlineplus/ency/article/001243.htm.
"Autoimmune disorders: MedlinePlus Medical Encyclopedia," 2013, p. 1-4, accessed online Oct. 7, 2014; http://www.nlm.nih.gov/medlineplus/ency/article/000816.htm.
"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/page1, 5 pgs.

(Continued)

*Primary Examiner* — Paul V Ward
(74) *Attorney, Agent, or Firm* — Fish & Richardson P.C.

(57) ABSTRACT

The present invention provides pyrimidinones that modulate the activity of phosphoinositide 3-kinases (PI3Ks) and are useful in the treatment of diseases related to the activity of PI3Ks including, for example, inflammatory disorders, immune-based disorders, cancer, and other diseases.

51 Claims, 2 Drawing Sheets

(56) References Cited

U.S. PATENT DOCUMENTS

| | | |
|---|---|---|
| 9,527,848 B2 | 12/2016 | Li et al. |
| 2003/0008898 A1 | 1/2003 | Mahboobi et al. |
| 2003/0157052 A1 | 8/2003 | Choe et al. |
| 2004/0058930 A1 | 3/2004 | Belema et al. |
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikian et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player et al. |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto et al. |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298334 A1 | 11/2010 | Rodgers et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0059951 A1 | 3/2011 | Rodgers et al. |
| 2011/0098248 A1 | 4/2011 | Halcomb et al. |
| 2011/0105508 A1 | 5/2011 | Allen et al. |
| 2011/0166164 A1 | 7/2011 | Brewster |
| 2011/0183985 A1 | 7/2011 | Li et al. |
| 2011/0190319 A1 | 8/2011 | Combs et al. |
| 2011/0224155 A1 | 9/2011 | Tachdjian et al. |
| 2011/0224190 A1 | 9/2011 | Huang et al. |
| 2011/0281884 A1 | 11/2011 | Combs et al. |
| 2011/0312979 A1 | 12/2011 | Li et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2013/0018034 A1 | 1/2013 | Yao et al. |
| 2013/0029982 A1 | 1/2013 | Castro et al. |
| 2013/0045963 A1 | 2/2013 | Rodgers et al. |
| 2013/0059835 A1 | 3/2013 | Li et al. |
| 2013/0261101 A1 | 10/2013 | Combs et al. |
| 2014/0005166 A1 | 1/2014 | Rodgers et al. |
| 2014/0031355 A1 | 1/2014 | Fisher et al. |
| 2014/0057912 A1 | 2/2014 | Combs et al. |
| 2014/0066448 A1 | 3/2014 | Combs et al. |
| 2014/0121198 A1 | 5/2014 | Li et al. |
| 2014/0121222 A1 | 5/2014 | Li et al. |
| 2014/0249132 A1 | 9/2014 | Li et al. |
| 2014/0275127 A1 | 9/2014 | Combs et al. |
| 2014/0343030 A1 | 11/2014 | Li et al. |
| 2015/0284390 A1 | 10/2015 | Li et al. |
| 2015/0361094 A1 | 12/2015 | Li et al. |
| 2016/0022685 A1 | 1/2016 | Li et al. |
| 2016/0024117 A1 | 1/2016 | Li et al. |
| 2016/0257689 A1 | 9/2016 | Qiao et al. |
| 2016/0264580 A1 | 9/2016 | Combs et al. |
| 2016/0362424 A1 | 12/2016 | Li et al. |
| 2016/0362425 A1 | 12/2016 | Li et al. |
| 2016/0362426 A1 | 12/2016 | Zhou et al. |
| 2017/0158696 A1 | 6/2017 | Li et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 2050749 | 4/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011511761 | 4/2011 |
| JP | 2011136925 | 7/2011 |
| RU | 2233842 | 8/2004 |
| SU | 1712359 | 2/1992 |
| WO | WO 1993/16076 | 8/1993 |
| WO | WO 1993/22291 | 11/1993 |
| WO | WO 1993/25524 | 12/1993 |
| WO | WO 1999/43651 | 9/1999 |
| WO | WO 1999/43672 | 9/1999 |
| WO | WO 2000/09495 | 2/2000 |
| WO | WO 2000/044750 | 8/2000 |
| WO | WO 2000/053595 | 9/2000 |
| WO | WO 2001/014402 | 3/2001 |
| WO | WO 2001/064639 | 9/2001 |
| WO | WO 2001/064655 | 9/2001 |
| WO | WO 2001/072709 | 10/2001 |
| WO | WO 2002/000196 | 1/2002 |
| WO | WO 2002/006477 | 1/2002 |
| WO | WO 2002/024685 | 3/2002 |
| WO | WO 2002/064599 | 8/2002 |
| WO | WO 2002/066478 | 8/2002 |

(56) References Cited

FOREIGN PATENT DOCUMENTS

| | | |
|---|---|---|
| WO | WO 2002/078701 | 10/2002 |
| WO | WO 2003/020721 | 3/2003 |
| WO | WO 2003/024967 | 3/2003 |
| WO | WO 2003/029209 | 4/2003 |
| WO | WO 2003/037347 | 5/2003 |
| WO | WO 2003/044014 | 5/2003 |
| WO | WO 2003/049678 | 6/2003 |
| WO | WO 2003/050064 | 6/2003 |
| WO | WO 2003/068750 | 8/2003 |
| WO | WO 2003/074497 | 9/2003 |
| WO | WO 2003/099771 | 12/2003 |
| WO | WO 2004/005281 | 1/2004 |
| WO | WO 2004/024693 | 3/2004 |
| WO | WO 2004/046120 | 6/2004 |
| WO | WO 2004/048365 | 6/2004 |
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/095588 | 8/2007 |
| WO | WO 2007/102392 | 9/2007 |
| WO | WO 2007/114926 | 10/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/064157 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |
| WO | WO 2008/118454 | 10/2008 |
| WO | WO 2008/118468 | 10/2008 |
| WO | WO 2009/026701 | 3/2009 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/085230 | 7/2009 |
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2013/033569 | 3/2013 |
| WO | WO 2013/052699 | 4/2013 |
| WO | WO 2013/151930 | 10/2013 |
| WO | WO 2015/191677 | 12/2015 |
| WO | WO 2016/183063 | 6/2016 |
| WO | WO 2016/138363 | 9/2016 |
| WO | WO 2016/183060 | 11/2016 |
| WO | WO 2016/183062 | 11/2016 |

OTHER PUBLICATIONS

Ali, et al., "Essential role for the p110δ phosphoinositide 3-kinase in the allergic response," Nature. 2004, 431(7011):1007-11.

Allen, et al., "Synthesis of C-6 substituted pyrazolo[1,5-a]pyridines with potent activity against herpesviruses," *Bioorganic & Medicinal Chemistry* (2006), 14(4), 944-954.

Apsel et al., "Targeted polypharmacology: discovery of dual inhibitors of tyrosine and phosphoinositide kinases," Nat. Chem. Biol., 2008, 4(11): 691-699.

Bader, et al., "Cancer-specific mutations in PIK3CA are oncogenic in vivo," Proc Natl Acad Sci U S A. 2006, 103(5):1475-9.

Baek et al., "Complete remission induced by rituximab in refractory, seronegative, muscle-specific, kinase-positive myasthenia gravis," J Neurol Neurosurg Psychiatry, 2007, 78(7):771.

Ball, "PI3K inhibitors as potential therapeutics for autoimmune disease," Drug Discovery Today, 2014, pp. 1195-119.

Barber, et al., "PI3Kγ inhibition blocks glomerulonephritis and extends lifespan in a mouse model of systemic lupus," Nat Med. 2005, 11(9):933-5.

Barragan et al., "Protein Kinases in the Regulation of Apoptosis in B-cell Chronic Lymphocytic Leukemia," *Leukemia and Lymphoma*, 2003, 44(11):1865-1870.

Belema, et al., "Synthesis and structure-activity relationship of imidazo(1,2-a)thieno(3,2-e)pyrazines as IKK-β inhibitors," *Bioorganic & Medicinal Chemistry Letters* (2007), 17(15), 4284-4289.

(56) References Cited

OTHER PUBLICATIONS

Bendell, J.C., "Phase I, dose-escalation study of BKM120, an oral pan-Class I PI3K inhibitor, in patients with advanced solid tumors," Journal of Clincial Oncology (2011): JCO-2011.
Benistant, et al., "A specific function for phosphatidylinositol 3-kinase α (p85α-p110α) in cell survival and for phosphatidylinositol 3-kinase β (p85α-p110β) in de novo DNA synthesis of human colon carcinoma cells," Oncogene, 2000, 19(44):5083-90.
Bennasar, et al., "Generation and Intermolecular Reactions of 2-Indolylacyl Radicals," *Organic Letters* (2001), 3(11), 1697-1700, CODEN: ORLEF7; ISSN: 1523-7060.
Berge et al., "Pharmaceutical Salts," J Pharma Sci, 1977, 66(1):1-19.
Bergman, et al., "Synthesis of indolocarbazole quinones; potent aryl hydrocarbon receptor ligands," *Tetrahedron* (2002), 58(7), 1443-1452.
Bhatia and Rose, "Autoimmunity and autoimmune disease," Principles of Med Biol., 1996, 6:239-263, 244.
Bhovi, et al., "1,3-dipolar cycloaddition reaction: Synthesis and antimicrobial activity of some new3-ethoxycarbonyl-5-methoxy-6-bromo-2-triazolylmethylindoles," *Indian Journal of Heterocyclic Chemistry* (2004), 14(1), 15-18 CODEN: IJCHEI; ISSN: 0971-1627.
Billottet, et al., "A selective inhibitor of the p110δ isoform of PI 3-kinase inhibits AML cell proliferation and survival and increases the cytotoic effects of VP16," Oncogene. 2006, 25(50):6648-59.
Biswas, et al., "Synthesis of a trifluoromethylindolocarbazole, novel cyclic 27- and 36-membered N-benzyltri- and -tetraindoles, and an N-benzyltetraindolyltrimethane," *Monatshefte fuer Chemie* (1999), 130(10), 1227-1239, CODEN: MOCMB7; ISSN: 0026-9247.
Blom et al., Preparative LC-MS Purification: Improved Compound Specific Method Optimization, J. Combi. Chem. 2004, 6(6), 874-883.
Blom et al., "Two-Pump at Column Dilution Configuration for Preparative LC-MS," 2002, 4: 295.
Blom et al., "Optimizing Preparative LC-MS Configurations and Methods for Parallel Synthesis Purification," 2003, 5: 670.
Boger, et al., "First and Second Generation Total Synthesis of the Teicoplanin Aglycon," JACS, 123(9), 1862-1871, 2001.
Brachmann et al., "PI3K and mTOR inhibitors—a new generation of targeted anticancer agents," Current Opinion Cell Biol., 2009, 21:194-198.
Bringmann, et al., "Novel concepts in directed biaryl synthesis. Part 65. Synthesis and structure of a novel twofold lactone-bridged ternaphthyl," *Tetrahedron Letters* (1998), 39(12), 1545-1548 CODEN: TELEAY; ISSN: 0040-4039.
Brock et al., "Roles of Gβγ in membrane recruitment and activation of p110γ/p101 phosphoinositide 3-kinaseγ," J Cell Biol., 2003, 160(1):89-99.
Brown, et al., "Small molecule inhibitors of IgE synthesis," *Bioorganic & Medicinal Chemistry Letters* (2006), 16(17), 4697-4699.
Cacoub et al., "Anti-CD20 monoclonal antibody (rituximab) treatment for cryoglobulinemic vasculitis: where do we stand?," Ann Rheum Dis, Mar. 2008, 67: 283-287.
Camps, et al., "Blockade of PI3Kγ suppresses joint inflammation and damage in mouse models of rheumatoid arthritis," Nat Med. 2005, 11(9):936-43.
Canadian Examination Report in Canadian Application No. 2,766,100, dated Jan. 31, 2017, 3 pages.
Cannon, Burger's Medicinal Chemistry and Drug Discovery, Fifth Edition, vol. 1 Principles and Practice, Wiley-Interscience 1995, Ch. 19, pp. 783-803, 784.
Cantley, "The Phosphoinositide 3-Kinase Pathway," Science, (2002) 296 (5573):1655-7.
Castillo-Trivino, et al., "Rituximab in relapsing and progressive forms of multiple sclerosis: a systematic review," The PLoS One. Jul. 2013; 8(7):e66308. doi: 10.1371/journal.pone.0066308. Print 2013.

Chai, et al., "Synthesis and in vitro anti-hepatitis B virus activities of some ethyl 6-bromo-5-hydroxy-1H-indole-3-carboxylates," *Bioorganic & Medicinal Chemistry* (2006), 14(4), 911-917.
Chang, K-Y., "Novel phosphoinositide 3-kinase/mTOR dual inhibitor, NVP-BGT226, displays potent growth-inhibitory activity against human head and neck cancer cells in vitro and in vivo," Clinical Cancer Research 17.22 (2011): 7116-7126.
Chen, X., "Targeting oxidative stress in embryonal rhabdomyosarcoma," Cancer cell 24.6 (2013): 710-724.
Clayton, et al., "A Crucial Role for the p110δ Subunit of Phosphatidylinositol 3-Kinase in B Cell Development and Activation," J Exp Med. 2002, 196(6):753-63.
Collins et al., "Rituximab treatment of fibrillary glomerulonephritis," Am J Kidney Dis., 2008, 52(6):1158-62.
Coughlin et al., Approaches and limitations of phosphatidylinositol-3-kinase pathway activation status as a predictive biomarker in the clinical development of targeted theraphy, Breast Cancer Res Treatment, 2010, 124:1-11.
Courtney et al., "The PI3K Pathway as Drug Target in Human Cancer," J Clinc Oncol., 2010, 29:1075-1083.
Crabbe, "The PI3K inhibitor arsenal: choose your weapon!" Trends Biochem Sci., 2007, 32(10):450-56.
Dagia et al., A preferential p110α/γ PI3K inhibitor attenuates experimental inflammation by suppressing the production of proinflammatory mediators in a NF-κB-dependent manner, Am J Physiol—Cell Physiol., 2010, 298:929-941.
DeBerardinis et al., "The Biology of Cancer: Metabolic Reprogramming Fuels Cell Growth and Proliferation," Cell Metabolism, Jan. 2008, 7:11-20.
Delmas and Meunier, "The Management of Paget's Disease of Bone," N Engl J Med., 1997, 336:558-566.
Devauchelle-Pensec, "Treatment of Primary Sjogren Syndrome with Rituximab," Annal Internal Med., 2014, 160:233-242.
Dolezal et al., "Preparation and biological activity of 6-benzylaminopurine derivatives in plants and human cancer cells," *Bioorganic & Medicinal Chemistry* (2006), 14(3), 875-884.
Dolezal et al., "Preparation, biological activity and endogenous occurrence of N6-benzyladenosines," *Bioorganic & Medicinal Chemistry* (2007), 15(11), 3737-3747.
Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya (1993), (11), 1932-7.
Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 328(3):758-765, 2009.
Dushianthan et al., "Acute respiratory distress syndrome and acute lung injury," Post Graduate Med J., 2011, 87:612-622.
Engelman, "Targeting PI3K signalling in cancer: opportunities, challenges and limitations," Nature Rev: Cancer, 2009, 9:550-562.
Fadeyeva, et al., "Inhibitors of early virus-cell interaction stages among 3-ethoxycarbonyl-5-hydroxy-bromoindole derivatives," *Khimiko-Farmatsevticheskii Zhurnal* (1992), 26(9-10), 17-20 (with English abstract).
Fine et al., "Neoplasms of the Central Nervous System," Cancer Principles Practice Oncol., 2005, 2:1834-1887.
Flinn et al., "Preliminary evidence of clinical activity in a phase I study of CAL-101, a selective inhibitor of the p110δ isoform of phosphatidylinositol 3-kinase (PI3K), in patients with select hematologic malignancies," Journal of Clinical Oncology, (abstract), 27(15S):3543, 2009.
Floberg et al., "Extractive alkylation of 6-mercaptopurine and determination in plasma by gas chromatography-mass spectrometry," *Journal of Chromatography, Biomedical Applications*, (1981), 225(1), 73-81.
Fruman and Bismuth, "Fine Tuning the Immune Response with PI3K," *Immunological Revs.*, 2006, 228:253-272.
Garvey, "Rituximab in the treatment of autoimmune haematolgoical disorders," British Journal of Haematology, 2008, 141: 149-169.

(56) References Cited

OTHER PUBLICATIONS

Gati et al., "(125I)Iodohydroxynitrobenzylthioinosine: a new high-affinity nucleoside transporter probe," *Biochemistry and Cell Biology* (1987), 65(5), 467-73.

Geng, et al., "Exploring 9-benzyl purines as inhibitors of glutamate racemase (MurI) in Gram-positive bacteria", Bioorganic & Medicinal Chemistry Letters (2008),18(15), 4368-4372.

Ghigo et al., "PI3K inhibition in inflammation: Toward tailored therapies for specific diseases," BioEssays, 2010, 32:185-196.

Godeau et al., "Rituximab efficacy and safety in adult splenectomy candidates with chronic immune thrombocytopenic purpura: results of a prospective multicenter phase 2 study," Blood, 2008, 112(4): 999-1004.

Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.

Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).

Greene and P. G. M. Wuts, Protective Groups in Organic Synthesis, 3rd Ed., Wiley & Sons, Inc., New York (1999).

Wuts and Greene, Protective Groups in Organic Synthesis, 4th ed., John Wiley & Sons: New Jersey, pp. 696-887,2007.

Harley, "Medical Management of Acute Renal Failure," Renal Failure Replacement Therapies, 2008, pp. 26-32.

Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.

Hauser et al., "B-Cell Depletion with Rituximab in Relapsing-Remitting Multiple Sclerosis," The New England Journal of Medicine, 358(7):676-688, 2008.

Hayter and Cook, "Updated assessment of the prevalence, spectrum and case definition of autoimmune disease," Autoimmunity Reviews, 2012, 11:754-765.

Hickey, et al., "BCR-ABL Regulates Phosphatidylinositol 3-Kinase-p110γ Transcription and Activation and is Required for Proliferation and Drug Resistance," J Biol Chem. 2006, 281(5):2441-50.

Hirose, et al., "Pyridone-carboxylic acids as antibacterial agents. I. Synthesis and antibacterial activity of 1-alkyl-1,4-dihydro-4-oxo-1,8- and -1,6-naphthyridine-3-carboxylic acids", Chemical & Pharmaceutical Bulletin (1982), 30(7), 2399-409.

Hirota, "Efficient synthesis of 2,9-disubstituted 8-hydroxyadenine derivatives", Organic & Biomolecular Chemistry (2003), 1(8), 1354-1365.

Hirsch et al., "Taming the PI3K team to hold inflammation and cancer at bay," Pharmacology & Therapeutics, 2008, 118: 192-205.

Hosalkar et al., "Skeletal Trauma and Common Orthopedic Problems," Chpt 10, Khurana (ed.) Bone Pathology, 2009, 93 pages.

Huang et al., "Design and synthesis of a pyrido[2,3-d]pyrimidin-5-one class of anti-inflammatory FMS inhibitors,", *Bioorganic & Medicinal Chemistry Letters* (2008), 18(7), 2355-2361.

Huang et al., "Synthesis and bioassay of a fluorine-containing cytokinin, N6-pentafluoro-benzyladenosine," *Youji Huaxue* (1988), 8(2), 147-8 (with English abstract).

Ihle et al., "Inhibitors of phosphatidylinositol-3-kinase in cancer therapy", *Molecular Aspects of Medicine*, 31(2):135-144, 2010.

Irie, et al., "Discovery of selective and nonpeptidic cathepsin S inhibitors," *Bioorganic & Medicinal Chemistry Letters* (2008), 18(14), 3959-3962.

Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.

Itaya, et al., "Syntheses of the marine ascidian purine aplidiamine and its 9-β-D-ribofuranoside," Tetrahedron Letters (1998), 39(26), 4695-4696.

Itaya, et al., "Synthesis and structure of the marine ascidian 8-oxoadenine aplidiamine," *Chemical & Pharmaceutical Bulletin* (1999), 47(9), 1297-1300.

Jager et al., "Molecular recognition. II Discrimination of specific and non-specific intermolecular interactions by means of magnetic resonance spectroscopy," *Magnetic Resonance in Chemistry* (1998), 36(3), 205-210, CODEN: MRCHEG; ISSN: 0749-1581.

Jager, et al., "Molecular recognition analyzed by EPR, ENDOR, and NMR spectroscopy," *Angewandte Chemie*, International Edition in English (1996), 35(16), 1815-1818.

Japanese Office Action in Japanese Application No. 2014-528654, dated Mar. 29, 2016, 5 pages (English Translation).

Jimenez, et al, "The p85 Regulator Subunit Controls Sequential Activation of Phosphoinositide 3-Kinase by Tyr Kinases and Ras," J Biol Chem., 2002, 277(44):41556-62.

Jou, et al., "Essential, Nonredundant Role for the Phosphoinositide 3-Kinase p110δ in Signaling by the B-Cell Receptor Complex," Mol Cell Biol. 2002, 22(24):8580-91.

Kang et al., "Aplidiamine, a unique zwitterionic benzyl hydroxyadenine from the Western Australian marine ascidian *Aplidiopsis sp.*," Tetrahedron Letters (1997), 38(6), 941-944.

Kang, et al., "Phosphtidylinositol 3-kinase mutations identified in human cancer are oncogenic," Proc Natl Acad Sci U S A. 2005, 102(3):802-7.

Karpouzas, et al., "Rituximab Therapy Induces Durable Remissions in Hispanic and African American Patients with Refractory Systemic Lupus Erythematosus (SLE)," Presented at 73th Annual Scientific Meeting of the American College of Rheumatology, Oct. 2009; Philadelphia, PA.

Kasibhatla, "Rationally Designed High-Affinity 2-Amino-6-halopurine Heat Shock Protein 90 Inhibitors That Exhibit Potent Antitumor Activity",Journal of Medicinal Chemistry (2007), 50(12),2767-2778.

Katritzky, et al., "Facile Synthesis of 2-Substituted Indoles and Indolo[3,2-b]carbazoles from 2-(Benzotriazol-1-ylmethyl)indole," *Journal of Organic Chemistry* (1995), 60(11), 3401-4.

Kim et al., "A signaling network in Phenylephrine-Induced Benign Prostatic Hyperplasia," Endocrinology, 2009, 150:3576-3583.

Kim, et al., "A new structural class of S-adenosylhomocysteine hydrolase inhibitors", Bioorganic & Medicinal Chemistry (2009), 17(18), 6707-6714.

Kim, et al., "Synthesis and evaluation of antitumor activity of novel 1,4-naphthoquinone derivatives," *Archives of Pharmacal Research* (2006), 29(2), 123-130 CODEN: APHRDQ; ISSN: 0253-6269.

Knobbe, et al., "Genetic alteration and expression of the phosphoinositol-3-kinase/Akt pathway genes *PIK3CA* and *PIKE* in human glioblastomas," Neuropathol Appl Neurobiol. 2005, 31(5):486-90.

Kolasa, et al., "Synthesis of indolylalkoxyiminoalkylcarboxylates as leukotriene biosynthesis inhibitors," *Bioorganic & Medicinal Chemistry* (1997), 5(3), 507-514.

Kolliputi and Waxman, "IL-6 cytoprotection in hyperoxic acute lung injury occurs via PI3K/Akt-mediated Bax phosphorylation," Am J Physiol Lung Cellular Mole Physiol., 2009, 297:L6-L16.

Kong and Yamori, "Phosphatidylinositol 3-kinase inhibitors: promising drug candidates for cancer theraphy," Cancer Sci., 2008, 9:1734-1740.

Kong and Yamori, "Advances in Development of Phosphatidylinositol 3-Kinase Inhibitors," Current Medicinal Chemistry, 16:2839-2854, 2009.

Kuduk et al., "Heterocyclic fused pyridone carboxylic acid M1 positive allosteric modulators," *Bioorganic & Medicinal Chemistry Letters* (2010), 20(8), 2533-2537.

Kung et al., "Characterization of a Murine Model of Allergic Pulmonary Inflammation," Int. Arch. Allergy Immunol., (abstract), 105(1):83-90, 1994.

Kurimoto, et al., "Synthesis and Biological Evaluation of 8-Oxoadenine Derivatives as Toll-like Receptor 7 Agonists Introducing the Antedrug Concept", *Journal of Medicinal Chemistry* (2010), 53(7),2964-2972.

Kuster (ed), Kinase Inhibitors: Methods and Protocols Methods in Molecular Biology, 2012, 795:1-44.

(56) References Cited

OTHER PUBLICATIONS

Kutney, et al., "Dihydropyridines in synthesis and biosynthesis. IV. Dehydrosecodine, in vitro precursor of indole alkaloids," *Canadian Journal of Chemistry* (1982), 60(11), 1269-78.

Lee, et al., "Inhibition of phosphoinositide 3-kinase δ attenuates allergic airway inflammation and hyperresponsiveness in murine asthma model," FASEB J. 2006, 20(3):455-65.

Li et al., "Design, synthesis and antitumor activities of novel 4-anilino-5H-pyridazino[4,5-b]indoles," *Zhongnan Yaoxue* (2008), 6(2), 144-148, CODEN: ZYHAC6; ISSN: 1672-2981, Publisher: Zhongnan Yaoxue Zazhishe (with English abstract within the article).

Li et al., "Synthesis and antitumor activities of novel 1-anilino 5H-pyridazino[4,5-b]indoles," *Zhongguo Yaowu Huaxue Zazhi* (2007), 17(6), 339-343, CODEN: ZYHZEF; ISSN: 1005-0108 (with English abstract within the article).

Li, et al., "Optimization of the heterocyclic core of the quinazolinone-derived CXCR3 antagonists," *Bioorganic & Medicinal Chemistry Letters* (2008), 18(2), 688-693.

Li, et al., "Synthesis and anti-tumor activities of a novel series of tricyclic 1-anilino-5H-pyridazino[4,5-b]indoles," *Archiv der Pharmazie* (Weinheim, Germany) (2007), 340(8), 424-428, CODEN: ARPMAS; ISSN: 0365-6233.

Lindsay, et al., "SmI2-Promoted Radical Addition Reactions with N-(2-Indolylacyl)oxazolidinones: Synthesis of Bisindole Compounds," *Journal of Organic Chemistry* (2007), 72(11), 4181-4188, CODEN: JOCEAH; ISSN: 0022-3263.

Link, J. T., "The intramolecular Heck reaction," *Organic Reactions* (Hoboken, NJ, United States) (2002), 60, No pp. given CODEN: ORHNBA URL: http://www3.interscience.wiley.com/cgi-bin/mrwhome/107610747/HOME.

Lipsky, "Systemic lupus erythematosus: an autoimmune disease of B cell hyperactivity," Nat Immunol., 2001, 2(9):764-6.

Liu et al., "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.

Liu et al., "mTOR mediated anti-cancer drug discovery," Drug Discovery Today: Therapeutic Strategies, 2009, 6:47-55.

Lovric et al., "Rituximab as rescue therapy in anti-neutrophil cytoplasmic antibody-associated vasculitis: a single-centre expereince with 15 patients," Nephrol Dial Transplant, 2009, 24: 179-185.

Lucas, et al., "Rauwolfia alkaloids. XXXI. The synthesis and activity of some reserpine analogs," *Journal of the American Chemical Society* (1959), 81, 1928-32.

Luo et al., "Principles of Cancer Therapy: Oncogene and Non-oncogene Addiction," Cell, 2009, 36:823-837.

Ma, et al., "Bromophenols Coupled with Nucleoside Bases and Brominated Tetrahydroisoquinolines from the Red Alga Rhodomela confervoides", Journal of Natural Products (2007), 70(3), 337-341.

Ma, et al., "Two new constituents from Artemisia capillaris Thunb", Molecules (2008), 13(2), 267-271.

Mahboobi, et al., "Bis(1H-2-indolyl)methanones as a Novel Class of Inhibitors of the Platelet-Derived Growth Factor Receptor Kinase," Journal of Medicinal Chemistry (2002), 45(5):1002-1018.

Martelli et al., "Targeting the PI3K/AKT/mTOR signaling network in acute myelogenous leukemia," Expert Opin Investig Drugs. Sep. 2009;18(9):1333-49.

Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", *J Medicinal Chem* (1975), 18(1), 74-9.

McDermott and Settleman, "Personalized Cancer Theraphy with Selective Kinase Inhibitors: An Emerging Paradigm in Medical Oncology," J Clinical Oncol., 2009, 27:5650-5659.

McLean, et al., "Discovery of covalent inhibitors for MIF tautomerase via cocrystal structures with phantom hits from virtual screening ," *Bioorganic & Medicinal Chemistry Letters* (2009), 19(23), 6717-6720.

McMahon, G., "VEGF Receptor Signaling in Tumor Angiogenesis," The Oncologist, 5(1):3-10, 2000.

Meade, et al., "Anxiolytic activity of analogs of 4-benzylamino-2-methyl-7H-pyrrolo[2,3-d]pyrimidines," *European Journal of Medicinal Chemistry* (1998), 33(5), 363-374.

MedicineNet.com' [online]. "Definition of Cancer," Sep. 18, 2004, retrieved on Sep. 16, 2005. Retrieved from the Internet: http://www.medterms.com, 1 page.

medpagetoday.com' [online] "Current Role of Rituximab in Systematic Lupus," Jan. 2015, [retrieved Apr. 23, 2015]. Retrieved from the Internet: URL <http://www.medpagetoday.com/Rheumatology/Lupus/49398#./49398?&_suid=142974298438809105451304289684>. 10 pages.

Meijer et al., "Treatment of primary Sjögren syndrome with rituximab: extended follow-up, safety and efficacy of retreatment," Ann. Rheum. Dis., 68(2):284-285, 2009.

Medeot et al., "Rituximab therapy in adult patients with relapsed or refractory immune thrombocytopenic purpura: long-term follow-up results," European Journal of Haematology, 2008, 81: 165-169.

Merrill, "Efficacy and safety of rituximab in moderately-to-severely active systemic lupus erythematosus: The randomized, double-blind, phase ii/iii systemic lupus erythematosus evaluation of rituximab trial," Arthritis & Rheumatism, 2010, 61(1):222-233.

Miki, et al., "Reaction of 1-benzylindole-2,3-dicarboxylic anhydride with 3-bromo-4-lithiopyridine: formal synthesis of ellipticine," *Heterocycles* (1998), 48(8), 1593-1597.

Miki, et al., "Reaction of indole-2,3-dicarboxylic anhydride with (3-bromo-4-pyridyl)triisopropoxytitanium: synthesis of ellipticine," *Tetrahedron Letters* (1996), 37(43), 7753-7754.

Miki, et al., "Synthesis of caulersin and its isomers by reaction of indole-2,3-dicarboxylic anhydrides with methyl indoleacetates," *Tetrahedron Letters* (2006), 47(29), 5215-5218, CODEN: TELEAY; ISSN: 0040-4039.

Miki, et al., "Synthesis of ellipticine by reaction of 1-(4-methoxybenzyl)indole-2,3-dicarboxylic anhydride with (3-bromo-4-pyridyl)triisopropoxytitanium," *Journal of the Chemical Society*, Perkin Transactions 1 (2001), (18), 2213-2216.

Mishra et al., "Decanuclear Copper Framework Supported by a Tripodal Adenine Ligand," *Inorganic Chemistry* (Washington, DC, United States), (2010), 49(8), 3691-3693.

Mizoguchi, et al., "Genetic Alterations of Phosphoinositide 3-kinase Subunit Genes in Human Glioblastomas," Brain Pathol. 2004, 14(4):372-7.

Moffett, "Antiulcer agents. p-Aminobenzamido aromatic compounds", Journal of Medicinal Chemistry (1971), 14(10), 963-8.

Mohammadizadeh, et al., "A novel and expedient synthesis of 7-pyrimidinylpyrimido[4,5-d]pyrimidinones," *Helvetica Chimica Acta* (2010), 93(1), 153-157.

Morrison, et al., "Pyrimido[4,5-c]pyridazines. 1. Cyclizations with α-keto esters", *Journal of Organic Chemistry* (1978), 43(25), 4844-9.

Mukhopadhyay, et al., "An ionic liquid {[secbmim]+ Br-} as a "dual reagent catalyst" for the multicomponent synthesis of (quinolinyl- and isoquinolinyl-amino) alkylnaphthols, their bis-analogs and a facile route to naphthoxazines," ARKIVOC (Gainesville, FL, United States) (2010), (10), 291-304.

Musmuca, et al., "Small-Molecule Interferon Inducers. Toward the Comprehension of the Molecular Determinants through Ligand-Based Approaches", Journal of Chemical Information and Modeling (2009),49(7), 1777-1786.

Najiwara, et al., "Behavior of naphthoyloxyl and methoxynaphthoyloxyl radicals generated from the photocleavage of dinaphthoyl peroxides and 1-(naphthoyloxy)-2-pyridones," *Bulletin of the Chemical Society of Japan* (2003), 76(3), 575-585.

Najiwara, et al., Generation and behavior of naphthoyloxyl radicals in photocleavage of 1-(naphthoyloxy)-2-pyridones, Chemistry Letters (2001), (10), 1064-1065.

Nettekoven, M., "A combinatorial approach towards 2-acyl-3-amino-indole derivatives," *Tetrahedron Letters* (2000), 41(43), 8251-8254.

Norman, P., "Selective PI3Kδ inhibitors , a review of the patent literature", Expert Opinion on Therapeutic Patents, Informa Healthcare, 21(11):1773-1790, 2011.

(56) References Cited

OTHER PUBLICATIONS

Oki, et al., "Reactivities of Stable Rotamers. XLII. Generation and Fates of Rotameric [1-(9-Fluorenyl)-2-naphthyl]methyl Radicals," *Bulletin of the Chemical Society of Japan* (1999), 72(10), 2327-2336.
Okkenhaug, et al., "Impaired B and T Cell Antigen Receptor Signaling in p110δ PI 3-Kinase Mutant Mice," Science, 2002, 297(5583):1031-4).
Park et al., Analytical Biochemistry 1999, 269, 94-104.
Park et al., "Phosphoinositide 3-kinase δ inhibitor as a novel therapeutic agent in asthma," Respirology, 13:764-771, 2008.
Phillips, et al., "The reaction of anils with 8-quinolinol," *Journal of Organic Chemistry* (1954), 19, 907-9 CODEN: JOCEAH; ISSN: 0022-3263.
Pinedo and Slamon, "Translational Research: The Role of VEGF in Tumor Angiogenesis," The Oncologist, 5(1):1-2, 2000.
Platts, et al., "A concise synthesis of HIV integrase inhibitors bearing the dipyridone acid motif," *Tetrahedron Letters* (2011), 52(4), 512-514.
Portnaya, et al., "Azomethine dyes. IV. Indoaniline dyes derived from heterocyclic N-substituted 1-hydroxy-2-naphthamides," *Ts. Vses. Nauchn.-Issled. Kinofotoinst.* (1960), (No. 40), 106-18 (with English abstract).
Prezent, et al., STN Abstract, Accession No. 2004:358794, "Boron chelates as intermediates in the synthesis of new functionalized pyridines and pyrimidines from α,α-dioxoketene aminals," *Boron Chemistry at the Beginning of the 21st Century*, [Proceedings of the International Conference on the Chemistry of Boron], 11th, Moscow, Russian Federation, Jul. 28-Aug. 1, 2002 (2003), Meeting Date 2002, 91-93. Editor(s): Bubnov, Yu. N. A. N. Nesmeyanov Institute of Organoelement Compounds, Russian Academy of Sciences: Moscow, Russia.
Puri and Gold, "Selective inhibitors of phosphoinositide 3-kinase delta: modulators of B-cell function with potential for treating autoimmune inflammatory diseases and B-cell malignancies," Frontiers in Immunology, 3(256):1-16, 2012.
Ramos-Casals et al., "Rituximab in systemic lupus erythematosus; A systematic review of off-label use in 188 cases," Lupus, 18:767-776, 2009.
Randis, et al., "Role of PI3Kδ and PI3Kγ in inflammatory arthritis and tissue localization of neutrophils," Eur. J. Immunol., 2008, 38(5):1215-24.
Reich, et al., "Preparation of a,b-unsaturated carbonyl compounds and nitriles by selenoxide elimination ," *Organic Reactions* (Hoboken, NJ, United States) (1993), 44, No pp. given.
Remington's Pharmaceutical Sciences, 17th ed., Mack Publishing Company, Easton, Pa., 1985, p. 1418.
Ringshausen et al., "Constitutively Actived phosphatidylinositol-3-kinase (PI-3K) is involved in the defect of apoptosis is B-CLL: assocaite with protein kinase C delta," Blood, 2002, 100:3741-3748.
Roxas-Duncan, et al., "Identification and biochemical characterization of small-molecule inhibitors of Clostridium botulinum neurotoxin serotype A," *Antimicrobial Agents and Chemotherapy* (2009), 53(8), 3478-3486.
Sahoo, et al., "Antispasmodic compounds. IV," Journal of the Indian Chemical Society (1959), 36, 421-4.
Sako, M., "Product class 19: pyridopyrimidines," *Science of Synthesis* (2004), 16, 1155-1267.
Samuels and Ericson, "Oncogenic PI3K and its role in cancer," Curr Opin Oncol., 2006, 18(1):77-82.
Samuels, et al., "High Frequency of Mutations of the PIK3CA Gene in Human Cancers," Science, 2004, 304(5670):554.
Sasaki, et al., "Function of PI3Kγ in Thymocyte Development, T Cell Activation, and Neutrophil Migration," Science, 2000, 287(5455):1040-6.
Sawyers, "The cancer biomarker problem," Nature, 2008, 452:548-552.
Saxena, et al., "Pharmacophore-based virtual screening and docking studies on Hsp90 inhibitors", SAR and QSAR in Environmental Research (2010), 21(5-6), 445-462.
Schafer and Kolkhof, "Failure is an option: learning from unsuccessful proof-of-concept trials," Drug Discovery Today, Nov. 2008, 13(21/22):913-916.
Schell, et al., "Versatile Solid-Phase Synthesis of Trisubstituted 1H-Pyrido[2,3-d]pyrimidin-4-ones and Related Heterocycles," *Journal of Combinatorial Chemistry* (2005), 7(1), 96-98.
Selig et al., "The application of Stille cross-coupling reactions with multiple nitrogen containing heterocycles," Tetrahedron, Sep. 2011, 67(47): 9204-9213.
Segarra et al., "Successful treatment of membranous glomerulonephritis with rituximab in calcineurin inhibitor-dependent patients," Clin J Am Soc Nephrol., 2009, 4(6):1083-8.
Sen, et al., "Reaction of aldehydes and amines with 8-hydroxyquinaldine and 8-quinolinol. II," *Journal of the Indian Chemical Society* (1960), 37, 640-2.
Shi, et al., "Synthesis and preliminary cytotoxic evaluation of substituted indoles as potential anticancer agents," *Chinese Chemical Letters* (2007), 18(8), 899-901, CODEN: CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 18(1):2686-2714, 2011.
Silverman, R. B., "The organic Chemistry of Drugs Design and Drug Action." Elsevier. Northwestern University. Second Edition. Evanstons Illinois. 2004. p. 29 and table 2.2.
Singh et al., "Application of Nazarov cyclization to access [6-5-6] and [6-5-5]tricyclic core embedded new heterocycles: an easy entry to structures related to Taiwaniaquinoids," *Organic & Biomolecular Chemistry* (2009), 7(9), 1858-1867, CODEN: OBCRAK; ISSN: 1477-0520.
Steliou, et al., "Does diatomic sulfur(S2) react as a free species?", *Journal of the American Chemical Society* (1992), 114(4), 1456-62.
Stüve et al., "Long-term B-Lymphocyte Depletion With Rituximab in Patients With Relapsing-Remitting Multiple Sclerosis," Arch. Neurol., 66(2):259-261, 2009.
Sujobert, et al., "Essential role for the p110δ isoform in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," *Bioorganic & Medicinal Chemistry* (2009), 17(5), 1938-1947.
Terrier, et al., "Tolerance and Efficacy of Rituximab (RTX) in Systemic Lupus Erythematosus (SLE): Data of 104 Patients From the AIR (Auto-immunity and Rituximab) Registry," Presented at 73th Annual Scientific Meeting of the American College of Rheumatology, Oct. 2009; Philadelphia, PA.
Thomas, et al., "Airway inflammation: chemokine-induced neutrophilia and the class I phosphoinositide 3-kinases," Eur J Immunol. 2005, 35(4):1283-91.
Travnickek, et al., "2-Chloro-6-[(4-hydroxy-3,5-dimethoxybenzyl)amino]-9-isopropylpurine," *Acta Crystallographica*, Section E: Structure Reports Online (2007), E63(2), o728-o730 CODEN: ACSEBH; ISSN: 1600-5368 URL: http://journals.iucr.org/e/issues/2007/02/00/lh2285/lh2285.pdf.
Umar, A., "Future directions in cancer prevention," Nature Reviews Cancer, 12.12 (2012): 835-848.
Uddin et al., "Role of phosphatidylinositol 3'-kinase/AKT pathway in diffuse large B-cell lymphomas survival," Blood, 2006, 108:4178-4186.
Vanhaesebroeck et al., "Signalling by PI3K isoforms: insights from gene-targeted mice," Trends Biochem Sci., 2005, 30(4):194-204.
Vasil'ev, et al, "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).
Venet et al., "Lymphocytes in the Development of Lung Inflammation: A role of Regulatory CD4+ T Cells in Indirect Pulmonary Lung Injury," J Immunol., 2009, 183:6472-3480.
Wallin, J.J., "GDC-0980 is a novel class I PI3K/mTOR kinase inhibitor with robust activity in cancer models driven by the PI3K pathway," Molecular cancer therapeutics 10.12 (2011): 2426-2436.

(56) References Cited

OTHER PUBLICATIONS

Walsh and Jayne, "Rituximab in the treatment of anti-neutrophil cytoplasm antibody associated vasculitis and systemic lupus erythematosis: past, present and future," Kidney International, 2007, 72: 676-682.
WebMD. Arthritis Health Center: What is Inflammation? Jul. 6, 2012, www.webmd.com/arthritis/about-inflammation?page=2, 4 pages.
WebMD. Bladder Cancer Health Center: Bladder Cancer-Prevention, Apr. 30, 2013, www.webmd.com/cancer/bladder-cancer/bladder-cancer-prevention, 1 page.
WebMD. Lung Disease & Respiratory Health Center: ARDS, May 21, 2014, www.webmd.com/lung/ards-acute-respiratory-distress-syndrome?page=2, 4 pages.
WebMD. Lung Disease & Respiratory Health Center: Lung Disease Overview, May 23, 2014, www.webmd.com/lung/lung-diseases-overview, 3 pages.
WebMD. Osteoarthritis Health Center: Osteoarthritis-prevention, Apr. 9, 2013, www.webmd.com/osteoarthritis/tc/osteoarthritis-prevention, 2 pages.
WebMD. Psoriasis Health Center: Psoriasis-prevention, Jan. 9, 2012, www.webmd.com/skin-problems-and-treatments/psoriasis/psoriasis-prevention, 1 page.
Xu et al., "Activation of the PI3K/AKT/mTOR pathway in diffuse large B cell lymphoma: clinical significance and inhibitory effect of rituximab," Ann Hematol., 2013, 92:1351-1358.
Yaguchi et al., "Antitumor Activity of ZSTK474, a new Phosphatidinylinositol 3-Kinase Inhibitor," *J Natl. Cancer Inst.*, 2006, 98(8):545-556.
Yahay-Zadeh, "Synthesis of 9-Aryl-6-aminopurines from 5-Amino-1-aryl-1H-imidazole-4-carbonitriles", Russian Journal of Organic Chemistry (Translation of Zhurnal Organicheskoi Khimii) (2003), 39(11),1649-1651.
Yahyazadeh, et al., "Synthesis of 9-benzyl-6-aminopurines from 5-amino-1-benzyl-4-cyanoimidazoles", Bulletin of the Korean Chemical Society (2003), 24(12), 1723-1724.
Yamada et al., "Alpha-1 Adrenoceptors in Human Prostate: Characterization and Alteration in Benign Prostatic Hypertrophy," J Pharmacol Experimental Therapeutics, 1987, 242(1):326-330.
Yanni, A. S., "Synthesis of some new 5-iodo-7-substituted-aminomethyl-8-hydroxyquinoline," *Revue Roumaine de Chimie* (1994), 39(7), 833-6 CODEN: RRCHAX; ISSN: 0035-3930.
Yanni, et al., "Synthesis and biological activity of some 7-substituted aminomethyl-8-hydroxyquinoline-5- sulfonic acids," *Indian Journal of Chemistry, Section B: Organic Chemistry Including Medicinal Chemistry* (1982), 21B(7), 705-6.
Yoo, et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," *Archives of Pharmacal Research* (2008), 31(2), 142-147 CODEN: APHRDQ; ISSN: 0253-6269.
Yoon et al., "Impact of fluoroquinolones on the diagnosis of pulmonary tuberculosis initially treated as bacterial pneumonia," Int'l J Tuberculosis and Lung Dis, 2005, 9:1215-1219.
Yoshida, et al., "MexAB-OprM specific efflux pump inhibitors in Pseudomonas aeruginosa. Part 5: Carbon-substituted analogues at the C-2 position," *Bioorganic & Medicinal Chemistry* (2006), 14(6), 1993-2004.
Yuan, T.L., "PI3K pathway alterations in cancer: variations on a theme," Oncogene, 2008, 27.41: 5497-551.
Zhang et al., "Advances in preclinical small molecules for the treatment of NSCLC", Expert Opinion on Therapeutic Patents, 19(6):731-751, 2009.
Zhao and Vogt, "Class I PI3K in oncogenic cellular transformation," Oncogene, 2008, 27:5486-5496.
Zhao, et al., "Synthesis and in vitro anti-hepatitis B virus activities of some ethyl 5-hydroxy-1H-indole-3-carboxylates," *Bioorganic & Medicinal Chemistry* (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/030310 dated Oct. 1, 2013 (7pgs.).
International Preliminary Report on Patentability for PCT/US2012/028915 dated Sep. 17, 2013 (6pgs.).
International Preliminary Report on Patentability for PCT/US2012/053398, dated Mar. 4, 2014 (6 pgs.).
International Search Report dated Jul. 11, 2013 for International Appln. No. PCT/US2013/034803 (15 pgs.).
International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).
International Search Report for PCT/US2011/032213 dated Jun. 14, 2011 (11 pgs.).
STN Search Report, dated Dec. 1, 2010, 132 pages.
STN Search Report, dated Dec. 16, 2009, 72 pages.
STN Search Report, dated prior to Jun. 21, 2011, 224 pages.
STN Search Report, dated Apr. 5, 2010, 513 pages.
STN Search Report, dated Apr. 24, 2009, 43 pages.
STN Search Report, dated Dec. 7, 2010, 213 pages.
STN Search Report, dated Aug. 29, 2011, 181 pages.
STN Search Report, dated May 27, 2009, 2 pages.
STN Search Report, dated May 28, 2009, 81 pages.
STN Search Report, dated Apr. 2, 2010, 141 pages.
STN Search Report, dated Aug. 30, 2011, 61 pages.
Office Action in CO Application No. 11-179.464, 17 pages.
Office Action in JP Application No. 2012-518563, dated Jul. 8, 2014, 6 pages (with English translation).
Office Action in JP Application No. 2013-546274, dated Sep. 15, 2015, 7 pages (with English Translation).
Office Action in JP Application No. 2014-223540, dated Jul. 21, 2015, 5 pages (with English Translation).
International Search Report and Written Opinion in International Application No. PCT/US2016/031606, dated Jun. 20, 2016, 10 pages.
International Search Report and Written Opinion in International Application No. PCT/US2016/031611, dated Jun. 20, 2016, 10 pages.
International Search Report and Written Opinion in International Application No. PCT/US2016/031603, dated Jun. 22, 2016, 11 pages.
International Search Report and Written Opinion in International Application No. PCT/US2015/035046, dated Aug. 27, 2015, 9 pages.
International Search Report and Written Opinion in International Application No. PCT/US2016/019741, dated Aug. 2, 2016, 16 pages.
International Preliminary Report on Patentability in International Application No. PCT/US2015/035046, dated Dec. 22, 2016, 7 pages.

(56) References Cited

OTHER PUBLICATIONS

Malaysian Office Action in Malaysian Application No. PI 2011006255, dated Mar. 15, 2017, 2 pages.
European Search Report in European Application No. 16199883.6, dated Jun. 4, 2017, 7 pages.
Taiwan Office Action in Taiwan Application No. 105111882, dated Mar. 8, 2017, 5 pages (English Translation).
Vietnamese Office Action in Vietnamese Application No. 2012-00241, dated May 9, 2017, 3 pages (English Translation).
International Preliminary Report on Patentability in International Application No. PCT/US2016/019741, dated Aug. 29, 2017, 10 pages.

\* cited by examiner

PYRIMIDINONES AS PI3K INHIBITORS

This application is a continuation of U.S. Ser. No. 14/146,169, filed Jan. 2, 2014, which is a continuation of U.S. Ser. No. 12/824,924, filed Jun. 28, 2010, which claims the benefit of priority of U.S. Prov. Appl. No. 61/221,160, filed on Jun. 29, 2009, and U.S. Prov. Appl. No. 61/259,765, filed on Nov. 10, 2009, each of which is incorporated herein by reference in its entirety.

FIELD OF THE INVENTION

The present invention provides pyrimidinones that modulate the activity of phosphoinositide 3-kinases (PI3Ks) and are useful in the treatment of diseases related to the activity of PI3Ks including, for example, inflammatory disorders, immune-based disorders, cancer, and other diseases.

BACKGROUND OF THE INVENTION

The phosphoinositide 3-kinases (PI3Ks) belong to a large family of lipid signaling kinases that phosphorylate phosphoinositides at the D3 position of the inositol ring (Cantley, Science, 2002, 296(5573): 1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (pi 10) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4): 194-204).

The differential tissue distribution of the PI3K isoforms factors in their distinct biological functions. Genetic ablation of either PI3Kα or PI3Kβ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et al., Science, 2000, 287(5455): 1040-6). PI3Kδ-mutant mice have specific defects in B cell signaling that lead to impaired B cell development and reduced antibody responses after antigen stimulation (Clayton, et al., J. Exp. Med. 2002, 196(6):753-63; Jou, et al., Mol. Cell Biol. 2002, 22(24):8580-91; Okkenhaug, et al., Science, 2002, 297(5583): 1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat Med. 2005, 11(9):936-43; Thomas, et al., Eur. J. Immunol., 2005, 35(4): 1283-91). In addition, treatment of wild-type mice with a selective inhibitor of PI3Kγ was shown to reduce glomerulonephritis and prolong survival in the MRL-lpr model of systemic lupus nephritis (SLE) and to suppress joint inflammation and damage in models of RA (Barber, et al., Nat Med. 2005, 11(9):933-5; Camps, et al., 2005). Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011): 1007-11; Lee, et al., FASEB J. 2006, 20(3):455-65) and to have attenuated disease in a model of RA (Randis, et al., Eur. J. Immunol., 2008, 38(5): 1215-24).

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr. Opin. Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc. Natl. Acad. Sci. U.S.A. 2005, 102(3):802-7; Bader, et al., Proc. Natl. Acad. Sci. U.S. Pat. No. 2,006,103(5): 1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3): 1063-6) and inhibitors of PI3Kδ can prevent the growth of leukemic cells (Billottet, et al., Oncogene. 2006, 25(50): 6648-59). Elevated expression of PI3Kγ is seen in chronic myeloid leukemia (Hickey, et al., J. Biol. Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44):5083-90; Mizoguchi, et al., Brain Pathol. 2004, 14(4):372-7; Knobbe, et al., Neuropathol. Appl. Neurobiol. 2005, 31(5):486-90). Further, these isoforms have all been shown to be oncogenic in cell culture (Kang, et al., 2006).

Thus, new or improved agents which inhibit kinases such as PI3K are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease, nephritis), diseases involving a hyperactive inflammatory response (e.g., eczema), allergies, lung diseases, cancer (e.g., prostate, breast, leukemia, multiple myeloma), and some immune reactions (e.g., skin rash or contact dermatitis or diarrhea) caused by other therapeutics. The compounds, compositions, and methods described herein are directed toward these needs and other ends.

SUMMARY OF THE INVENTION

The present invention provides, inter alia, compounds of Formula I or II:

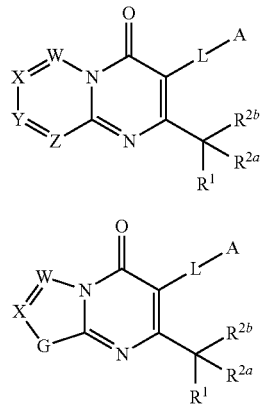

or pharmaceutically acceptable salts thereof, wherein constituent members are defined herein.

The present invention further provides pharmaceutical compositions comprising a compound of Formula I or II, or a pharmaceutically acceptable salt thereof, and at least one pharmaceutically acceptable carrier.

The present invention further provides methods of modulating an activity of one or more kinases (such as a PI3K) comprising contacting the kinase with a compound of Formula I or II, or a pharmaceutically acceptable salt thereof.

The present invention further provides methods of treating a disease or a disorder associated with abnormal kinase expression or activity in a patient by administering to a patient a therapeutically effective amount of a compound of Formula I or II, or a pharmaceutically acceptable salt of the same.

The present invention further provides methods of treating diseases such as immune-based diseases, cancer, and lung diseases in a patient by administering to the patient a therapeutically effective amount of a compound of Formula I or II, or a pharmaceutically acceptable salt thereof.

The present invention further provides a compound of Formula I or II, or a pharmaceutically acceptable salt thereof, for use in therapy.

The present invention further provides use of a compound of Formula I or II, or a pharmaceutically acceptable salt thereof, for the production of a medicament for use in therapy.

DETAILED DESCRIPTION

Figure 1:
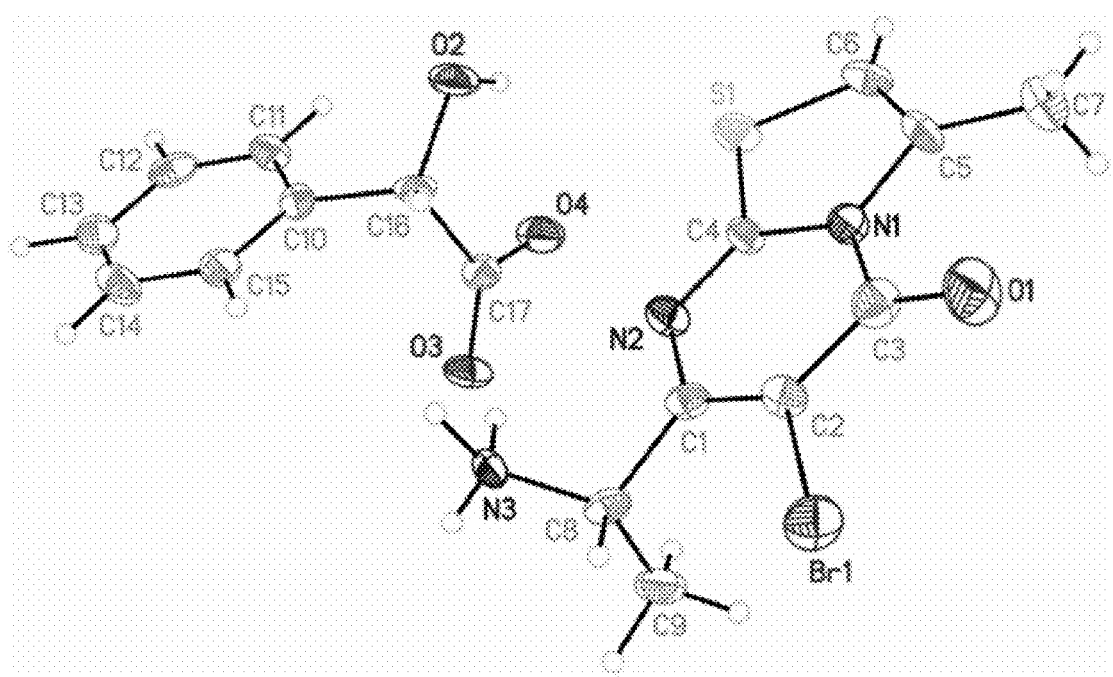
FIG. 1. X-ray crystal structure of Example 15, step 5.

The present invention provides, inter alia, compounds that modulate the activity of one or more PI3Ks and are useful, for example, in the treatment of various diseases such as those associated with expression or activity of one or more PI3Ks. The compounds of the invention include those of Formula I or II:

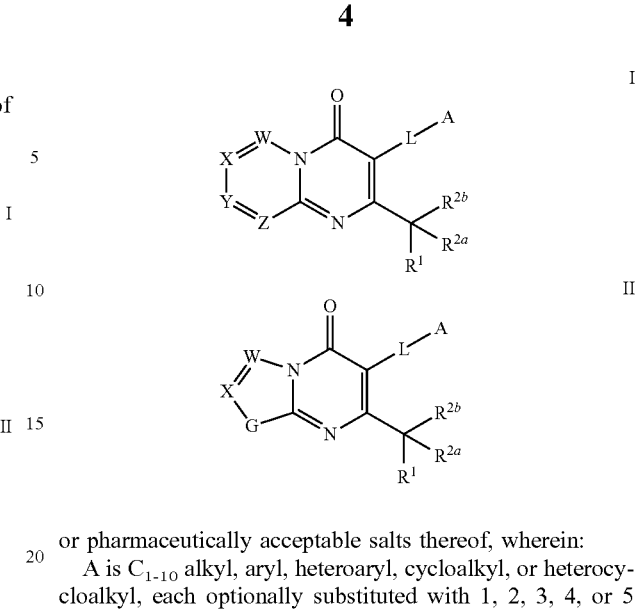

or pharmaceutically acceptable salts thereof, wherein:

A is $C_{1-10}$ alkyl, aryl, heteroaryl, cycloalkyl, or heterocycloalkyl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

L is absent, $(CR^{7a}R^{7b})_m$, $(CR^{7a}R^{7b})_pO(CR^{7a}R^{7b})_q$, $(CR^{7a}R^{7b})_pS(CR^{7a}R^{7b})_q$, $(CR^{7a}R^{7b})_pS(O)(CR^{7a}R^{7b})_q$, $(CR^{7a}R^{7b})_pS(O)_2(CR^{7a}R^{7b})_q$, $(CR^{7a}R^{7b})_pNR^{7c}(CR^{7a}R^{7b})_q$, $(CR^{7a}R^{7b})_pNR^{7c}C(O)NR^{7c}(CR^{7a}R^{7b})_q$, $(CR^{7a}R^{7b})_pNR^{7c}C(O)O(CR^{7a}R^{7b})_q$, $(CR^{7a}R^{7b})_pNR^{7c}C(=NR^{7d})NR^{7c}(CR^{7a}R^{7b})_q$, or $(CR^{7a}R^{7b})_pNR^{7c}S(O)_2(CR^{7a}R^{7b})_q$;

W is N or $CR^3$;
X is N or $CR^4$;
Y is N or $CR^5$;
Z is N or $CR^6$;
G is O, S, or $NR^N$;
$R^1$ is $OR^A$, $SR^A$, $S(O)R^A$, $S(O)_2R^A$, $NR^AR^B$, $NR^CC(O)NR^AR^B$, $NR^CC(O)OR^A$, $NR^CC(=NR^E)NR^AR^B$, $NR^CS(O)_2R^A$, $NR^CS(O)_2NR^CR^A$, heterocycloalkyl, or heteroaryl, wherein the heterocycloalkyl or heteroaryl is optionally substituted with 1, 2, or 3 substituents independently selected from $-(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^{2a}$ and $R^{2b}$ are independently selected from H, halo, OH, CN, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e}$)NR$^{c2}$R$^{d2}$, NR$^{c2}$C(=NR$^{e}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

or R$^{2a}$ and R$^{2b}$ together with the carbon atom to which they are attached form a 3-, 4-, 5-, 6-, or 7-membered cycloalkyl ring or a 3-, 4-, 5-, 6-, or 7-membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e}$)NR$^{c2}$R$^{d2}$, NR$^{c2}$C(=NR$^{e}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

R$^3$, R$^4$, R$^5$, and R$^6$ are independently selected from H, halo, CN, NO$_2$, OR$^{a3}$, SR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$S(O)$_2$R$^{b3}$, NR$_{c3}$S(O)$_2$NR$_{c3}$R$^{d3}$, S(O)$_2$NR$^{c3}$R$^{d3}$, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e}$)NR$^{c3}$R$^{d3}$, NR$^{c3}$C(=NR$^{e}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

R$^{7a}$ and R$^{7b}$ are independently selected from H, halo, or $C_{1-4}$ alkyl;

R$^{7c}$ is H or $C_{1-4}$ alkyl;

R$^{7d}$ is H, CN, NO$_2$, OR$^{a5}$, SR$^{b5}$, S(O)$_2$R$^{b5}$, C(O)R$^{b5}$, S(O)$_2$NR$^{c5}$R$^{d5}$, or C(O)NR$^{c5}$R$^{d5}$;

R$^A$ is heteroaryl, heterocycloalkyl, heteroarylalkyl, or heterocycloalkylalkyl, each optionally substituted with 1, 2, 3, 4, or 5 substituents independently selected from —(C$_{1-4}$ alkyl)$_r$-Cy$^1$, halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e}$)NR$^{c1}$R$^{d1}$, NR$^{c1}$C(=NR$^{e}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^B$ and R$^C$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{f}$)NR$^{c5}$R$^{d5}$, NR$^{c5}$C(=NR$^{f}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

R$^E$ is H, CN, NO$_2$, OR$^{a5}$, SR$^{b5}$, S(O)$_2$R$^{b5}$, C(O)R$^{b5}$, S(O)$_2$NR$^{c5}$R$^{d5}$, or C(O)NR$^{c5}$R$^{d5}$;

R$^N$ is H or $C_{1-4}$ alkyl;

Cy$^1$ is aryl, heteroaryl, cycloalkyl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e}$)NR$^{c1}$R$^{d1}$, NR$^{c1}$C(=NR$^{e}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^a$, R$^b$, R$^c$, and R$^d$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{f}$)NR$^{c5}$R$^{d5}$, NR$^{c5}$C(=NR$^{f}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or R$^c$ and R$^d$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{f}$)NR$^{c5}$R$^{d5}$, NR$^{c5}$C(=NR$^{f}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

R$^{a1}$, R$^{b1}$, R$^{c1}$, and R$^{d1}$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{f}$)NR$^{c5}$R$^{d5}$, NR$^{c5}$C(=NR$^{f}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or R$^{c1}$ and R$^{d1}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{f}$)NR$^{c5}$R$^{d5}$, NR$^{c5}$C(=NR$^{f}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

R$^{a2}$, R$^{b2}$, R$^{c2}$, and R$^{d2}$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or $R^{c2}$ and $R^{d2}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$R^{a3}$, $R^{b3}$, $R^{c3}$, and $R^{d3}$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or $R^{c3}$ and $R^{d3}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, halo, $C_{1-6}$ haloalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$R^e$ and $R^f$ are independently selected from H, CN, $NO_2$, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

$R^{a5}$, $R^{b5}$, $R^{c5}$, and $R^{d5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$ haloalkoxy;

or $R^{c5}$ and $R^{d5}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$ haloalkoxy;

m is 1, 2, 3, 4, 5, 6, 7, 8, 9, or 10;
p is 0, 1, 2, 3, or 4;
q is 0, 1, 2, 3, or 4; and
r is 0 or 1.

In some embodiments, the compounds of the invention have Formula I.

In some embodiments, the compounds of the invention have Formula II.

In some embodiments, A is $C_{1-10}$ alkyl optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR_a$, $SR_a$, $C(O)R^b$, $C(O)NR^cR^d$, $C(O)OR^a$, $OC(O)R_b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, A is aryl, heteroaryl, cycloalkyl, or heterocycloalkyl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, A is aryl or heteroaryl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NRCC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, L is absent.

In some embodiments, L is $(CR^{7a}R^{7b})_m$, $(CR^{7a}R^{7b})_pO(CR^{7a}R^{7b})_q$, $(CR^{7a}R^{7b})_pS(CR^{7a}R^{7b})_q$, $(CR^{7a}R^{7b})_pS(O)$ $(CR^{7a}R^{7b})_q$, $(CR^{7a}R^{7b})_pS(O)_2(CR^{7a}R^{7b})_q$, $(CR^{7a}R^{7b})_pNR^{7c}(CR^{7a}R^{7b})_q$, $(CR^{7a}R^{7b})_pNR^{7c}C(O)NR^{7c}(CR^{7a}R^{7b})_q$, $(CR^{7a}R^{7b})_pNR^{7c}C(O)O(CR^{7a}R^{7b})_q$, $(CR^{7a}R^{7b})_pNR^{7c}C(=NR^{7d})NR^{7c}(CR^{7a}R^{7b})_q$, or $(CR^{7a}R^{7b})_pNR^{7c}S(O)_2(CR^{7a}R^{7b})_q$.

In some embodiments, L is $(CR^{7a}R^{7b})_m$.

In some embodiments, W is N.

In some embodiments, W is $CR^3$.

In some embodiments, X is N.

In some embodiments, X is $CR^4$.

In some embodiments, Y is N.

In some embodiments, Y is $CR^5$.

In some embodiments, Z is N.

In some embodiments, Z is $CR^6$.

In some embodiments, not more than 2 of W, X, Y, or Z are N.

In some embodiments, not more than 3 of W, X, Y, or Z are N.

In some embodiments, one of W and X is N.

In some embodiments, G is O.

In some embodiments, G is S.

In some embodiments, G is $NR^N$.

In some embodiments, $R^1$ is heteroaryl optionally substituted with 1, 2, or 3 substituents independently selected from $-(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^1$ is $NR^AR^B$.

In some embodiments, $R^{2a}$ and $R^{2b}$ are independently selected from H and $C_{1-6}$ alkyl optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^e)NR^{c2}R^{d2}$, $NR^{c2}C(=NR^e)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, at least one of $R^{2a}$ and $R^{2b}$ is other than H.

In some embodiments, $R^3$, $R^4$, $R^5$, and $R^6$ are independently selected from H or $C_{1-6}$ alkyl optionally substituted with 1, 2, 3, 4, or 5 substituents independently selected from $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^e)NR^{c3}R^{d3}$, $NR^{c3}C(=NR^e)NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$.

In some embodiments, $R^3$ is $C_{1-6}$ alkyl optionally substituted with 1, 2, 3, 4, or 5 substituents independently selected from $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^e)NR^{c3}R^{d3}$, $NR^{c3}C(=NR^e)NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$.

In some embodiments, $R^4$, $R^5$, and $R^6$ are each H.

In some embodiments, $R^{7a}$, $R^{7b}$, $R^{7c}$, and $R^{7d}$ are each H.

In some embodiments, $R^4$ is heteroaryl optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$.

In some embodiments, $R^B$ and $R^C$ are independently selected from H and $C_{1-6}$ alkyl.

In some embodiments, A is other than phenyl substituted at the 4-position by halogen.

In some embodiments, r is 0.

In some embodiments, r is 1.

In some embodiments, the compounds of the invention have Formula Ia, Ib, Ic, Id, Ie, IIa, IIb, or IIc:

Ia
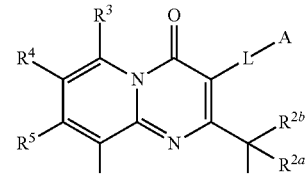

Ib
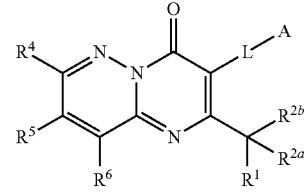

Ic
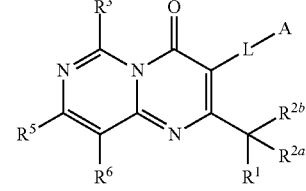

Id
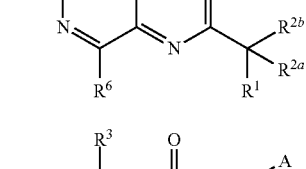

Ie
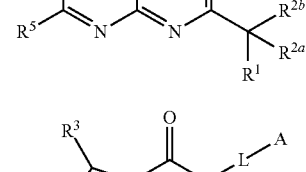

IIa
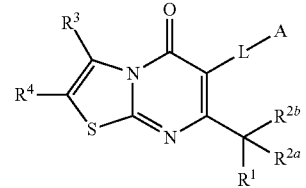

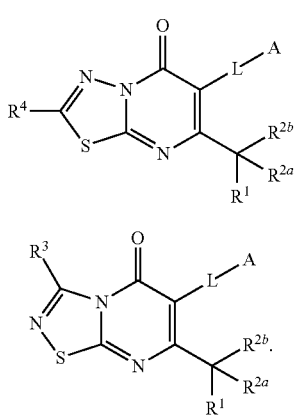

In some embodiments, the compounds of the invention have Formula If or IId:

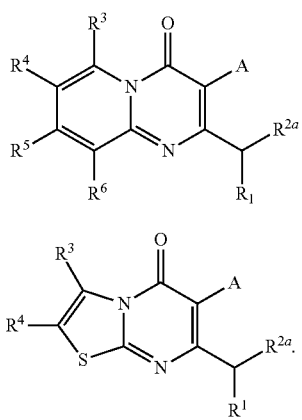

In some embodiments of compounds of Formulas I, Ia-If, II, and IIa-IId:

A is aryl, heteroaryl, cycloalkyl, or heterocycloalkyl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

$R^1$ is $OR^A$, $SR^A$, $S(O)_2R^A$, $NR^AR^B$, $NR^CC(O)NR^AR^B$, $NR^CC(O)OR^A$, $NR^CC(=NR^E)NR^AR^B$, $NR^CS(O)_2R^A$, $NR^CS(O)_2NR^CR^A$, heterocycloalkyl, or heteroaryl, wherein the heterocycloalkyl or heteroaryl is optionally substituted with 1, 2, or 3 substituents independently selected from —$(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^{2a}$ is H, halo, OH, CN, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^e)NR^{c2}R^{d2}$, $NR^{c2}C(=NR^e)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^3$, $R^4$, $R^5$, and $R^6$ are independently selected from H, halo, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}S(O)_2R^{b3}$, $NR^{c3}S(O)_2NR^{c3}R^{d3}$, $S(O)_2NR^{c3}R^{d3}$, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^e)NR^{c3}R^{d3}$, $NR^{c3}C(=NR^e)NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

$R^A$ is heteroaryl, heterocycloalkyl, heteroarylalkyl, or heterocycloalkylalkyl, each optionally substituted with 1, 2, 3, 4, or 5 substituents independently selected from —$(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^B$ and $R^C$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$R^E$ is H, CN, $NO_2$, $OR^{a5}$, $SR^{b5}$, $S(O)_2R^{b5}$, $C(O)R^{b5}$, $S(O)_2NR^{c5}R^{d5}$, or $C(O)NR^{c5}R^{d5}$;

$Cy^1$ is aryl, heteroaryl, cycloalkyl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^a$, $R^b$, $R^c$, and $R^d$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or $R^c$ and $R^d$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2NR^{c5}R^{d5}$, and $S(O)_2NR^{c5}R^{d5}$;

$R^{a1}$, $R^{b1}$, $R^{c1}$, and $R^{d1}$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or $R^{c1}$ and $R^{d1}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$R^{a2}$, $R^{b2}$, $R^{c2}$, and $R^{d2}$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or $R^{c2}$ and $R^{d2}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$R^{a3}$, $R^{b3}$, $R^{c3}$, and $R^{d3}$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or $R^{c3}$ and $R^{d3}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, halo, $C_{1-6}$ haloalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$R^e$ and $R^f$ are independently selected from H, CN, $NO_2$, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

$R^{a5}$, $R^{b5}$, $R^{c5}$, and $R^{d5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$ haloalkoxy;

or $R^{c5}$ and $R^{d5}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$ haloalkoxy; and r is 0 or 1.

In some embodiments of compounds of Formulas I and Ia-If, when A is 3-fluorophenyl; $R^{2a}$ is H; $R^3$ is methyl; and $R^4$, $R^5$, and $R^6$ are H; then $R^1$ is other than 4-amino-3-iodo-1H-pyrazolo[3,4-d]pyrimidin-1-yl.

In some embodiments of compounds of Formulas I and Ia-If, when A is 1,3-dioxolan-2-yl; $R^{2a}$, $R^3$, $R^4$, and $R^6$ are H; then $R^1$ is other than 1-(tert-butoxycarbonyl)piperidin-4-yl.

In some embodiments of compounds of Formulas I and Ia-If, $R^1$ is other than a substituted or unsubstituted pyrazolo[3,4-d]pyrimidin-1-yl group.

In some embodiments of compounds of Formulas I and Ia-If, $R^1$ is other than a substituted or unsubstituted piperidinyl group.

In some embodiments, the compound has Formula Ia.
In some embodiments, the compound has Formula Ib.
In some embodiments, the compound has Formula Ic.
In some embodiments, the compound has Formula Id.
In some embodiments, the compound has Formula Ie.
In some embodiments, the compound has Formula If.
In some embodiments, the compound has Formula IIa.
In some embodiments, the compound has Formula IIb.
In some embodiments, the compound has Formula IIc.
In some embodiments, the compound has Formula IId.

In some embodiments of compounds of Formulas I, Ia-If, II, and IIa-IId, A is cycloalkyl or heterocycloalkyl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments of compounds of Formulas I, Ia-If, II, and IIa-IId, A is aryl or heteroaryl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments of compounds of Formulas I, Ia-If, II, and IIa-IId, A is aryl optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments of compounds of Formulas I, Ia-If, II, and IIa-IId, A is phenyl optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments of compounds of Formulas I, Ia-If, II, and IIa-IId, A is phenyl optionally substituted with 1, 2, 3, 4, or 5 substituents independently selected from halo, $C_{1-6}$ alkyl, or $C_{1-6}$ haloalkyl.

In some embodiments of compounds of Formulas I, Ia-If, II, and IIa-IId, A is phenyl.

In some embodiments of compounds of Formulas I, Ia-If, II, and IIa-IId, A is heteroaryl optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments of compounds of Formulas I, Ia-If, II, and IIa-IId, A is 6-membered heteroaryl optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments of compounds of Formulas I, Ia-If, II, and IIa-IId, A is pyridyl optionally substituted with 1, 2, or 3 substituents independently selected from halo, $C_{1-6}$ alkyl, or $C_{1-6}$ haloalkyl.

In some embodiments of compounds of Formulas I, Ia-If, II, and IIa-IId, A is 5-membered heteroaryl optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments of compounds of Formulas I, Ia-If, II, and IIa-IId, A is pyrazolyl optionally substituted with 1 or 2 substituents independently selected from halo, $C_{1-6}$ alkyl, or $C_{1-6}$ haloalkyl.

In some embodiments of compounds of Formulas I, Ia-If, II, and IIa-IId, $R^1$ is heteroaryl optionally substituted with 1, 2, or 3 substituents independently selected from $-(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments of compounds of Formulas I, Ia-If, II, and IIa-IId, $R^1$ is bicyclic heteroaryl optionally substituted with 1, 2, or 3 substituents independently selected from $-(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments of compounds of Formulas I, Ia-If, II, and IIa-IId, $R^1$ is purinyl optionally substituted with $-(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)$ $NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$.

In some embodiments of compounds of Formulas I, Ia-If, II, and IIa-IId, $R^1$ is $OR^A$, $SR^A$, $S(O)R^A$, $S(O)_2R^A$, $NR^AR^B$, $NR^CC(O)NR^AR^B$, $NR^CC(O)OR^A$, $NR^CC(=NR^E)NR^AR^B$, $NR^CS(O)_2R^A$, or $NR^CS(O)_2NR^CR^A$.

In some embodiments of compounds of Formulas I, Ia-If, II, and IIa-IId, $R^1$ is $NR^AR^B$.

In some embodiments of compounds of Formulas I, Ia-If, II, and IIa-IId, $R^4$ is heteroaryl optionally substituted with 1, 2, 3, 4, or 5 substituents independently selected from $-(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments of compounds of Formulas I, Ia-If, II, and IIa-IId, $R^4$ is bicyclic heteroaryl optionally substituted with 1, 2, 3, 4, or 5 substituents independently selected from $-(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments of compounds of Formulas I, Ia-If, II, and IIa-IId, $R^4$ is purinyl optionally substituted with 1 or 2 substituents independently selected from $-(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments of compounds of Formulas I, Ia-If, II, and IIa-IId, $R^4$ is purinyl optionally substituted with 1 or 2 substituents independently selected from $C_{1-6}$ alkyl, $C_{1-6}$ haloalkyl, $NR^{c5}R^{d5}$, $NR^{c5}C(O)R^{b5}$, $NR^{c5}C(O)NR^{c5}R^{d5}$, $NR^{c5}C(O)OR^{a5}$, $NR^{c5}C(=NR^f)NR^{c5}R^{d5}$, $NR^{c5}S(O)_2R^{b5}$, $NR^{c5}S(O)_2NR^{c5}R^{d5}$, and $S(O)_2NR^{c5}R^{d5}$.

In some embodiments of compounds of Formulas I, Ia-If, II, and IIa-IId, $R^4$ is:

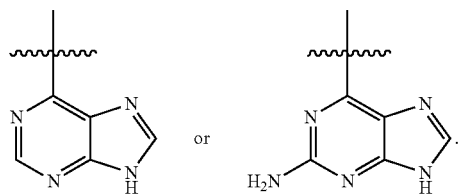 [SMILES: *c1ncnc2[nH]cnc12 ; *c1nc(N)nc2[nH]cnc12]

In some embodiments, $R^A$ is selected from:

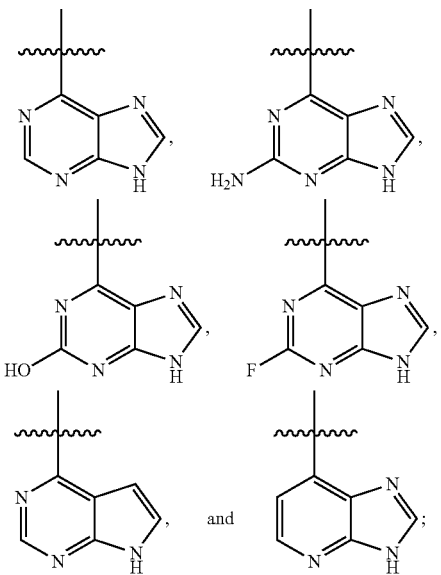

In some embodiments of compounds of Formulas I, Ia-If, II, and IIa-IId, $R^A$ is bicyclic heteroaryl optionally substituted with 1, 2, 3, 4, or 5 substituents independently selected from —$(C_{1-4}$ alkyl$)_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^e$)NR$^{c1}$R$^{d1}$, NR$^{c1}$C(=NR$^e$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$.

In some embodiments of compounds of Formulas I, Ia-If, II, and IIa-IId, $R^B$ and $R^C$ are independently selected from H and $C_{1-6}$ alkyl.

In some embodiments of compounds of Formulas I, Ia-If, II, and IIa-IId, $R^B$ and $R^C$ are each H.

In some embodiments of compounds of Formulas I, Ia-If, II, and IIa-IId, $R^{2a}$ is H, halo, OH, CN, $C_{1-6}$ alkyl, $C_{1-6}$ haloalkyl, $C_{2-6}$ alkenyl, or $C_{2-6}$ alkynyl, wherein the $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^e$)NR$^{c2}$R$^{d2}$, NR$^{c2}$C(=NR$^e$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments of compounds of Formulas I, Ia-If, II, and IIa-IId, $R^{2a}$ is halo, OH, CN, $C_{1-6}$ alkyl, $C_{1-6}$ haloalkyl, $C_{2-6}$ alkenyl, or $C_{2-6}$ alkynyl, wherein the $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^e$)NR$^{c2}$R$^{d2}$, NR$^{c2}$C(=NR$^e$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments of compounds of Formulas I, Ia-If, II, and IIa-IId, $R^{2a}$ is H, halo, OH, CN, $C_{1-6}$ alkyl, $C_{1-6}$ haloalkyl, $C_{2-6}$ alkenyl, or $C_{2-6}$ alkynyl.

In some embodiments of compounds of Formulas I, Ia-If, II, and IIa-IId, $R^{2a}$ is $C_{1-6}$ alkyl.

In some embodiments of compounds of Formulas I, Ia-If, II, and IIa-IId, $R^{2a}$ is methyl or ethyl.

In some embodiments of compounds of Formulas I, Ia-If, II, and IIa-IId, $R^3$ is halo, CN, NO$_2$, OR$^{a3}$, SR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$S(O)$_2$R$^{b3}$, NR$^{c3}$S(O)$_2$NR$^{c3}$R$^{d3}$, S(O)$_2$NR$^{c3}$R$^{d3}$, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^e$)NR$^{c3}$R$^{d3}$, NR$^{c3}$C(=NR$^e$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$.

In some embodiments of compounds of Formulas I, Ia-If, II, and IIa-IId, $R^3$ is H, halo, CN, NO$_2$, OR$^{a3}$, SR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$S(O)$_2$R$^{b3}$, S(O)$_2$NR$^{c3}$R$^{d3}$, or $C_{1-6}$ alkyl, wherein the $C_{1-6}$ alkyl, is optionally substituted with 1, 2, 3, 4, or 5 substituents independently selected from halo, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^e$)NR$^{c3}$R$^{d3}$, NR$^{c3}$C(=NR$^e$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, and S(O)$_2$NR$^{c3}$R$^{d3}$.

In some embodiments of compounds of Formulas I, Ia-If, II, and IIa-IId, $R^3$ is H or $C_{1-6}$alkyl.

In some embodiments of compounds of Formulas I, Ia-If, II, and IIa-IId, $R^3$ is $C_{1-6}$ alkyl.

In some embodiments of compounds of Formulas I, Ia-If, II, and IIa-IId, $R^3$ is methyl.

In some embodiments of compounds of Formulas I, Ia-If, II, and IIa-IId, $R^4$, $R^5$, and $R^6$ are independently selected from H, halo, $C_{1-6}$ alkyl, or $C_{1-6}$ haloalkyl.

In some embodiments of compounds of Formulas I, Ia-If, II, and IIa-IId, $R^4$, $R^5$, and $R^6$ are each H.

In some embodiments of compounds of Formulas I, Ia-If, II, and IIa-IId, $R^4$ is H.

In some embodiments of compounds of Formulas I, Ia-If, II, and IIa-IId, $R^5$ is H.

In some embodiments of compounds of Formulas I, Ia-If, II, and IIa-IId, $R^6$ is H.

In some embodiments, the compounds of the invention have Formula Ig or IIe:

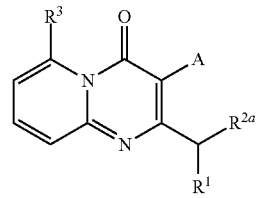

Ig

21
-continued

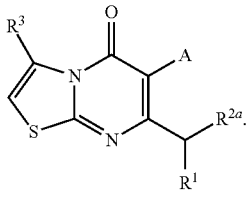

IIe

In some embodiments of compounds of Formulas Ig and IIe, $R^1$ is according to any of the previously recited embodiments for $R^1$.

In some embodiments, the compounds of the invention have Formula Ih or IIf:

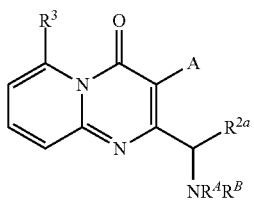

Ih

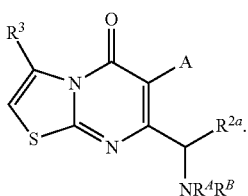

IIf

In some embodiments, of compounds of Formulas Ih and IIf, $R^A$ is according to any of the previously recited embodiments for $R^A$.

In some embodiments, the compounds of the invention have Formula Ii or IIg:

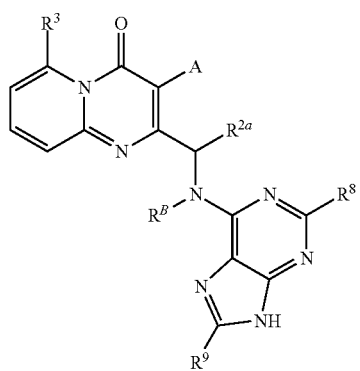

Ii

22
-continued

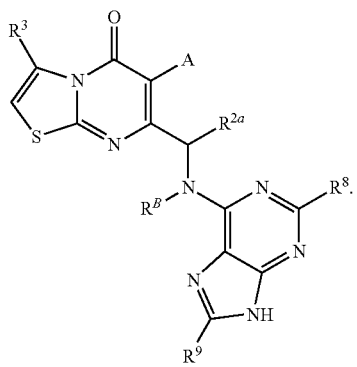

IIg wherein $R^8$ and $R^9$ are independently selected from H, $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$.

In some embodiments, $R^8$ and $R^9$ are independently selected from H, $C_{1-6}$ alkyl, $C_{1-6}$ haloalkyl, $NR^{c5}R^{d5}$, $NR^{c5}C(O)R^{b5}$, $NR^{c5}C(O)NR^{c5}R^{d5}$, $NR^{c5}C(O)OR^{a5}$, $NR^{c5}C(=NR^f)NR^{c5}R^{d5}$, $NR^{c5}S(O)_2R^{b5}$, and $NR^{c5}S(O)_2NR^{c5}R^{d5}$.

In some embodiments, $R^8$ and $R^9$ are independently selected from H and $C_{1-6}$ alkyl.

In some embodiments of compounds of Formulas Ig-Ii and IIe-IIg, A is according to any of the previously recited embodiments for A.

In some embodiments of compounds of Formulas Ig-Ii and IIe-IIg, $R^3$ is according to any of the previously recited embodiments for $R^3$.

In some embodiments of compounds of Formulas Ig-Ii and IIe-IIg, $R^{2a}$ is according to any of the previously recited embodiments for $R^{2a}$.

In some embodiments of compounds of Formulas Ig-Ii and IIe-IIg, $R^B$ is according to any of the previously recited embodiments for $R^B$.

In some embodiments of compounds of Formula If or IId:

A is aryl or heteroaryl, each optionally substituted with 1, 2, or 3 substituents independently selected from halo, $C_{1-6}$ alkyl, $C_{1-6}$ haloalkyl, CN, and $OR^a$;

$R^1$ is $NR^AR^B$ or heteroaryl; wherein the heteroaryl is optionally substituted with 1, 2, or 3 substituents independently selected from halo, $C_{1-6}$ alkyl, $C_{1-6}$ haloalkyl, CN, and ORAL;

$R^{2a}$ is $C_{1-6}$ alkyl;

$R^3$, $R^4$, $R^5$, and $R^6$ are independently selected from H, halo, CN, $NO_2$, $OR^{a3}$, and $C_{1-6}$ alkyl; wherein the $C_{1-6}$ alkyl is optionally substituted with 1, 2, 3, 4, or 5 substituents independently selected from halo;

$R^A$ is heteroaryl, which is optionally substituted with 1, 2, 3, 4, or 5 substituents independently selected from halo, $C_{1-6}$ alkyl, CN, $OR^{a1}$, and $NR^{c1}R^{d1}$;

$R^B$ is H;

each $R^a$ is independently selected from H and $C_{1-6}$ alkyl;

each $R^{a1}$, $R^{c1}$, and $R^{d1}$ is independently selected from H and $C_{1-6}$ alkyl, wherein the $C_{1-6}$ alkyl is optionally substituted with 1, 2, 3, 4, or 5 substituents independently selected from halo; and each $R^{a3}$ is independently selected from H and $C_{1-6}$ alkyl, wherein the $C_{1-6}$ alkyl is optionally substituted with 1, 2, 3, 4, or 5 substituents independently selected from halo.

In some embodiments of compounds of Formula If or IId:

A is phenyl, 5-membered heteroaryl or 6-membered heteroaryl, each optionally substituted with 1, 2, or 3 substituents independently selected from halo, $C_{1-6}$ alkyl, $C_{1-6}$ haloalkyl, CN, and $OR^a$;

$R^1$ is $NR^AR^B$ or

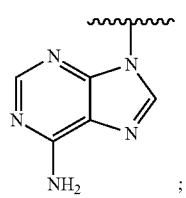 [SMILES: *n1cnc2c(N)ncnc21]
;

$R^{2a}$ is $C_{1-6}$ alkyl;

$R^3$, $R^4$, $R^5$, and $R^6$ are independently selected from H, halo, CN, $NO_2$, $OR^{a3}$, and $C_{1-6}$ alkyl; wherein the $C_{1-6}$ alkyl is optionally substituted with 1, 2, 3, 4, or 5 substituents independently selected from halo;

$R^A$ is selected from:

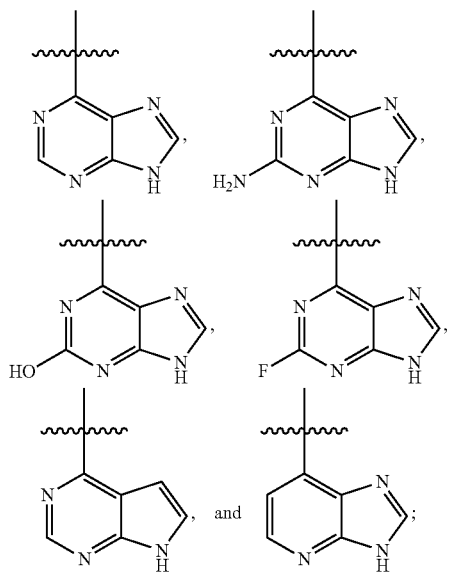 [SMILES: *c1ncnc2[nH]cnc12 ; *c1nc(N)nc2[nH]cnc12 ; *c1nc(O)nc2[nH]cnc12 ; *c1nc(F)nc2[nH]cnc12 ; *c1ncnc2[nH]ccc12 ; *c1ccnc2[nH]cnc12]

$R^B$ is H;

each $R^a$ is independently selected from H and $C_{1-6}$ alkyl; and each $R^{a3}$ is independently selected from H and $C_{1-6}$ alkyl, wherein the $C_{1-6}$ alkyl is optionally substituted with 1, 2, 3, 4, or 5 substituents independently selected from halo.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, linking substituents are described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, sec-butyl, t-butyl), pentyl (e.g., n-pentyl, isopentyl, sec-pentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more carbon-carbon double bonds. Example alkenyl groups include ethenyl, propenyl, cyclohexenyl, and the like.

As used herein, "alkynyl" refers to an alkyl group having one or more carbon-carbon triple bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "halosulfanyl" refers to a sulfur group having one or more halogen substituents. Example halosulfanyl groups include pentahalosulfanyl groups such as $SF_5$.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of cyclopentane, cyclopentene, cyclohexane, and the like. A cycloalkyl group containing a fused aromatic ring can be attached through any ring-forming atom including a ring-forming atom of the fused aromatic ring.

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. Examples of bicyclic heteroaryl groups include without limitation, purinyl, indolyl, and the like. In some embodiments, any ring-forming N in a heteroaryl moiety can be substituted by oxo. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 9 to about 10, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles having one or more ring-forming heteroatoms such as an O, N, or S atom. Heterocycloalkyl groups include monocyclic and polycyclic (e.g., having 2, 3 or 4 fused rings) systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. The heterocycloalkyl group can be attached through a ring-forming carbon atom or a ring-forming heteroatom. The heterocycloalkyl group containing a fused aromatic ring can be attached through any ring-forming atom including a ring-forming atom of the fused aromatic ring. In some embodiments, the heterocycloalkyl group has from 1 to about 20 carbon atoms, and in further embodiments from about 3 to about 20 carbon atoms. In some embodiments, the heterocycloalkyl group contains 3 to about 14, 4 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double or triple bonds. In some embodiments, the heterocycloalkyl group contains 0 to 2 double or triple bonds.

As used herein, "halo" or "halogen" includes fluoro, chloro, bromo, and iodo.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

As used herein, "amino" refers to NH$_2$.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-(haloalkyl) group.

As used herein, "alkylthio" refers to an —S-alkyl group. Example alkylthio groups include meththio, ethylthio, propylthio (e.g., n-propylthio and isopropylthio), and the like.

As used herein, "alkylamino" refers to an —NH-alkyl group. Example alkylamino groups include methylamino, ethylamino, propylamino (e.g., n-propylamino and isopropylamino), and the like.

As used herein, "di(alkyl)amino" refers to an —N(alkyl)$_2$ group. Example di(alkyl)amino groups include dimethylamino, diethylamino, dipropylamino (e.g., di(n-propyl) amino and di(isopropyl)amino), and the like.

It should be further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone— enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2, 4-triazole, 1H- and 2H-isoindole, and 1H- and 2H-pyrazole. Tautomeric forms can be in equilibrium or sterically locked into one form by appropriate substitution. For example, purine includes the 9H and a 7H tautomeric forms:

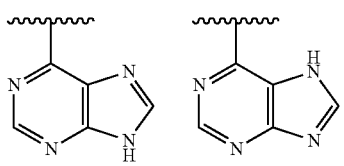

Compounds of the invention can include both the 9H and 7H tautomeric forms.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%), or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Example synthetic methods for preparing compounds of the invention are provided in the Schemes below. For instance, compounds of the invention can be prepared by the general synthetic procedure shown in Scheme 1. Heteroaryl compounds of formula 1 can react with 4-halo-3-oxo-pentanoates 2 in the presence of polyphosphoric acid (PPA) to provide the compounds of formula 3 via a cyclocondensation reaction. These can be subjected to halogenation reaction under suitable conditions, to provide halogenated compounds 4. Compounds of formula 4 can be transformed to the compounds of formula 5 through any variation of a sequence of steps. $X^1$ can be replaced with either an azide, an amine, or a heterocyclic group through an $S_N2$ displacement and eventually transformed to the $R^1$ group. $X^2$ can be converted to a desired cyclic moiety (Cy) through any of the standard cross-coupling reactions, known to one skilled in the art, e.g., using boronic acid derivatives of the desired cyclic moiety.

Scheme 1

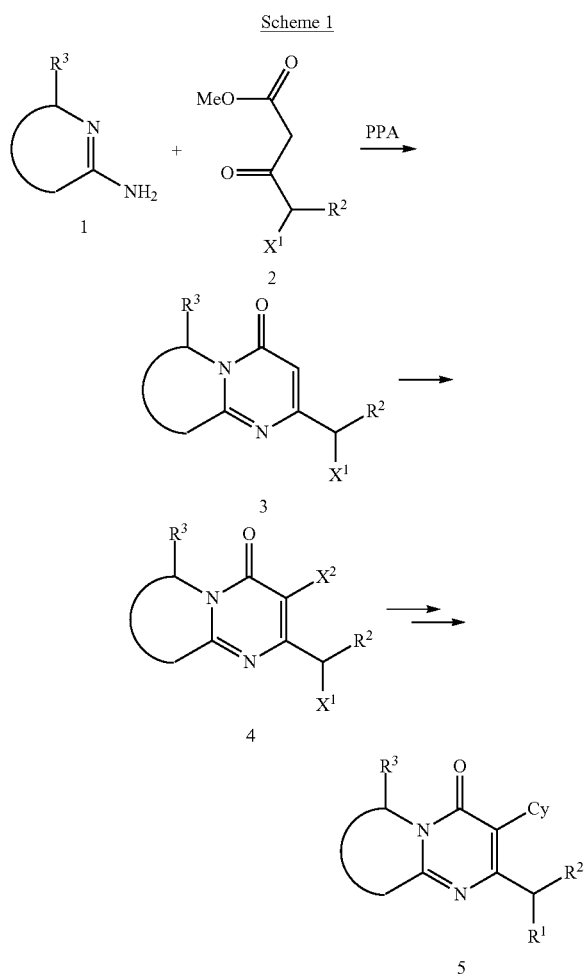

As shown in Scheme 2, the pyrido[1,2-a]pyrimidin-4-ones of the invention can be prepared by cyclocondensation of aminopyrimidines 6 with a β-keto ester 2. Halogenation of the resultant pyridopyridinones 7 under suitable conditions (such as NBS or bromine) provides compounds of formula 8. The latter can be transformed to the compounds of formula 9 through an $S_N2$ substitution of $X^1$ with a heterocycle $R^1$ followed by a coupling reaction of $X^2$ with L-A moiety (such as a Negishi coupling of organozinc reagent; a Suzuki or Stille coupling of an arylboronic acid or arylstanne, respectively). Alternatively, $X^1$ can be replaced with either an amine or an azide which can be reduced to amine. The amine can then be subjected to coupling reaction with a $R^1$ moiety to give compounds of formula 9.

Scheme 2

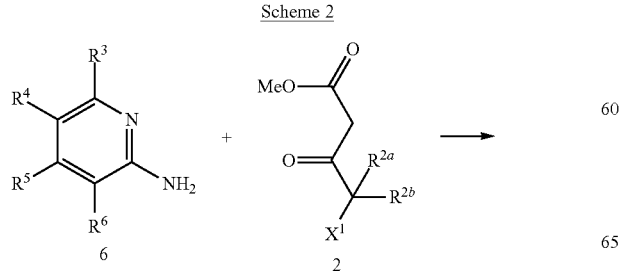

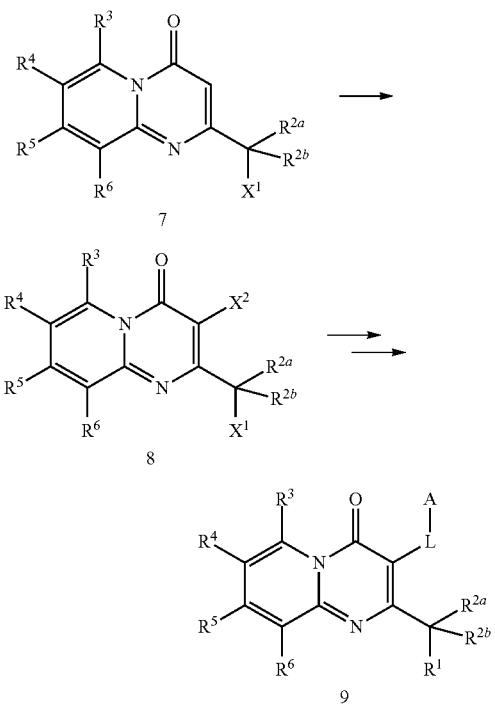

The thiazolo[3,2-a]pyrimidin-5-ones of the invention can be prepared according to Scheme 3. 2-Aminothiazole 10 condensed with a β-keto ester 2 provides thiazolopyrimidinone 11. Compounds of formula 11 can be converted to compounds of formula 13 through any variations of a sequence of steps as described above.

Scheme 3

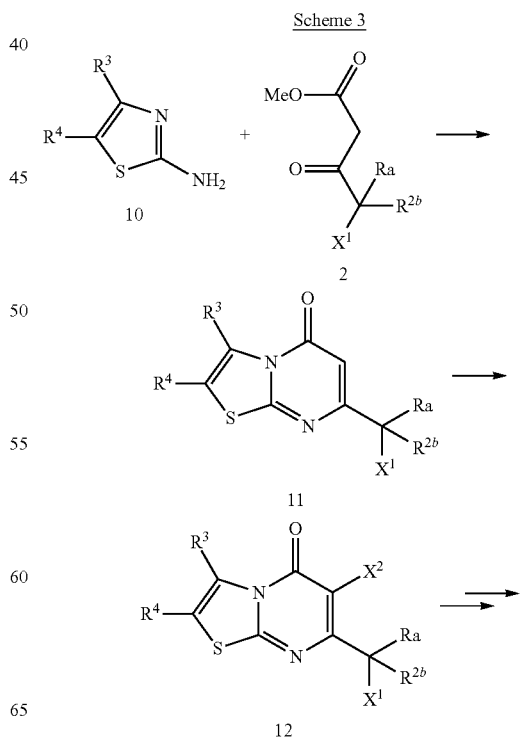

31

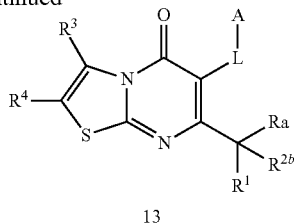

13

Alternatively, compounds of the invention can be synthesized by reacting amino heterocycles 14 with an α-substituted β-keto ester 15 shown in Scheme 4. The cyclocondensation derivatives 16 can then be subjected to halogenation (such as NBS or bromine) or oxidation (such as SeO$_2$) to afford halogen compounds 17 ($X^1$=halogen), or alcohol compounds 17 (X=OH), respectively. Compounds of formula 17 can then be transformed to compounds of formula 18 through any variations of a sequence of steps. $X^1$ can be coupled directly with a heterocycles under any of the cross coupling conditions know to one skilled in the art (such as Buchwald-Hartwig cross coupling conditions) or converted to a halogen then the latter can be coupled with a heterocycles through $S_N2$ substitutions.

Scheme 4

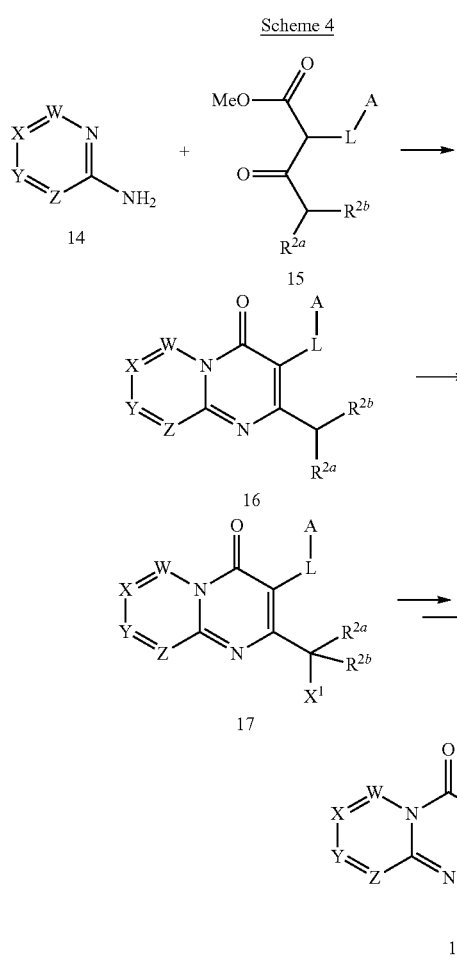

Compounds of Formula II of the invention can be prepared according to Scheme 5. Amino heterocycles 19 condensed with α-substituted β-ketone ester 15 affords compounds of formula 20. The latter can be transformed to compounds of Formula II through any variation of steps described above.

Scheme 5

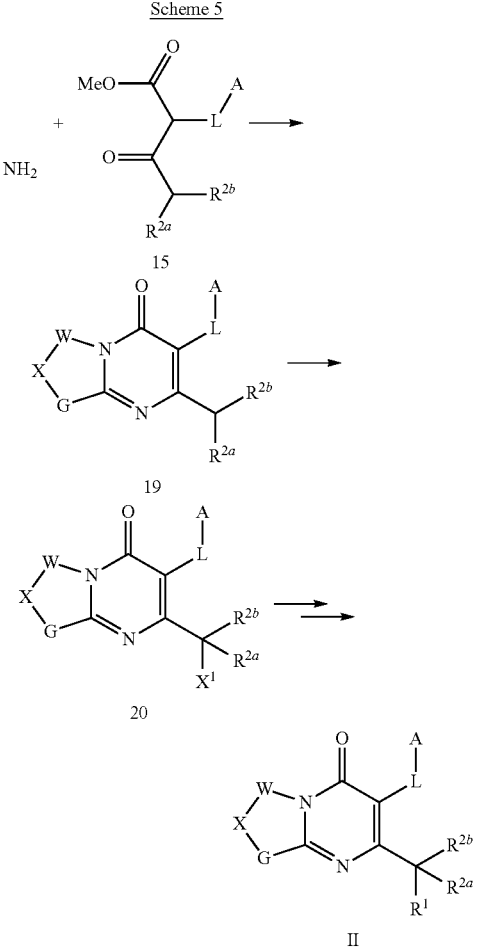

It should noted that in all of the Schemes described herein, if there are functional groups present on a substituent group, further modification can be made if appropriate and desired. For example, a CN group can be hydrolyzed to afford an amide group; a carboxylic acid can be converted to a ester, which in turn can be reduced to an alcohol, which in turn can be further modified. In another example, an OH group can be converted into a better leaving group such as mesylate, which in turn is suitable for nucleophilic substitution, such as by CN. Furthermore, an OH group can be subjected to Mitsunobu reaction conditions with phenol, or heteroaryl alcohol, to afford aryl or heteroaryl ether compounds. One skilled in the art will recognize further modifications.

It should be further noted that the reaction sequences described above can be modified to suit different target molecules. For instance, Cy-boronic acid can be reacted with 4 to generate the Suzuki product first. The $X^1$ group of the Suzuki product can then be further functionalized with a nucleophilic reagent such as an azide or a heterocyclic amine.

Methods

The compounds of the invention can modulate activity of one or more of various kinases including, for example, phosphoinositide 3-kinases (PI3Ks). The term "modulate" is meant to refer to an ability to increase or decrease the activity of one or more members of the PI3K family. Accordingly, the compounds of the invention can be used in methods of modulating a PI3K by contacting the PI3K with any one or more of the compounds or compositions described herein. In some embodiments, compounds of the present invention can act as inhibitors of one or more PI3Ks. In further embodiments, the compounds of the invention can be used to modulate activity of a PI3K in an individual in need of modulation of the receptor by administering a modulating amount of a compound of the invention, or a pharmaceutically acceptable salt thereof. In some embodiments, modulating is inhibiting.

Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate (e.g., inhibit) include any member of the PI3K family. In some embodiments, the PI3K is PI3Kα, PI3Kβ, PI3Kγ, and PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one compound of the invention is used to inhibit the activity of one kinase (e.g., PI3Kγ or PI3Kδ).

In some embodiments, more than one compound of the invention is used to inhibit more than one kinase, such as at least two kinases (e.g., PI3Kγ or PI3Kδ).

In some embodiments, one or more of the compounds is used in combination with another kinase inhibitor to inhibit the activity of one kinase (e.g., PI3Kγ or PI3Kδ).

In some embodiments, one or more of the compounds is used in combination with another kinase inhibitor to inhibit the activities of more than one kinase (e.g., PI3Kγ or PI3Kδ), such as at least two kinases.

The compounds of the invention can be selective. By "selective" is meant that the compound binds to or inhibits a kinase with greater affinity or potency, respectively, compared to at least one other kinase. In some embodiments, the compounds of the invention are selective inhibitors of PI3Kγ or PI3Kδ over PI3Kα and/or PI3Kβ. In some embodiments, the compounds of the invention are selective inhibitors of PI3Kδ (e.g., over PI3Kα, PI3Kβ, and PI3Kγ). In some embodiments, the compounds of the invention are selective inhibitors of PI3Kγ (e.g., over PI3Kα, PI3Kβ, and PI3Kδ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase (such as PI3K)-associated disease or disorder in an individual (e.g., patient) by administering to the individual in need of such treatment a therapeutically effective amount or dose of one or more compounds of the present invention or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjoegren's syndrome, and the like.

The present invention further provides a compound described herein, or a pharmaceutically acceptable salt thereof, for use in any of the methods described herein.

The present invention further provides use of a compound described herein, or a pharmaceutically acceptable salt thereof, for the production of a medicament for use in any of the methods described herein.

As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, EGFR, HER2, JAK, c-MET, VEGFR, PDGFR, cKit, IGF-1R, RAF and FAK kinase inhibitors such as, for example, those described in WO 2006/056399, or other agents such as, therapeutic antibodies can be used in combination with the compounds of the present invention for treatment of PI3K-associated diseases, disorders or conditions. The one or more additional pharmaceutical agents can be administered to a patient simultaneously or sequentially.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, Cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent. Furthermore, resistance of multiple myeloma cells to agents such as dexamethasone may be reversible upon treatment with the PI3K inhibitor of the present invention. The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some further embodiments, combinations of the compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compounds or compositions of the invention contain from about 5 to about 50 mg of the active ingredient. One having ordinary skill in the art will appreciate that this embodies compounds or compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compounds or compositions of the invention contain from about 50 to about 500 mg of the active ingredient. One having ordinary skill in the art will appreciate that this embodies compounds or compositions containing about 50 to about 100, about 100 to about 150, about 150 to about 200, about 200 to about 250, about 250 to about 300, about 350 to about 400, or about 450 to about 500 mg of the active ingredient.

In some embodiments, the compounds or compositions of the invention contain from about 500 to about 1000 mg of the active ingredient. One having ordinary skill in the art will appreciate that this embodies compounds or compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro PI3K labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^{3}$H, $^{14}$C, $^{125}$I, $^{35}$S and $^{82}$Br.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3K inhibitors according to at least one assay described herein.

EXAMPLES

The example compounds below containing one or more chiral centers were obtained in racemate form or as isomeric mixtures, unless otherwise specified.

Example 1. 2-[1-(6-amino-9H-purin-9-yl)ethyl]-6-methyl-3-phenyl-4H-pyrido[1,2-a]pyrimidin-4-one

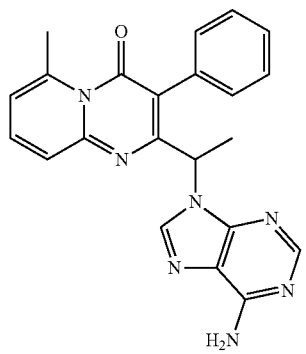 [SMILES: Cc1cccc2nc(C(C)n3cnc4c(N)ncnc43)c(-c3ccccc3)c(=O)n12]

Step 1. methyl 4-chloro-3-oxopentanoate

To a solution of 3-oxopentanoic acid, methyl ester (Aldrich, 26.0 mL, 207.2 mmol) in methylene chloride (300 mL) was added in portions, N,N,N-trimethyl(phenyl) methanaminium dichloroiodanuide (75.71 g, 217.5 mmol). The reaction mixture was stirred at room temperature (rt) for 2 h, then washed with saturated sodium thiosulfate, brine, dried over magnesium sulfate and concentrated. The crude product was used directly in next step (23 g, 67.4%).

Step 2. 2-(1-chloroethyl)-6-methyl-4H-pyrido[1,2-a]pyrimidin-4-one

To a manually stirred polyphosphoric acid (30 g, 200 mmol) in a 200 mL beaker was added 6-methyl-2-pyridinamine (Aldrich, 4.7 g, 43 mmol), followed by methyl 4-chloro-3-oxopentanoate (8.584 g, 52.15 mmol). The mixture was heated with stirring at 110° C. for 5 h. After being cooled, the dark slurry was transferred on to 100 g of ice. The pH of the mixture was adjusted to 6-7 with 10% sodium hydroxide. The mixture was extracted with methylene chloride. The combined organic layers were washed with water, brine, dried over magnesium sulfate and evaporated to dryness. The residue was purified on silica gel, eluting with 0-10% methanol in methylene chloride, to yield the desired product (3.16 g, 32.1%). LCMS calculated for $C_{11}H_{12}ClN_2O(M+H)^+$: m/z=223.1. Found: 223.2.

Step 3. 3-bromo-2-(1-chloroethyl)-6-methyl-4H-pyrido[1,2-a]pyrimidin-4-one

To a stirred solution of 2-(1-chloroethyl)-6-methyl-4H-pyrido[1,2-a]pyrimidin-4-one (3.16 g, 14.2 mmol) in methylene chloride (30 mL) was added drop-wise bromine (0.804 mL, 15.6 mmol) in methylene chloride (7 mL). The reaction mixture was stirred at room temperature for 2 h. The product precipitated out and was collected by filtration (2.42 g, 56.6%). LCMS calculated for $C_{11}H_{11}BrClN_2O(M+H)^+$: m/z=301.0. Found: 301.1.

Step 4. 2-[1-(6-amino-9H-purin-9-yl)ethyl]-3-bromo-6-methyl-4H-pyrido[1,2-a]pyrimidin-4-one A mixture of 3-bromo-2-(1-chloroethyl)-6-methyl-4H-pyrido[1,2-a]pyrimidin-4-one (1.24 g, 4.11 mmol), adenine (Sigma, 1.08 g, 8.04 mmol), and potassium carbonate (1.11 g, 8.04 mmol) in N,N-dimethylformamide (20 mL) was stirred at room temperature overnight. The suspension was then poured into water and extracted with methylene chloride. The combined organic layers were washed with water, brine, and then the organic layers dried and evaporated to dryness. The residue was chromatographed on silica gel, eluting with 0 to 10% MeOH in methylene chloride, to provide the desired product (176 mg, 10.7%). LCMS calculated for $C_{16}H_{15}BrN_7O(M+H)^+$: m/z=400.1. Found: 400.1. $^1$H NMR (DMSO-$d_6$, 300 MHz) δ 8.44 (1H, s), 8.07 (1H, s), 7.67 (1H, dd, J=8.7 and 7.2 Hz), 7.30 (1H, br d, J=8.7 Hz), 7.20 (2H, s), 6.99 (1H, br d, J=12 Hz), 6.15 (1H, q, J=12 Hz), 2.91 (3H, s), 1.84 (3H, d, J=12 Hz) ppm.

Step 5. 2-[1-(6-amino-9H-purin-9-yl)ethyl]-6-methyl-3-phenyl-4H-pyrido[1,2-a]pyrimidin-4-one To a mixture of 2-[1-(6-amino-9H-purin-9-yl)ethyl]-3-bromo-6-methyl-4H-pyrido[1,2-a]pyrimidin-4-one (0.030 g, 0.075 mmol) and phenylboronic acid (11.0 mg, 0.0899 mmol) in 1,4-dioxane (0.6 mL) was added a 1 M solution of sodium carbonate (9.53 mg, 0.0899 mmol) in water (0.089 mL) and tetrakis(triphenylphosphine)palladium (0) (4.33 mg, 0.00375 mmol). The reaction mixture was heated at 100° C. overnight. After cooling to rt, the mixture was diluted with EtOAc, washed with water, brine, dried over MgSO$_4$, and concentrated. The residue was purified on RP-HPLC at pH 10 (XBridge C18 column, eluting with a gradient of acetonitrile/water containing 0.15% NH$_4$OH) to provide the desired product. LCMS calculated for C$_{22}$H$_{20}$N$_7$O(M+H)$^+$: m/z=398.2. Found: 398.3. $^1$H NMR (DMSO-d$_6$, 300 MHz) δ 8.37 (1H, s), 7.97 (1H, s), 7.56 (1H, dd, J=8.7 and 6.6 Hz), 7.41-7.36 (5H, m), 7.26 (1H, br d, J=9.0 Hz), 7.09 (2H, br s), 6.85 (1H, br d, J=12 Hz), 5.59 (1H, q, J=12 Hz), 2.80 (3H, s), 1.64 (3H, d, J=12 Hz) ppm.

Example 2. 6-methyl-3-phenyl-2-[1-(9H-purin-6-ylamino)propyl]-4H-pyrido[1,2-a]pyrimidin-4-one

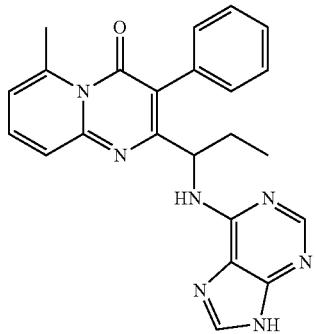 [SMILES: CCC(Nc1ncnc2[nH]cnc12)c1nc2cccc(C)n2c(=O)c1-c1ccccc1]

Step 1. methyl 4-bromo-3-oxohexanoate

Under a nitrogen atmosphere, a solution of bromine (8.61 mL, 167 mmol) in chloroform (20 mL) was added drop-wise over a period of 2 h to a solution of methyl 3-oxohexanoate (Fluka, 24.1 g, 167 mmol) in chloroform (147 mL), at 0° C. (ice bath). The reaction mixture was stirred for 30 min at 0° C. and then allowed to warm to room temperature overnight. While stirring, a stream of air was bubbled through the solution for 1 hour. The reaction mixture was dried over sodium sulfate and the solvent evaporated under reduced pressure to provide the desired compound.

Step 2. 2-(1-bromopropyl)-6-methyl-4H-pyrido[1,2-a]pyrimidin-4-one

To a manually stirred polyphosphoric acid (80 g, 800 mmol) in a 1000 mL beaker at room temperature was added 6-methyl-2-pyridinamine (15 g, 140 mmol), followed by methyl 4-bromo-3-oxohexanoate (37.3 g, 167 mmol). The mixture was heated with stirring at 110° C. for 5 h. After cooling, the dark slurry was transferred into 300 g of ice. The pH of the mixture was adjust to 6-7 with 10% sodium hydroxide. The precipitate was collected by filtration under reduced pressure, washed with water, and air dried to yield the desired product (25.4 g, 64.8%). LCMS calculated for C$_{12}$H$_{14}$BrN$_2$O(M+H)$^+$: m/z=281.0. Found: 281.2. $^1$H NMR (DMSO-d$_6$, 300 MHz) δ 7.66 (1H, d, J=9.0 and 6.9 Hz), 7.39 (1H, d, J=9.0 Hz), 6.90 (1H, d, J=6.9 Hz), 6.33 (1H, s), 4.91 (1H, t, J=7.5 Hz), 2.91 (3H, s), 2.15 (2H, qd, J=7.5 and 7.5 Hz), 0.93 (3H, t, J=7.5 Hz) ppm.

Step 3. 2-(1-bromopropyl)-3-iodo-6-methyl-4H-pyrido[1,2-a]pyrimidin-4-one

A mixture of 2-(1-bromopropyl)-6-methyl-4H-pyrido[1,2-a]pyrimidin-4-one (3.46 g, 12.3 mmol) and N-iodosuccinimide (4.15 g, 18.4 mmol) in acetonitrile (100 mL) was stirred at 80° C., under nitrogen, overnight. After removal of acetonitrile in vacuum, the resulting solid was dissolved in methylene chloride, washed with water, saturated Na$_2$S$_2$O$_3$, saturated sodium bicarbonate, and brine; and then the organic layers dried over sodium sulfate and then filtered. The filtrate was concentrated under reduced pressure to provide the desired product (4.53 g, 90.4%). LCMS calculated for C$_{12}$H$_{13}$BrIN$_2$O(M+H)$^+$: m/z=406.9. Found: 407.1.

Step 4. 2-(1-azidopropyl)-3-iodo-6-methyl-4H-pyrido[1,2-a]pyrimidin-4-one

A mixture of 2-(1-bromopropyl)-3-iodo-6-methyl-4H-pyrido[1,2-a]pyrimidin-4-one (4.50 g, 11.0 mmol) and sodium azide (3.59 g, 55.3 mmol) in DMF was stirred at room temperature for 2 h. After diluting with ethyl acetate, the mixture was washed with water, brine, dried over sodium sulfate, and evaporated under reduced pressure to provide the crude product, which was used directly in next step (3.35 g, 82.1%). LCMS calculated for C$_{12}$H$_{13}$IN$_5$O(M+H)$^+$: m/z=370.0. Found: 370.2.

Step 5. 2-(1-azidopropyl)-6-methyl-3-phenyl-4H-pyrido[1,2-a]pyrimidin-4-one

To a mixture of 2-(1-azidopropyl)-3-iodo-6-methyl-4H-pyrido[1,2-a]pyrimidin-4-one (0.11 g, 0.29 mmol) and phenylboronic acid (42.9 mg, 0.352 mmol) in 1,4-dioxane (2 mL) was added a 1 M solution of sodium carbonate (37.3 mg, 0.352 mmol) in water (0.35 mL) and tetrakis(triphenylphosphine)palladium (0) (16.9 mg, 0.0147 mmol). The reaction mixture was heated at 100° C. overnight. After cooling to rt, the mixture was diluted with EtOAc, washed with water, brine, dried over MgSO$_4$, and concentrated. The residue was purified on silica gel, eluting with 0 to 40% EtOAc in hexane, to provide the desired product (50 mg, 53.4%). LCMS calculated for C$_{18}$H$_{18}$N$_5$O(M+H)$^+$: m/z=320.2. Found: 320.3.

Step 6. 2-(1-aminopropyl)-6-methyl-3-phenyl-4H-pyrido[1,2-a]pyrimidin-4-one

To a stirred solution of 2-(1-azidopropyl)-6-methyl-3-phenyl-4H-pyrido[1,2-a]pyrimidin-4-one (0.030 g, 0.094 mmol) in tetrahydrofuran (0.24 mL) and water (0.06 mL) was added 1.0 M of trimethylphosphine in tetrahydrofuran (0.11 mL) at room temperature and the mixture was stirred at room temperature for 1 hour. To the mixture was added methylene chloride and the mixture was washed with brine, dried over magnesium sulfate, and evaporated to dryness under reduced pressure. The crude residue was used directly in next step. LCMS calculated for C$_{18}$H$_{20}$N$_3$O(M+H)$^+$: m/z=294.2. Found: 294.3.

Step 7. 6-methyl-3-phenyl-2-[1-(9H-purin-6-ylamino)propyl]-4H-pyrido[1,2-a]pyrimidin-4-one A mixture of 6-bromo-9H-purine (Aldrich, 0.0152 g, 0.07656 mmol), 2-(1-aminopropyl)-6-methyl-3-phenyl-4H-pyrido[1,2-a]pyrimidin-4-one (0.019 g, 0.064 mmol), and N,N-diisopropylethylamine (0.0134 mL, 0.07666 mmol) in ethanol (0.5 mL) was refluxed under nitrogen overnight. The mixture was cooled and purified on RP-HPLC at pH 10 (XBridge C18 column, eluting with a gradient of acetonitrile/water containing 0.15% NH$_4$OH) to provide the product as the free base. LCMS calculated for C$_{23}$H$_{22}$N$_7$O(M+H)$^+$: m/z=412.2. Found: 412.4. $^1$H NMR (DMSO-d$_6$, 300 MHz) δ 8.07 (2H, m), 7.60 (1H, dd, J=9.0 and 6.9 Hz), 7.39-7.32 (7H, m), 7.00 (1H, m), 6.85 (1H, br d, J=6.9 Hz), 5.13 (1H, m), 2.81 (3H, s), 1.72 (2H, m), 0.65 (3H, t, J=7.2 Hz) ppm.

Example 3. 3-(5-fluoropyridin-3-yl)-6-methyl-2-[1-(9H-purin-6-ylamino)propyl]-4H-pyrido[1,2-a]pyrimidin-4-one

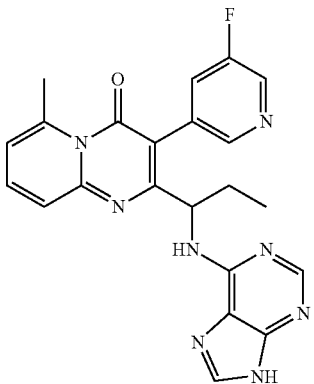 [SMILES: CCC(Nc1ncnc2[nH]cnc12)c1nc2cccc(C)n2c(=O)c1-c1cncc(F)c1]

Step 1. 2-(1-aminopropyl)-3-iodo-6-methyl-4H-pyrido[1,2-a]pyrimidin-4-one

To a stirred solution of 2-(1-azidopropyl)-3-iodo-6-methyl-4H-pyrido[1,2-a]pyrimidin-4-one (3.10 g, 8.40 mmol) in tetrahydrofuran (20 mL) and water (6.06 mL) was added a 1.0 M solution of trimethylphosphine in tetrahydrofuran (0.1 mmol) at room temperature and stirred for 1 hour. To the mixture was added EtOAc and the mixture was extracted twice with 1 N HCl. The combined extracts were neutralized with solid sodium bicarbonate and extracted with methylene chloride. The combined organic layers were washed with brine, dried over magnesium sulfate, and concentrated under reduced pressure. The residue was used directly in next step (2.58 g, 89.5%). LCMS calculated for C$_{12}$H$_{15}$IN$_3$O(M+H)$^+$: m/z=344.0. Found: 344.2.

Step 2. 3-iodo-6-methyl-2-[1-(9H-purin-6-ylamino)propyl]-4H-pyrido[1,2-a]pyrimidin-4-one A mixture of 6-bromo-9H-purine (1.65 g, 0.008270 mol), 2-(1-aminopropyl)-3-iodo-6-methyl-4H-pyrido[1,2-a]pyrimidin-4-one (2.58 g, 0.00752 mol), and N,N-diisopropylethylamine (1.571 mL, 0.009022 mol) in ethanol (60 mL) was refluxed under nitrogen overnight. The mixture was concentrated and the resulting residue was purified on silica gel, eluting with 0 to 10% methanol in methylene chloride, to provide the desired product (2.86 g, 82.5%). LCMS calculated for C$_{17}$H$_{17}$IN$_7$O(M+H)$^+$: m/z=462.1. Found: 462.2. $^1$H NMR (DMSO-d$_6$, 300 MHz) δ 8.31 (2H, m), 8.19 (1H, s), 8.15 (1H, s), 7.69 (1H, dd, J=8.7 and 6.9 Hz), 7.44 (1H, d, J=8.7 Hz), 6.99 (1H, d, J=6.9 Hz), 5.69 (1H, m), 2.89 (3H, s), 1.91 (2H, m), 0.95 (3H, t, J=7.2 Hz) ppm.

Step 3. 3-(5-fluoropyridin-3-yl)-6-methyl-2-[1-(9H-purin-6-ylamino)propyl]-4H-pyrido[1,2-a]pyrimidin-4-one To a mixture of 3-iodo-6-methyl-2-[1-(9H-purin-6-ylamino)propyl]-4H-pyrido[1,2-a]pyrimidin-4-one (0.030 g, 0.065 mmol) and (5-fluoropyridin-3-yl)boronic acid (Combi-Blocks, 11.0 mg, 0.0780 mmol) in 1,4-dioxane (0.5 mL) was added a 1 M solution of sodium carbonate (8.27 mg, 0.0780 mmol) in water (0.077 mL) and tetrakis(triphenylphosphine)palladium (0) (3.76 mg, 0.00325 mmol). The reaction mixture was heated at 100° C. overnight. After cooling to rt, the mixture was diluted with EtOAc, washed with water, brine, dried over MgSO$_4$, and concentrated. The residue was purified on RP-HPLC at pH 10 conditions (XBridge C18 column, eluting with a gradient of acetonitrile/water containing 0.15% NH$_4$OH) to provide the desired product. LCMS calculated for C$_{22}$H$_{20}$FN$_8$O(M+H)$^+$: m/z=431.2. Found: 431.3.

Example 4. 3-(3-fluorophenyl)-6-methyl-2-[1-(9H-purin-6-ylamino)propyl]-4H-pyrido[1,2-a]pyrimidin-4-one

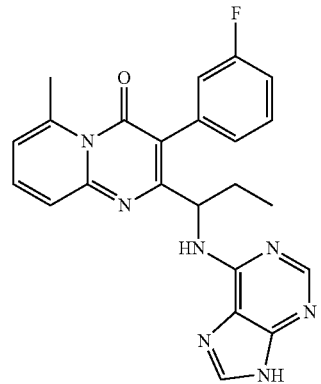 [SMILES: CCC(Nc1ncnc2[nH]cnc12)c1nc2cccc(C)n2c(=O)c1-c1cccc(F)c1]

To a mixture of 3-iodo-6-methyl-2-[1-(9H-purin-6-ylamino)propyl]-4H-pyrido[1,2-a]pyrimidin-4-one (from example 3, step 2; 0.030 g, 0.065 mmol) and (3-fluorophenyl)boronic acid (Aldrich, 10.9 mg, 0.0780 mmol) in 1,4-dioxane (0.5 mL) was added a 1 M solution of sodium carbonate (8.27 mg, 0.0780 mmol) in water (0.077 mL) and tetrakis(triphenylphosphine)palladium (0) (3.76 mg, 0.00325 mmol). The reaction mixture was heated at 100° C. overnight. After cooling to rt, the mixture was diluted with EtOAc, washed with water, brine, dried over MgSO$_4$, and concentrated. The residue was purified on RP-HPLC at pH 10 conditions (XBridge C18 column, eluting with a gradient of acetonitrile/water containing 0.15% NH$_4$OH) to provide the desired product. LCMS calculated for C$_{23}$H$_{21}$FN$_7$O(M+H)$^+$: m/z=430.2. Found: 430.3. $^1$H NMR (DMSO-d$_6$, 300 MHz) δ 8.11 (2H, m), 7.65 (1H, m), 7.45 (2H, m), 7.24 (4H, m), 7.08 (1H, m), 6.91 (1H, m), 5.17 (1H, m), 2.87 (3H, s), 1.79 (2H, m), 0.72 ((3H, t, J=7.2 Hz) ppm. $^{19}$F NMR (DMSO-d$_6$, 282 MHz) δ−114 ppm.

Example 5. 3-(3,5-difluorophenyl)-6-methyl-2-[1-(9H-purin-6-ylamino)propyl]-4H-pyrido[1,2-a]pyrimidin-4-one

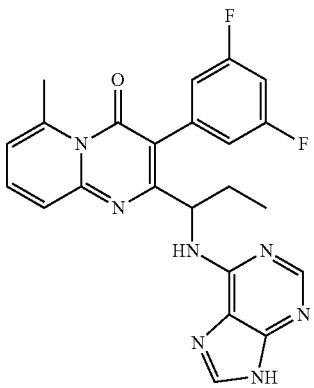 [SMILES: CCC(Nc1ncnc2[nH]cnc12)c1nc2cccc(C)n2c(=O)c1-c1cc(F)cc(F)c1]

To a mixture of 3-iodo-6-methyl-2-[1-(9H-purin-6-ylamino)propyl]-4H-pyrido[1,2-a]pyrimidin-4-one (from example 3, step 2; 0.030 g, 0.065 mmol) and (3,5-difluorophenyl)boronic acid (Aldrich, 12.3 mg, 0.0780 mmol) in 1,4-dioxane (0.5 mL) was added a 1 M solution of sodium carbonate (8.27 mg, 0.0780 mmol) in water (0.077 mL) and tetrakis(triphenylphosphine)palladium (0) (3.76 mg, 0.00325 mmol). The reaction mixture was heated at 100° C. overnight. After cooling to rt, the mixture was diluted with EtOAc, washed with water, brine, dried over MgSO$_4$, and concentrated. The residue was purified on RP-HPLC at pH 10 conditions (XBridge C18 column, eluting with a gradient of acetonitrile/water containing 0.15% NH$_4$OH) to provide the desired product. LCMS calculated for $C_{23}H_{20}F_2N_7O$ (M+H)$^+$: m/z=448.2. Found: 448.3. $^1$H NMR (DMSO-d$_6$, 300 MHz) δ 8.06 (2H, m), 7.61 (1H, m), 7.38 (1H, m), 7.14 (5H, m), 6.88 (1H, m), 5.08 (1H, m), 2.83 (3H, s), 1.75 (2H, m), 0.70 ((3H, t, J=7.8 Hz) ppm. 19F NMR (DMSO-d$_6$, 282 MHz) δ -111 ppm.

Example 6. 3-(2-fluoropyridin-3-yl)-6-methyl-2-[1-(9H-purin-6-ylamino)propyl]-4H-pyrido[1,2-a]pyrimidin-4-one

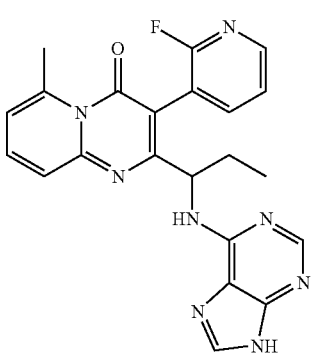 [SMILES: CCC(Nc1ncnc2[nH]cnc12)c1nc2cccc(C)n2c(=O)c1-c1cccnc1F]

To a mixture of 3-iodo-6-methyl-2-[1-(9H-purin-6-ylamino)propyl]-4H-pyrido[1,2-a]pyrimidin-4-one (from example 3, step 2; 0.030 g, 0.065 mmol) and (2-fluoropyridin-3-yl)boronic acid (Alfa Aesar, 11.0 mg, 0.0780 mmol) in 1,4-dioxane (0.5 mL) was added a 1 M solution of sodium carbonate (8.27 mg, 0.0780 mmol) in water (0.077 mL) and tetrakis(triphenylphosphine)palladium (0) (3.76 mg, 0.00325 mmol). The reaction mixture was heated at 100° C. overnight. After cooling to rt, the mixture was diluted with EtOAc, washed with water, brine, dried over MgSO$_4$, and concentrated. The residue was purified on RP-HPLC at pH 2 conditions (XBridge C18 column, eluting with a gradient of acetonitrile/water containing 0.05% TFA) to provide the desired product as a TFA salt. LCMS calculated for free base $C_{22}H_{20}FN_8O$(M+H)$^+$: m/z=431.2. Found: 431.3.

Example 7. 6-methyl-2-[1-(9H-purin-6-ylamino)propyl]-3-(1H-pyrazol-4-yl)-4H-pyrido[1,2-a]pyrimidin-4-one

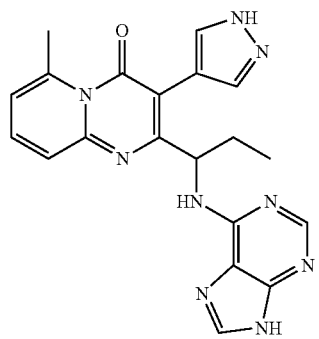 [SMILES: CCC(Nc1ncnc2[nH]cnc12)c1nc2cccc(C)n2c(=O)c1-c1cn[nH]c1]

To a mixture of 3-iodo-6-methyl-2-[1-(9H-purin-6-ylamino)propyl]-4H-pyrido[1,2-a]pyrimidin-4-one (from example 3, step 2; 0.030 g, 0.065 mmol) and 4-(4,4,5,5-tetramethyl-1,3,2-dioxaborolan-2-yl)-1H-pyrazole (Aldrich, 15.1 mg, 0.0780 mmol) in 1,4-dioxane (0.5 mL) was added a 1 M solution of sodium carbonate (8.27 mg, 0.0780 mmol) in water (0.077 mL) and tetrakis(triphenylphosphine)palladium (0) (3.76 mg, 0.00325 mmol). The reaction mixture was heated at 100° C. overnight. After cooling to rt, the mixture was diluted with EtOAc, washed with water, brine, dried over MgSO$_4$, and concentrated. The residue was purified on RP-HPLC at pH 2 conditions (XBridge C18 column, eluting with a gradient of acetonitrile/water containing 0.05% TFA) to provide the desired product as a TFA salt. LCMS calculated for free base $C_{20}H_{20}N_9O$(M+H)$^+$: m/z=402.2. Found: 402.1.

Example 8. 3-methyl-6-phenyl-7-[1-(9H-purin-6-ylamino)ethyl]-5H-[1,3]thiazolo[3,2-a]pyrimidin-5-one

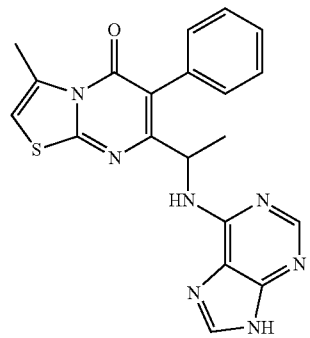

Step 1. methyl 4-bromo-3-oxopentanoate

Under a nitrogen atmosphere, a solution of bromine (8.61 mL, 167 mmol) in chloroform (20 mL, 200 mmol) was added dropwise over a period of 2 h to a solution of 3-oxopentanoic acid, methyl ester (Aldrich, 21.0 mL, 167 mmol) in chloroform (147 mL, 1840 mmol), at 0° C. (ice bath). The reaction mixture was stirred for 30 min at 0° C. and then allowed to stand at room temperature overnight. While stirring, a stream of air was bubbled through the solution for 1 hour. After drying over sodium sulfate, the solvent was evaporated under reduced pressure leaving the desired compound.

Step 2. 7-(1-bromoethyl)-3-methyl-5H-[1,3]thiazolo[3,2-a]pyrimidin-5-one

To a manually stirred polyphosphoric acid (80 g, 800 mmol) in a 1000 mL beaker was added 4-methyl-1,3-thiazol-2-amine (Aldrich, 16 g, 140 mmol), followed by methyl 4-bromo-3-oxopentanoate (34.9 g, 167 mmol). The mixture was heated with stirring at 110° C. for 5 h. After cooling, the dark slurry was transferred into 300 g of ice. The pH of the mixture was adjust to 6-7 with 10% sodium hydroxide. The aqueous layer was discarded and the dark oil layer was diluted with methylene chloride and washed with 1 N NaOH, brine, dried over magnesium sulfate, and evaporated to dryness to yield the desired product (16.2 g, 42.6%). LCMS calculated for $C_9H_{10}BrN_2OS(M+H)^+$: m/z=273.0. Found: 273.1.

Step 2. 6-bromo-7-(1-bromoethyl)-3-methyl-5H-[1,3]thiazolo[3,2-a]pyrimidin-5-one A mixture of 7-(1-bromoethyl)-3-methyl-5H-[1,3]thiazolo[3,2-a]pyrimidin-5-one (16.2 g, 59.3 mmol) and N-bromosuccinimide (15.8 g, 89.0 mmol) in acetonitrile (500 mL) was stirred at 80° C., under nitrogen, overnight. After removal of acetonitrile in vacuum, the resulting solid was dissolved in methylene chloride, washed with water, saturated $Na_2S_2O_3$, saturated sodium bicarbonate, and brine; and then the organic layers dried over sodium sulfate and filtered. The filtrate was concentrated under reduced pressure to provide the desired product (19.5 g, 93.4%). LCMS calculated for $C_9H_9Br_2N_2OS(M+H)^+$: m/z=350.9. Found: 351.0.

Step 3. 7-(1-azidoethyl)-6-bromo-3-methyl-5H-[1,3]thiazolo[3,2-a]pyrimidin-5-one A mixture of 6-bromo-7-(1-bromoethyl)-3-methyl-5H-[1,3]thiazolo[3,2-a]pyrimidin-5-one (11.1 g, 31.5 mmol) and sodium azide (6.15 g, 94.6 mmol) in dimethyl formamide (DMF) (100 mL) was stirred at room temperature for 2 h. After diluting with EtOAc, the mixture was washed with water, brine, dried over sodium sulfate, and evaporated under reduced pressure. The crude residue was purified on silica gel, eluting with 0 to 80% EtOAc in hexane, to provide the product (8.68 g, 87.6%). LCMS calculated for $C_9H_9BrN_5OS(M+H)^+$: m/z=314.0. Found: 313.9. $^1H$ NMR (DMSO-$d_6$, 300 MHz) δ 7.15 (1H, s), 4.83 (1H, q, J=6.6 Hz), 2.69 (3H, s), 1.48 (3H, d, J=6.6 Hz) ppm.

Step 4. 7-(1-azidoethyl)-3-methyl-6-phenyl-5H-[1,3]thiazolo[3,2-a]pyrimidin-5-one To a mixture of 7-(1-azidoethyl)-6-bromo-3-methyl-5H-[1,3]thiazolo[3,2-a]pyrimidin-5-one (0.100 g, 0.318 mmol) and phenylboronic acid (46.6 mg, 0.382 mmol) in 1,4-dioxane (2 mL) was added a 1 M solution of sodium carbonate (40.5 mg, 0.382 mmol) in water (0.38 mL) and tetrakis(triphenylphosphine)palladium (0) (18.4 mg, 0.0159 mmol). The reaction mixture was heated at 100° C. overnight. After cooling to rt, the mixture was diluted with EtOAc, washed with water, brine, dried over $MgSO_4$, and concentrated. The residue was purified on silica gel, eluting with 0 to 50% EtOAc in hexane, to provide the desired product (44 mg, 44.4%). LCMS calculated for $C_{15}H_{14}N_5OS$ $(M+H)^+$: m/z=312.1. Found: 312.3.

Step 5. 7-(1-aminoethyl)-3-methyl-6-phenyl-5H-[1,3]thiazolo[3,2-a]pyrimidin-5-one To a stirred solution of 7-(1-azidoethyl)-3-methyl-6-phenyl-5H-[1,3]thiazolo[3,2-a]pyrimidin-5-one (0.044 g, 0.14 mmol) in tetrahydrofuran (0.4 mL) and water (0.102 mL) was added 1.0 M of trimethylphosphine in tetrahydrofuran (0.17 mL) at room temperature and the mixture was stirred at room temperature for 1 hour. To the mixture was added EtOAc and the mixture was extracted twice with 1 N HCl. The combined extracts were neutralized with solid sodium bicarbonate and extracted with methylene chloride. The combined organic layers were washed with brine, dried over magnesium sulfate, and concentrated under reduced pressure. The residue was used directly in next step (36 mg, 89.3%). LCMS calculated for $C_{15}H_{16}N_3OS(M+H)^+$: m/z=286.1. Found: 286.0.

Step 6. 3-methyl-6-phenyl-7-[1-(9H-purin-6-ylamino)ethyl]-5H-[1,3]thiazolo[3,2-a]pyrimidin-5-one A mixture of 6-bromo-9H-purine (0.01504 g, 0.0076 mmol), 7-(1-aminoethyl)-3-methyl-6-phenyl-5H-[1,3]thiazolo[3,2-a]pyrimidin-5-one (0.018 g, 0.063 mmol), and N,N-diisopropylethylamine (0.013 mL, 0.0076 mol) in ethanol (0.5 mL) was refluxed under nitrogen overnight. The mixture was concentrated under reduced pressure and the residue was purified on RP-HPLC at pH 2 to provide the product as a TFA salt. LCMS calculated for free base $C_{20}H_{18}N_7OS(M+H)^+$: m/z=404.1. Found: 404.3. $^1H$ NMR (DMSO-$d_6$, 300 MHz) for a TFA salt: δ 8.54 (2H, m), 8.41 (2H, m), 7.44-7.36 (5H, m), 7.08 (1H, d, J=1.2 Hz), 5.21 (1H, m), 2.64 (3H, s), 1.38 (3H, d, J=6.6 Hz) ppm.

Example 9. 7-{1-[(2-amino-9H-purin-6-yl)amino]ethyl}-3-methyl-6-phenyl-5H-[1,3]thiazolo[3,2-a]pyrimidin-5-one

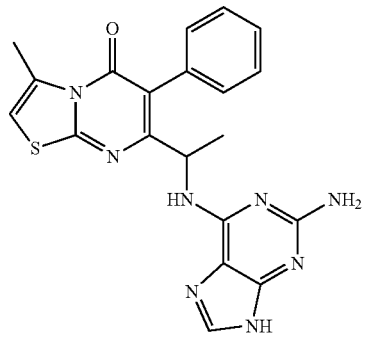 [SMILES: Cc1csc2nc(C(C)Nc3nc(N)nc4[nH]cnc34)c(-c3ccccc3)c(=O)n12]

A mixture of 2-amino-6-bromopurine (Aldrich, 0.01618 g, 0.007558 mmol), 7-(1-aminoethyl)-3-methyl-6-phenyl-5H-[1,3]thiazolo[3,2-a]pyrimidin-5-one (from example 8, step 5; 0.018 g, 0.063 mmol), and N,N-diisopropylethylamine (0.01318 mL, 0.007569 mmol) in ethanol (0.5 mL) was refluxed under nitrogen overnight. The mixture was evaporated and the resulting residue was purified on RP-HPLC at pH 2 to provide the product as a TFA salt. LCMS calculated for $C_{20}H_{19}N_8OS(M+H)^+$: m/z=419.3. Found: 419.3. $^1$H NMR (DMSO-$d_6$, 300 MHz) for TFA salt: δ 8.74 (1H, m), 8.16 (1H, s), 7.46-7.33 (6H, m), 7.14-7.11 (3H, m), 5.20 (1H, m), 2.66 (3H, d, J=1.5 Hz), 1.32 (3H, d, J=6.6 Hz) ppm.

Example 10. 6-(3-fluorophenyl)-3-methyl-7-[1-(9H-purin-6-ylamino)ethyl]-5H-[1,3]thiazolo[3,2-a]pyrimidin-5-one

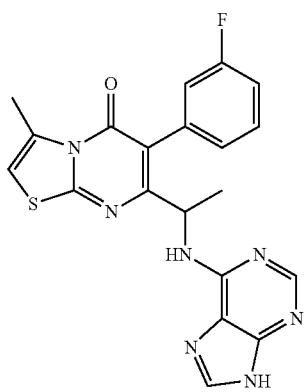 [SMILES: Cc1csc2nc(C(C)Nc3ncnc4[nH]cnc34)c(-c3cccc(F)c3)c(=O)n12]

Step 1. 7-(1-azidoethyl)-6-(3-fluorophenyl)-3-methyl-5H-[1,3]thiazolo[3,2-a]pyrimidin-5-one To a mixture of 7-(1-azidoethyl)-6-bromo-3-methyl-5H-[1,3]thiazolo[3,2-a]pyrimidin-5-one (from example 8, step 3; 0.100 g, 0.318 mmol) and (3-fluorophenyl)boronic acid (53.4 mg, 0.382 mmol) in 1,4-dioxane (2 mL) was added a 1 M solution of sodium carbonate (40.5 mg, 0.382 mmol) in water (0.38 mL) and tetrakis(triphenylphosphine)palladium(0) (18.4 mg, 0.0159 mmol). The reaction mixture was heated at 100° C. overnight. After cooling to rt, the mixture was diluted with EtOAc, washed with water, brine, dried over MgSO$_4$, and concentrated. The residue was purified on silica gel, eluting with 0 to 50% EtOAc in hexane, to provide the desired product (35 mg, 33.4%). LCMS calculated for $C_{15}H_{13}FN_5OS(M+H)^+$: m/z=330.1. Found: 330.2.

Step 2. 7-(1-aminoethyl)-6-(3-fluorophenyl)-3-methyl-5H-[1,3]thiazolo[3,2-a]pyrimidin-5-one To a stirred solution of 7-(1-azidoethyl)-6-(3-fluorophenyl)-3-methyl-5H-[1,3]thiazolo[3,2-a]pyrimidin-5-one (0.037 g, 0.11 mmol) in tetrahydrofuran (0.3 mL) and water (0.0811 mL) was added 1.0 M of trimethylphosphine in tetrahydrofuran (0.13 mmol) at room temperature and stirred for 1 hour. To the mixture was added EtOAc and was extracted twice with 1 N HCl. The combined extracts were neutralized with solid sodium bicarbonate and extracted with methylene chloride. The combined organic layers were washed with brine, dried over magnesium sulfate, and concentrated under reduced pressure. The residue was used directly in next step (31 mg, 90.9%). LCMS calculated for $C_{15}H_{15}FN_3OS(M+H)^+$: m/z=304.1. Found: 304.3.

Step 3. 6-(3-fluorophenyl)-3-methyl-7-[1-(9H-purin-6-ylamino)ethyl]-5H-[1,3]thiazolo[3,2-a]pyrimidin-5-one A mixture of 6-bromo-9H-purine (0.01258 g, 0.006320 mmol), 7-(1-aminoethyl)-6-(3-fluorophenyl)-3-methyl-5H-[1,3]thiazolo[3,2-a]pyrimidin-5-one (0.016 g, 0.053 mmol), and N,N-diisopropylethylamine (0.011 mL, 0.006329 mmol) in ethanol (0.4 mL) was refluxed under nitrogen overnight. The mixture was evaporated and the resulting residue was purified on RP-HPLC at pH 2 to provide the product as a TFA salt. LCMS calculated for $C_{20}H_{17}FN_7OS(M+H)^+$: m/z=422.1. Found: 422.3. $^1$H NMR (DMSO-$d_6$, 300 MHz) for TFA salt: δ 8.55 (2H, m), 8.40 (2H, m), 7.48 (1H, m), 7.25-7.22 (3H, m), 7.09 (1H, s), 5.19 (1H, m), 2.64 (3H, d, J=0.9 Hz), 1.40 (3H, d, J=6.6 Hz) ppm. $^{19}$F NMR (DMSO-$d_6$, 282 MHz) for TFA salt: δ−74.2, −114.0 ppm.

Example 11. 7-{1-[(2-amino-9H-purin-6-yl)amino]ethyl}-6-(3-fluorophenyl)-3-methyl-5H-[1,3]thiazolo[3,2-a]pyrimidin-5-one

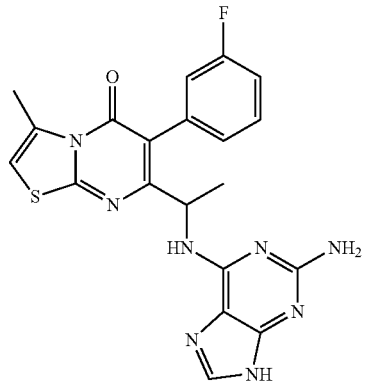 [SMILES: Cc1csc2nc(C(C)Nc3nc(N)nc4[nH]cnc34)c(-c3cccc(F)c3)c(=O)n12]

A mixture of 2-amino-6-bromopurine (0.01353 g, 0.006320 mmol), 7-(1-aminoethyl)-6-(3-fluorophenyl)-3-methyl-5H-[1,3]thiazolo[3,2-a]pyrimidin-5-one (from example 10, step 2; 0.016 g, 0.053 mmol), and N,N-diisopropylethylamine (0.01102 mL, 0.006329 mmol) in ethanol (0.4 mL) was refluxed under nitrogen overnight. The mixture was evaporated and the resultant residue was purified on RP-HPLC at pH 2 to provide the product as a TFA salt. LCMS calculated for $C_{20}H_{18}FN_8OS(M+H)^+$: m/z=437.1. Found: 437.3. $^1$H NMR (DMSO-$d_6$, 300 MHz) for TFA salt: δ 8.74 (1H, m), 8.16 (1H, s), 7.46 (1H, m), 7.20-7.13 (7H, m), 5.18 (1H, m), 2.66 (3H, s), 1.33 (3H, d, J=6.9 Hz) ppm. 19F NMR (DMSO-$d_6$, 282 MHz) for TFA salt: δ−74.0, −114.0 ppm.

Example 12. 6-(3,5-difluorophenyl)-3-methyl-7-[1-(9H-purin-6-ylamino)ethyl]-5H-[1,3]thiazolo[3,2-a]pyrimidin-5-one

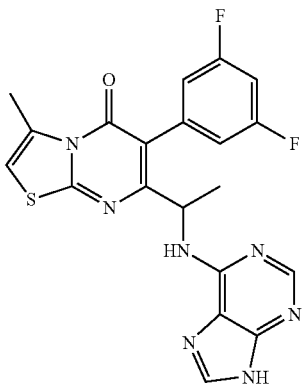 [SMILES: Cc1csc2nc(C(C)Nc3ncnc4[nH]cnc34)c(-c3cc(F)cc(F)c3)c(=O)n12]

Step 1. 7-(1-azidoethyl)-6-(3,5-difluorophenyl)-3-methyl-5H-[1,3]thiazolo[3,2-a]pyrimidin-5-one To a mixture of 7-(1-azidoethyl)-6-bromo-3-methyl-5H-[1,3]thiazolo[3,2-a]pyrimidin-5-one (0.10 g, 0.318 mmol) and (3,5-difluorophenyl)boronic acid (60.3 mg, 0.382 mmol) in 1,4-dioxane (2 mL) was added a 1 M solution of sodium carbonate (40.5 mg, 0.382 mmol) in water (0.38 mL) and tetrakis(triphenylphosphine)palladium (0) (18.4 mg, 0.0159 mmol). The reaction mixture was heated at 100° C. overnight. After cooling to rt, the mixture was diluted with EtOAc, washed with water, brine, dried over MgSO$_4$, and concentrated. The residue was purified on silica gel, eluting with 0 to 40% EtOAc in hexane, to provide the desired product (42 mg, 38.0%). LCMS calculated for $C_{15}H_{12}F_2N_5OS(M+H)^+$: m/z=348.1. Found: 348.2.

Step 2. 7-(1-aminoethyl)-6-(3,5-difluorophenyl)-3-methyl-5H-[1,3]thiazolo[3,2-a]pyrimidin-5-one To a stirred solution of 7-(1-azidoethyl)-6-(3,5-difluorophenyl)-3-methyl-5H-[1,3]thiazolo[3,2-a]pyrimidin-5-one (0.042 g, 0.12 mmol) in tetrahydrofuran (0.3 mL) and water (0.0873 mL) was added 1.0 M of trimethylphosphine in tetrahydrofuran (0.14 mmol) at room temperature and stirred for 1 hour. To the mixture was added EtOAc and the mixture was extracted twice with 1 N HCl. The combined extracts were neutralized with solid sodium bicarbonate, and extracted with methylene chloride. The combined organic layers were washed with brine, dried over magnesium sulfate, and concentrated under reduced pressure. The residue was used directly in next step (36 mg, 92.7%). LCMS calculated for $C_{15}H_{14}F_2N_3OS(M+H)^+$: m/z=322.1. Found: 322.3.

Step 3. 6-(3,5-difluorophenyl)-3-methyl-7-[1-(9H-purin-6-ylamino)ethyl]-5H-[1,3]thiazolo[3,2-a]pyrimidin-5-one A mixture of 6-bromo-9H-purine (0.01258 g, 0.006320 mmol), 7-(1-aminoethyl)-6-(3,5-difluorophenyl)-3-methyl-5H-[1,3]thiazolo[3,2-a]pyrimidin-5-one (0.017 g, 0.053 mmol), and N,N-diisopropylethylamine (0.011 mL, 0.006329 mmol) in ethanol (0.4 mL) was refluxed under nitrogen overnight. The mixture was concentrated under reduced pressure and the resultant residue was purified on RP-HPLC at pH 2 to provide the product as a TFA salt. LCMS calculated for $C_{20}H_{16}F_2N_7OS(M+H)^+$: m/z=440.1. Found: 440.3. $^1$H NMR (DMSO-d$_6$, 300 MHz) for TFA salt: δ 8.55 (1H, m), 8.39 (2H, m), 7.29 (1H, m), 7.15-7.11 (3H, m), 5.17 (1H, m), 2.64 (3H, d, J=1.2 Hz), 1.42 (3H, d, J=6.9 Hz) ppm.

Example 13. 7-{1-[(2-amino-9H-purin-6-yl)amino]ethyl}-6-(3,5-difluorophenyl)-3-methyl-5H-[1,3]thiazolo[3,2-a]pyrimidin-5-one

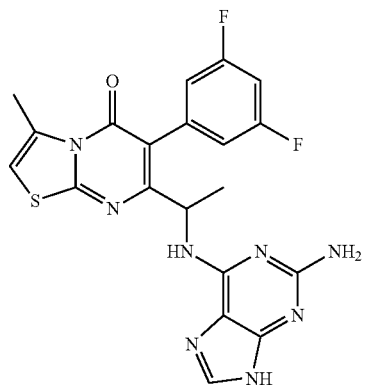 [SMILES: Cc1csc2nc(C(C)Nc3nc(N)nc4[nH]cnc34)c(-c3cc(F)cc(F)c3)c(=O)n12]

A mixture of 2-amino-6-bromopurine (0.01436 g, 0.006712 mmol), 7-(1-aminoethyl)-6-(3,5-difluorophenyl)-3-methyl-5H-[1,3]thiazolo[3,2-a]pyrimidin-5-one (from example 12, step 2; 0.018 g, 0.056 mmol), and N,N-diisopropylethylamine (0.01171 mL, 0.006722 mmol) in ethanol (0.4 mL) was refluxed under nitrogen overnight. The mixture was evaporated and the resultant residue was purified on RP-HPLC at pH 2 to provide the product as a TFA salt. LCMS calculated for $C_{20}H_{17}F_2N_8OS(M+H)^+$: m/z=455.1. Found: 455.3. $^1$H NMR (DMSO-d$_6$, 300 MHz) for TFA salt: δ 8.74 (1H, m), 8.16 (1H, s), 7.26-7.06 (6H, m), 5.16 (1H, m), 2.66 (3H, d, J=1.2 Hz), 1.36 (3H, d, J=6.9 Hz) ppm.

Example 14. 3-methyl-7-[1-(9H-purin-6-ylamino)ethyl]-6-pyridin-2-yl-5H-[1,3]thiazolo[3,2-a]pyrimidin-5-one

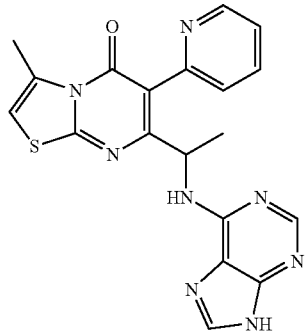 [SMILES: Cc1csc2nc(C(C)Nc3ncnc4[nH]cnc34)c(-c3ccccn3)c(=O)n12]

Step 1. 7-(1-azidoethyl)-3-methyl-6-pyridin-2-yl-5H-[1,3]thiazolo[3,2-a]pyrimidin-5-one A mixture of 2-(tributylstannyl)pyridine (Aldrich, 0.176 g, 0.382 mmol), 7-(1-azidoethyl)-6-bromo-3-methyl-5H-[1,3]thiazolo[3,2-a]pyrimidin-5-one (from example 8, step 3; 0.10 g, 0.318 mmol), and tetrakis(triphenylphosphine)palladium (0) (0.0184 g, 0.0159 mmol) in 1,4-dioxane (0.5 mL) was heated at 65° C. overnight. After being cooled and quenched with saturated ammonium chloride, the resulting mixture was extracted with EtOAc. The organic layers were combined, washed with brine, dried and evaporated to dryness. The residue was purified on silica gel, eluting with 0 to 100% EtOAc in hexane, to provide the desired product (13 mg, 13%). LCMS calculated for $C_{14}H_{13}N_6OS(M+H)^+$: m/z=313.1. Found: 313.0.

Step 2. 7-(1-aminoethyl)-3-methyl-6-pyridin-2-yl-5H-[1,3]thiazolo[3,2-a]pyrimidin-5-one To a stirred solution of 7-(1-azidoethyl)-3-methyl-6-pyridin-2-yl-5H-[1,3]thiazolo[3,2-a]pyrimidin-5-one (0.012 g, 0.039 mmol) in tetrahydrofuran (0.1 mL) and water (0.0285 mL) was added 1.0 M of trimethylphosphine in tetrahydrofuran (0.047 mmol) at room temperature and stirred for 1 hour. To the mixture was added EtOAc and the mixture was extracted twice with 1 N HCl. The combined extracts were neutralized with solid sodium bicarbonate and extracted with methylene chloride. The combined organic layers were washed with brine, dried over magnesium sulfate, and concentrated under reduced pressure. The residue was used directly in next step. LCMS calculated for $C_{14}H_{15}N_4OS(M+H)^+$: m/z=287.1. Found: 287.0.

Step 3. 3-methyl-7-[1-(9H-purin-6-ylamino)ethyl]-6-pyridin-2-yl-5H-[1,3]thiazolo[3,2-a]pyrimidin-5-one A mixture of 6-bromo-9H-purine (9.300 mg, 0.004673 mmol), 7-(1-aminoethyl)-3-methyl-6-pyridin-2-yl-5H-[1,3]thiazolo[3,2-a]pyrimidin-5-one (11 mg, 0.039 mmol), and N,N-diisopropylethylamine (8.152 µL, 0.004680 mmol) in ethanol (0.3 mL) was refluxed under nitrogen overnight. The mixture was concentrated under reduced pressure and the residue was purified on RP-HPLC (eluting with a gradient of methanol/water containing 1% TFA) to provide the product as a TFA salt. LCMS calculated for $C_{19}H_{17}N_8OS(M+H)^+$: m/z=405.1. Found: 405.3.

Example 15. (S)-7-(1-(9H-purin-6-ylamino)ethyl)-6-(3-fluorophenyl)-3-methyl-5H-thiazolo[3,2-a]pyrimidin-5-one

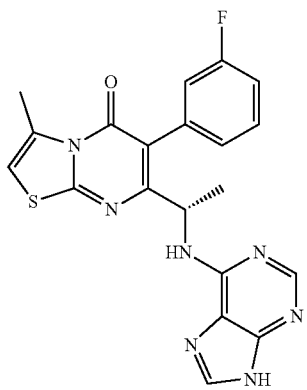

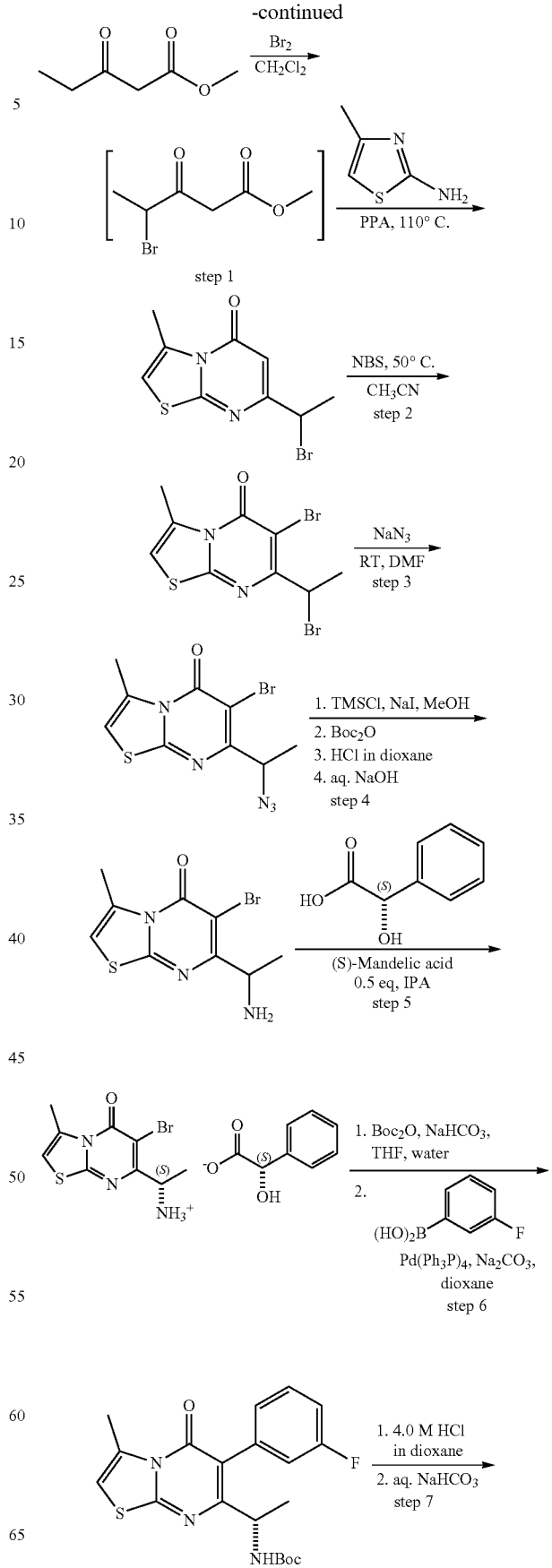

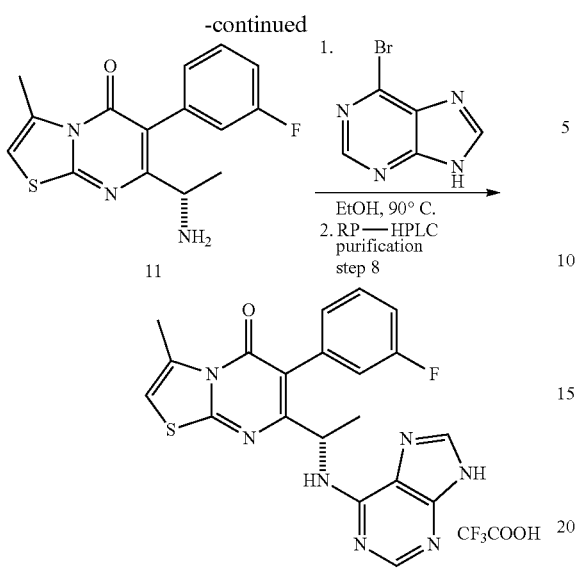

Step 1. 7-(1-Bromoethyl)-3-methyl-5H-thiazolo[3,2-a]pyrimidin-5-one

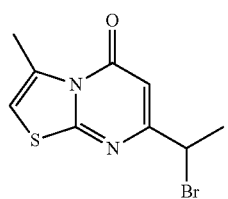

A solution of 3-oxopentanoic acid methyl ester (12.5 g, 96.0 mmol) in methylene chloride (50 mL) was cooled with an ice water bath. The outlet of the flask was attached to a NaOH trap. Bromine (5.19 mL, 101 mmol) in methylene chloride (10 mL, 200 mmol) was added dropwise over a 20-min period, and the reaction mixture was allowed to warm to room temperature and then stirred overnight. The reaction mixture was bubbled with nitrogen for 30 min and then concentrated to give an oil. This oil was used in the next step without further purification. $^1$H NMR (400 MHz, DMSO-$d_6$) δ 4.89 (q, J=6.9 Hz, 1H), 3.85 (s, 2H), 3.63 (s, 3H), 1.64 (d, J=6.7 Hz, 3H).

Into a 3-neck flask fitted with a condenser, a thermometer, and a nitrogen inlet was added polyphosphoric acid (50.0 g, 458 mmol). The flask was heated to ~70° C. to give a liquid that was easy to stir. 4-Methyl-1,3-thiazol-2-amine (10.0 g, 87.6 mmol) was added in small portions with stirring. The internal temperature slowly increased to 78° C. upon mixing. The crude oil obtained above was then added to the flask via a pipette and the mixture was heated to 110° C. under nitrogen. After 6 h of heating, HPLC indicated that the reaction was complete.

The reaction mixture was cooled to ~35° C. Water (70 mL) and EtOAc (200 mL) were added. The mixture was stirred until all solids dissolved. The organic layer was separated. The aqueous layer was extracted with EtOAc (200 mL×2). The combined organic extracts were washed with 1 N aqueous HCl (40 mL×2) with sat. NaHCO$_3$ (50 mL×2) and brine (30 mL). The organic layer was dried and concentrated to give 7-(1-bromoethyl)-3-methyl-5H-thiazolo[3,2-a]pyrimidin-5-one as a yellow solid (11.8 g, 49.3%). LCMS calculated for $C_9H_{10}BrN_2OS$ (M+H)$^+$: m/z 274.96, 272.96. Found: 274.75, 272.75. $^1$H NMR (400 MHz, DMSO-$d_6$) δ 7.05 (m, 1H), 6.27 (s, 1H), 5.17 (q, J=6.9 Hz, 1H), 2.65 (s, 3H), 1.85 (d, J=6.9 Hz, 3H).

Step 2. 6-Bromo-7-(1-bromoethyl)-3-methyl-5H-thiazolo[3,2-a]pyrimidin-5-one

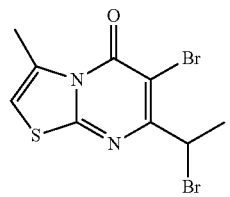

Under nitrogen, a suspension of 7-(1-bromoethyl)-3-methyl-5H-[1,3]thiazolo[3,2-a]pyrimidin-5-one(13.2 g, 48.3 mmol) in acetonitrile (100 mL, 2000 mmol) was stirred until a clear solution was obtained. N-Bromosuccinimide (9.891 g, 55.57 mmol) was then added and the reaction mixture was stirred at 50° C. After 20 min, HPLC indicated that the reaction was complete. A solution of sodium sulfite (3.046 g, 24.16 mmol) in water (50 mL) was added and the mixture was stirred at room temperature for 20 min. Water (200 mL) was added slowly and the mixture stirred at room temperature for 30 min. and then filtered. The solid was washed with water (100 mL×3) and dried to give 6-bromo-7-(1-bromoethyl)-3-methyl-5H-thiazolo[3,2-a]pyrimidin-5-one as an off-white solid (15.61 g, 91%). LCMS calculated for $C_9H_9Br_2N_2OS$ (M+H)$^+$: m/z 352.87, 354.87. Found: 352.65, 354.60. $^1$H NMR (400 MHz, DMSO-$d_6$) δ 7.15 (q, J=1.3 Hz, 1H), 5.51 (q, J=6.7 Hz, 1H), 2.66 (d, J=1.2 Hz, 3H), 1.90 (d, J=6.7 Hz, 3H).

Step 3. 7-(1-Azidoethyl)-6-bromo-3-methyl-5H-thiazolo[3,2-a]pyrimidin-5-one

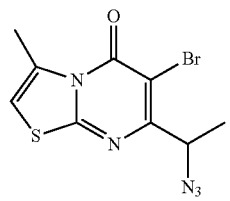 [SMILES: Cc1csc2nc(C(C)N=[N+]=[N-])c(Br)c(=O)n12]

To a suspension of 6-bromo-7-(1-bromoethyl)-3-methyl-5H-[1,3]thiazolo[3,2-a]pyrimidin-5-one (6.85 g, 19.4 mmol) in N,N-dimethylformamide (30.1 mL) was added sodium azide (1.45 g, 22.4 mmol). The mixture slowly turned clear after 5-10 min. After 50 min, a solution of sodium bicarbonate (4.7 g, 56 mmol) in water (90 mL) was added dropwise with stirring. The mixture was stirred at room temperature for 1 h and the solid precipitates were filtered off. The solid was then washed with water (30 mL×3), and dried to give 7-(1-azidoethyl)-6-bromo-3-methyl-5H-thiazolo[3,2-a]pyrimidin-5-one as an off-white solid (5.94 g, 97.2%). LCMS calculated for $C_9H_9BrN_5OS$ (M+H)$^+$: m/z 313.96, 315.96. Found: 313.75, 315.75. $^1$H NMR (400 MHz, DMSO-d$_6$) δ 7.15 (q, J=1.3 Hz, 1H), 4.83 (q, J=6.8 Hz, 1H), 2.67 (d, J=1.4 Hz, 3H), 1.48 (d, J=6.8 Hz, 3H).

Step 4. 7-(1-Aminoethyl)-6-bromo-3-methyl-5H-thiazolo[3,2-a]pyrimidin-5-one

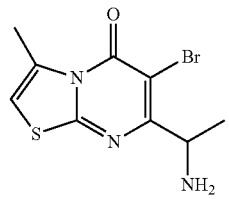

7-(1-Azidoethyl)-6-bromo-3-methyl-5H-thiazolo[3,2-a]pyrimidin-5-one (22.6 g, 71.9 mmol) was mixed with methanol (200 mL). Sodium iodide (64.7 g, 432 mmol) was added and stirred at room temperature for 10 min. Chlorotrimethylsilane (54.8 mL, 432 mmol) was dissolved in methanol (29.1 mL) and added dropwise over 10 min. at 5-25° C. The reaction mixture was stirred at room temperature for 10 min. HPLC and TLC showed that the reaction was complete. The reaction was quenched by addition of a solution of sodium thiosulfate (69.4 g, 439 mmol) in water (259 ml) while maintaining the batch temperature at 5-25° C. A large amount of solid was formed, and the pH of the mixture was 3. The mixture was stirred at 0-5° C. for 30 min. The pH was adjusted to 11 using 3 N aqueous sodium hydroxide (85 mL). In order to facilitate product purification and isolation, the N-Boc derivative of the product was prepared. To the mixture was added di-t-butyldicarbonate (28.3 g, 129 mmol) and the reaction mixture was stirred at room temperature for 2 h. HPLC indicated a small amount of amine remained unreacted. Additional di-t-butyldicarbonate (10.0 g, 45.8 mmol) was added followed by 3 N aqueous sodium hydroxide (15 mL) to adjust the pH to 11. The reaction mixture was stirred at room temperature for 30 min. The reaction mixture was extracted with ethyl acetate (150 mL×3). The organic solution which contained the N-Boc derivative of the product was dried over anhydrous sodium sulfate, filtered, and concentrated under reduced pressure to give a residue. The residue was added to a 4 M solution of hydrogen chloride in 1,4-dioxane (206 mL, 824 mmol) and stirred at room temperature for 1.5 h. HPLC indicated the N-Boc-deprotection was complete. The hydrochloride salt of the product was isolated by filtration, the solid washed with MTBE, dried by suction filtration for 1 h to give 7-(1-aminoethyl)-6-bromo-3-methyl-5H-thiazolo[3,2-a]pyrimidin-5-one hydrochloride salt (25.1 g) as a purple powder.

The hydrochloride salt was dissolved in water (50 mL) and a 50% solution of sodium hydroxide (about 5 mL) was added to adjust the pH to 11. The mixture was stirred at room temperature for 20 min. The product precipitated and was isolated by filtration. The wet solid was washed with water (10 mL) and dried on the filter under vacuum for 18 h to give 7-(1-aminoethyl)-6-bromo-3-methyl-5H-thiazolo[3,2-a]pyrimidin-5-one (18.8 g, 65.2 mmol, 90.7% yield) as a yellow powder. LCMS calculated for C$_9$H$_{11}$BrN$_3$OS (M+H)$^+$: m/z 287.97, 289.97. Found: 287.75, 289.75. $^1$H NMR (400 MHz, DMSO-d$_6$) 7.08 (q, J=1.3 Hz, 1H), 4.19 (q, J=6.7 Hz, 1H), 2.65 (d, J=1.3 Hz, 3H), 1.17 (d, J=6.7 Hz, 3H).

Step 5. (S)-1-(6-bromo-3-methyl-5-oxo-5H-thiazolo[3,2-a]pyrimidin-7-yl)ethanaminium (S)-2-hydroxy-2-phenylacetate

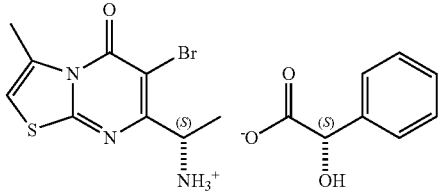

7-(1-Aminoethyl)-6-bromo-3-methyl-5H-thiazolo[3,2-a]pyrimidin-5-one (18.8 g, 65.2 mmol) was dissolved in isopropanol (375 mL) at reflux and then (S)-(+)-mandelic acid (4.84 g, 31.8 mmol) in isopropanol (375 mL) was added dropwise to the amine solution over 35 min. The reaction mixture was allowed to cool to about 72° C. and solid precipitation was observed. The slurry was cooled to room temperature and stirred for 1 hour. The solid product was collected by filtration. The wet cake was washed with isopropanol (100 mL) and dried on the filter under suction for 1 h to give the product (S)-1-(6-bromo-3-methyl-5-oxo-5H-thiazolo[3,2-a]pyrimidin-7-yl)ethanaminium (S)-2-hydroxy-2-phenyl acetate (11.9 g) as a white solid. Chiral HPLC analysis was performed on a Lux Cellulose-2, 4.6×250 mm, 5 micron column using 60% ethanol/40% hexanes as the mobile phase at a flow rate of 1 mL/min. The major enantiomer eluted at retention time 11.21 min (99.0 area %). The minor enantiomer eluted at retention time 14.31 min (0.96 area %). The e.e. of the desired product was 98.08%.

The product at 98.08% e.e. (11.9 g) was suspended in isopropanol (750 mL) and heated under reflux for 30 min. The slurry was cooled to room temperature with stirring. The solid was collected by filtration. The wet solid was washed with isopropanol (100 mL) and dried on the filter under suction for 18 h to give 10.9 g of white solid. Chiral HPLC by the method described above gave e.e. of 98.48%.

The product at 98.48% e.e. (10.9 g) was stirred in a solution of sodium carbonate (3.9 g, 37 mmol) in water (100 mL) at room temperature for 30 min. The solid free base was collected by filtration, washed with water (20 mL) and dried on the filter under suction for 2 h to give a slightly wet cake (13 g). The wet solid was dissolved in isopropanol (325 mL) at reflux and a solution of (S)-(+)-mandelic acid (3.613 g, 23.75 mmol) in isopropanol (325 mL) was added dropwise over 20 min to the free base solution. The solution was cooled to room temperature with stirring. The solid product was collected by filtration, washed with isopropanol (100 mL) and dried on the filter under suction for 48 h to give pure product (S)-1-(6-bromo-3-methyl-5-oxo-5H-thiazolo[3,2-a]pyrimidin-7-yl)ethanaminium (5)-2-hydroxy-2-phenylacetate (8.4 g, 19.08 mmol, 29.3% yield) as a white solid. The e.e. of this sample was determined to be 100% as no minor enantiomer (retention time=14.31 min) was detected. LCMS calculated for C$_9$H$_{11}$BrN$_3$OS (M+H)$^+$ for the free base: m/z 289.97, 287.97. Found: 289.75, 287.75. $^1$H NMR (400 MHz, DMSO-d$_6$) δ 7.33 (d, J=7.5 Hz, 2H), 7.22 (dd, J=7.1, 7.5 Hz, 2H), 7.16 (m, 2H), 4.61 (s, 1H), 4.47 (q, J=6.9 Hz, 1H), 2.68 (d, J=1.1 Hz, 3H), 1.31 (d, J=6.8 Hz, 3H).

In order to determine the absolute stereochemistry of the product, a sample was sublimed at about 105° C. to provide colorless needles suitable for X-ray crystal structure analysis. The study determined the absolute configuration of the amine bearing carbon (C-8) is S (see Example 16 and FIG. 1).

Step 6. (S)-tert-Butyl 1-(6-(3-fluorophenyl)-3-methyl-5-oxo-5H-thiazolo[3,2-a]pyrimidin-7-yl)ethylcarbamate

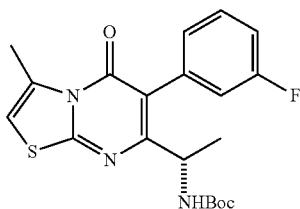 [SMILES: Cc1csc2nc([C@H](C)NC(=O)OC(C)(C)C)c(-c3cccc(F)c3)c(=O)n12]

(S)-1-(6-Bromo-3-methyl-5-oxo-5H-thiazolo[3,2-a]pyrimidin-7-yl)ethanaminium (S)-2-hydroxy-2-phenylacetate (4.93 g, 11.2 mmol) was dissolved in THF (100 mL) and water (33 mL). Di-t-butyldicarbonate (3.03 g, 13.9 mmol) was added, followed by sodium bicarbonate (1.88 g, 22.4 mmol). The reaction mixture was stirred at room temperature for 30 min. at which point the HPLC showed the reaction was near complete. Additional di-t-butyldicarbonate (0.49 g, 2.24 mmol) was then added and the reaction mixture was stirred at room temperature for 1 hour. The reaction was shown to be complete by HPLC. The reaction mixture was diluted with water (100 mL) and extracted with ethyl acetate (2×100 mL). The ethyl acetate solution was concentrated to give (S)-tert-butyl 1-(6-bromo-3-methyl-5-oxo-5H-thiazolo[3,2-a]pyrimidin-7-yl)ethylcarbamate (5.46 g, 14.1 mmol, 126% yield) which was used in the subsequent Suzuki coupling reaction without further purification.

(S)-tert-Butyl 1-(6-bromo-3-methyl-5-oxo-5H-thiazolo[3,2-a]pyrimidin-7-yl)ethylcarbamate (5.46 g, 14.1 mmol) and (3-fluorophenyl)boronic acid (2.95 g, 21.1 mmol) were suspected in 1,4-dioxane (110 mL). A solution of sodium carbonate (4.47 g, 42.2 mmol) in water (27 mL) was added to the mixture followed by tetrakis(triphenylphosphine)palladium(0) catalyst (0.81 g, 0.70 mmol). The reaction mixture was degassed and heated under nitrogen at 100° C. for 16 h. HPLC indicated the starting material was consumed. The reaction mixture was cooled to room temperature and water (100 mL) was added. The resultant mixture was extracted with ethyl acetate (2×100 mL). The ethyl acetate solution was washed with saturated aqueous sodium bicarbonate (100 mL), dried over anhydrous sodium sulfate, filtered, and concentrated under reduced pressure to give a residue. The residue was purified by flash column chromatography on silica gel using 1-50% ethyl acetate in hexane as eluent to give (S)-tert-butyl 1-(6-(3-fluorophenyl)-3-methyl-5-oxo-5H-thiazolo[3,2-a]pyrimidin-7-yl)ethylcarbamate (4.34 g, 10.8 mmol, 76%) as an off-white solid. LCMS calculated for $C_{20}H_{23}FN_3O_3S$ (M+H)$^+$: m/z 404.1. Found 404.1. $^1$H NMR (500 MHz, DMSO-$d_6$) δ 7.48 (ddd, J=8.1, 7.8, 6.2 Hz, 1H), 7.18 (m, 3H), 7.05 (q, J=1.3 Hz, 1H), 6.96 (d, J=7.5 Hz, 1H), 4.41 (m, 1H), 2.66 (d, J=1.3 Hz, 3H), 1.33 (s, 9H), 1.13 (d, J=6.8 Hz, 3H).

Step 7. (S)-7-(1-Aminoethyl)-6-(3-fluorophenyl)-3-methyl-5H-thiazolo[3,2-a]pyrimidin-5-one

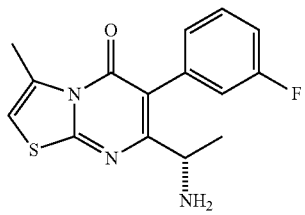 [SMILES: Cc1csc2nc([C@H](C)N)c(-c3cccc(F)c3)c(=O)n12]

(S)-tert-Butyl 1-(6-(3-fluorophenyl)-3-methyl-5-oxo-5H-thiazolo[3,2-a]pyrimidin-7-yl)ethylcarbamate (4.15 g, 10.3 mmol) was dissolved in a 4.0 M solution of hydrogen chloride in 1,4-dioxane (25.7 mL, 102.8 mmol) and the solution was stirred at room temperature for 45 min. HPLC indicated that the reaction was complete. To the solution was added water (10 mL) followed by 3 N aqueous sodium hydroxide solution at 0-5° C. to adjust the pH to 10. The aqueous mixture was extracted with ethyl acetate (2×30 mL). The ethyl acetate solution was dried over anhydrous sodium sulfate, filtered, and concentrated under reduced pressure to give (S)-7-(1-Aminoethyl)-6-(3-fluorophenyl)-3-methyl-5H-thiazolo[3,2-a]pyrimidin-5-one (3.30 g, 10.88 mmol, 103% yield). LCMS calculated for $C_{15}H_{15}FN_3OS$ (M+H)$^+$: m/z 304.08. Found 303.9. $^1$H NMR (400 MHz, DMSO-$d_6$) δ 7.45 (ddd, J=8.1, 7.9, 5.9 Hz, 1H), 7.19 (m, 1H), 7.12 (m, 2H) 7.04 (q, J=1.1 Hz, 1H), 3.57 (q, J=6.6 Hz, 1H), 2.64 (d, J=1.3 Hz, 3H), 1.10 (d, J=6.7 Hz, 3H)

Step 8. (S)-7-(1-(9H-purin-6-ylamino)ethyl)-6-(3-fluorophenyl)-3-methyl-5H-thiazolo[3,2-a]pyrimidin-5-one trifluoroacetic acid salt

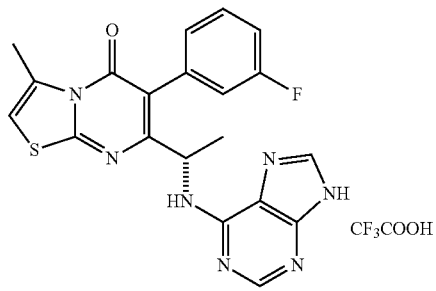

(S)-7-(1-Aminoethyl)-6-(3-fluorophenyl)-3-methyl-5H-thiazolo[3,2-a]pyrimidin-5-one (2.30 g, 7.58 mmol), 6-bromo-9H-purine (2.716 g, 13.65 mmol), N,N-diisopropylethylamine (6.60 mL, 37.9 mmol) were dissolved in ethanol (15 mL) and the resultant mixture was heated at reflux under a nitrogen atmosphere for 17 h. HPLC indicated the reaction was complete. The reaction mixture was concentrated under reduced pressure to give a residue. The residue was purified by flash column chromatography on silica gel using gradient elution starting at 100% DCM with increasing polarity to 25% of a mixture of DCM/MeOH/aq.NH$_4$OH (100:5:0.5, v/v/v) in DCM. After the silica chromatography, 2.1 g of crude product was obtained. This crude product was further purified by preparative reversed phase HPLC using 0.1% TFA in water and acetonitrile as mobile phases at a flow rate of 60 mL/min. on a SunFire C18, 5 μM, 30×100 mm column. Pure (S)-7-(1-(9H-purin-6-ylamino)ethyl)-6-(3-fluorophenyl)-3-methyl-5H-thiazolo[3,2-a]pyrimidin-5-one trifluoroacetic acid salt (trifluoroacetic acid salt) (1.86 g, 3.47 mmol, 45.8% yield) was obtained as a white solid after lyophilization. LCMS calculated for $C_{20}H_{17}FN_7OS$ (M+H)$^+$ for the free base: m/z 422.1. Found: 422.0). $^1$H NMR (500 MHz, DMSO-d$_6$) δ 9.03 (br s, 1H), 8.53 (s, 1H), 8.51 (s, 1H), 7.47 (m, 1H), 7.21 (m, 3H), 7.09 (s, 1H), 5.23 (m, 1H), 2.65 (d, J=1.3 Hz, 3H), 1.43 (d, J=7.0 Hz, 3H). $^{13}$C NMR (125 MHz, DMSO-d$_6$) δ 164.0, 162.1 ($J_{CF}$=244.9 Hz), 160.5, 160.3, 150.9, 147.6, 147.5, 144.4, 135.9, 135.9, 130.2 ($J_{CF}$=8.3 Hz), 126.9, 117.4 ($J_{CF}$=22.6 Hz), 116.1, 114.8 ($J_{CF}$=21.5 Hz), 111.1, 107.8, 48.5, 19.6, 18.0. Reversed phase analytical HPLC showed purity at 99.8 area %. Chiral HPLC analysis was performed on Chiralcel OJ-H, 4.6×250 mm, 5 micron column using 60% ethanol/40% hexanes as eluent at a flow rate of 0.5 mL/min. The peak for the desired enantiomer (S)-7-(1-(9H-purin-6-ylamino)ethyl)-6-(3-fluorophenyl)-3-methyl-5H-thiazolo[3,2-a]pyrimidin-5-one was observed at a retention time of 21.171 min. (99.1 area %). The minor peak for the undesired enantiomer (R)-7-(1-(9H-purin-6-ylamino)ethyl)-6-(3-fluorophenyl)-3-methyl-5H-thiazolo[3,2-a]pyrimidin-5-one was observed at a retention time of 13.358 min (0.9 area %). The enantiomeric excess of the desired enantiomer was 98.2%.

Example 15A. (S)-7-(1-(9H-purin-6-ylamino)ethyl)-6-(3-fluorophenyl)-3-methyl-5H-thiazolo[3,2-a]pyrimidin-5-one

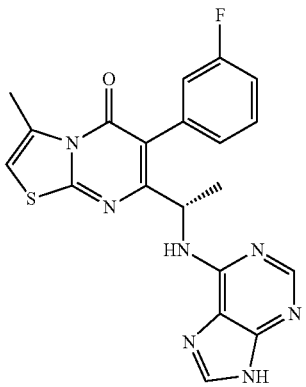 [SMILES: Cc1csc2nc([C@H](C)Nc3ncnc4[nH]cnc34)c(-c3cccc(F)c3)c(=O)n12]

A mixture of (S)-7-(1-aminoethyl)-6-(3-fluorophenyl)-3-methyl-5H-thiazolo[3,2-a]pyrimidin-5-one (108.2 g, 357 mmol), 6-chloropurine (71.73 g, 464.1 mmol), and N,N-diisopropylethylamine (74.6 mL, 428.4 mmol) in 1-butanol (952 mL) was degassed with nitrogen bubbling for 5 minutes. The reaction mixture was heated at 105° C. under nitrogen for 15 hours, at which point HPLC indicated amine was consumed. The reaction mixture was cooled down to room temperature before being treated with water (200 mL) at room temperature. The resulting mixture was concentrated under reduced pressure to give an oily residue and the residue was treated with $CH_2Cl_2$ (1000 mL) to give a brownish clear solution. The resulting solution was washed with 2.5% aqueous sodium carbonate solution ($Na_2CO_3$, 250 mL×2) and the organic layer was concentrated under reduced pressure to afford the crude desired product as a brownish solid. The solution of the crude desired product in $CH_2Cl_2$ was absorbed onto silica gel (300 g) and the dried silica gel was loaded onto a flash column. The flash column was eluted with pure $CH_2Cl_2$ and a mixture of $CH_2Cl_2$, MeOH and aqueous $NH_4OH$ (2000:10:5) to afford pure desired product. The fractions containing pure desired product were combined and concentrated under reduced pressure. The resulting yellowish solid (90.3 g) was dissolved in a mixture of $CH_2Cl_2$ and methanol (500:50 mL). The resulting solution was treated with ethyl acetate (900 mL) and the resulting mixture was distilled until the internal solution temperature reached 68° C. The mixture was then cooled to room temperature and subsequently to 0-5° C. for 1 hour. The solids were collected by filtration, washed with cold ethyl acetate (100 mL), and dried overnight on the filter under vacuum to afford (S)-7-(1-(9H-purin-6-ylamino)ethyl)-6-(3-fluorophenyl)-3-methyl-5H-thiazolo[3,2-a]pyrimidin-5-one (89.5 g, 59.4% yield, 99.4% ee) as a light yellowish solid. LCMS calculated for $C_{20}H_{17}FN_7OS$ (M+H)$^+$ for the free base: m/z 422.1. Found: 422.0; $^1$H NMR (500 MHz, DMSO-d$_6$) δ 8.40 (s, 1H), 7.99 (br s, 1H), 7.45 (m, 1H), 7.21-7.12 (m, 3H), 6.8 (m, 1H), 6.42 (s, 1H), 5.52 (br s, 1H), 2.79 (d, J=1.3 Hz, 3H), 1.43 (d, J=7.0 Hz, 3H).

Example 16. X-Ray Crystallography of (S)-1-(6-bromo-3-methyl-5-oxo-5H-thiazolo[3,2-a]pyrimidin-7-yl)ethanaminium (S)-2-hydroxy-2-phenylacetate (From Example 15, Step 5)

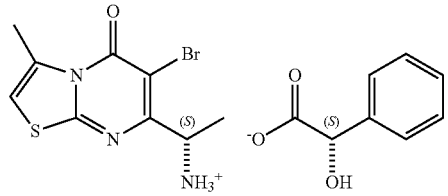

In order to determine the absolute stereochemistry of the product from Example 15, step 5, a sample was sublimed at about 105° C. to provide colorless needles suitable for X-ray crystal structure analysis. The study determined the absolute configuration of the amine bearing carbon (C-8) is S.

DATA COLLECTION: Bruker SMART APEX-II CCD system, MoKalpha radiation, standard focus tube, anode power=50 kV×42 mA, crystal to plate distance=5.0 cm, 512×512 pixels/frame, beam center=(256.13, 253.14), total frames=1081, oscillation/frame=0.50°, exposure/frame=300.1 sec/frame, SAINT integration, hkl min/max= (−4, 7, −14, 14, −31, 35), data input to shelx=11285, unique data=3870, two-theta range=3.82 to 53.64°, completeness to two-theta 53.64=99.70%, R(int-xl)=0.0908, SADABS correction applied.

SOLUTION AND REFINEMENT: Structure solved using XS(Shelxtl), refined using shelxtl software package, refinement by full-matrix least squares on $F^2$, scattering factors from Int. Tab. Vol C Tables 4.2.6.8 and 6.1.1.4, number of data=3870, number of restraints=0, number of parameters=309, data/parameter ratio=12.52, goodness-of-fit on $F^2$=0.99, R indices[I>4sigma(I)] R1=0.0455, wR2=0.0674, R indices (all data) R1=0.1059, wR2=0.0825, max difference peak and hole=0.420 and −0.863 e/Å$^3$, refined flack parameter=0.025(11). All of the hydrogen atoms have been found from a difference map and fully refined.

CRYSTAL DATA: C17H18 Br N3 O4 S, from sublimation @ 105° C., colorless, needle, ~0.160×0.020×0.020 mm, orthorhombic, P212121, a=5.5572(18) Å, b=11.547(4) Å, c=28.207(10) Å, Vol=1810.1(11) Å$^3$, Z=4, T=−100.° C., Formula weight=440.31, Density=1.616 g/cm$^3$, μ(Mo)=2.41 mm$^{-1}$.

Figure 2:
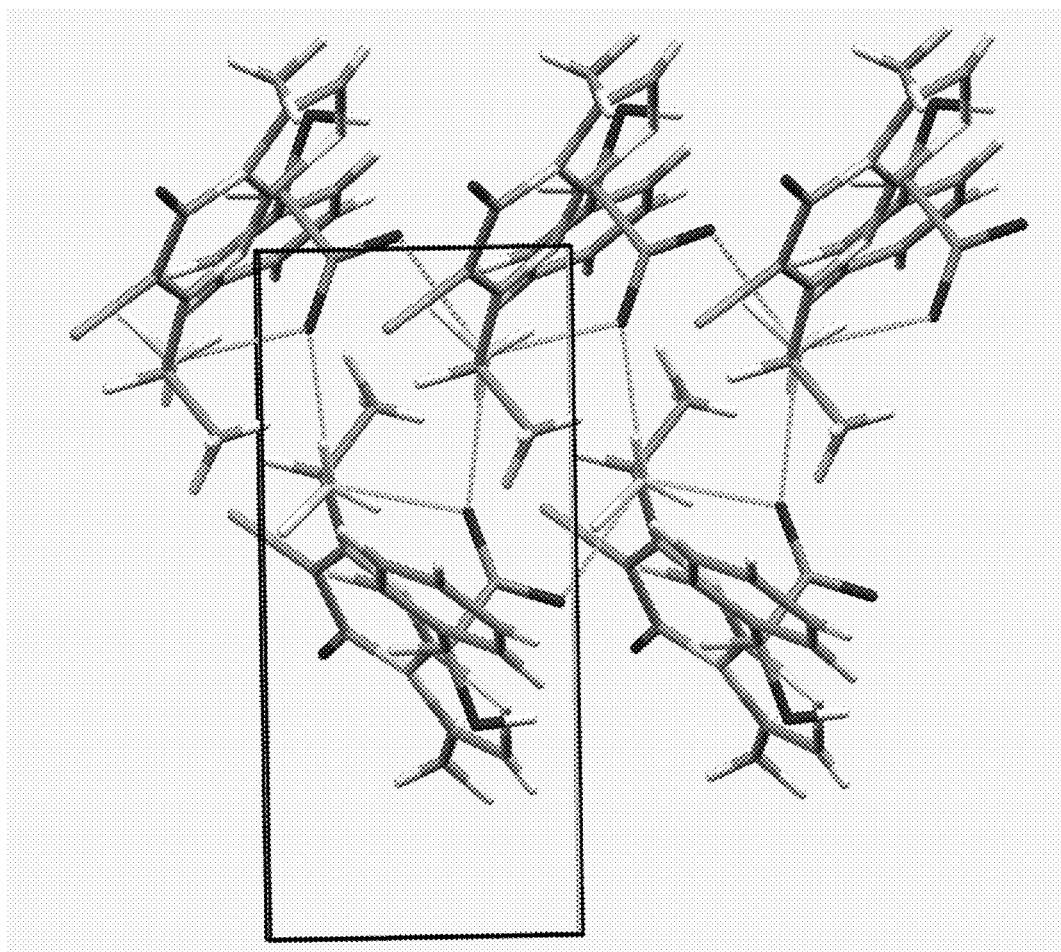
FIG. 2. X-ray crystal structure lattice of Example 15, step 5.

RESULTS: This study determined the structure of C17, H18,N3,O4,S1,Br1 for the product of Example 15, step 5. The asymmetric unit contains one of each molecule as shown in FIG. 1 with thermal ellipsoids drawn to the 50% probability level. The predicted structure was confirmed. The molecules form an infinite hydrogen bonded chain via the NH3's along the a-axis which is the needle axis, as shown in FIG. 2. The absolute configuration was determined to be S at both C8 and C16 based upon the refinement of the flack parameter=0.02(5). The configuration of C16 was known to be S.

TABLE A1

Atomic coordinates (×10$^4$) and equivalent isotropic displacement parameters (Å$^2$ × 10$^3$). U(eq) is defined as one third of the trace of the orthogonalized Uij tensor.

| | x | y | z | U(eq) |
|---|---|---|---|---|
| Br(1) | 5816(1) | 1172(1) | 1875(1) | 34(1) |
| S(1) | −2800(2) | −1679(1) | 1030(1) | 28(1) |
| O(1) | 2992(7) | −875(4) | 2278(1) | 48(1) |
| O(2) | −1818(7) | −1946(3) | −193(1) | 33(1) |
| O(3) | −1693(5) | 1147(3) | −24(1) | 27(1) |
| O(4) | −4576(7) | −176(3) | 77(1) | 32(1) |
| N(1) | 285(6) | −1133(4) | 1670(1) | 22(1) |
| N(2) | 444(8) | 26(3) | 965(1) | 25(1) |
| N(3) | 2679(10) | 1576(4) | 395(2) | 23(1) |
| C(1) | 2242(9) | 648(4) | 1173(2) | 20(1) |
| C(2) | 3198(8) | 351(4) | 1606(2) | 22(1) |
| C(3) | 2267(10) | −571(4) | 1891(2) | 29(1) |
| C(4) | −474(9) | −820(4) | 1219(2) | 20(1) |
| C(5) | −1135(9) | −2023(4) | 1878(2) | 25(1) |
| C(6) | −2805(11) | −2394(5) | 1565(2) | 26(1) |
| C(7) | −807(18) | −2456(6) | 2365(2) | 41(2) |
| C(8) | 2920(10) | 1736(4) | 917(2) | 23(1) |
| C(9) | 1254(13) | 2703(5) | 1078(3) | 32(2) |
| C(10) | −755(11) | −530(4) | −802(2) | 21(1) |
| C(11) | −2631(10) | −858(4) | −1102(2) | 26(1) |
| C(12) | −2597(11) | −528(5) | −1570(2) | 28(1) |
| C(13) | −732(12) | 127(4) | −1755(2) | 31(1) |
| C(14) | 1149(11) | 434(5) | −1457(2) | 31(1) |
| C(15) | 1156(10) | 102(4) | −981(2) | 26(1) |
| C(16) | −926(12) | −817(4) | −274(2) | 24(1) |
| C(17) | −2506(10) | 130(4) | −50(2) | 23(1) |

TABLE A2

Bond lengths [Å] and angles (deg)

| | |
|---|---|
| Br(1)—C(2) | 1.896(5) |
| S(1)—C(4) | 1.714(5) |
| S(1)—C(6) | 1.719(6) |
| O(1)—C(3) | 1.215(6) |
| O(2)—C(16) | 1.413(6) |
| O(3)—C(17) | 1.260(6) |
| O(4)—C(17) | 1.256(6) |
| N(1)—C(4) | 1.387(6) |
| N(1)—C(3) | 1.422(6) |
| N(1)—C(5) | 1.423(6) |
| N(2)—C(4) | 1.314(6) |
| N(2)—C(1) | 1.362(6) |
| N(3)—C(8) | 1.489(6) |
| C(1)—C(2) | 1.375(7) |
| C(1)—C(8) | 1.497(7) |
| C(2)—C(3) | 1.431(7) |
| C(5)—C(6) | 1.350(8) |
| C(5)—C(7) | 1.474(8) |
| C(8)—C(9) | 1.521(8) |
| C(10)—C(15) | 1.385(8) |
| C(10)—C(11) | 1.395(7) |
| C(10)—C(16) | 1.529(7) |
| C(11)—C(12) | 1.375(7) |
| C(12)—C(13) | 1.385(8) |
| C(13)—C(14) | 1.388(8) |
| C(14)—C(15) | 1.394(8) |
| C(16)—C(17) | 1.538(7) |
| C(4)—S(1)—C(6) | 90.4(3) |
| C(4)—N(1)—C(3) | 121.2(4) |
| C(4)—N(1)—C(5) | 113.4(4) |
| C(3)—N(1)—C(5) | 125.4(4) |
| C(4)—N(2)—C(1) | 116.3(5) |
| N(2)—C(1)—C(2) | 122.2(5) |
| N(2)—C(1)—C(8) | 114.8(5) |
| C(2)—C(1)—C(8) | 122.7(5) |
| C(1)—C(2)—C(3) | 123.0(5) |
| C(1)—C(2)—Br(1) | 121.9(4) |
| C(3)—C(2)—Br(1) | 115.1(4) |
| O(1)—C(3)—N(1) | 121.2(5) |
| O(1)—C(3)—C(2) | 126.8(5) |
| N(1)—C(3)—C(2) | 111.9(5) |
| N(2)—C(4)—N(1) | 125.1(5) |
| N(2)—C(4)—S(1) | 123.6(4) |
| N(1)—C(4)—S(1) | 111.3(3) |
| C(6)—C(5)—N(1) | 110.0(5) |
| C(6)—C(5)—C(7) | 125.9(5) |
| N(1)—C(5)—C(7) | 124.1(5) |
| C(5)—C(6)—S(1) | 114.8(5) |
| N(3)—C(8)—C(1) | 110.5(4) |
| N(3)—C(8)—C(9) | 109.4(5) |
| C(1)—C(8)—C(9) | 108.6(4) |
| C(15)—C(10)—C(11) | 119.6(5) |
| C(15)—C(10)—C(16) | 121.2(5) |
| C(11)—C(10)—C(16) | 119.1(5) |
| C(12)—C(11)—C(10) | 119.8(5) |
| C(11)—C(12)—C(13) | 121.5(6) |
| C(12)—C(13)—C(14) | 118.4(5) |
| C(13)—C(14)—C(15) | 121.0(5) |
| C(10)—C(15)—C(14) | 119.6(5) |
| O(2)—C(16)—C(10) | 112.3(4) |
| O(2)—C(16)—C(17) | 113.0(5) |
| C(10)—C(16)—C(17) | 106.3(4) |
| O(4)—C(17)—O(3) | 125.1(5) |
| O(4)—C(17)—C(16) | 116.1(5) |
| O(3)—C(17)—C(16) | 118.8(5) |

TABLE A3

Anisotropic displacement parameters (Å$^2$ × 10$^3$) (symmetry transformations used to generate equivalent atoms. The anisotropic displacement factor exponent takes the form:
$-2\pi^2 [h^2 a^{*2} U11 + \ldots + 2 h k a^* b^* U12]$

| | U11 | U22 | U33 | U23 | U13 | U12 |
|---|---|---|---|---|---|---|
| Br(1) | 27(1) | 40(1) | 36(1) | −4(1) | −6(1) | −9(1) |
| S(1) | 27(1) | 24(1) | 33(1) | 2(1) | −5(1) | −7(1) |
| O(1) | 54(3) | 56(3) | 33(3) | 9(2) | −21(2) | −11(2) |
| O(2) | 41(3) | 13(2) | 46(3) | 3(2) | 6(2) | 4(2) |
| O(3) | 33(2) | 14(2) | 35(2) | 5(2) | −7(1) | 0(2) |
| O(4) | 31(3) | 21(2) | 44(3) | −1(2) | 8(2) | 0(2) |
| N(1) | 22(2) | 22(2) | 21(2) | 1(2) | −3(2) | −3(2) |
| N(2) | 26(3) | 21(2) | 26(3) | 5(2) | −2(2) | 0(2) |
| N(3) | 27(3) | 22(3) | 19(3) | 4(2) | 3(2) | −8(2) |
| C(1) | 16(3) | 19(3) | 26(3) | −4(2) | 0(2) | −3(2) |
| C(2) | 13(3) | 23(3) | 29(3) | 1(3) | 1(2) | −2(2) |
| C(3) | 29(3) | 31(3) | 27(3) | −1(3) | −5(3) | 2(3) |
| C(4) | 23(3) | 17(3) | 20(3) | 4(2) | 0(2) | 1(2) |
| C(5) | 26(3) | 22(3) | 29(3) | 11(3) | 6(3) | −2(2) |
| C(6) | 22(3) | 17(3) | 40(4) | 4(3) | 0(3) | −4(3) |
| C(7) | 56(5) | 36(4) | 31(4) | 11(3) | 1(4) | −2(4) |
| C(8) | 23(3) | 21(3) | 26(3) | −7(3) | −4(2) | −4(2) |
| C(9) | 34(5) | 21(3) | 41(5) | −3(3) | 6(3) | −9(3) |

TABLE A3-continued

Anisotropic displacement parameters (Å² × 10³) (symmetry transformations used to generate equivalent atoms. The anisotropic displacement factor exponent takes the form:
$-2\pi^2 [h^2 a^{*2} U11 + \ldots + 2 h k a^* b^* U12]$

| | U11 | U22 | U33 | U23 | U13 | U12 |
|---|---|---|---|---|---|---|
| C(10) | 23(3) | 17(3) | 23(3) | 1(2) | 6(3) | 9(3) |
| C(11) | 26(3) | 22(3) | 31(4) | 1(3) | 3(3) | −6(3) |
| C(12) | 26(3) | 19(3) | 38(4) | −7(3) | −4(3) | 11(3) |
| C(13) | 37(3) | 22(3) | 32(4) | 3(2) | 5(3) | 8(3) |
| C(14) | 22(4) | 25(3) | 45(4) | 8(3) | 10(3) | 0(3) |
| C(15) | 27(3) | 20(3) | 33(3) | −1(3) | 7(3) | 6(3) |
| C(16) | 30(3) | 10(3) | 31(3) | −2(2) | 1(3) | 3(3) |
| C(17) | 29(3) | 18(3) | 22(3) | 1(2) | −3(3) | 6(3) |

TABLE A4

Hydrogen coordinates (×10⁴) and isotropic displacement parameters (Å² × 10³)

| | x | y | z | U(eq) |
|---|---|---|---|---|
| H(2) | −3600(200) | −1860(80) | −110(30) | 160(40) |
| H(3) | 4250(110) | 910(50) | 254(19) | 59(17) |
| H(3A) | 1260(150) | 1240(60) | 310(20) | 80(20) |
| H(3B) | 2910(100) | 2160(50) | 266(19) | 27(18) |
| H(6) | −3610(100) | −2890(40) | 1579(18) | 25(18) |
| H(7) | −2240(160) | −3020(80) | 2480(30) | 120(30) |
| H(7A) | −1360(90) | −1900(50) | 2583(17) | 30(17) |
| H(7B) | 640(120) | −2750(50) | 2426(19) | 41(19) |
| H(8) | 4800(80) | 1970(40) | 1003(17) | 28(15) |
| H(9) | 2070(100) | 3440(50) | 950(20) | 56(19) |
| H(9A) | 1570(110) | 2790(50) | 1430(20) | 60(20) |
| H(9B) | −210(100) | 2520(50) | 1035(19) | 34(19) |
| H(11) | −3890(80) | −1350(40) | −963(14) | 16(12) |
| H(12) | −3720(100) | −740(50) | −1780(20) | 60(20) |
| H(13) | −670(100) | 380(40) | −2129(18) | 40(15) |
| H(14) | 2390(110) | 910(50) | −1573(18) | 45(17) |
| H(15) | 2710(120) | 320(50) | −760(20) | 70(20) |
| H(16) | 780(100) | 840(40) | −125(18) | 50(16) |

TABLE A5

Torsion angles [deg].

| | |
|---|---|
| C(4)—N(2)—C(1)—C(2) | 5.5(7) |
| C(4)—N(2)—C(1)—C(8) | −168.8(4) |
| N(2)—C(1)—C(2)—C(3) | −5.2(8) |
| C(8)—C(1)—C(2)—C(3) | 168.7(5) |
| N(2)—C(1)—C(2)—Br(1) | 176.5(4) |
| C(8)—C(1)—C(2)—Br(1) | −9.6(7) |
| C(4)—N(1)—C(3)—O(1) | −177.1(5) |
| C(5)—N(1)—C(3)—O(1) | 4.4(8) |
| C(4)—N(1)—C(3)—C(2) | 3.3(7) |
| C(5)—N(1)—C(3)—C(2) | −175.2(4) |
| C(1)—C(2)—C(3)—O(1) | −179.0(5) |
| Br(1)—C(2)—C(3)—O(1) | −0.7(8) |
| C(1)—C(2)—C(3)—N(1) | 0.6(7) |
| Br(1)—C(2)—C(3)—N(1) | 179.0(3) |
| C(1)—N(2)—C(4)—N(1) | −1.5(7) |
| C(1)—N(2)—C(4)—S(1) | 178.2(4) |
| C(3)—N(1)—C(4)—N(2) | −3.0(7) |
| C(5)—N(1)—C(4)—N(2) | 175.6(5) |
| C(3)—N(1)—C(4)—S(1) | 177.2(4) |
| C(5)—N(1)—C(4)—S(1) | −4.1(5) |
| C(6)—S(1)—C(4)—N(2) | −177.2(5) |
| C(6)—S(1)—C(4)—N(1) | 2.5(4) |
| C(4)—N(1)—C(5)—C(6) | 3.8(6) |
| C(3)—N(1)—C(5)—C(6) | −177.6(5) |
| C(4)—N(1)—C(5)—C(7) | −175.8(6) |
| C(3)—N(1)—C(5)—C(7) | 2.8(8) |
| N(1)—C(5)—C(6)—S(1) | −1.8(6) |
| C(7)—C(5)—C(6)—S(1) | 177.7(5) |
| C(4)—S(1)—C(6)—C(5) | −0.4(5) |

TABLE A5-continued

Torsion angles [deg].

| | |
|---|---|
| N(2)—C(1)—C(8)—N(3) | −34.3(6) |
| C(2)—C(1)—C(8)—N(3) | 151.4(5) |
| N(2)—C(1)—C(8)—C(9) | 85.7(6) |
| C(2)—C(1)—C(8)—C(9) | −88.6(6) |
| C(15)—C(10)—C(11)—C(12) | −1.5(8) |
| C(16)—C(10)—C(11)—C(12) | 174.9(5) |
| C(10)—C(11)—C(12)—C(13) | 0.0(8) |
| C(11)—C(12)—C(13)—C(14) | 1.0(8) |
| C(12)—C(13)—C(14)—C(15) | −0.6(8) |
| C(11)—C(10)—C(15)—C(14) | 1.9(8) |
| C(16)—C(10)—C(15)—C(14) | −174.4(5) |
| C(13)—C(14)—C(15)—C(10) | −0.9(8) |
| C(15)—C(10)—C(16)—O(2) | −141.3(5) |
| C(11)—C(10)—C(16)—O(2) | 42.3(7) |
| C(15)—C(10)—C(16)—C(17) | 94.7(6) |
| C(11)—C(10)—C(16)—C(17) | −81.7(6) |
| O(2)—C(16)—C(17)—O(4) | −15.1(7) |
| C(10)—C(16)—C(17)—O(4) | 108.4(5) |
| O(2)—C(16)—C(17)—O(3) | 167.6(4) |
| C(10)—C(16)—C(17)—O(3) | −68.9(6) |

Example 17. 6-(3,5-difluorophenyl)-3-methyl-7-[1-(7H-pyrrolo[2,3-d]pyrimidin-4-ylamino)ethyl]-5H-[1,3]thiazolo[3,2-a]pyrimidin-5-one

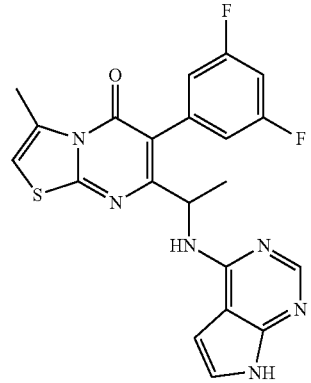 [SMILES: Cc1csc2nc(C(C)Nc3ncnc4[nH]ccc34)c(-c3cc(F)cc(F)c3)c(=O)n12]

A mixture of 7-(1-aminoethyl)-6-(3,5-difluorophenyl)-3-methyl-5H-[1,3]thiazolo[3,2-a]pyrimidin-5-one hydrochloride (0.030 g, 0.084 mmol), 4-chloropyrrolo[2,3-d]pyrimidine (0.013 g, 0.084 mmol), and N,N-diisopropylethylamine (0.044 mL, 0.25 mmol) in isopropyl alcohol (0.2 mL) was heated at 100° C., in a sealed tube, for three days. The resultant mixture was applied on RP-HPLC (XBridge C18 Column, eluting with a gradient of acetonitrile/water containing 0.15% $NH_4OH$) to give the desired product. LCMS calculated for $C_{21}H_{17}F_2N_6OS(M+H)^+$: m/z=439.1. Found: 439.1.

Example 18. 6-(3,5-difluorophenyl)-7-{1-[(2-fluoro-9H-purin-6-yl)amino]ethyl}-3-methyl-5H-[1,3]thiazolo[3,2-a]pyrimidin-5-one

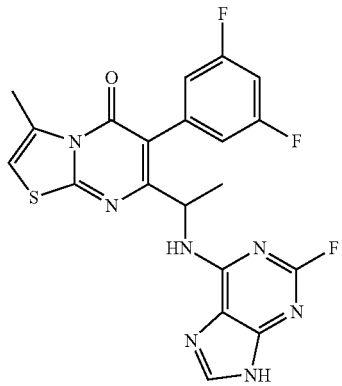 [SMILES: Cc1csc2nc(C(C)Nc3nc(F)nc4[nH]cnc34)c(-c3cc(F)cc(F)c3)c(=O)n12]

A mixture of 7-(1-aminoethyl)-6-(3,5-difluorophenyl)-3-methyl-5H-[1,3]thiazolo[3,2-a]pyrimidin-5-one hydrochloride (0.030 g, 0.084 mmol), 2-fluoro-6-chloropurine (0.015 g, 0.084 mmol), and N,N-diisopropylethylamine (0.044 mL, 0.25 mmol) in isopropyl alcohol (0.2 mL) was heated at 100° C. for three days, in a sealed tube. The resultant mixture was purified on RP-HPLC (XBridge C18 Column, eluting with a gradient of acetonitrile/water containing 0.15% NH$_4$OH) to give the desired product. LCMS calculated for C$_{20}$H$_{15}$F$_3$N$_7$OS(M+H)$^+$: m/z=458.1. Found: 458.0.

Example 19. 3-methyl-7-[1-(9H-purin-6-ylamino)ethyl]-6-pyridin-4-yl-5H-[1,3]thiazolo[3,2-a]pyrimidin-5-one

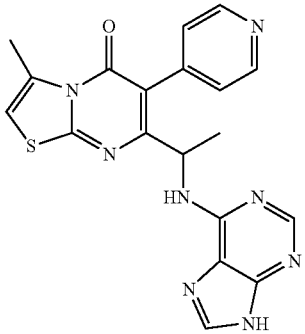 [SMILES: Cc1csc2nc(C(C)Nc3ncnc4[nH]cnc34)c(-c3ccncc3)c(=O)n12]

Step 1. 7-(1-aminoethyl)-3-methyl-6-pyridin-4-yl-5H-[1,3]thiazolo[3,2-a]pyrimidin-5-one

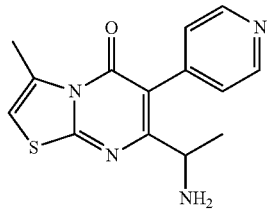 [SMILES: Cc1csc2nc(C(C)N)c(-c3ccncc3)c(=O)n12]

To a stirred solution of 7-(1-azidoethyl)-3-methyl-6-pyridin-4-yl-5H-[1,3]thiazolo[3,2-a]pyrimidin-5-one (0.050 g, 0.16 mmol) in tetrahydrofuran (0.5 mL) and water (0.12 mL) was added 1.00 M of trimethylphosphine in tetrahydrofuran (0.19 mL, 0.19 mmol) at room temperature and the mixture was stirred at room temperature for 1 hour. To the mixture was added ethyl acetate (EtOAc) and the mixture was extracted with 1 N HCl two times. The combined extracts were neutralized with solid sodium bicarbonate, and extracted with dichloromethane. The combined organic layers were washed with brine, dried over magnesium sulfate, and concentrated under reduced pressure. The residue, shown two peaks with same desired mass, was used directly in next step. LCMS calculated for C$_{14}$H$_{15}$N$_4$OS(M+H)$^+$: m/z=287.1. Found: 287.0.

Step 2. 3-methyl-7-[1-(9H-purin-6-ylamino)ethyl]-6-pyridin-4-yl-5H-[1,3]thiazolo[3,2-a]pyrimidin-5-one

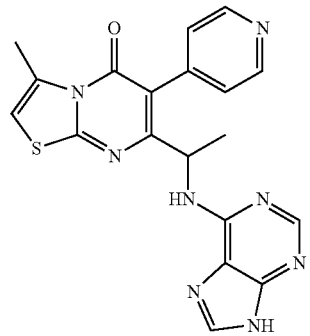 [SMILES: Cc1csc2nc(C(C)Nc3ncnc4[nH]cnc34)c(-c3ccncc3)c(=O)n12]

A mixture of 6-bromo-9H-purine (0.064 g, 0.32 mmol), 7-(1-aminoethyl)-3-methyl-6-pyridin-4-yl-5H-[1,3]thiazolo[3,2-a]pyrimidin-5-one (0.046 g, 0.16 mmol), and N,N-diisopropylethylamine (0.056 mL, 0.32 mmol) in ethanol (0.5 mL) was heated at reflux under nitrogen overnight. The mixture was evaporated and the resultant residue was purified on RP-HPLC (XBridge C18 Column, eluting with a gradient of acetonitrile/water containing 0.15% NH$_4$OH) to give the product as the free base. LCMS calculated for C$_{19}$H$_{17}$N$_8$OS(M+H)$^+$: m/z=405.1. Found: 405.1.

Example 20. 3-methyl-7-[1-(9H-purin-6-ylamino)ethyl]-6-(1,3-thiazol-2-yl)-5H-[1,3]thiazolo[3,2-a]pyrimidin-5-one trifluoroacetic acid salt

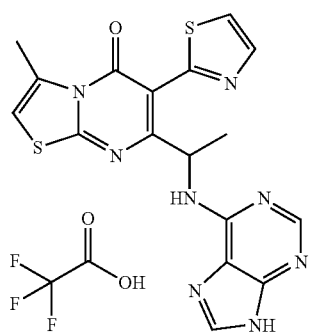 [SMILES: Cc1csc2nc(C(C)Nc3ncnc4[nH]cnc34)c(-c3nccs3)c(=O)n12 ; O=C(O)C(F)(F)F]

Step 1. 7-(1-azidoethyl)-3-methyl-6-(1,3-thiazol-2-yl)-5H-[1,3]thiazolo[3,2-a]pyrimidin-5-one

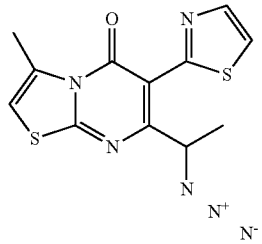

To a mixture of 7-(1-azidoethyl)-6-bromo-3-methyl-5H-[1,3]thiazolo[3,2-a]pyrimidin-5-one (0.10 g, 0.32 mmol), and 2-(tributylstannyl)-1,3-thiazole (143 mg, 0.382 mmol) in 1,4-dioxane (3 mL) was added tetrakis(triphenylphosphine)palladium(0) (18 mg, 0.016 mmol). The reaction mixture was heated at 120° C. overnight. After cooling to room temperature, the mixture concentrated under reduced pressure. The crude mixture was purified on silica gel, eluting with 0 to 60% ethyl acetate in hexane, to give the desired product (73 mg, 72%). LCMS calculated for $C_{12}H_{11}N_6OS_2(M+H)^+$: m/z=319.0. Found: 319.0.

Step 2. 7-(1-aminoethyl)-3-methyl-6-(1,3-thiazol-2-yl)-5H-[1,3]thiazolo[3,2-a]pyrimidin-5-one

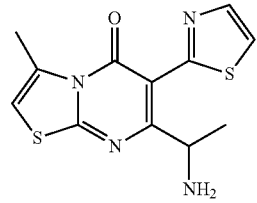 [SMILES: Cc1csc2nc(C(C)N)c(-c3nccs3)c(=O)n12]

To a stirred solution of 7-(1-azidoethyl)-3-methyl-6-(1,3-thiazol-2-yl)-5H-[1,3]thiazolo[3,2-a]pyrimidin-5-one (0.030 g, 0.094 mmol) in tetrahydrofuran (0.3 mL) and water (0.068 mL) was added 1.00 M of trimethylphosphine in tetrahydrofuran (0.11 mL, 0.11 mmol) at room temperature and the mixture was stirred at room temperature for 1 hour. To the mixture was added ethyl acetate and the mixture was extracted with 1 N HCl two times. The combined extracts were neutralized with solid sodium bicarbonate, and extracted with dichloromethane. The combined organic layers were washed with brine, dried over magnesium sulfate, and concentrated under reduced pressure. The residue was used directly in next step. LCMS calculated for $C_{12}H_{13}N_4OS_2(M+H)^+$: m/z=293.1. Found: 293.0.

Step 3. 3-methyl-7-[1-(9H-purin-6-ylamino)ethyl]-6-(1,3-thiazol-2-yl)-5H-[1,3]thiazolo[3,2-a]pyrimidin-5-one trifluoroacetic acid salt

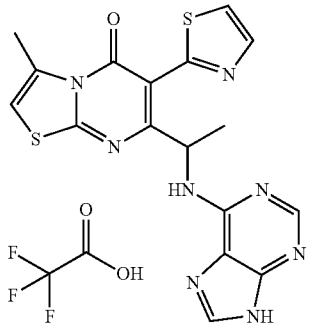 [SMILES: Cc1csc2nc(C(C)Nc3ncnc4[nH]cnc34)c(-c3nccs3)c(=O)n12 ; O=C(O)C(F)(F)F]

A mixture of 6-bromo-9H-purine (0.038 g, 0.19 mmol), 7-(1-aminoethyl)-3-methyl-6-(1,3-thiazol-2-yl)-5H-[1,3]thiazolo[3,2-a]pyrimidin-5-one (0.028 g, 0.096 mmol), and N,N-diisopropylethylamine (0.033 mL, 0.19 mmol) in ethanol (0.3 mL) was heated at reflux under nitrogen overnight. The mixture was evaporated and the resultant residue was purified on RP-HPLC (XBridge C18 Column, eluting with a gradient of acetonitrile/water containing 0.05% trifluoroacetic acid (TFA)) to give the product as a TFA salt. LCMS calculated for $C_{17}H_{15}N_8OS_2(M+H)^+$: m/z=411.1. Found: 411.0.

Example 21. 3-methyl-7-[1-(9H-purin-6-ylamino)ethyl]-6-(1,3-thiazol-4-yl)-5H-[1,3]thiazolo[3,2-a]pyrimidin-5-one trifluoroacetic acid salt

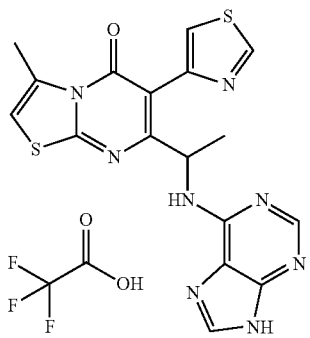 [SMILES: Cc1csc2nc(C(C)Nc3ncnc4[nH]cnc34)c(-c3cscn3)c(=O)n12 ; O=C(O)C(F)(F)F]

Step 1. 7-(1-azidoethyl)-3-methyl-6-(1,3-thiazol-4-yl)-5H-[1,3]thiazolo[3,2-a]pyrimidin-5-one

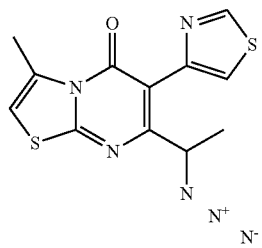

To a mixture of 7-(1-azidoethyl)-6-bromo-3-methyl-5H-[1,3]thiazolo[3,2-a]pyrimidin-5-one (0.10 g, 0.32 mmol) and 4-(tributylstannyl)-1,3-thiazole (143 mg, 0.382 mmol) in 1,4-dioxane (3 mL) was added tetrakis(triphenylphosphine)palladium(0) (18.4 mg, 0.0159 mmol). The reaction mixture was heated at 120° C. overnight. After cooling to room temperature, the mixture concentrated under reduced pressure. The crude mixture was purified on silica gel, eluting with 0 to 60% EtOAc in hexane, to give the desired product (82 mg, 81%). LCMS calculated for $C_{12}H_{11}N_6OS_2$ $(M+H)^+$: m/z=319.0. Found: 319.0.

Step 2. 7-(1-aminoethyl)-3-methyl-6-(1,3-thiazol-4-yl)-5H-[1,3]thiazolo[3,2-a]pyrimidin-5-one

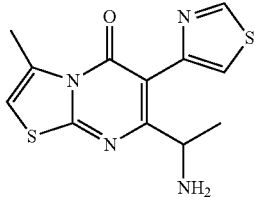 [SMILES: Cc1csc2nc(C(C)N)c(-c3cscn3)c(=O)n12]

To a stirred solution of 7-(1-azidoethyl)-3-methyl-6-(1,3-thiazol-4-yl)-5H-[1,3]thiazolo[3,2-a]pyrimidin-5-one (0.030 g, 0.094 mmol) in tetrahydrofuran (0.3 mL) and water (0.068 mL) was added 1.00 M of trimethylphosphine in tetrahydrofuran (0.113 mL, 0.113 mmol) at room temperature and the mixture was stirred at room temperature for 1 hour. To the mixture was added ethyl acetate and the mixture was extracted with 1 N HCl two times. The combined extracts were neutralized with solid sodium bicarbonate, and extracted with dichloromethane. The combined organic layers were washed with brine, dried over magnesium sulfate, and concentrated under reduced pressure. The residue was used directly in next step. LCMS calculated for $C_{12}H_{13}N_4OS_2(M+H)^+$: m/z=293.1. Found: 293.0.

Step 3. 3-methyl-7-[1-(9H-purin-6-ylamino)ethyl]-6-(1,3-thiazol-4-yl)-5H-[1,3]thiazolo[3,2-a]pyrimidin-5-one trifluoroacetic acid salt

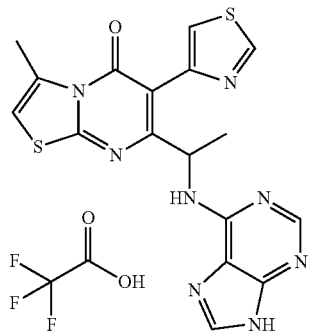 [SMILES: Cc1csc2nc(C(C)Nc3ncnc4[nH]cnc34)c(-c3cscn3)c(=O)n12 ; O=C(O)C(F)(F)F]

A mixture of 6-bromo-9H-purine (0.038 g, 0.19 mmol), 7-(1-aminoethyl)-3-methyl-6-(1,3-thiazol-4-yl)-5H-[1,3]thiazolo[3,2-a]pyrimidin-5-one (0.028 g, 0.096 mmol), and N,N-diisopropylethylamine (0.033 mL, 0.19 mmol) in ethanol (0.3 mL) was heated at reflux under nitrogen overnight. The mixture was evaporated and the resultant residue was purified on RP-HPLC (XBridge C18 Column, eluting with a gradient of acetonitrile/water containing 0.05% TFA) to give the product as a TFA salt. LCMS calculated for $C_{17}H_{15}N_8OS_2(M+H)^+$: m/z=411.1. Found: 411.0.

Example 22. 6-(4-fluorophenyl)-3-methyl-7-[1-(9H-purin-6-ylamino)ethyl]-5H-[1,3]thiazolo[3,2-a]pyrimidin-5-one trifluoroacetic acid salt

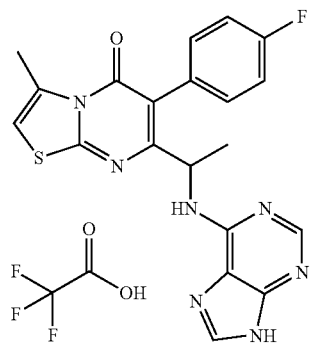

Step 1. 7-(1-azidoethyl)-6-(4-fluorophenyl)-3-methyl-5H-[1,3]thiazolo[3,2-a]pyrimidin-5-one

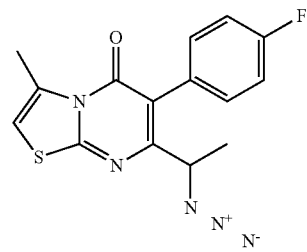

To a mixture of 7-(1-azidoethyl)-6-bromo-3-methyl-5H-[1,3]thiazolo[3,2-a]pyrimidin-5-one (0.10 g, 0.32 mmol) and 4-fluorophenylboronic acid (53 mg, 0.38 mmol) in 1,4-dioxane (2 mL) was added a 1 M solution of sodium carbonate in water (0.38 mL, 0.38 mmol) and tetrakis(triphenylphosphine)palladium(0) (18 mg, 0.016 mmol). The reaction mixture was heated at 100° C. overnight. After cooling to room temperature, the mixture was diluted with ethyl acetate, washed with water, brine, dried over MgSO$_4$, and concentrated. The crude mixture was purified on silica gel, eluting with 0 to 40% EtOAc in hexane, to give desired product (69 mg, 66%). LCMS calculated for $C_{15}H_{13}FN_5OS(M+H)^+$: m/z=330.1. Found: 330.0.

Step 2. 7-(1-aminoethyl)-6-(4-fluorophenyl)-3-methyl-5H-[1,3]thiazolo[3,2-a]pyrimidin-5-one

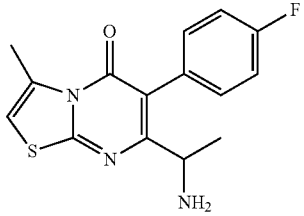 [SMILES: Cc1csc2nc(C(C)N)c(-c3ccc(F)cc3)c(=O)n12]

To a stirred solution of 7-(1-azidoethyl)-6-(4-fluorophenyl)-3-methyl-5H-[1,3]thiazolo[3,2-a]pyrimidin-5-one (0.062 g, 0.19 mmol) in tetrahydrofuran (0.6 mL) and water (0.14 mL,) was added 1.00 M of trimethylphosphine in tetrahydrofuran (0.226 mL, 0.226 mmol) at room temperature, and the mixture was stirred at room temperature for 1 hour. To the mixture was added ethyl acetate, and then the mixture was extracted with 1 N HCl two times. The combined extracts were neutralized with solid sodium bicarbonate and extracted with dichloromethane. The combined organic layers were washed with brine, dried over magnesium sulfate, and concentrated under reduced pressure. The residue was used directly in next step. LCMS calculated for $C_{15}H_{15}FN_3OS(M+H)^+$: m/z=304.1. Found: 304.1.

Step 3. 6-(4-fluorophenyl)-3-methyl-7-[1-(9H-purin-6-ylamino)ethyl]-5H-[1,3]thiazolo[3,2-a]pyrimidin-5-one trifluoroacetic acid salt

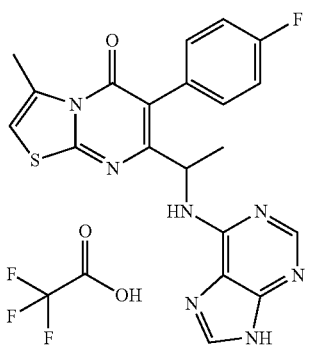 [SMILES: Cc1csc2nc(C(C)Nc3ncnc4[nH]cnc34)c(-c3ccc(F)cc3)c(=O)n12 ; O=C(O)C(F)(F)F]

A mixture of 6-bromo-9H-purine (0.076 g, 0.38 mmol), 7-(1-aminoethyl)-6-(4-fluorophenyl)-3-methyl-5H-[1,3]thiazolo[3,2-a]pyrimidin-5-one (0.058 g, 0.19 mmol), and N,N-diisopropylethylamine (0.066 mL, 0.38 mmol) in ethanol (0.6 mL) was heated at reflux under nitrogen overnight. The mixture was evaporated, and the resultant residue was purified on RP-HPLC (XBridge C18 Column, eluting with a gradient of acetonitrile/water containing 0.05% TFA) to give the product as a TFA salt. LCMS calculated for $C_{20}H_{17}FN_7OS(M+H)^+$: m/z=422.1. Found: 422.1.

Example 23. 7-{1-[(2-amino-9H-purin-6-yl)amino]ethyl}-6-(3,5-difluorophenyl)-3-methyl-5H-[1,3]thiazolo[3,2-a]pyrimidin-5-one

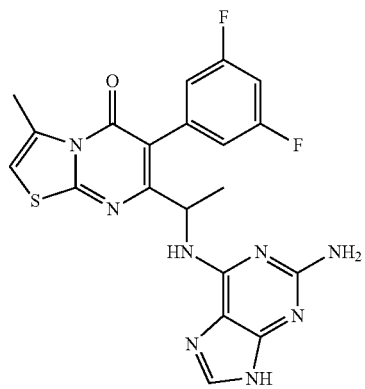 [SMILES: Cc1csc2nc(C(C)Nc3nc(N)nc4[nH]cnc34)c(-c3cc(F)cc(F)c3)c(=O)n12]

Step 1. 7-(1-azidoethyl)-6-(3,5-difluorophenyl)-3-methyl-5H-[1,3]thiazolo[3,2-a]pyrimidin-5-one

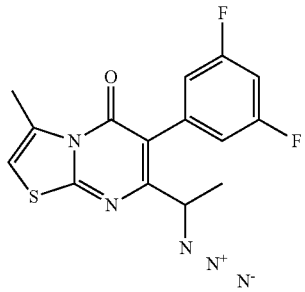

To a mixture of 7-(1-azidoethyl)-6-bromo-3-methyl-5H-[1,3]thiazolo[3,2-a]pyrimidin-5-one (1.24 g, 3.95 mmol) and (3,5-difluorophenyl)boronic acid (0.748 g, 4.74 mmol) in 1,4-dioxane (25 mL) was added a 1 N solution of sodium carbonate in water (5.92 mL, 5.92 mmol) and tetrakis(triphenylphosphine)palladium(0) (0.27 g, 0.24 mmol). The mixture was heated at 100° C. overnight. After cooling, the mixture was diluted with ethyl acetate, washed with water and brine, dried over $MgSO_4$, and concentrated. The residue was purified on silica gel (0-40% EtOAc/Hex) to give the desired product (0.42 g, 31%). LCMS calculated for $C_{15}H_{12}F_2N_5OS(M+H)^+$: m/z=348.1. Found: 348.0. The product was subjected to chiral HPLC separation (ChiralPak IA Column: 20×250 mm, 5 μm; Mobile Phase: 5% Ethanol—95% Hexanes; Flow Rate: 15 mL/min) to give two enantiomers. On analytic HPLC (ChiralPak IA Column: 4.6×250 mm, 5 μm; Mobile Phase: 5% Ethanol-95% Hexanes; Flow Rate: 1 mL/min), the first enantiomer has retention time of 7.78 min and the second peak has retention time of 8.61 minutes.

Step 2. 7-(1-aminoethyl)-6-(3,5-difluorophenyl)-3-methyl-5H-[1,3]thiazolo[3,2-a]pyrimidin-5-one

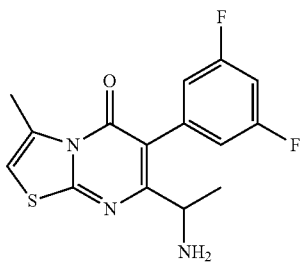 [SMILES: Cc1csc2nc(C(C)N)c(-c3cc(F)cc(F)c3)c(=O)n12]

To a stirred solutions of 7-(1-azidoethyl)-6-(3,5-difluorophenyl)-3-methyl-5H-[1,3]thiazolo[3,2-a]pyrimidin-5-one (0.15 g, 0.43 mmol) (1 st peak from chiral separation) in tetrahydrofuran (2 mL) and water (0.5 mL) were added 1.00 M of trimethylphosphine in tetrahydrofuran (0.52 mL, 0.52 mmol) at room temperature and the mixtures were stirred at room temperature for 1 hour. To the mixture was added EtOAc and the mixture was extracted with aqueous 1 N HCl solution (three times). The combined extracts were neutralized with solid $Na_2CO_3$ and extracted with dichloromethane (two times). The combined organic layers were washed with brine, dried over $Na_2SO_4$, and concentrated to give the desired product (134 mg, 96.6%). LCMS calculated for $C_{15}H_{14}F_2N_3OS(M+H)^+$: m/z=322.1. Found: 322.0.

Step 3. 7-{1-[(2-amino-9H-purin-6-yl)amino]ethyl}-6-(3,5-difluorophenyl)-3-methyl-5H-[1,3]thiazolo[3,2-a]pyrimidin-5-one

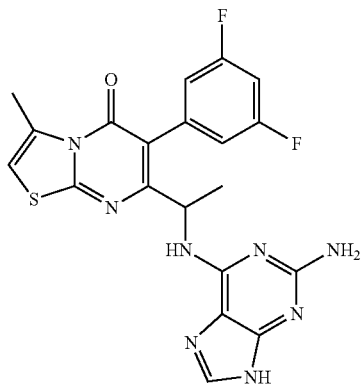

A mixture of optical pure 7-(1-aminoethyl)-6-(3,5-difluorophenyl)-3-methyl-5H-[1,3]thiazolo[3,2-a]pyrimidin-5-one (0.13 g, 0.40 mmol) made from above, 2-amino-6-bromopurine (0.10 g, 0.47 mmol), and N,N-diisopropylethylamine (0.085 mL, 0.49 mmol) in ethanol (1 mL) was heated at 110° C. overnight. LCMS showed incomplete conversion. An additional 0.5 equivalent of 2-amino-6-bromopurine and 1.0 equivalent of N,N-diisopropylethylamine was added, and the mixture was stirred at 110° C. for another day. The solid was shown to be 2-amino-6-bromopurine by LCMS. The mixture was filtered, and the filtrates were purified on preparative-LCMS ((XBridge C18 Column, eluting with a gradient of acetonitrile/water containing 0.15% $NH_4OH$) to give the desired product (0.095 g, 52%). LCMS calculated for $C_{20}H_{17}F_2N_8OS(M+H)^+$: m/z=455.1. Found: 455.1 $^1$H NMR (DMSO-$d_6$, 400 MHz) δ 7.67 (1H, s), 7.27 (1H, m), 7.17 (3H, m), 7.07 (1H, s), 6.89 (1H, br s), 5.45 (2H, br s), 5.03 (1H, m), 2.63 (3H, s), 1.30 (3H, d, J=6.8 Hz) ppm. $^{19}$F NMR (DMSO-$d_6$, 376.3 MHz) δ−111 ppm.

Example 24. 7-{1-[(2-amino-9H-purin-6-yl)amino]ethyl}-6-(3,5-difluorophenyl)-5H-[1,3]thiazolo[3,2-a]pyrimidin-5-one

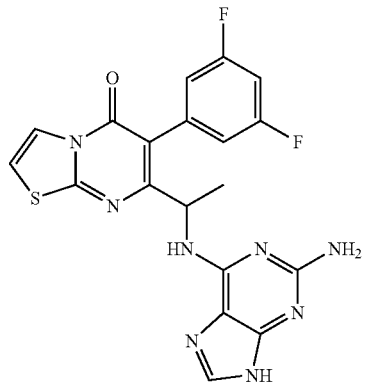 [SMILES: CC(Nc1nc(N)nc2[nH]cnc12)c1nc2sccn2c(=O)c1-c1cc(F)cc(F)c1]

Step 1. 7-(1-bromoethyl)-5H-[1,3]thiazolo[3,2-a]pyrimidin-5-one

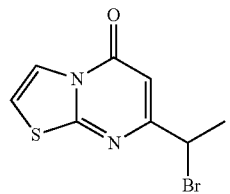

A mixture of polyphosphoric acid (73.8 g, 677 mmol), 1,3-thiazol-2-amine (12.3 g, 123 mmol), and methyl 4-bromo-3-oxopentanoate (34.8 g, 166 mmol) was stirred at 110° C. overnight. After cooling, an ice-cold 10% aq. NaOH solution was slowly added to adjust the pH to 7. The mixture was filtered, and the collected precipitate was air-dried to give crude product which was directly used in next step. LCMS calculated for $C_8H_8BrN_2OS(M+H)^+$: m/z=259.0. Found: 259.0.

Step 2. 6-bromo-7-(1-bromoethyl)-5H-[1,3]thiazolo[3,2-a]pyrimidin-5-one

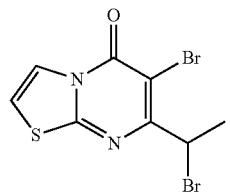

A mixture of 7-(1-bromoethyl)-5H-[1,3]thiazolo[3,2-a]pyrimidin-5-one (17.5 g, 67.5 mmol) and A-bromosuccinimide (14.2 g, 79.8 mmol) in acetonitrile (400 mL) was stirred at 80° C. under N₂ overnight. After removal of the solvent under reduced pressure, the resulting solid was dissolved in dichloromethane, washed sequentially with water, saturated aqueous Na₂S₂O₃ and NaHCO₃ solution and brine, dried over Na₂SO₄, and then concentrated to give crude product (3.7 g), which was used in the next step without further purification. LCMS calculated for $C_8H_7Br_2N_2OS(M+H)^+$: m/z=336.9. Found: 336.9.

Step 3. 7-(1-azidoethyl)-6-bromo-5H-[1,3]thiazolo[3,2-a]pyrimidin-5-one

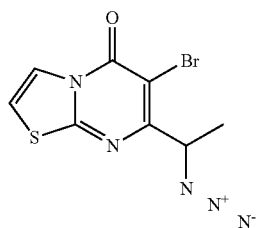

A mixture of 6-bromo-7-(1-bromoethyl)-5H-[1,3]thiazolo[3,2-a]pyrimidin-5-one (3.7 g, 11 mmol) and sodium azide (1.4 g, 22 mmol) in N,N-dimethylformamide (30 mL) was stirred at room temperature for 1.5 hour. After diluted with ethyl acetate, the mixture was washed with water, dried over Na₂SO₄, concentrated and purified on silica gel (0-60% ethyl acetate/hexanes) to give the desired product (2.16 g). LCMS calculated for $C_8H_7BrN_5OS(M+H)^+$: m/z=300.0. Found: 300.0.

Step 4. 7-(1-azidoethyl)-6-(3,5-difluorophenyl)-5H-[1,3]thiazolo[3,2-a]pyrimidin-5-one

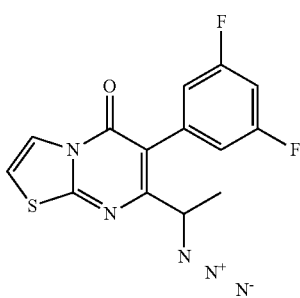

To a mixture of 7-(1-azidoethyl)-6-bromo-5H-[1,3]thiazolo[3,2-a]pyrimidin-5-one (0.50 g, 1.7 mmol) and (3,5-difluorophenyl)boronic acid (0.31 g, 2.0 mmol) in 1,4-dioxane (10 mL) was added a 1 N solution of sodium carbonate in water (2.2 mL, 2.2 mmol) and tetrakis(triphenylphosphine)palladium(0) (0.096 g, 0.083 mmol). The mixture was stirred at 100° C. overnight. After cooling, the mixture was diluted with ethyl acetate, washed with water and brine, dried over MgSO₄, concentrated, and purified on silica gel (0-45% ethyl acetate/hexanes) to give the desired product (0.30 g, 53%). LCMS calculated for $C_{14}H_{10}F_2N_5OS$ $(M+H)^+$: m/z=334.1. Found: 334.0.

Step 5. 7-(1-aminoethyl)-6-(3,5-difluorophenyl)-5H-[1,3]thiazolo[3,2-a]pyrimidin-5-one

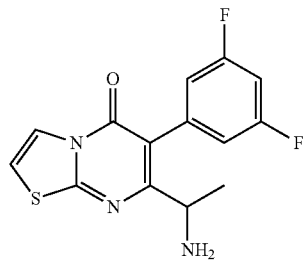 [SMILES: CC(N)c1nc2sccn2c(=O)c1-c1cc(F)cc(F)c1]

To a stirred solution of 7-(1-azidoethyl)-6-(3,5-difluorophenyl)-5H-[1,3]thiazolo[3,2-a]pyrimidin-5-one (0.295 g, 0.885 mmol) in tetrahydrofuran (5 mL) and water (1 mL) was added 1.00 M of trimethylphosphine in tetrahydrofuran (1.06 mL, 1.06 mmol) at room temperature and the mixture was stirred at room temperature for 1 hour. To the mixture was added ethyl acetate, and the mixture was extracted with aqueous 1 N HCl solution (three times). The combined extract was neutralized with solid NaHCO₃ and extracted with dichloromethane (two times). The combined organic layers were washed with brine, dried over Na₂SO₄, and concentrated to give the desired compound (0.241 g, 88.6%), which was used directly in next step. LCMS calculated for $C_{14}H_{12}F_2N_3OS(M+H)^+$: m/z=308.1. Found: 308.0.

Step 6. 7-{1-[(2-amino-9H-purin-6-yl)amino]ethyl}-6-(3,5-difluorophenyl)-5H-[1,3]thiazolo[3,2-a]pyrimidin-5-one

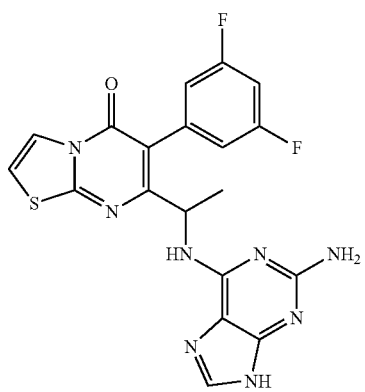

A mixture of 7-(1-aminoethyl)-6-(3,5-difluorophenyl)-5H-[1,3]thiazolo[3,2-a]pyrimidin-5-one (0.040 g, 0.13 mmol), 2-amino-6-bromopurine (0.056 g, 0.26 mmol), and N,N-diisopropylethylamine (0.045 mL, 0.26 mmol) in ethanol (0.5 mL) was heated at 110° C. overnight. The mixture was filtered, and the filtrate was purified on preparative-LCMS (XBridge C18 Column, eluting with a gradient of acetonitrile/water containing 0.15% NH₄OH), to give the desired product. LCMS calculated for $C_{19}H_{15}F_2N_8OS(M+H)^+$: m/z=441.1. Found: 441.1.

Example 25. 6-(3,5-difluorophenyl)-7-[1-(9H-purin-6-ylamino)ethyl]-5H-[1,3]thiazolo[3,2-a]pyrimidin-5-one

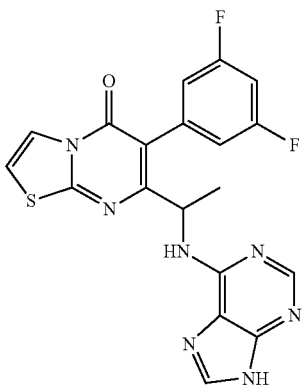 [SMILES: CC(Nc1ncnc2[nH]cnc12)c1nc2sccn2c(=O)c1-c1cc(F)cc(F)c1]

A mixture of 7-(1-aminoethyl)-6-(3,5-difluorophenyl)-5H-[1,3]thiazolo[3,2-a]pyrimidin-5-one (0.037 g, 0.12 mmol), 6-bromo-9H-purine (0.048 g, 0.24 mmol), and N,N-diisopropylethylamine (0.042 mL, 0.24 mmol) in ethanol (0.5 mL) was heated at 110° C. overnight. The mixture was filtered, and the filtrate was purified on preparative-LCMS (XBridge C18 Column, eluting with a gradient of acetonitrile/water containing 0.15% NH$_4$OH) to give the desired product. LCMS calculated for C$_{19}$H$_{14}$F$_2$N$_7$OS(M+H)$^+$: m/z=426.1. Found: 426.0. $^1$H NMR (DMSO-d$_6$, 400 MHz) δ 7.99 (1H, d, J=4.8 Hz), 7.63 (1H, s), 7.53 (1H, d, J=4.8 Hz), 7.24 (1H, m), 7.16 (2H, m), 6.88 (1H, br s), 5.41 (2H, br s), 5.05 (1H, m), 1.27 (3H, d, J=6.8 Hz) ppm. $^{19}$F NMR (DMSO-d$_6$, 376.3 MHz) δ−111 ppm.

Example 26. 7-{1-[(2-amino-9H-purin-6-yl)amino]ethyl}-6-(3-fluorophenyl)-5H-[1,3]thiazolo[3,2-a]pyrimidin-5-one

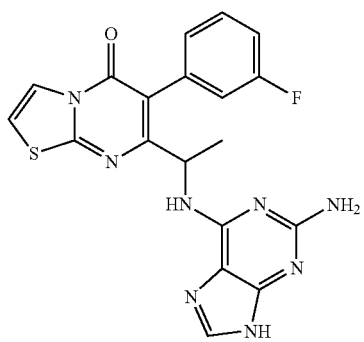 [SMILES: CC(Nc1nc(N)nc2[nH]cnc12)c1nc2sccn2c(=O)c1-c1cccc(F)c1]

Step 1. 7-(1-azidoethyl)-6-(3-fluorophenyl)-5H-[1,3]thiazolo[3,2-a]pyrimidin-5-one

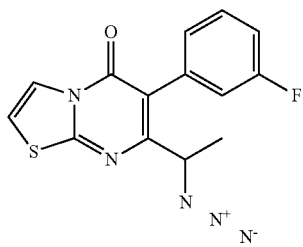

To a mixture of 7-(1-azidoethyl)-6-bromo-5H-[1,3]thiazolo[3,2-a]pyrimidin-5-one (0.48 g, 1.6 mmol) and (3-fluorophenyl)boronic acid (0.27 g, 2.0 mmol) in 1,4-dioxane (10 mL) was added a 1 N solution of sodium carbonate in water (2.1 mL, 2.1 mmol) and tetrakis(triphenylphosphine)palladium(0) (0.092 g, 0.080 mmol). The mixture was stirred at 100° C. overnight. After cooling, the mixture was diluted with ethyl acetate, washed with water and brine, dried over MgSO$_4$, concentrated, and purified on silica gel (0-50% ethyl acetate/hexanes) to give the desired compound (0.32 g, 63%). LCMS calculated for C$_{14}$H$_{11}$FN$_5$OS(M+H)$^+$: m/z=316.1. Found: 316.0.

Step 2. 7-(1-aminoethyl)-6-(3-fluorophenyl)-5H-[1,3]thiazolo[3,2-a]pyrimidin-5-one

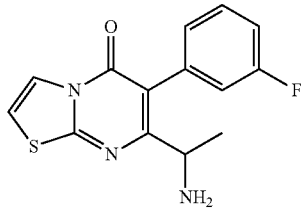 [SMILES: CC(N)c1nc2sccn2c(=O)c1-c1cccc(F)c1]

To a stirred solution of 7-(1-azidoethyl)-6-(3-fluorophenyl)-5H-[1,3]thiazolo[3,2-a]pyrimidin-5-one (0.32 g, 1.0 mmol) in tetrahydrofuran (5 mL) and water (1 mL) was added 1.00 M of trimethylphosphine in tetrahydrofuran (1.22 mL, 1.22 mmol) at room temperature, and the mixture was stirred at room temperature for 1 hour. To the mixture was added ethyl acetate, and the mixture was extracted with aqueous 1 N HCl solution (three times). The combined extract was neutralized with solid NaHCO$_3$ and extracted with dichloromethane (two times). The combined organic layer was washed with brine, dried over Na$_2$SO$_4$, and concentrated to give the desired product (0.17 g, 58%). LCMS calculated for C$_{14}$H$_{13}$FN$_3$OS(M+H)$^+$: m/z=290.1. Found: 290.0.

Step 3. 7-{1-[(2-amino-9H-purin-6-yl)amino]ethyl}-6-(3-fluorophenyl)-5H-[1,3]thiazolo[3,2-a]pyrimidin-5-one

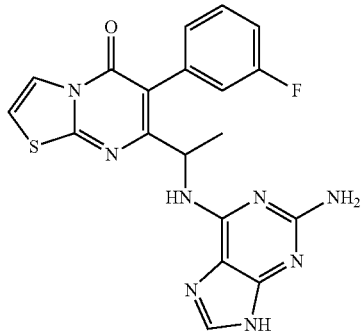 [SMILES: CC(Nc1nc(N)nc2[nH]cnc12)c1nc2sccn2c(=O)c1-c1cccc(F)c1]

A mixture of 7-(1-aminoethyl)-6-(3-fluorophenyl)-5H-[1,3]thiazolo[3,2-a]pyrimidin-5-one (0.025 g, 0.086 mmol), 2-amino-6-bromopurine (0.033 g, 0.16 mmol), and N,N-diisopropylethylamine (0.027 mL, 0.16 mmol) in ethanol (0.5 mL) was heated at 110° C. overnight. The mixture was filtered and the filtrate was purified on preparative-LCMS (XBridge C18 Column, eluting with a gradient of acetonitrile/water containing 0.15% NH$_4$OH) to give the desired product. LCMS calculated for C$_{19}$H$_{16}$FN$_8$OS(M+H)$^+$: m/z=423.1. Found: 423.0. $^1$H NMR (DMSO-d$_6$, 400 MHz) δ 7.98 (1H, d, J=4.8 Hz), 7.63 (1H, s), 7.52 (1H, d, J=4.8 Hz), 7.46 (1H, m), 7.20 (2H, m), 6.84 (1H, br s), 5.41 (1H, br s), 5.07 (1H, m), 1.26 (3H, d, J=6.8 Hz) ppm. $^{19}$F NMR (DMSO-d$_6$, 376.3 MHz) δ−114 ppm.

Example 27. 7-{1-[(2-amino-9H-purin-6-yl)amino]ethyl}-6-phenyl-5H-[1,3]thiazolo[3,2-a]pyrimidin-5-one

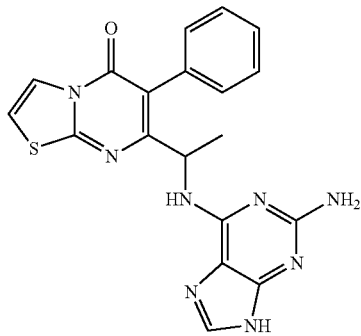 [SMILES: CC(Nc1nc(N)nc2[nH]cnc12)c1nc2sccn2c(=O)c1-c1ccccc1]

Step 1. 7-(1-azidoethyl)-6-phenyl-5H-[1,3]thiazolo[3,2-a]pyrimidin-5-one

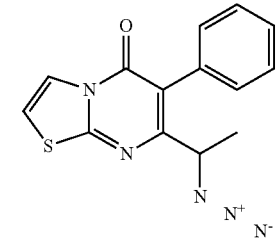

To a mixture of 7-(1-azidoethyl)-6-bromo-5H-[1,3]thiazolo[3,2-a]pyrimidin-5-one (0.34 g, 1.1 mmol) and phenylboronic acid (0.16 g, 1.4 mmol) in 1,4-dioxane (10 mL) was added a 1 N solution of sodium carbonate in water (1.5 mL, 1.5 mmol) and tetrakis(triphenylphosphine)palladium (0) (0.065 g, 0.057 mmol). The mixture was stirred at 100° C. overnight. After cooling, the mixture was diluted with ethyl acetate, washed with water and brine, dried over MgSO$_4$, concentrated, and purified on silica gel (0-50% ethyl acetate/hexanes) to give the desired product (0.23 g, 68%). LCMS calculated for C$_{14}$H$_{12}$N$_5$OS(M+H)$^+$: m/z=298.1. Found: 298.0.

Step 2. 7-(1-aminoethyl)-6-phenyl-5H-[1,3]thiazolo[3,2-a]pyrimidin-5-one

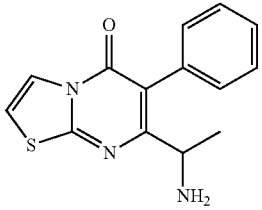 [SMILES: CC(N)c1nc2sccn2c(=O)c1-c1ccccc1]

To a stirred solution of 7-(1-azidoethyl)-6-phenyl-5H-[1,3]thiazolo[3,2-a]pyrimidin-5-one (0.23 g, 0.77 mmol) in tetrahydrofuran (5 mL) and water (1 mL) was added 1.00 M of trimethylphosphine in tetrahydrofuran (0.93 mL, 0.93 mmol) at room temperature, and the mixture was stirred at room temperature for 1 hour. To the mixture was added ethyl acetate, and the mixture was extracted with aqueous 1 N HCl solution (three times). The combined extract was neutralized with solid NaHCO$_3$ and extracted with dichloromethane (two times). The combined organic layer was washed with brine, dried over Na$_2$SO$_4$, and concentrated to give the desired compound (0.13 g, 62%). LCMS calculated for C$_{14}$H$_{14}$N$_3$OS(M+H)$^+$: m/z=272.1. Found: 272.0.

Step 3. 7-{1-[(2-amino-9H-purin-6-yl)amino]ethyl}-6-phenyl-5H-[1,3]thiazolo[3,2-a]pyrimidin-5-one

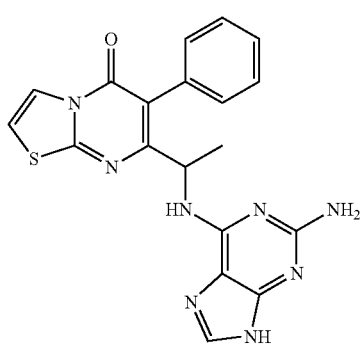 [SMILES: CC(Nc1nc(N)nc2[nH]cnc12)c1nc2sccn2c(=O)c1-c1ccccc1]

A mixture of 7-(1-aminoethyl)-6-phenyl-5H-[1,3]thiazolo[3,2-a]pyrimidin-5-one (0.025 g, 0.092 mmol), 2-amino-6-bromopurine (0.035 g, 0.16 mmol), and N,N-diisopropylethylamine (0.029 mL, 0.16 mmol) in ethanol (0.5 mL) was heated at 110° C. overnight. The mixture was filtered, and the filtrate was purified on preparative-LCMS (XBridge C18 Column, eluting with a gradient of acetonitrile/water containing 0.15% NH$_4$OH) to give the desired product. LCMS calculated for C$_{19}$H$_{17}$N$_8$OS(M+H)$^+$: m/z=405.1. Found: 405.1. $^1$H NMR (DMSO-d$_6$, 400 MHz) δ 80.1 (1H, d, J=4.8 Hz), 7.65 (1H, s), 7.55 (1H, d, J=4.8 Hz), 7.47 (2H, m), 7.40 (3H, m), 6.79 (1H, br s), 5.48 (2H, br s), 5.13 (1H, m), 1.29 (3H, d, J=6.8 Hz) ppm.

Example 28. 6-(3-fluorophenyl)-7-[1-(9H-purin-6-ylamino)ethyl]-5H-[1,3]thiazolo[3,2-a]pyrimidin-5-one

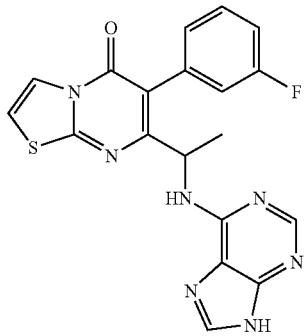 [SMILES: CC(Nc1ncnc2[nH]cnc12)c1nc2sccn2c(=O)c1-c1cccc(F)c1]

A mixture of 7-(1-aminoethyl)-6-(3-fluorophenyl)-5H-[1,3]thiazolo[3,2-a]pyrimidin-5-one (0.025 g, 0.086 mmol), 6-bromo-9H-purine (0.031 g, 0.16 mmol), and N,N-diisopropylethylamine (0.027 mL, 0.16 mmol) in ethanol (0.5 mL) was heated at 110° C. overnight. The mixture was filtered and the filtrate was purified on preparative-LCMS (XBridge C18 Column, eluting with a gradient of acetonitrile/water containing 0.15% NH$_4$OH) to give the desired product. LCMS calculated for C$_{19}$H$_{15}$FN$_7$OS(M+H)$^+$: m/z=408.1. Found: 408.0.

Example 29. 6-phenyl-7-[1-(9H-purin-6-ylamino)ethyl]-5H-[1,3]thiazolo[3,2-a]pyrimidin-5-one

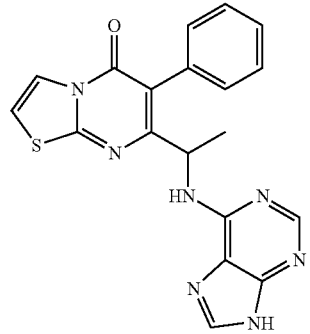 [SMILES: CC(Nc1ncnc2[nH]cnc12)c1nc2sccn2c(=O)c1-c1ccccc1]

A mixture of 7-(1-aminoethyl)-6-phenyl-5H-[1,3]thiazolo[3,2-a]pyrimidin-5-one (0.025 g, 0.092 mmol), 6-bromo-9H-purine (0.033 g, 0.16 mmol), and N,N-diisopropylethylamine (0.029 mL, 0.16 mmol) in ethanol (0.5 mL) was heated at 110° C. overnight. The mixture was filtered, and the filtrate was purified on preparative-LCMS (XBridge C18 Column, eluting with a gradient of acetonitrile/water containing 0.15% NH$_4$OH) to give the desired product. LCMS calculated for C$_{19}$H$_{16}$N$_7$OS(M+H)$^+$: m/z=390.1. Found: 390.1. $^1$H NMR (DMSO-d$_6$, 400 MHz) δ 8.08 (1H, s), 8.06 (1H, s), 7.97 (1H, d, J=4.8 Hz), 7.51 (1H, d, J=4.8 Hz), 7.44~7.33 (6H, m), 5.15 (1H, m), 1.29 (3H, d, J=12 Hz) ppm.

Example 30. 6-(3-fluorophenyl)-3-methyl-7-[1-(9H-purin-6-ylamino)ethyl]-5H-[1,3]thiazolo[3,2-a]pyrimidin-5-one

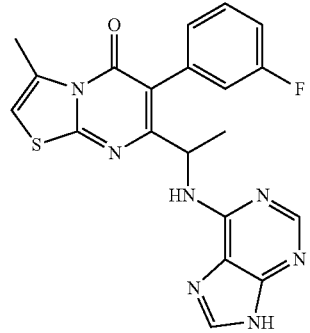

Step 1. 7-(1-azidoethyl)-6-(3-fluorophenyl)-3-methyl-5H-[1,3]thiazolo[3,2-a]pyrimidin-5-one

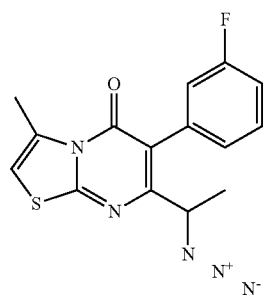

To a mixture of 7-(1-azidoethyl)-6-bromo-3-methyl-5H-[1,3]thiazolo[3,2-a]pyrimidin-5-one (0.50 g, 1.6 mmol) and (3-fluorophenyl)boronic acid (0.27 g, 1.9 mmol) in 1,4-dioxane (10 mL) was added 1 N solution of sodium carbonate in water (2.1 mL, 2.1 mmol) and tetrakis(triphenylphosphine)palladium(0) (0.092 g, 0.080 mmol). The mixture was stirred at 100° C. overnight. After cooling, the mixture was diluted with ethyl acetate, washed with water, dried over $Na_2SO_4$, concentrated and purified on silica gel (0-40% ethyl acetate/hexanes) to give the desired product (0.32 g, 61%). LCMS calculated for $C_{15}H_{13}FN_5OS(M+H)^+$: m/z=330.1. Found: 330.0. The product was subjected to chiral HPLC separation (ChiralPak IA Column: 20×250 mm, 5 µm; Mobile Phase: 10% Ethanol—90% Hexanes; Flow Rate: 18 mL/min) to give two enantiomers. On analytic HPLC (ChiralPak IA Column: 4.6×250 mm, 5 µm; Mobile Phase: 10% Ethanol-90% Hexanex; Flow Rate: 1 mL/min), the first enantiomer has retention time of 6.38 minutes and the second peak has retention time of 6.99 minutes.

Step 2. 7-(1-aminoethyl)-6-(3-fluorophenyl)-3-methyl-5H-[1,3]thiazolo[3,2-a]pyrimidin-5-one

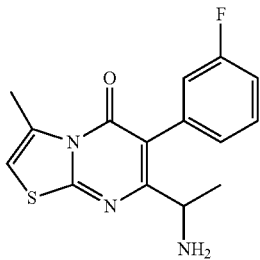 [SMILES: Cc1csc2nc(C(C)N)c(-c3cccc(F)c3)c(=O)n12]

To a stirred solution of 7-(1-azidoethyl)-6-(3-fluorophenyl)-3-methyl-5H-[1,3]thiazolo[3,2-a]pyrimidin-5-one (0.14 g, 0.42 mmol) (1st peak from chiral separation) in tetrahydrofuran (3 mL) and water (0.5 mL) was added 1.00 M of trimethylphosphine in tetrahydrofuran (0.52 mL, 0.52 mmol), and the mixture was stirred at room temperature for 1 hour. To the mixtures were added ethyl acetate and the mixtures were extracted with aqueous 1 N HCl solution (three times). The combined extracts were neutralized with solid $NaHCO_3$, and extracted with dichloromethane (three times). The combined organic layers were washed with brine, dried over $MgSO_4$, and concentrated to give the crude product (0.125 g) used directly in next step. LCMS calculated for $C_{15}H_{15}FN_3OS(M+H)^+$: m/z=304.1. Found: 304.0.

Step 3. 6-(3-fluorophenyl)-3-methyl-7-[1-(9H-purin-6-ylamino)ethyl]-5H-[1,3]thiazolo[3,2-a]pyrimidin-5-one

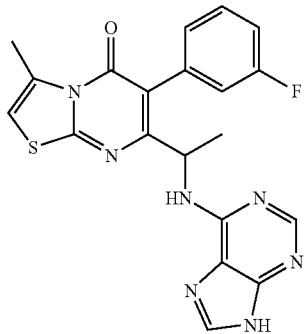 [SMILES: Cc1csc2nc(C(C)Nc3ncnc4[nH]cnc34)c(-c3cccc(F)c3)c(=O)n12]

A mixture of single enantiomer 7-(1-aminoethyl)-6-(3-fluorophenyl)-3-methyl-5H-[1,3]thiazolo[3,2-a]pyrimidin-5-one (0.125 g, 0.412 mmol) made from above, 6-bromo-9H-purine (0.148 g, 0.742 mmol), and N,N-diisopropylethylamine (0.144 mL, 0.824 mmol) in ethanol (1.5 mL) was heated at 110° C. overnight. The mixture was filtered, and the filtrate was purified on preparative-LCMS (XBridge C18 Column, eluting with a gradient of acetonitrile/water containing 0.15% $NH_4OH$) to give the desired product (0.076 g, 44%). LCMS calculated for $C_{20}H_{17}FN_7OS(M+H)^+$: m/z=422.1. Found: 422.0. $^1H$ NMR (DMSO-$d_6$, 500 MHz) δ 8.05 (2H, s), 7.43 (1H, m), 7.24~7.14 (5H, m), 6.99 (1H, s), 5.08 (1H, m), 2.59 (3H, s), 1.29 (3H, d, J=6.5 Hz) ppm. 19F NMR (DMSO-$d_6$, 376.3 MHz) δ−114 ppm.

Example 31. 3-methyl-6-(4-methylphenyl)-7-[1-(9H-purin-6-ylamino)ethyl]-5H-[1,3]thiazolo[3,2-a]pyrimidin-5-one trifluoroacetic acid salt

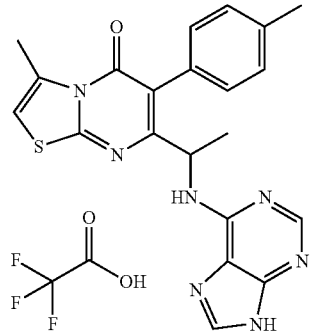 [SMILES: Cc1ccc(-c2c(C(C)Nc3ncnc4[nH]cnc34)nc3scc(C)n3c2=O)cc1 ; O=C(O)C(F)(F)F]

Step 1. 7-(1-azidoethyl)-3-methyl-6-(4-methylphenyl)-5H-[1,3]thiazolo[3,2-a]pyrimidin-5-one

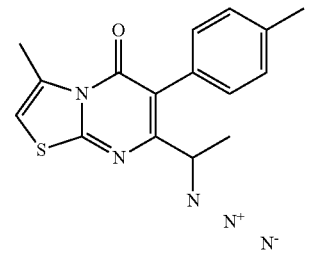

To a mixture of 7-(1-azidoethyl)-6-bromo-3-methyl-5H-[1,3]thiazolo[3,2-a]pyrimidin-5-one (0.080 g, 0.25 mmol) and (4-methylphenyl)boronic acid (0.042 g, 0.31 mmol) in 1,4-dioxane (2 mL) was added 1 N solution of sodium carbonate in water (0.38 mL, 0.38 mmol) and dichloro (bis{di-tert-butyl[4-(dimethylamino)phenyl]phosphoranyl})palladium (0.011 g, 0.015 mmol). The mixture was heated at 100° C. overnight. After cooling to room temperature, the mixture was diluted with ethyl acetate, washed with water, dried over $MgSO_4$, concentrated and then purified on silica gel (0-25% ethyl acetate/hexane) to give the desired product (50 mg). LCMS calculated for $C_{16}H_{16}N_5OS(M+H)^+$: m/z=326.1. Found: 326.0.

Step 2. 7-(1-aminoethyl)-3-methyl-6-(4-methylphenyl)-5H-[1,3]thiazolo[3,2-a]pyrimidin-5-one

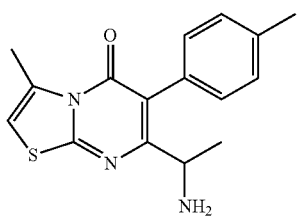 [SMILES: Cc1ccc(-c2c(C(C)N)nc3scc(C)n3c2=O)cc1]

To a solution of 7-(1-azidoethyl)-3-methyl-6-(4-methylphenyl)-5H-[1,3]thiazolo[3,2-a]pyrimidin-5-one (0.050 g, 0.15 mmol) in tetrahydrofuran (2 mL) was added 1.00 M of trimethylphosphine in tetrahydrofuran (0.23 mL, 0.23 mmol) and the mixture was stirred at room temperature for 1 hour. The mixture was concentrated to give the crude product (40 mg), which was used directly in next step. LCMS calculated for $C_{16}H_{18}N_3OS(M+H)^+$: m/z=300.1. Found: 300.1.

Step 3. 3-methyl-6-(4-methylphenyl)-7-[1-(9H-purin-6-ylamino)ethyl]-5H-[1,3]thiazolo[3,2-a]pyrimidin-5-one

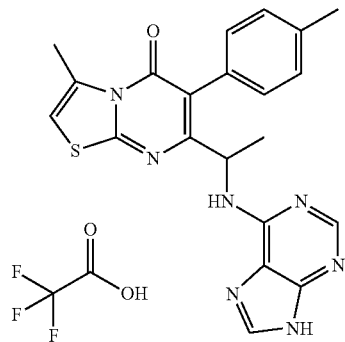 [SMILES: O=C(O)C(F)(F)F ; Cc1ccc(-c2c(C(C)Nc3ncnc4[nH]cnc34)nc3scc(C)n3c2=O)cc1]

A mixture of 7-(1-aminoethyl)-3-methyl-6-(4-methylphenyl)-5H-[1,3]thiazolo[3,2-a]pyrimidin-5-one (0.040 g, 0.13 mmol), 6-bromo-9H-purine (0.040 g, 0.20 mmol), and N,N-diisopropylethylamine (0.046 mL, 0.27 mmol) in ethanol (0.3 mL) was heated at 110° C. overnight. The mixture was filtered and the filtrate was purified on preparative-LCMS (XBridge C18 Column, eluting with a gradient of acetonitrile/water containing 0.05% TFA), to give the desired product as a TFA salt. LCMS calculated for $C_{21}H_{20}N_7OS$ $(M+H)^+$: m/z=418.1. Found: 418.1. $^1H$ NMR (DMSO-$d_6$, 400 MHz) δ 8.57 (1H, br s), 8.39 (1H, s), 8.38 (1H, s), 7.19 (4H, s), 7.02 (1H, d, J=1.2 Hz), 5.17 (1H, m), 2.59 (3H, s), 2.30 (3H, s), 1.32 (3H, d, J=6.8 Hz) ppm.

Example 32. 7-{1-[(2-amino-9H-purin-6-yl)amino]ethyl}-6-(3-chlorophenyl)-3-methyl-5H-[1,3]thiazolo[3,2-a]pyrimidin-5-one trifluoroacetic acid salt

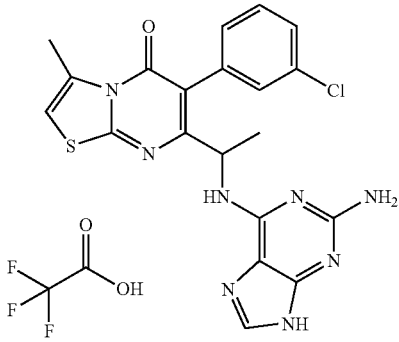 [SMILES: O=C(O)C(F)(F)F ; Cc1csc2nc(C(C)Nc3nc(N)nc4[nH]cnc34)c(-c3cccc(Cl)c3)c(=O)n12]

Step 1. 7-(1-azidoethyl)-6-(3-chlorophenyl)-3-methyl-5H-[1,3]thiazolo[3,2-a]pyrimidin-5-one

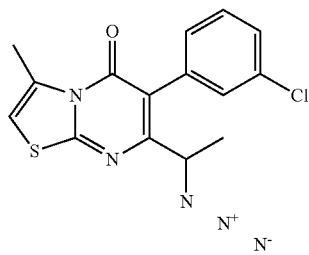

To a mixture of 7-(1-azidoethyl)-6-bromo-3-methyl-5H-[1,3]thiazolo[3,2-a]pyrimidin-5-one (0.12 g, 0.38 mmol) and (3-chlorophenyl)boronic acid (0.072 g, 0.46 mmol) in 1,4-dioxane (3 mL) was added a 1 N solution of sodium carbonate in water (0.5 mL, 0.5 mmol) and tetrakis(triphenylphosphine)palladium(0) (0.022 g, 0.019 mmol). The mixture was stirred at 100° C. overnight. After cooling, the mixture was diluted with ethyl acetate, washed with water, dried over $Na_2SO_4$, concentrated, and purified on silica gel (0-30% ethyl acetate/hexanes) to give the desired product. LCMS calculated for $C_{15}H_{13}ClN_5OS(M+H)^+$: m/z=346.1. Found: 346.0.

Step 2. 7-(1-aminoethyl)-6-(3-chlorophenyl)-3-methyl-5H-[1,3]thiazolo[3,2-a]pyrimidin-5-one

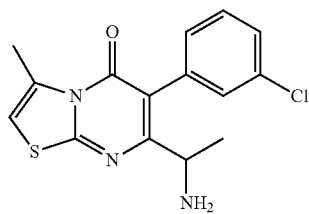 [SMILES: Cc1csc2nc(C(C)N)c(-c3cccc(Cl)c3)c(=O)n12]

To a stirred solution of 7-(1-azidoethyl)-6-(3-chlorophenyl)-3-methyl-5H-[1,3]thiazolo[3,2-a]pyrimidin-5-one (0.10 g, 0.29 mmol) in tetrahydrofuran (3 mL, 40 mmol) was added 1.00 M of trimethylphosphine in tetrahydrofuran (0.35 mL, 0.35 mmol), and the mixture was stirred at room temperature for 1 hour. The mixture was concentrated to give the crude product (0.090 g), which was used directly in next step. LCMS calculated for $C_{15}H_{15}ClN_3OS(M+H)^+$: m/z=320.1. Found: 320.0.

Step 3. 7-{1-[(2-amino-9H-purin-6-yl)amino]ethyl}-6-(3-chlorophenyl)-3-methyl-5H-[1,3]thiazolo[3,2-a]pyrimidin-5-one trifluoroacetic acid salt

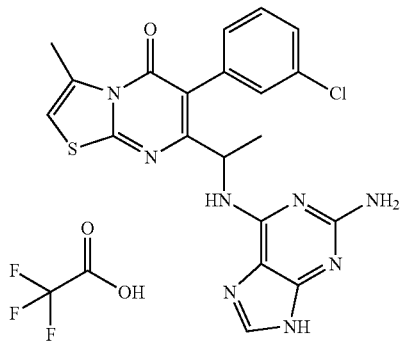 [SMILES: O=C(O)C(F)(F)F ; Cc1csc2nc(C(C)Nc3nc(N)nc4[nH]cnc34)c(-c3cccc(Cl)c3)c(=O)n12]

A mixture of 7-(1-aminoethyl)-6-(3-chlorophenyl)-3-methyl-5H-[1,3]thiazolo[3,2-a]pyrimidin-5-one (0.045 g, 0.14 mmol), 2-amino-6-bromopurine (0.060 g, 0.28 mmol), and N,N-diisopropylethylamine (0.049 mL, 0.28 mmol) in ethanol (0.5 mL) was heated at 110° C. overnight. The mixture was filtered and the filtrate was purified on preparative-LCMS (XBridge C18 Column, eluting with a gradient of acetonitrile/water containing 0.05% TFA) to give the desired product as a TFA salt. LCMS calculated for $C_{20}H_{18}ClN_8OS(M+H)^+$: m/z=453.1. Found: 453.1. $^1H$ NMR (DMSO-$d_6$, 400 MHz) δ 8.13 (1H, s), 7.48-7.12 (8H, s), 6.55 (1H, br s), 5.14 (1H, m), 1.33 (3H, d, J=6.8 Hz) ppm.

Example 33. 7-{1-[(2-amino-9H-purin-6-yl)amino]ethyl}-6-(2-fluorophenyl)-3-methyl-5H-[1,3]thiazolo[3,2-a]pyrimidin-5-one trifluoroacetic acid salt

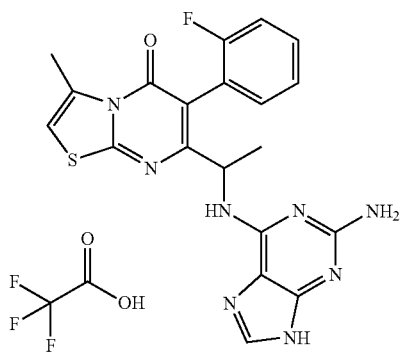 [SMILES: O=C(O)C(F)(F)F ; Cc1csc2nc(C(C)Nc3nc(N)nc4[nH]cnc34)c(-c3ccccc3F)c(=O)n12]

Step 1. 7-(1-azidoethyl)-6-(2-fluorophenyl)-3-methyl-5H-[1,3]thiazolo[3,2-a]pyrimidin-5-one

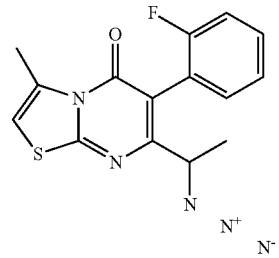

To a mixture of 7-(1-azidoethyl)-6-bromo-3-methyl-5H-[1,3]thiazolo[3,2-a]pyrimidin-5-one (0.12 g, 0.38 mmol) and (2-fluorophenyl)boronic acid (0.064 g, 0.46 mmol) in 1,4-dioxane (4 mL) was added a 1 N solution of sodium carbonate in water (0.8 mL, 0.8 mmol) and dichloro(bis{di-tert-butyl[4-(dimethylamino)phenyl]phosphoranyl})palladium (0.014 g, 0.019 mmol). The mixture was stirred at 100° C. overnight. After cooling, the mixture was diluted with ethyl acetate, washed with water, dried over $Na_2SO_4$, concentrated, and purified on silica gel (0-35% ethyl acetate/hexane) to give the desired product (87 mg). LCMS calculated for $C_{15}H_{13}FN_5OS(M+H)^+$: m/z=330.1. Found: 330.0.

Step 2. 7-(1-aminoethyl)-6-(2-fluorophenyl)-3-methyl-5H-[1,3]thiazolo[3,2-a]pyrimidin-5-one

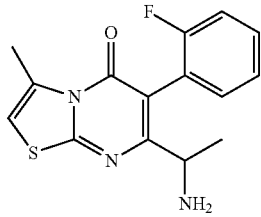

To a stirred solution of 7-(1-azidoethyl)-6-(2-fluorophenyl)-3-methyl-5H-[1,3]thiazolo[3,2-a]pyrimidin-5-one (0.087 g, 0.26 mmol) in tetrahydrofuran (3 mL) was added 1.00 M of trimethylphosphine in tetrahydrofuran (0.32 mL, 0.32 mmol), and the mixture was stirred at room temperature for 1 hour. The mixture was concentrated to give the crude product (0.080 g), which was used directly in next step. LCMS calculated for $C_{15}H_{15}FN_3OS(M+H)^+$: m/z=304.1. Found: 304.0.

Step 3. 7-{1-[(2-amino-9H-purin-6-yl)amino]ethyl}-6-(2-fluorophenyl)-3-methyl-5H-[1,3]thiazolo[3,2-a]pyrimidin-5-one trifluoroacetic acid salt

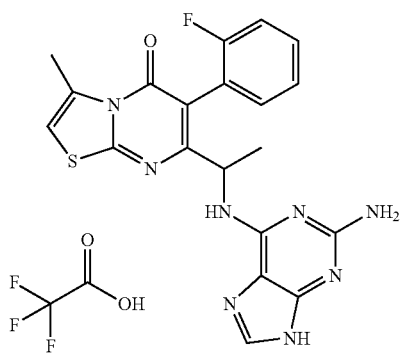 [SMILES: O=C(O)C(F)(F)F ; Cc1csc2nc(C(C)Nc3nc(N)nc4[nH]cnc34)c(-c3ccccc3F)c(=O)n12]

A mixture of 7-(1-aminoethyl)-6-(2-fluorophenyl)-3-methyl-5H-[1,3]thiazolo[3,2-a]pyrimidin-5-one (0.040 g, 0.13 mmol), 2-amino-6-bromopurine (0.056 g, 0.26 mmol), and N,N-diisopropylethylamine (0.046 mL, 0.26 mmol) in ethanol (0.5 mL) was heated at 110° C. overnight. The mixture was filtered, and the filtrate was purified on preparative-LCMS (XBridge C18 Column, eluting with a gradient of acetonitrile/water containing 0.05% TFA) to give the desired product as a diastereoisomeric mixture (TFA salts). LCMS calculated for $C_{20}H_{18}FN_8OS(M+H)^+$: m/z=437.1. Found: 437.1. $^1H$ NMR (DMSO-$d_6$, 400 MHz) δ 8.77 (1H, br s), 8.14 (1H, m), 7.45 (2H, m), 7.28 (4H, m), 7.14 (1H, m), 5.13 (1H, m), 2.65 (3H, s), 1.42 (1.5H, d, J=6.8 Hz), 1.28 (1.5H, d, J=6.8 Hz) ppm. $^{19}F$ NMR (DMSO-$d_6$, 376.3 MHz) δ −113.8, −114 ppm.

Example 34. 7-{1-[(2-amino-9H-purin-6-yl)amino]ethyl}-6-(2,3-difluorophenyl)-3-methyl-5H-[1,3]thiazolo[3,2-a]pyrimidin-5-one trifluoroacetic acid salt

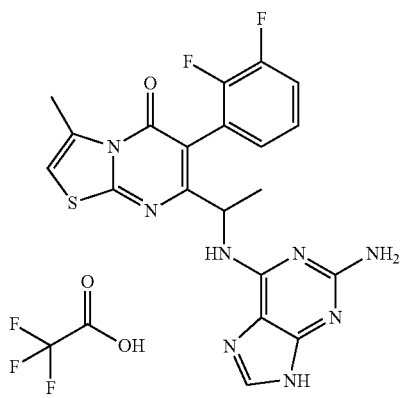 [SMILES: O=C(O)C(F)(F)F ; Cc1csc2nc(C(C)Nc3nc(N)nc4[nH]cnc34)c(-c3cccc(F)c3F)c(=O)n12]

Step 1. 7-(1-azidoethyl)-6-(2,3-difluorophenyl)-3-methyl-5H-[1,3]thiazolo[3,2-a]pyrimidin-5-one

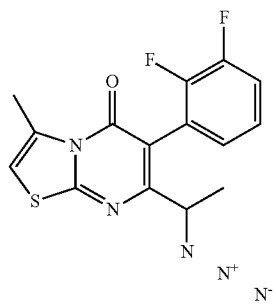

To a mixture of 7-(1-azidoethyl)-6-bromo-3-methyl-5H-[1,3]thiazolo[3,2-a]pyrimidin-5-one (0.12 g, 0.38 mmol) and (2,3-difluorophenyl)boronic acid (0.072 g, 0.46 mmol) in 1,4-dioxane (3 mL) was added a 1 N solution of sodium carbonate in water (0.57 mL, 0.57 mmol) and dichloro(bis{di-tert-butyl[4-(dimethylamino)phenyl]phosphoranyl})palladium (0.014 g, 0.019 mmol). The mixture was stirred at 100° C. overnight. After cooling, the mixture was diluted with ethyl acetate, washed with water, dried over $Na_2SO_4$, concentrated, and purified on silica gel (0-30% ethyl acetate/hexane) to give the desired product (83 mg). LCMS calculated for $C_{15}H_{12}F_2N_5OS(M+H)^+$: m/z=348.1. Found: 348.0.

Step 2. 7-(1-aminoethyl)-6-(2,3-difluorophenyl)-3-methyl-5H-[1,3]thiazolo[3,2-a]pyrimidin-5-one To a solution of 7-(1-azidoethyl)-6-(2,3-difluorophenyl)-3-methyl-5H-[1,3]thiazolo[3,2-a]pyrimidin-5-one (0.083 g, 0.24 mmol) in tetrahydrofuran (3 mL) was added 1.00 M of trimethylphosphine in tetrahydrofuran (0.29 mL, 0.29 mmol), and the mixture was stirred at room temperature for 1 hour. The mixture was concentrated to give the crude product (0.076 g), which was used directly in next step. LCMS calculated for $C_{15}H_{14}F_2N_3OS(M+H)^+$: m/z=322.1. Found: 322.0.

Step 3. 7-{1-[(2-amino-9H-purin-6-yl)amino]ethyl}-6-(2,3-difluorophenyl)-3-methyl-5H-[1,3]thiazolo[3,2-a]pyrimidin-5-one trifluoroacetic acid salt Step 1. 7-(1-azidoethyl)-6-(3-chloro-5-fluorophenyl)-3-methyl-5H-[1,3]thiazolo[3,2-a]pyrimidin-5-one

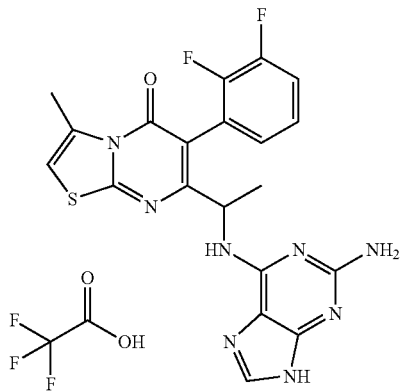 [SMILES: O=C(O)C(F)(F)F ; Cc1csc2nc(C(C)Nc3nc(N)nc4[nH]cnc34)c(-c3cccc(F)c3F)c(=O)n12]

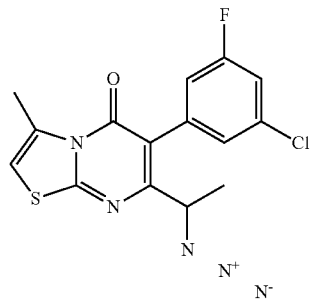

To a mixture of 7-(1-azidoethyl)-6-bromo-3-methyl-5H-[1,3]thiazolo[3,2-a]pyrimidin-5-one (0.12 g, 0.38 mmol) and (3-chloro-5-fluorophenyl)boronic acid (0.080 g, 0.46 mmol) in 1,4-dioxane (3 mL) was added a 1 N solution of sodium carbonate in water (0.5 mL, 0.5 mmol) and tetrakis(triphenylphosphine)palladium(0) (0.022 g, 0.019 mmol). The mixture was heated at 100° C. overnight. After cooling, the mixture was diluted with ethyl acetate, washed with water, dried over $Na_2SO_4$, concentrated and purified on silica gel (0-25% ethyl acetate/hexanes) to give the desired product (0.077 g, 55%). LCMS calculated for $C_{15}H_{12}ClFN_5OS(M+H)^+$: m/z=364.0. Found: 364.0.

A mixture of 7-(1-aminoethyl)-6-(2,3-difluorophenyl)-3-methyl-5H-[1,3]thiazolo[3,2-a]pyrimidin-5-one (0.038 g, 0.12 mmol), 2-amino-6-bromopurine (0.051 g, 0.24 mmol), and N,N-diisopropylethylamine (0.041 mL, 0.24 mmol) in ethanol (0.5 mL) was heated at 110° C. overnight. The mixture was filtered and the filtrate was purified on preparative-LCMS (XBridge C18 Column, eluting with a gradient of acetonitrile/water containing 0.05% TFA) to give the desired product as a mixture of two diastereomers (TFA salt). LCMS calculated for $C_{20}H_{17}F_2N_8OS(M+H)^+$: m/z=455.1. Found: 455.1. $^1$H NMR (DMSO-$d_6$, 400 MHz) δ 8.12 (1H, d, J=9.6 Hz), 7.45 (1H, m), 7.30~7.23 (3H, m), 7.18~7.11 (3H, m), 6.56 (1H, s), 5.16 (1H, m), 2.66 (3H, s), 1.44 (1.5H, d, J=6.8 Hz), 1.30 (1.5H, d, J=6.8 Hz) ppm.

Step 2. 7-(1-aminoethyl)-6-(3-chloro-5-fluorophenyl)-3-methyl-5H-[1,3]thiazolo[3,2-a]pyrimidin-5-one Example 35. 7-{1-[(2-amino-9H-purin-6-yl)amino]ethyl}-6-(3-chloro-5-fluorophenyl)-3-methyl-5H-[1,3]thiazolo[3,2-a]pyrimidin-5-one trifluoroacetic acid salt

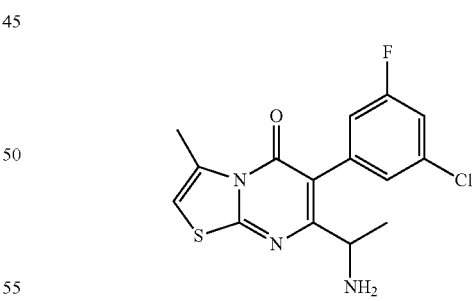

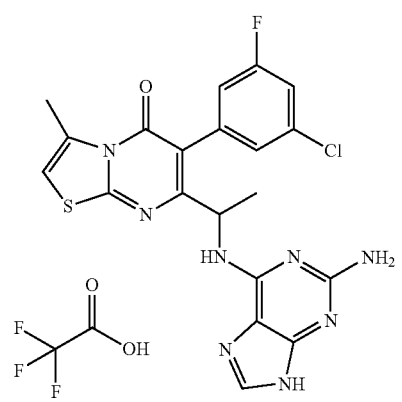 [SMILES: O=C(O)C(F)(F)F ; Cc1csc2nc(C(C)Nc3nc(N)nc4[nH]cnc34)c(-c3cc(F)cc(Cl)c3)c(=O)n12]

To a stirred solution of 7-(1-azidoethyl)-6-(3-chloro-5-fluorophenyl)-3-methyl-5H-[1,3]thiazolo[3,2-a]pyrimidin-5-one (0.077 g, 0.21 mmol) in tetrahydrofuran (3 mL) was added 1.00 M of trimethylphosphine in tetrahydrofuran (0.25 mL, 0.25 mmol) and the mixture was stirred at room temperature for 1 hour. The mixture was concentrated to give crude product (0.070 g), which was used directly in the next step. LCMS calculated for $C_{15}H_{14}ClFN_3OS(M+H)^+$: m/z=338.1. Found: 338.0.

Step 3. 7-{1-[(2-amino-9H-purin-6-yl)amino]ethyl}-6-(3-chloro-5-fluorophenyl)-3-methyl-5H-[1,3]thiazolo[3,2-a]pyrimidin-5-one trifluoroacetic acid salt

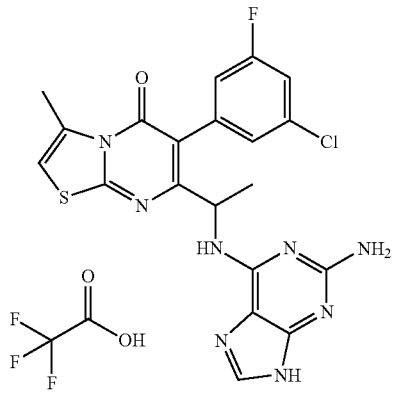

A mixture of 7-(1-aminoethyl)-6-(3-chloro-5-fluorophenyl)-3-methyl-5H-[1,3]thiazolo[3,2-a]pyrimidin-5-one (0.035 g, 0.10 mmol), 2-amino-6-bromopurine (0.058 g, 0.27 mmol), and N,N-diisopropylethylamine (0.047 mL, 0.27 mmol) in ethanol (0.5 mL) was heated at 110° C. overnight. The mixture was filtered, and the filtrate was purified on preparative-LCMS (XBridge C18 Column, eluting with a gradient of acetonitrile/water containing 0.05% TFA) to give the desired product as a TFA salt. LCMS calculated for $C_{20}H_{17}ClFN_8OS(M+H)^+$: m/z=471.1. Found: 471.0. $^1$H NMR (DMSO-$d_6$, 400 MHz) δ 8.79 (1H, d, J=7.2 Hz), 8.16 (1H, s), 7.39 (3H, m), 7.21 (2H, s), 7.18 (1H, m), 7.14 (1H, d, J=1.2 Hz), 5.13 (1H, m), 2.65 (3H, s), 1.37 (3H, d, J=6.8 Hz) ppm. 19F NMR (DMSO-$d_6$, 376.3 MHz) δ −112 ppm.

Example 36. 6-(3-chlorophenyl)-3-methyl-7-[1-(9H-purin-6-ylamino)ethyl]-5H-[1,3]thiazolo[3,2-a]pyrimidin-5-one trifluoroacetic acid salt

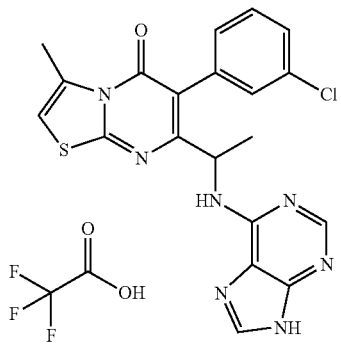 [SMILES: O=C(O)C(F)(F)F ; Cc1csc2nc(C(C)Nc3ncnc4[nH]cnc34)c(-c3cccc(Cl)c3)c(=O)n12]

A mixture of 7-(1-aminoethyl)-6-(3-chlorophenyl)-3-methyl-5H-[1,3]thiazolo[3,2-a]pyrimidin-5-one (0.045 g, 0.14 mmol), 6-bromo-9H-purine (0.056 g, 0.28 mmol), and N,N-diisopropylethylamine (0.049 mL, 0.28 mmol) in ethanol (0.5 mL) was heated at 110° C. overnight. The mixture was filtered and the filtrate was purified on preparative-LCMS (XBridge C18 Column, eluting with a gradient of acetonitrile/water containing 0.05% TFA), to give the desired product as a TFA salt. LCMS calculated for $C_{20}H_{17}ClN_7OS(M+H)^+$: m/z=438.1. Found: 438.0. $^1$H NMR (DMSO-$d_6$, 400 MHz) δ 8.29 (1H, s), 7.46 (3H, m), 7.37 (1H, m), 7.08 (1H, s), 5.14 (1H, m), 2.64 (3H, s), 1.37 (3H, d, J=6.8 Hz) ppm.

Example 37. 6-(3-chloro-5-fluorophenyl)-3-methyl-7-[1-(9H-purin-6-ylamino)ethyl]-5H-[1,3]thiazolo[3,2-a]pyrimidin-5-one trifluoroacetic acid salt

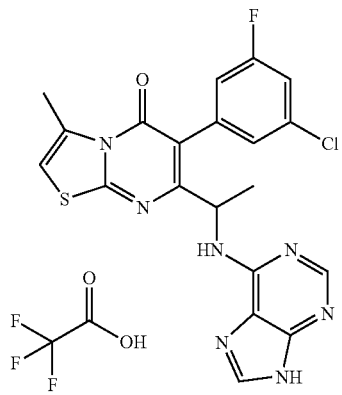 [SMILES: O=C(O)C(F)(F)F ; Cc1csc2nc(C(C)Nc3ncnc4[nH]cnc34)c(-c3cc(F)cc(Cl)c3)c(=O)n12]

A mixture of 7-(1-aminoethyl)-6-(3-chloro-5-fluorophenyl)-3-methyl-5H-[1,3]thiazolo[3,2-a]pyrimidin-5-one (0.035 g, 0.10 mmol), 6-bromo-9H-purine (0.041 g, 0.21 mmol), and N,N-diisopropylethylamine (0.036 mL, 0.21 mmol) in ethanol (0.5 mL) was heated at 110° C. overnight. The mixture was filtered, and the filtrate was purified on preparative-LCMS (XBridge C18 Column, eluting with a gradient of acetonitrile/water containing 0.05% TFA) to give the desired product as a TFA salt. LCMS calculated for $C_{20}H_{16}ClFN_7OS(M+H)^+$: m/z=456.1. Found: 456.0. $^1$H NMR (DMSO-$d_6$, 400 MHz) δ 8.52 (1H, br s), 8.39 (1H, s), 8.36 (1H, s), 7.43 (1H, d, J=8.0 Hz), 7.33~7.27 (3H, m), 7.10 (1H, s), 5.15 (1H, m), 2.64 (3H, s), 1.41 (3H, d, J=6.8 Hz) ppm. $^{19}$F NMR (DMSO-$d_6$, 376.3 MHz) δ −112 ppm.

Example 38. 7-{1-[(2-amino-9H-purin-6-yl)amino]ethyl}-6-(5-fluoropyridin-3-yl)-3-methyl-5H-[1,3]thiazolo[3,2-a]pyrimidin-5-one trifluoroacetic acid salt

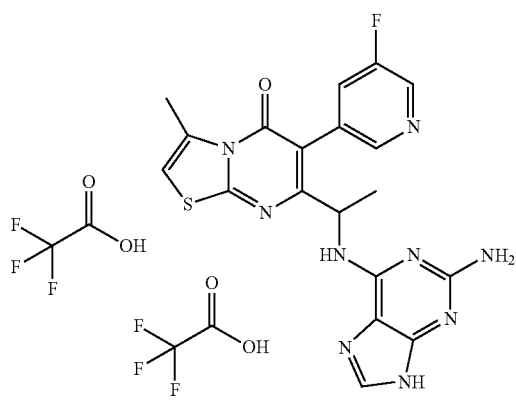 [SMILES: O=C(O)C(F)(F)F ; O=C(O)C(F)(F)F ; Cc1csc2nc(C(C)Nc3nc(N)nc4[nH]cnc34)c(-c3cncc(F)c3)c(=O)n12]

Step 1. 7-(1-azidoethyl)-6-(5-fluoropyridin-3-yl)-3-methyl-5H-[1,3]thiazolo[3,2-a]pyrimidin-5-one

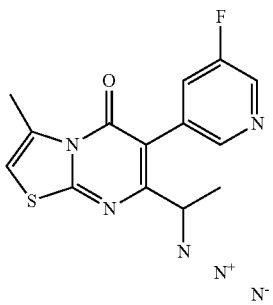

To a mixture of 7-(1-azidoethyl)-6-bromo-3-methyl-5H-[1,3]thiazolo[3,2-a]pyrimidin-5-one (0.12 g, 0.38 mmol) and 3-fluoro-5-(4,4,5,5-tetramethyl-1,3,2-dioxaborolan-2-yl)pyridine (0.10 g, 0.46 mmol) in 1,4-dioxane (3 mL) was added a 1 N solution of sodium carbonate in water (0.57 mL, 0.57 mmol) and dichloro(bis{di-tert-butyl[4-(dimethylamino)phenyl]phosphoranyl})palladium (0.014 g, 0.020 mmol). The mixture was heated at 100° C. overnight. After cooling, the mixture was diluted with ethyl acetate, washed with water, dried over Na$_2$SO$_4$, concentrated and purified on silica gel (0-45% ethyl acetate/hexanes) to give the desired product (0.020 g, 16%). LCMS calculated for C$_{14}$H$_{12}$FN$_{16}$OS(M+H)$^+$: m/z=331.1. Found: 331.0.

Step 2. 7-(1-aminoethyl)-6-(5-fluoropyridin-3-yl)-3-methyl-5H-[1,3]thiazolo[3,2-a]pyrimidin-5-one

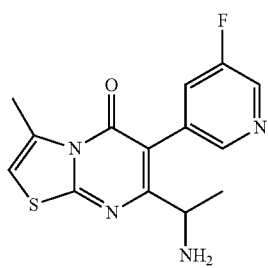 [SMILES: Cc1csc2nc(C(C)N)c(-c3cncc(F)c3)c(=O)n12]

To a solution of 7-(1-azidoethyl)-6-(5-fluoropyridin-3-yl)-3-methyl-5H-[1,3]thiazolo[3,2-a]pyrimidin-5-one (0.020 g, 0.060 mmol) in tetrahydrofuran (3 mL) was added 1.00 M of trimethylphosphine in tetrahydrofuran (0.079 mL, 0.079 mmol), and the mixture was stirred at room temperature for 1 hour. The mixture was concentrated to give the crude product (0.018 g), which was used directly in next step. LCMS calculated for C$_{14}$H$_{14}$FN$_4$OS(M+H)$^+$: m/z=305.1. Found: 305.0.

Step 3. 7-{1-[(2-amino-9H-purin-6-yl)amino]ethyl}-6-(5-fluoropyridin-3-yl)-3-methyl-5H-[1,3]thiazolo[3,2-a]pyrimidin-5-one trifluoroacetic acid salt

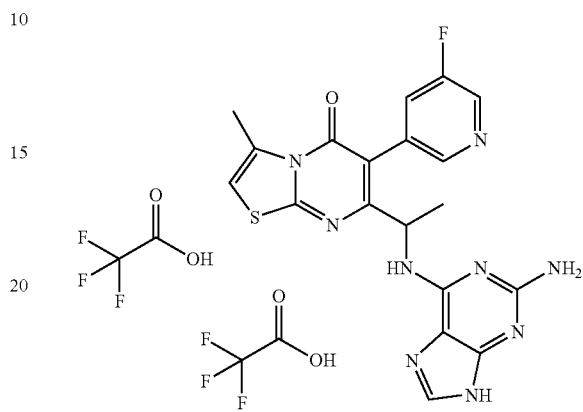

A mixture of 7-(1-aminoethyl)-6-(5-fluoropyridin-3-yl)-3-methyl-5H-[1,3]thiazolo[3,2-a]pyrimidin-5-one (9 mg, 0.03 mmol), 2-amino-6-bromopurine (9.5 mg, 0.044 mmol) and N,N-diisopropylethylamine (0.010 mL, 0.059 mmol) in ethanol (0.3 mL) was heated at 110° C. overnight. The mixture was filtered, and the filtrate was purified on prep-LCMS (XBridge C18 Column, eluting with a gradient of acetonitrile/water containing 0.05% TFA) to give the desired product as a TFA salt. LCMS calculated for C$_{19}$H$_{17}$FN$_9$OS (M+H)$^+$: m/z=438.1. Found: 438.0. $^1$H NMR (DMSO-d$_6$, 400 MHz) δ 8.82 (1H, br s), 8.59 (1H, d, J=2.8 Hz), 8.42 (1H, s), 8.16 (1H, s), 7.77 (1H, dt, J=9.6 and 2.4 Hz), 7.22-7.16 (4H, m), 5.08 (1H, m), 2.66 (3H, s), 1.37 (3H, d, J=6.8 Hz) ppm. $^{19}$F NMR (DMSO-d$_6$, 376.3 MHz) δ-128 ppm.

Example 39. 7-{1-[(2-amino-9H-purin-6-yl)amino]ethyl}-6-(2-chlorophenyl)-3-methyl-5H-[1,3]thiazolo[3,2-a]pyrimidin-5-one trifluoroacetic acid salt

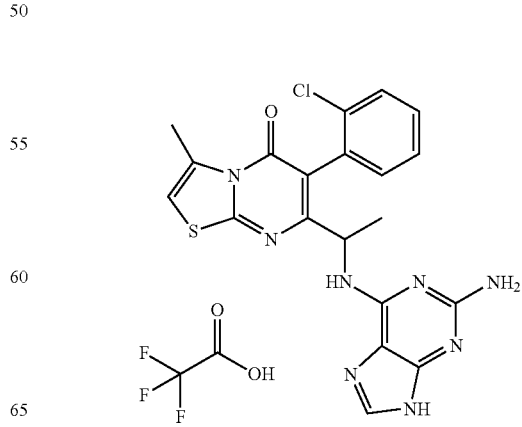

Step 1. 7-(1-azidoethyl)-6-(2-chlorophenyl)-3-methyl-5H-[1,3]thiazolo[3,2-a]pyrimidin-5-one

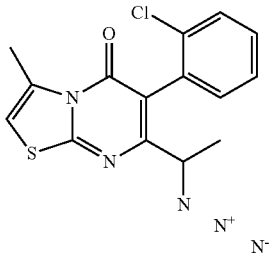

To a mixture of 7-(1-azidoethyl)-6-bromo-3-methyl-5H-[1,3]thiazolo[3,2-a]pyrimidin-5-one (0.12 g, 0.38 mmol) and (2-chlorophenyl)boronic acid (0.072 g, 0.46 mmol) in 1,4-dioxane (3 mL) was added a 1 N solution of sodium carbonate in water (0.57 mL, 0.57 mmol) and dichloro(bis{di-tert-butyl[4-(dimethylamino)phenyl]phosphoranyl})palladium (0.014 g, 0.019 mmol). The mixture was stirred at 105° C. overnight. After cooling, the mixture was diluted with ethyl acetate, washed with water, dried over $Na_2SO_4$, concentrated, and purified on silica gel (0-30% ethyl acetate/hexanes) to give the desired product (0.062 g). LCMS calculated for $C_{15}H_{13}ClN_5OS$ $(M+H)^+$: m/z=346.1. Found: 346.0.

Step 2. 7-(1-aminoethyl)-6-(2-chlorophenyl)-3-methyl-5H-[1,3]thiazolo[3,2-a]pyrimidin-5-one

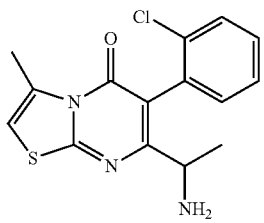 [SMILES: Cc1csc2nc(C(C)N)c(-c3ccccc3Cl)c(=O)n12]

To a stirred solution of 7-(1-azidoethyl)-6-(2-chlorophenyl)-3-methyl-5H-[1,3]thiazolo[3,2-a]pyrimidin-5-one (0.062 g, 0.18 mmol) in tetrahydrofuran (3 mL) was added 1.00 M of trimethylphosphine in tetrahydrofuran (0.22 mL, 0.22 mmol), and the mixture was stirred at room temperature for 1 hour. The mixture was concentrated to give the crude product (0.056 g), which was used directly in next step. $C_{15}H_{15}ClN_3OS(M+H)^+$: m/z=320.1. Found: 320.0.

Step 3. 7-{1-[(2-amino-9H-purin-6-yl)amino]ethyl}-6-(2-chlorophenyl)-3-methyl-5H-[1,3]thiazolo[3,2-a]pyrimidin-5-one trifluoroacetic acid salt

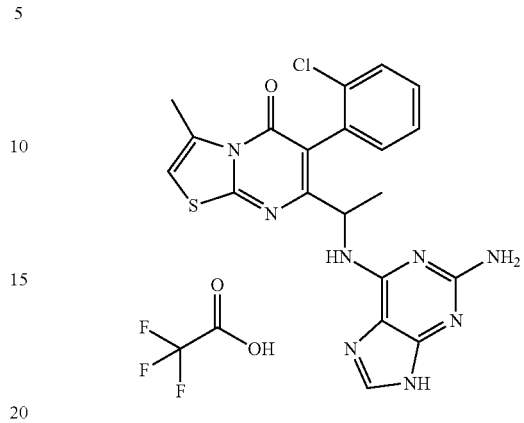

A mixture of 7-(1-aminoethyl)-6-(2-chlorophenyl)-3-methyl-5H-[1,3]thiazolo[3,2-a]pyrimidin-5-one (0.028 g, 0.088 mmol), 2-amino-6-bromopurine (0.037 g, 0.18 mmol), and N,N-diisopropylethylamine (0.030 mL, 0.18 mmol) in ethanol (0.4 mL) was heated at 110° C. overnight. The mixture was filtered and the filtrate was purified on preparative-LCMS (XBridge C18 Column, eluting with a gradient of acetonitrile/water containing 0.05% TFA) to give two diastereomers as a TFA salts. On analytic HPLC (Waters SunFire C18, 2.1×50 mm, 5 μM; injection volume 2 μL; flow rate 3 mL/min; at gradient from 2% to 80% acetonitile in water containing 0.15% $NH_4OH$ in 3 min): First peak has retention time 1.296 min; LCMS calculated for $C_{20}H_{18}ClN_8OS(M+H)^+$: m/z=453.1. Found: 453.0. Second peak has retention time 1.431 min; LCMS calculated for $C_{20}H_{18}ClN_8OS(M+H)^+$: m/z=453.1. Found: 453.0.

Example 40. 6-(2-fluorophenyl)-3-methyl-7-[1-(9H-purin-6-ylamino)ethyl]-5H-[1,3]thiazolo[3,2-a]pyrimidin-5-one trifluoroacetic acid salt

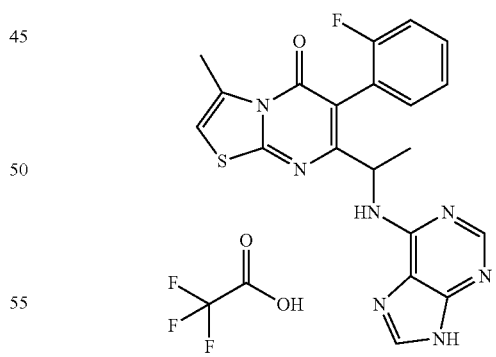

A mixture of 7-(1-aminoethyl)-6-(2-fluorophenyl)-3-methyl-5H-[1,3]thiazolo[3,2-a]pyrimidin-5-one (0.040 g, 0.13 mmol), 6-bromo-9H-purine (0.052 g, 0.26 mmol), and N,N-diisopropylethylamine (0.046 mL, 0.26 mmol) in ethanol (0.5 mL, 8 mmol) was heated at 110° C. overnight. The mixture was filtered, and the filtrate was purified on preparative-LCMS (XBridge C18 Column, eluting with a gradient of acetonitrile/water containing 0.05% TFA) to give the desired product as a diastereoisomeric mixture (TFA salt).

LCMS calculated for $C_{20}H_{17}FN_7OS(M+H)^+$: m/z=422.1. Found: 422.1. $^1$H NMR (DMSO-$d_6$, 400 MHz) δ 8.50 (1H, br s), 8.40 (1H, s), 8.38 (1H, s), 7.50 (1H, m), 7.36-7.25 (3H, m), 7.10 (1H, s), 5.14 (1H, m), 2.64 (3H, s), 1.48 (1.5H, d, J=6.8 Hz), 1.34 (1.5H, d, J=6.8 Hz) ppm. $^{19}$F NMR (DMSO-$d_6$, 376.3 MHz) δ–112, –114 ppm.

Example 41. 6-(2,3-difluorophenyl)-3-methyl-7-[1-(9H-purin-6-ylamino)ethyl]-5H-[1,3]thiazolo[3,2-a]pyrimidin-5-one trifluoroacetic acid salt

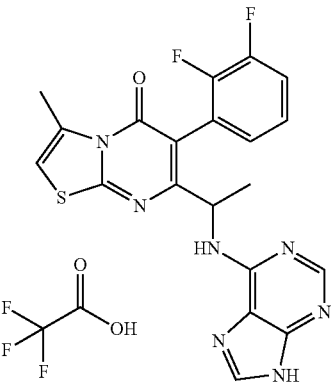 [SMILES: O=C(O)C(F)(F)F ; Cc1csc2nc(C(C)Nc3ncnc4[nH]cnc34)c(-c3cccc(F)c3F)c(=O)n12]

A mixture of 7-(1-aminoethyl)-6-(2,3-difluorophenyl)-3-methyl-5H-[1,3]thiazolo[3,2-a]pyrimidin-5-one (0.038 g, 0.12 mmol), 6-bromo-9H-purine (0.047 g, 0.24 mmol), and N,N-diisopropylethylamine (0.041 mL, 0.24 mmol) in ethanol (0.5 mL) was heated at 110° C. overnight. The mixture was filtered, and the filtrate was purified on prep-LCMS (XBridge C18 Column, eluting with a gradient of acetonitrile/water containing 0.05% TFA), to give the desired product as a mixture of two diastereomers (TFA salt). LCMS calculated for $C_{20}H_{16}F_2N_7OS(M+H)^+$: m/z=440.1. Found: 440.0. $^1$H NMR (DMSO-$d_6$, 400 MHz) δ 8.38~8.34 (3H, m), 7.49~7.10 (4H, m), 5.12 (1H, m), 2.64 (3H, s), 1.50 (1.5H, d, J=6.8 Hz), 1.36 (1.5H, d, J=6.8 Hz) ppm. $^{19}$F NMR (DMSO-$d_6$, 376.3 MHz) δ–137.8, –139.8, –140.0 ppm.

Example 42. 6-(5-fluoropyridin-3-yl)-3-methyl-7-[1-(9H-purin-6-ylamino)ethyl]-5H-[1,3]thiazolo[3,2-a]pyrimidin-5-one trifluoroacetic acid salt

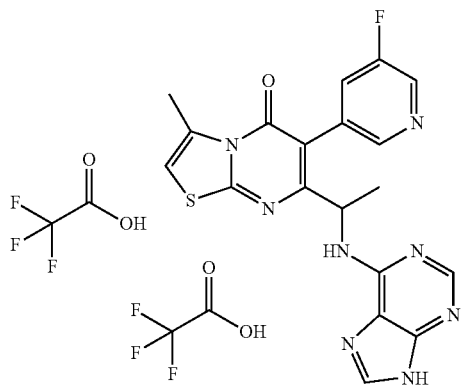 [SMILES: O=C(O)C(F)(F)F ; O=C(O)C(F)(F)F ; Cc1csc2nc(C(C)Nc3ncnc4[nH]cnc34)c(-c3cncc(F)c3)c(=O)n12]

A mixture of 7-(1-aminoethyl)-6-(5-fluoropyridin-3-yl)-3-methyl-5H-[1,3]thiazolo[3,2-a]pyrimidin-5-one (9 mg, 0.03 mmol), 6-bromo-9H-purine (8.8 mg, 0.044 mmol), and N,N-diisopropylethylamine (0.010 mL, 0.059 mmol) in ethanol (0.3 mL) was heated at 110° C. overnight. The mixture was filtered, and the filtrate was purified on preparative-LCMS (XBridge C18 Column, eluting with a gradient of acetonitrile/water containing 0.05% TFA), to give the desired product as a TFA salt. LCMS calculated for $C_{19}H_{16}FN_8OS(M+H)^+$: m/z=423.1. Found: 423.1. $^1$H NMR (DMSO-$d_6$, 400 MHz) δ 8.60 (1H, d, J=2.8 Hz), 8.47 (1H, s), 8.35 (1H, s), 8.33 (1H, s), 7.82 (1H, d, J=9.6 Hz), 7.12 (1H, s), 5.09 (1H, m), 2.64 (3H, s), 1.43 (3H, d, J=6.8 Hz) ppm. $^{19}$F NMR (DMSO-$d_6$, 376.3 MHz) δ–128 ppm.

Example 43. 6-(2-chlorophenyl)-3-methyl-7-[1-(9H-purin-6-ylamino)ethyl]-5H-[1,3]thiazolo[3,2-a]pyrimidin-5-one trifluoroacetic acid salt

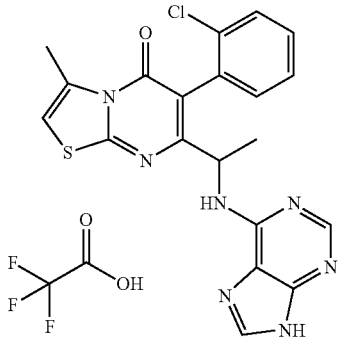 [SMILES: O=C(O)C(F)(F)F ; Cc1csc2nc(C(C)Nc3ncnc4[nH]cnc34)c(-c3ccccc3Cl)c(=O)n12]

A mixture of 7-(1-aminoethyl)-6-(2-chlorophenyl)-3-methyl-5H-[1,3]thiazolo[3,2-a]pyrimidin-5-one (0.028 g, 0.088 mmol), 6-bromo-9H-purine (0.035 g, 0.18 mmol), and N,N-diisopropylethylamine (0.030 mL, 0.18 mmol) in ethanol (0.4 mL) was heated at 110° C. overnight. The mixture was filtered, and the filtrate was purified on preparative-LCMS (XBridge C18 Column, eluting with a gradient of acetonitrile/water containing 0.05% TFA), to give two diastereomers as a TFA salts. On an analytic HPLC (Waters SunFire C18, 2.1×50 mm, 5 μM; injection volume 2 μL; flow rate 3 mL/min; at gradient from 2% to 80% acetonitrile in water containing 0.15% NH$_4$OH in 3 min): First peak has retention time 1.421 min; LCMS calculated for $C_{20}H_{17}ClN_7OS(M+H)^+$: m/z=438.1. Found: 438.0. Second peak has retention time 1.516 min; LCMS calculated for $C_{20}H_{17}ClN_7OS(M+H)^+$: m/z=438.1. Found: 438.0. $^1$H NMR (DMSO-$d_6$, 400 MHz) δ 8.36 (1H, s), 8.32 (1H, s), 7.57 (2H, m), 7.44 (2H, m), 7.11 (1H, s), 5.04 (1H, m), 2.64 (1H, s), 1.34 (3H, d, J=6.8 Hz) ppm.

Example 44. 6-(3,5-difluorophenyl)-3-methyl-7-[1-(9H-purin-6-ylamino)ethyl]-5H-[1,3]thiazolo[3,2-a]pyrimidin-5-one

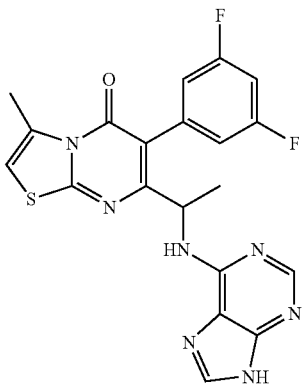 [SMILES: Cc1csc2nc(C(C)Nc3ncnc4[nH]cnc34)c(-c3cc(F)cc(F)c3)c(=O)n12]

A mixture of 7-(1-aminoethyl)-6-(3,5-difluorophenyl)-3-methyl-5H-[1,3]thiazolo[3,2-a]pyrimidin-5-one (0.105 g, 0.327 mmol) (1st peak from Example 23, step 1 chiral separation), 6-bromo-9H-purine (0.117 g, 0.588 mmol), and N,N-diisopropylethylamine (0.114 mL, 0.654 mmol) in ethanol (1.5 mL) was heated at 110° C. overnight. The mixture was filtered, and the filtrate was purified on preparative-LCMS (XBridge C18 Column, eluting with a gradient of acetonitrile/water containing 0.15% NH$_4$OH) to give the desired product (0.073 g, 51%). LCMS calculated for C$_{20}$H$_{16}$F$_2$N$_7$OS(M+H)$^+$: m/z=440.1. Found: 440.0. $^1$H NMR (DMSO-d$_6$, 500 MHz) δ 8.05 (2H, s), 7.34 (1H, br s), 7.18 (1H, m), 7.12 (2H, m), 6.84 (1H, s), 7.01 (1H, s), 5.07 (1H, m), 2.43 (3H, s), 1.31 (3H, d, J=7.0 Hz) ppm. $^{19}$F NMR (DMSO-d$_6$, 376.3 MHz) δ–111 ppm.

Example 45. 6-(2,5-difluorophenyl)-3-methyl-7-[1-(9H-purin-6-ylamino)ethyl]-5H-[1,3]thiazolo[3,2-a]pyrimidin-5-one trifluoroacetic acid salt

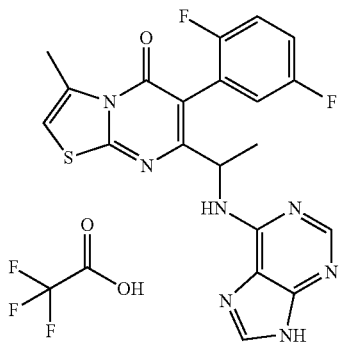 [SMILES: O=C(O)C(F)(F)F ; Cc1csc2nc(C(C)Nc3ncnc4[nH]cnc34)c(-c3cc(F)ccc3F)c(=O)n12]

Step 1. 7-(1-azidoethyl)-6-(2,5-difluorophenyl)-3-methyl-5H-[1,3]thiazolo[3,2-a]pyrimidin-5-one

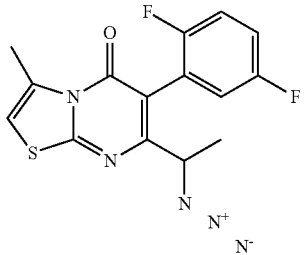

To a mixture of 7-(1-azidoethyl)-6-bromo-3-methyl-5H-[1,3]thiazolo[3,2-a]pyrimidin-5-one (0.080 g, 0.25 mmol) and (2,5-difluorophenyl)boronic acid (0.048 g, 0.30 mmol) in 1,4-dioxane (2 mL) was added a 1 N solution of sodium carbonate in water (0.38 mL, 0.38 mmol) and dichloro(bis{di-tert-butyl[4-(dimethylamino)phenyl]phosphoranyl})palladium (0.011 g, 0.015 mmol). The mixture was stirred at 100° C. overnight. After cooled to room temperature, the mixture was diluted with ethyl acetate, washed with water, dried over MgSO$_4$, then concentrated and purified on silica gel (0-25% ethyl acetate/hexane) to give the desired product as a diastereoisomer mixture (54 mg). LCMS calculated for C$_{15}$H$_{12}$F$_2$N$_5$OS(M+H)$^+$: m/z=348.1; Found: 348.0.

Step 2. 7-(1-aminoethyl)-6-(2,5-difluorophenyl)-3-methyl-5H-[1,3]thiazolo[3,2-a]pyrimidin-5-one

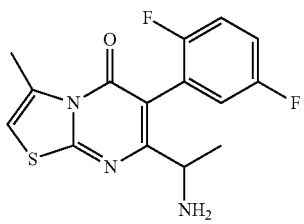 [SMILES: Cc1csc2nc(C(C)N)c(-c3cc(F)ccc3F)c(=O)n12]

To a solution of 7-(1-azidoethyl)-6-(2,5-difluorophenyl)-3-methyl-5H-[1,3]thiazolo[3,2-a]pyrimidin-5-one (0.054 g, 0.16 mmol) in tetrahydrofuran (2 mL) was added 1.00 M of trimethylphosphine in tetrahydrofuran (0.23 mL, 0.23 mmol), and the mixture was stirred at room temperature for 1 hour. The mixture was concentrated to give the crude product (45 mg), which was used directly in the next step. LCMS calculated for C$_{15}$H$_{14}$F$_2$N$_3$OS(M+H)$^+$: m/z=322.1. Found: 322.0.

Step 3. 6-(2,5-difluorophenyl)-3-methyl-7-[1-(9H-purin-6-ylamino)ethyl]-5H-[1,3]thiazolo[3,2-a]pyrimidin-5-one

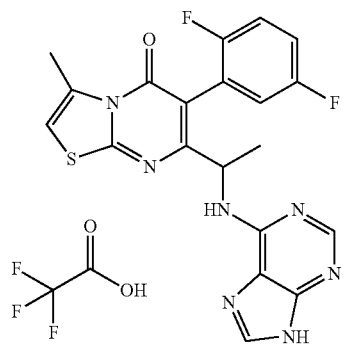 [SMILES: O=C(O)C(F)(F)F ; Cc1csc2nc(C(C)Nc3ncnc4[nH]cnc34)c(-c3cc(F)ccc3F)c(=O)n12]

A mixture of 7-(1-aminoethyl)-6-(2,5-difluorophenyl)-3-methyl-5H-[1,3]thiazolo[3,2-a]pyrimidin-5-one (0.045 g, 0.14 mmol), 6-bromo-9H-purine (0.042 g, 0.21 mmol), and N,N-diisopropylethylamine (0.049 mL, 0.28 mmol) in ethanol (0.3 mL) was heated at 110° C. overnight. The mixture was filtered, and the filtrate was purified on preparative-LCMS (XBridge C18 Column, eluting with a gradient of acetonitrile/water containing 0.05% TFA), to give the desired product as a mixture of two diastereomers (TFA salts). LCMS calculated for $C_{20}H_{16}F_2N_7OS(M+H)^+$: m/z=440.1. Found: 440.1. $^1$H NMR (DMSO-$d_6$, 400 MHz) δ 8.64 (1H, br s), 8.38 (1H, s), 8.36 (1H, s), 7.34~7.19 (3H, m), 7.08 (1H, m), 5.06 (1H, m), 2.60 (3H, s), 1.46 (1.5H, d, J=6.8 Hz), 1.33 (1.5H, d, J=6.8 Hz) ppm. $^{19}$F NMR (DMSO-$d_6$, 376.3 MHz) δ−117.8, −119.4, −119.8, −119.9 ppm.

Example 46. 6-(3-Fluorophenyl)-7-[(1S)-1-(3H-imidazo[4,5-6]pyridin-7-ylamino)ethyl]-3-methyl-5H-[1,3]thiazolo[3,2-a]pyrimidin-5-one

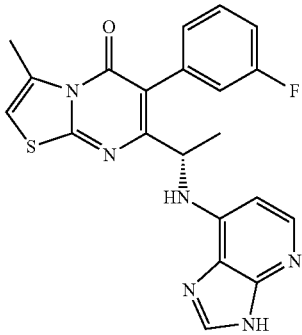 [SMILES: Cc1csc2nc([C@H](C)Nc3ccnc4[nH]cnc34)c(-c3cccc(F)c3)c(=O)n12]

A solution of 7-[(1S)-1-aminoethyl]-6-(3-fluorophenyl)-3-methyl-5H-[1,3]thiazolo[3,2-a]pyrimidin-5-one (50 mg, 0.16 mmol), 7-chloro-3H-imidazo[4,5-b]pyridine (51 mg, 0.33 mmol), and N,N-diisopropylethylamine (57 µL, 0.33 mmol) in 1-butanol (0.5 mL) in a sealable vial was degassed with nitrogen, sealed, and heated at 140° C. for 48 hours. The reaction mixture was diluted with methanol and purified by RP-HPLC (XBridge C18 column, eluting with a gradient of acetonitrile/water containing 0.1% ammonium hydroxide, at flow rate of 60 mL/min) to give the desired product (7 mg, 10%) as a white solid. LCMS for $C_{21}H_{18}FN_6OS$ (M+H)$^+$: m/z=420.8. $^1$H NMR (400 MHz, CD$_3$OD): δ 8.04 (s, 1H), 7.83 (d, J=5.9 Hz, 1H), 7.55-7.49 (m, 1H), 7.23-7.12 (m, 3H), 6.86 (d, J=1.2 Hz, 1H), 5.96 (d, J=5.9 Hz, 1H), 4.69-4.67 (m, 1H), 2.75 (s, 3H), 1.57 (d, J=6.4 Hz, 3H).

Example 47. 6-(3-Fluorophenyl)-7-{(1S)-1-[(2-hydroxy-9H-purin-6-yl)amino]ethyl}-3-methyl-5H-[1,3]thiazolo[3,2-a]pyrimidin-5-one

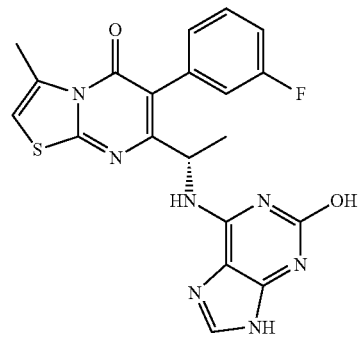 [SMILES: Cc1csc2nc([C@H](C)Nc3nc(O)nc4[nH]cnc34)c(-c3cccc(F)c3)c(=O)n12]

Step 1. 7-{(1S)-1-[(2-amino-9H-purin-6-yl)amino]ethyl}-6-(3-fluorophenyl)-3-methyl-5H-[1,3]thiazolo[3,2-a]pyrimidin-5-one

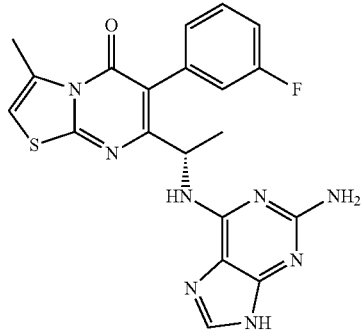 [SMILES: Cc1csc2nc([C@H](C)Nc3nc(N)nc4[nH]cnc34)c(-c3cccc(F)c3)c(=O)n12]

A solution of 7-[(1S)-1-aminoethyl]-6-(3-fluorophenyl)-3-methyl-5H-[1,3]thiazolo[3,2-a]pyrimidin-5-one (0.10 g, 0.33 mmol) and 2-amino-6-bromopurine (0.11 g, 0.49 mmol) in 1-butanol (0.66 mL) was treated with N,N-diisopropylethylamine (86 µL, 0.49 mmol), degassed with nitrogen for 5 min and heated at 100° C. for 18 hours. The reaction was not complete and was, therefore, heated at 115° C. for an additional 5 hours. The reaction mixture was diluted with methanol (10 mL), stirred, and filtered. The filtrate was purified by RP-HPLC (XBridge C18 column, eluting with a gradient of acetonitrile/water containing 0.1% ammonium hydroxide, at flow rate of 60 mL/min) to give the desired product (27 mg, 19%) as a white solid. LCMS for $C_{20}H_{18}FN_8OS$ (M+H)$^+$: m/z=437.0.

Step 2. 6-(3-Fluorophenyl)-7-{(1S)-1-[(2-hydroxy-9H-purin-6-yl)amino]ethyl}-3-methyl-5H-[1,3]thiazolo[3,2-a]pyrimidin-5-one A solution of 7-{(1S)-1-[(2-amino-9H-purin-6-yl)amino]ethyl}-6-(3-fluorophenyl)-3-methyl-5H-[1,3]thiazolo[3,2-a]

pyrimidin-5-one (27 mg, 62 µmol) in acetic acid (0.41 mL) and water (84 µL) at 0° C. was treated with a solution of sodium nitrite (13 mg, 0.19 mmol) in water (0.15 mL) dropwise and stirred at 0° C. for 30 minutes and at 20° C. for 16 hours. The reaction mixture was concentrated and purified by RP-HPLC (XBridge C18 column, eluting with a gradient of acetonitrile/water containing 0.1% ammonium hydroxide, at flow rate of 60 mL/min) to give the desired product (7 mg, 20%) as a white solid. LCMS for $C_{20}H_{17}FN_7O_2S$ (M+H)$^+$: m/z=437.8. $^1$H NMR (300 MHz, DMSO-d$_6$): δ 7.79 (br s, 1H), 7.68-7.61 (m, 1H), 7.50-7.38 (m, 3H), 7.23-7.14 (m, 2H), 7.06 (br s, 1H), 5.02-4.92 (m, 1H), 2.64 (s, 3H), 1.26 (d, J=6.7 Hz, 3H).

Example 48. 6-(3-Fluorophenyl)-7-[1-(9H-purin-6-ylamino)ethyl]-3-(trifluoromethyl)-5H-[1,3]thiazolo[3,2-a]pyrimidin-5-one

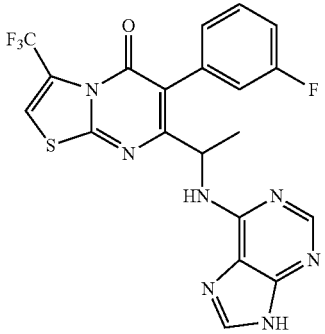 [SMILES: CC(Nc1ncnc2[nH]cnc12)c1nc2scc(C(F)(F)F)n2c(=O)c1-c1cccc(F)c1]

Step 1. 7-(1-Bromoethyl)-3-(trifluoromethyl)-5H-[1,3]thiazolo[3,2-a]pyrimidin-5-one

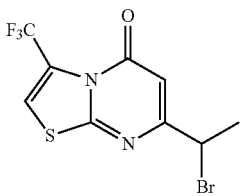 [SMILES: CC(Br)c1cc(=O)n2c(C(F)(F)F)csc2n1]

The desired compound was prepared according to the procedure of Example 8, step 2, using 4-(trifluoromethyl)-1,3-thiazol-2-amine as the starting material in 53% yield. LCMS for $C_9H_7BrF_3N_2OS$ (M+H)$^+$: m/z=326.8, 328.8.

Step 2. 6-Bromo-7-(1-bromoethyl)-3-(trifluoromethyl)-5H-[1,3]thiazolo[3,2-a]pyrimidin-5-one

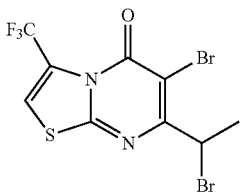 [SMILES: CC(Br)c1nc2scc(C(F)(F)F)n2c(=O)c1Br]

The desired compound was prepared according to the procedure of Example 8, step 3, using 7-(1-bromoethyl)-3-(trifluoromethyl)-5H-[1,3]thiazolo[3,2-a]pyrimidin-5-one as the starting material in quantitative yield. LCMS for $C_9H_6Br_2F_3N_2OS$ (M+H)$^+$: m/z=404.8, 406.7, 408.7.

Step 3. 7-(1-Azidoethyl)-6-bromo-3-(trifluoromethyl)-5H-[1,3]thiazolo[3,2-a]pyrimidin-5-one

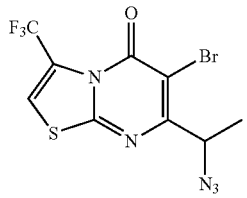

The desired compound was prepared according to the procedure of Example 8, step 4, using 6-bromo-7-(1-bromoethyl)-3-(trifluoromethyl)-5H-[1,3]thiazolo[3,2-a]pyrimidin-5-one as the starting material in 84% yield. LCMS for $C_9H_6BrF_3N_5OS$ (M+H)$^+$: m/z=367.7, 369.8.

Step 4. 7-(1-Azidoethyl)-6-(3-fluorophenyl)-3-(trifluoromethyl)-5H-[1,3]thiazolo[3,2-a]pyrimidin-5-one

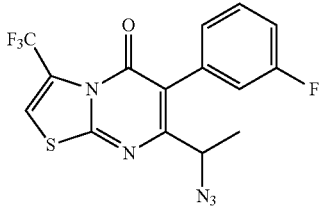

The desired compound was prepared according to the procedure of Example 8, step 5, using 7-(1-azidoethyl)-6-bromo-3-(trifluoromethyl)-5H-[1,3]thiazolo[3,2-a]pyrimidin-5-one and (3-fluorophenyl)boronic acid as the starting materials in 29% yield. LCMS for $C_{15}H_{10}F_4N_5OS$ (M+H)$^+$: m/z=383.9.

Step 5. 7-(1-Aminoethyl)-6-(3-fluorophenyl)-3-(trifluoromethyl)-5H-[1,3]thiazolo[3,2-a]pyrimidin-5-one trifluoroacetic acid salt

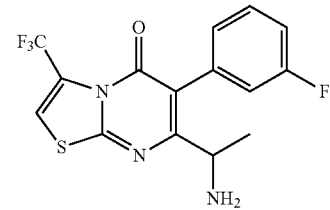 [SMILES: CC(N=[N+]=[N-])c1nc2scc(C(F)(F)F)n2c(=O)c1-c1cccc(F)c1]

The desired compound was prepared according to the procedure of Example 8, step 6, using 7-(1-azidoethyl)-6-(3-fluorophenyl)-3-(trifluoromethyl)-5H-[1,3]thiazolo[3,2- a]pyrimidin-5-one as the starting material in 79% yield after purification by RP-HPLC (XBridge C18 column, eluting with a gradient of acetonitrile/water containing 0.05% TFA, at flow rate of 30 mL/min). LCMS for $C_{15}H_{12}F_4N_3OS$ (M+H)$^+$: m/z=357.9.

Step 6. 6-(3-Fluorophenyl)-7-[1-(9H-purin-6-ylamino)ethyl]-3-(trifluoromethyl)-5H-[1,3]thiazolo[3,2-a]pyrimidin-5-one The desired compound was prepared according to the procedure of Example 8, step 7, using 7-(1-aminoethyl)-6-(3-fluorophenyl)-3-(trifluoromethyl)-5H-[1,3]thiazolo[3,2-a]pyrimidin-5-one trifluoroacetic acid salt as the starting material in 54% yield after purification by RP-HPLC (XBridge C18 column, eluting with a gradient of acetonitrile/water containing 0.1% ammonium hydroxide, at flow rate of 30 mL/min). LCMS for $C_{20}H_{14}F_4N_7OS$ (M+H)$^+$: m/z=475.9. $^1$H NMR (300 MHz, DMSO-d$_6$): δ 8.36 (s, 1H), 8.14-8.08 (m, 2H), 7.55-7.46 (m, 2H), 7.32-7.21 (m, 3H), 5.19-5.07 (m, 1H), 1.37 (d, J=7.0 Hz, 3H).

Example 49. 6-Methyl-3-phenyl-2-[1-(9H-purin-6-ylamino)ethyl]-4H-pyrido[1,2-a]pyrimidin-4-one trifluoroacetic acid salt

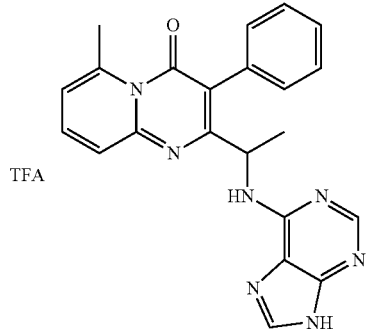 [SMILES: Cc1cccc2nc(C(C)Nc3ncnc4[nH]cnc34)c(-c3ccccc3)c(=O)n12]

Step 1. 2-(1-Bromoethyl)-6-methyl-4H-pyrido[1,2-a]pyrimidin-4-one

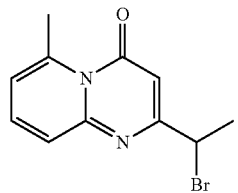

The desired compound was prepared according to the procedure of Example 8, step 2, using 6-methyl-2-pyridinamine as the starting material in 58% yield. LCMS for $C_{11}H_{12}BrN_2O$ (M+H)$^+$: m/z=267.0, 269.0.

Step 2. 2-(1-Bromoethyl)-3-iodo-6-methyl-4H-pyrido[1,2-a]pyrimidin-4-one

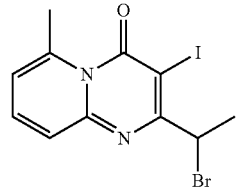 [SMILES: Cc1cccc2nc(C(C)Br)c(I)c(=O)n12]

The desired compound was prepared according to the procedure of Example 8, step 3, using 2-(1-bromoethyl)-6-methyl-4H-pyrido[1,2-a]pyrimidin-4-one and A-iodosuccinimide as the starting materials in 98% yield. LCMS for $C_{11}H_{11}BrIN_2O$ (M+H)$^+$: m/z=392.7, 394.7.

Step 3. 2-(1-Azidoethyl)-3-iodo-6-methyl-4H-pyrido[1,2-a]pyrimidin-4-one

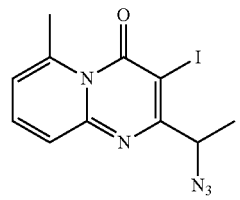 [SMILES: Cc1cccc2nc(C(C)N=[N+]=[N-])c(I)c(=O)n12]

The desired compound was prepared according to the procedure of Example 8, step 4, using 2-(1-bromoethyl)-3-iodo-6-methyl-4H-pyrido[1,2-a]pyrimidin-4-one as the starting material in 99% yield. LCMS for $C_{11}H_{11}IN_5O$ (M+H)$^+$: m/z=356.0.

Step 4. 2-(1-Azidoethyl)-6-methyl-3-phenyl-4H-pyrido[1,2-a]pyrimidin-4-one

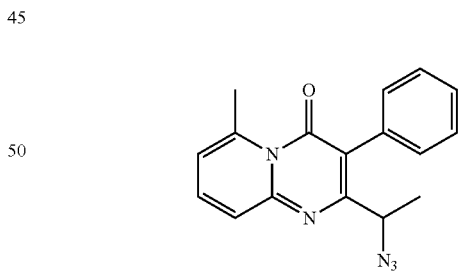

A solution of 2-(1-azidoethyl)-3-iodo-6-methyl-4H-pyrido[1,2-a]pyrimidin-4-one (100 mg, 0.28 mmol) and phenylboronic acid (48 mg, 0.39 mmol) in 1,4-dioxane (2 mL) was treated with sodium carbonate (45 mg, 0.42 mmol), water (0.50 mL), and dichloro(bis{di-tert-butyl[4-(dimethylamino)phenyl]phosphoranyl})palladium (2.0 mg, 28 μmol), degassed with nitrogen for 5 minutes, and heated at 110° C. for 18 hours. The reaction mixture was purified by RP-HPLC (XBridge C18 column, eluting with a gradient of acetonitrile/water containing 0.05% TFA, at flow rate of 30 mL/min). LCMS for $C_{17}H_{16}N_5O$ (M+H)$^+$: m/z=306.1.

Step 5. 6-Methyl-3-phenyl-2-[1-(9H-purin-6-ylamino)ethyl]-4H-pyrido[1,2-a]pyrimidin-4-one trifluoroacetic acid salt A solution of 2-(1-azidoethyl)-6-methyl-3-phenyl-4H-pyrido[1,2-a]pyrimidin-4-one (31 mg, 0.10 mmol) in tetrahydrofuran (1 mL) and water (0.2 mL) was treated with 1 M of trimethylphosphine in tetrahydrofuran (0.20 mL, 0.20 mmol) and stirred at 20° C. for 1 hour. The reaction mixture was diluted with brine (2 mL) and extracted with dichloromethane (3×15 mL). The combined organic extracts were dried with sodium sulfate, filtered, and concentrated to a crude residue. This intermediate amine was used without further purification. A solution of the amine in ethanol (1 mL) was treated with 6-bromo-9H-purine (31 mg, 0.16 mmol) and N,N-diisopropylethylamine (24 mL, 0.14 mmol) and then heated at 90° C. for 18 hours. The reaction mixture was purified by RP-HPLC (XBridge C18 column, eluting with a gradient of acetonitrile/water containing 0.05% TFA, at flow rate of 30 mL/min). LCMS for $C_{22}H_{20}N_7O$ (M+H)$^+$: m/z=398.1.

Example 50. 2-{1-[(2-Amino-9H-purin-6-yl)amino]ethyl}-6-methyl-3-phenyl-4H-pyrido[1,2-a]pyrimidin-4-one trifluoroacetic acid salt

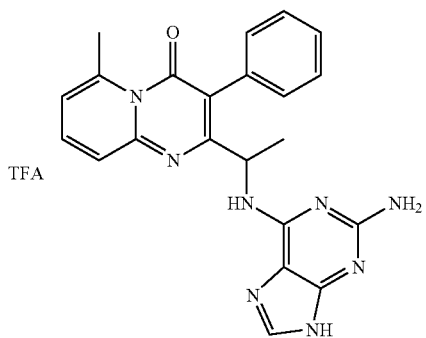 [SMILES: Cc1cccc2nc(C(C)Nc3nc(N)nc4[nH]cnc34)c(-c3ccccc3)c(=O)n12]

The desired compound was prepared according to the procedure of Example 49 using 2-amino-6-bromopurine (instead of 6-bromo-9H-purine in step 5). LCMS for $C_{22}H_{21}N_8O$ (M+H)$^+$: m/z=413.0.

Example 51. 6-Methyl-3-(3-methylphenyl)-2-[1-(9H-purin-6-ylamino)ethyl]-4H-pyrido[1,2-a]pyrimidin-4-one trifluoroacetic acid salt

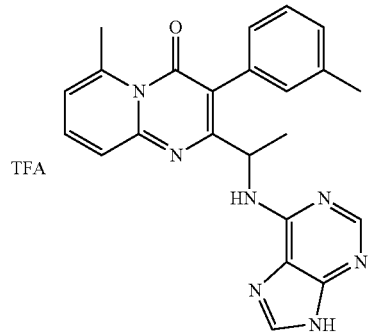 [SMILES: Cc1cccc(-c2c(C(C)Nc3ncnc4[nH]cnc34)nc3cccc(C)n3c2=O)c1]

The desired compound was prepared according to the procedure of Example 49 using (3-methylphenyl)boronic acid (instead of phenylboronic acid in step 4). LCMS for $C_{23}H_{22}N_7O$ (M+H)$^+$: m/z=411.9.

Example 52. 2-{1-[(2-Amino-9H-purin-6-yl)amino]ethyl}-6-methyl-3-(3-methylphenyl)-4H-pyrido[1,2-a]pyrimidin-4-one trifluoroacetic acid salt

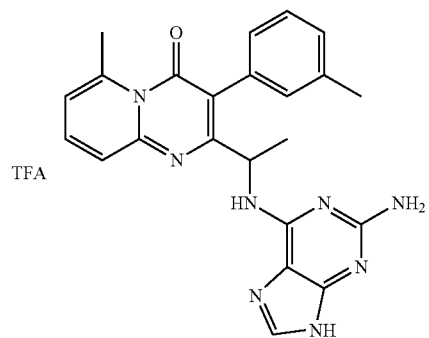 [SMILES: Cc1cccc(-c2c(C(C)Nc3nc(N)nc4[nH]cnc34)nc3cccc(C)n3c2=O)c1]

The desired compound was prepared according to the procedure of Example 49 using (3-methylphenyl)boronic acid (instead of phenylboronic acid in step 4) and 2-amino-6-bromopurine (instead of 6-bromo-9#-purine in step 5). LCMS for $C_{23}H_{23}N_8O$ (M+H)$^+$: m/z=427.0.

Example 53. 3-(3-Chlorophenyl)-6-methyl-2-[1-(9H-purin-6-ylamino)ethyl]-4H-pyrido[1,2-a]pyrimidin-4-one trifluoroacetic acid salt

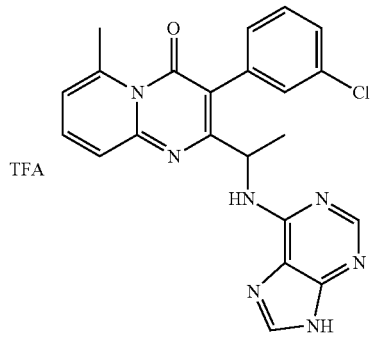 [SMILES: Cc1cccc2nc(C(C)Nc3ncnc4[nH]cnc34)c(-c3cccc(Cl)c3)c(=O)n12]

The desired compound was prepared according to the procedure of Example 49 using (3-chlorophenyl)boronic acid (instead of phenylboronic acid in step 4). LCMS for $C_{22}H_{19}ClN_7O$ (M+H)$^+$: m/z=432.1.

Example 54. 2-{1-[(2-Amino-9H-purin-6-yl)amino]ethyl}-3-(3-chlorophenyl)-6-methyl-4H-pyrido[1,2-a]pyrimidin-4-one trifluoroacetic acid salt

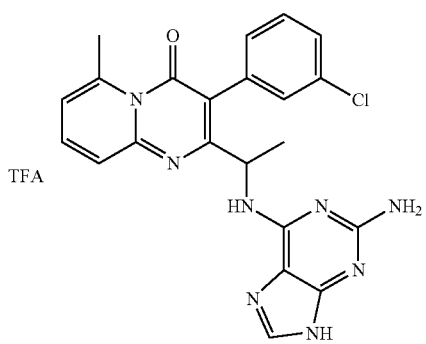 [SMILES: Cc1cccc2nc(C(C)Nc3nc(N)nc4[nH]cnc34)c(-c3cccc(Cl)c3)c(=O)n12]

The desired compound was prepared according to the procedure of Example 49 using (3-chlorophenyl)boronic acid (instead of phenylboronic acid in step 4) and 2-amino-6-bromopurine (instead of 6-bromo-9H-purine in step 5). LCMS for $C_{22}H_{20}ClN_8O$ (M+H)$^+$: m/z=447.1.

Example 55. 3-(4-Chlorophenyl)-6-methyl-2-[1-(9H-purin-6-ylamino)ethyl]-4H-pyrido[1,2-a]pyrimidin-4-one trifluoroacetic acid salt

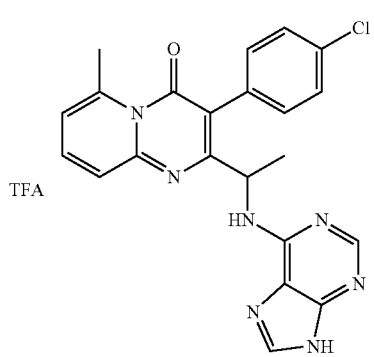 [SMILES: Cc1cccc2nc(C(C)Nc3ncnc4[nH]cnc34)c(-c3ccc(Cl)cc3)c(=O)n12]

The desired compound was prepared according to the procedure of Example 49 using (4-chlorophenyl)boronic acid (instead of phenylboronic acid in step 4). LCMS for $C_{22}H_{19}ClN_7O$ (M+H)$^+$: m/z=432.1.

Example 56. 2-{1-[(2-Amino-9H-purin-6-yl)amino]ethyl}-3-(4-chlorophenyl)-6-methyl-4H-pyrido[1,2-a]pyrimidin-4-one trifluoroacetic acid salt

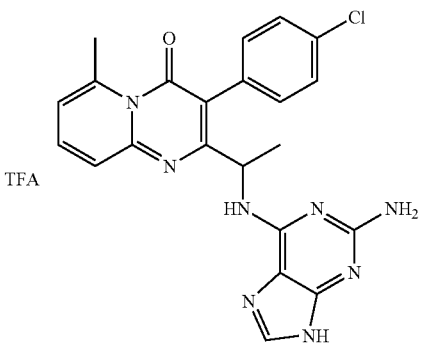 [SMILES: Cc1cccc2nc(C(C)Nc3nc(N)nc4[nH]cnc34)c(-c3ccc(Cl)cc3)c(=O)n12]

The desired compound was prepared according to the procedure of Example 49 using (4-chlorophenyl)boronic acid (instead of phenylboronic acid in step 4) and 2-amino-6-bromopurine (instead of 6-bromo-9H-purine in step 5). LCMS for $C_{22}H_{20}ClN_8O$ (M+H)$^+$: m/z=447.1.

Example 57. 3-(2-Chlorophenyl)-6-methyl-2-[1-(9H-purin-6-ylamino)ethyl]-4H-pyrido[1,2-a]pyrimidin-4-one trifluoroacetic acid salt

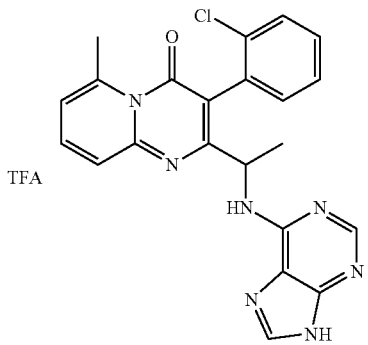 [SMILES: Cc1cccc2nc(C(C)Nc3ncnc4[nH]cnc34)c(-c3ccccc3Cl)c(=O)n12]

The desired compound was prepared according to the procedure of Example 49 using (2-chlorophenyl)boronic acid (instead of phenylboronic acid in step 4) as a mixture of atropisomers. LCMS for $C_{22}H_{19}ClN_7O$ (M+H)$^+$: m/z=432.1.

Example 58. 2-{1-[(2-Amino-9#-purin-6-yl)amino]ethyl}-3-(2-chlorophenyl)-6-methyl-4H-pyrido[1,2-a]pyrimidin-4-one trifluoroacetic acid salt

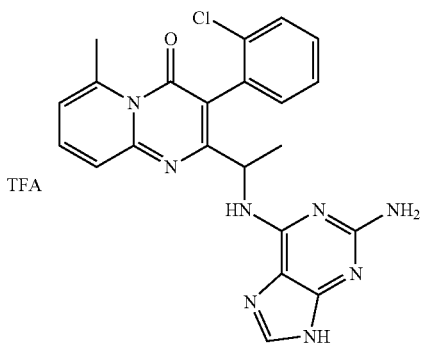 [SMILES: Cc1cccc2nc(C(C)Nc3nc(N)nc4[nH]cnc34)c(-c3ccccc3Cl)c(=O)n12]

The desired compound was prepared according to the procedure of Example 49 using (2-chlorophenyl)boronic acid (instead of phenylboronic acid in step 4) and 2-amino-6-bromopurine (instead of 6-bromo-9H-purine in step 5) as a mixture of atropisomers. LCMS for $C_{22}H_{20}ClN_8O$ (M+H)$^+$: m/z=447.1.

Example 59. 3-(2-Fluorophenyl)-6-methyl-2-[1-(9H-purin-6-ylamino)ethyl]-4H-pyrido[1,2-a]pyrimidin-4-one trifluoroacetic acid salt

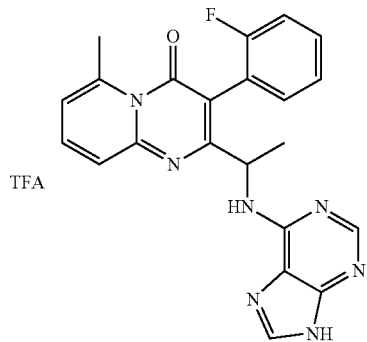 [SMILES: Cc1cccc2nc(C(C)Nc3ncnc4[nH]cnc34)c(-c3ccccc3F)c(=O)n12]

The desired compound was prepared according to the procedure of Example 49 using (2-fluorophenyl)boronic acid (instead of phenylboronic acid in step 4). LCMS for $C_{22}H_{19}FN_7O$ (M+H)$^+$: m/z=416.1.

Example 60. 2-{1-[(2-Amino-9#-purin-6-yl)amino]ethyl}-3-(2-fluorophenyl)-6-methyl-4H-pyrido[1,2-a]pyrimidin-4-one trifluoroacetic acid salt

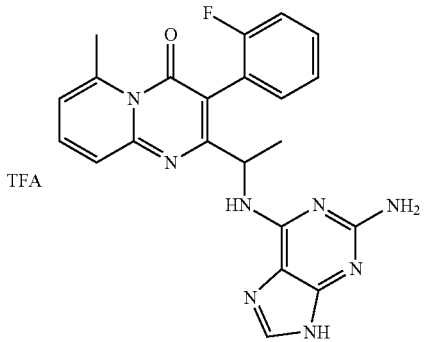

The desired compound was prepared according to the procedure of Example 49 using (2-fluorophenyl)boronic acid (instead of phenylboronic acid in step 4) and 2-amino-6-bromopurine (instead of 6-bromo-9H-purine in step 5). LCMS for $C_{22}H_{20}FN_8O$ (M+H)$^+$: m/z=431.1.

Example 61. 4-{6-Methyl-4-oxo-2-[1-(9H-purin-6-ylamino)ethyl]-4H-pyrido[1,2-a]pyrimidin-3-yl}benzonitrile trifluoroacetic acid salt

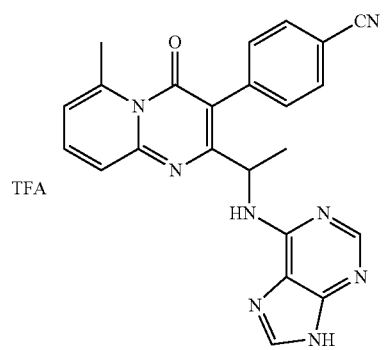 [SMILES: Cc1cccc2nc(C(C)Nc3ncnc4[nH]cnc34)c(-c3ccc(C#N)cc3)c(=O)n12]

The desired compound was prepared according to the procedure of Example 49 using (4-cyanophenyl)boronic acid (instead of phenylboronic acid in step 4). LCMS for $C_{23}H_{19}N_8O$ (M+H)$^+$: m/z=423.1.

Example 62. 4-(2-{1-[(2-Amino-9H-purin-6-yl)amino]ethyl}-6-methyl-4-oxo-4H-pyrido[1,2-a]pyrimidin-3-yl)benzonitrile trifluoroacetic acid salt

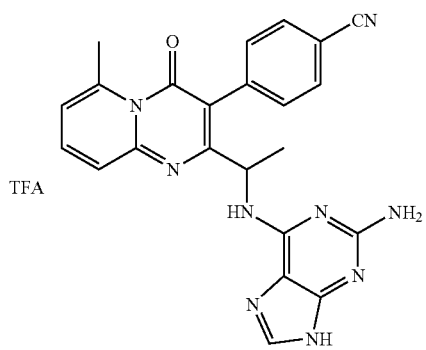 [SMILES: Cc1cccc2nc(C(C)Nc3nc(N)nc4[nH]cnc34)c(-c3ccc(C#N)cc3)c(=O)n12]

The desired compound was prepared according to the procedure of Example 49 using (4-cyanophenyl)boronic acid (instead of phenylboronic acid in step 4) and 2-amino-6-bromopurine (instead of 6-bromo-9#-purine in step 5). LCMS for $C_{23}H_{20}N_9O$ (M+H)$^+$: m/z=438.2.

Example 63. 6-Methyl-3-(2-methylphenyl)-2-[1-(9H-purin-6-ylamino)ethyl]-4H-pyrido[1,2-a]pyrimidin-4-one trifluoroacetic acid salt

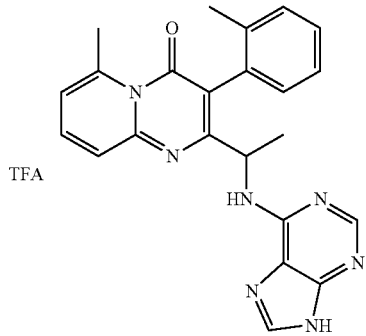 [SMILES: Cc1ccccc1-c1c(C(C)Nc2ncnc3[nH]cnc23)nc2cccc(C)n2c1=O]

The desired compound was prepared according to the procedure of Example 49 using (2-methylphenyl)boronic acid (instead of phenylboronic acid in step 4), [1,1'-bis(diphenylphosphino)ferrocene]dichloropalladium(II) complex with dichloromethane (1:1) (instead of dichloro(bis{di-tert-butyl[4-(dimethylamino)phenyl]phosphoranyl}) palladium in step 4), and potassium carbonate (instead of sodium carbonate in step 4). LCMS for $C_{23}H_{22}N_7O$ (M+H)$^+$: m/z=412.1.

Example 64. 6-Methyl-3-(4-methylphenyl)-2-[1-(9H-purin-6-ylamino)ethyl]-4H-pyrido[1,2-a]pyrimidin-4-one trifluoroacetic acid salt

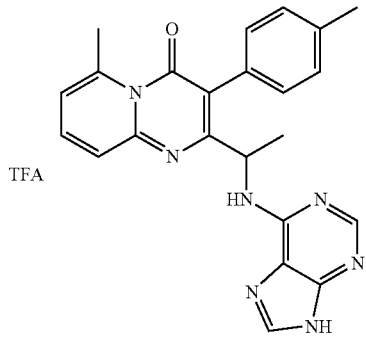 [SMILES: Cc1ccc(-c2c(C(C)Nc3ncnc4[nH]cnc34)nc3cccc(C)n3c2=O)cc1]

The desired compound was prepared according to the procedure of Example 49 using (4-methylphenyl)boronic acid (instead of phenylboronic acid in step 4), [1,1'-bis(diphenylphosphino)ferrocene]dichloropalladium(II) complex with dichloromethane (1:1) (instead of dichloro(bis{di-tert-butyl[4-(dimethylamino)phenyl]phosphoranyl}) palladium in step 4), and potassium carbonate (instead of sodium carbonate in step 4). LCMS for $C_{23}H_{22}N_7O$ (M+H)$^+$: m/z=412.1.

Example 65. 3-(3-Methoxyphenyl)-6-methyl-2-[1-(9H-purin-6-ylamino)ethyl]-4H-pyrido[1,2-a]pyrimidin-4-one trifluoroacetic acid salt

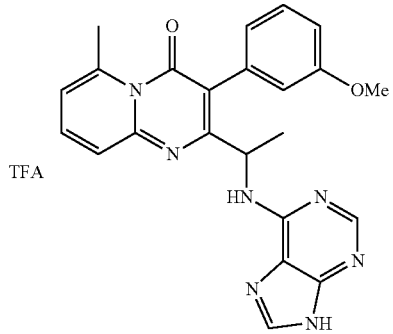 [SMILES: COc1cccc(-c2c(C(C)Nc3ncnc4[nH]cnc34)nc3cccc(C)n3c2=O)c1]

The desired compound was prepared according to the procedure of Example 49 using 3-methoxyphenylboronic acid (instead of phenylboronic acid in step 4), [1,1'-bis(diphenylphosphino)ferrocene]dichloropalladium(II) complex with dichloromethane (1:1) (instead of dichloro(bis{di-tert-butyl[4-(dimethylamino)phenyl]phosphoranyl}) palladium in step 4), and potassium carbonate (instead of sodium carbonate in step 4). LCMS for $C_{23}H_{22}N_7O_2$ (M+H)$^+$: m/z=428.1.

Example 66. 3-(2,3-Difluorophenyl)-6-methyl-2-[1-(9H-purin-6-ylamino)ethyl]-4H-pyrido[1,2-a]pyrimidin-4-one trifluoroacetic acid salt

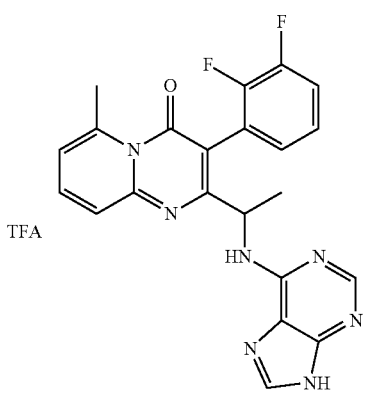 [SMILES: Cc1cccc2nc(C(C)Nc3ncnc4[nH]cnc34)c(-c3cccc(F)c3F)c(=O)n12]

The desired compound was prepared according to the procedure of Example 49 using (2,3-difluorophenyl)boronic acid (instead of phenylboronic acid in step 4), [1,1'-bis(diphenylphosphino)ferrocene]dichloropalladium(II) complex with dichloromethane (1:1) (instead of dichloro(bis{di-tert-butyl[4-(dimethylamino)phenyl]phosphoranyl}) palladium in step 4), and potassium carbonate (instead of sodium carbonate in step 4). LCMS for $C_{22}H_{18}F_2N_7O$ (M+H)$^+$: m/z=434.2.

Example 67. 3-(2,5-Difluorophenyl)-6-methyl-2-[1-(9H-purin-6-ylamino)ethyl]-4H-pyrido[1,2-a]pyrimidin-4-one trifluoroacetic acid salt

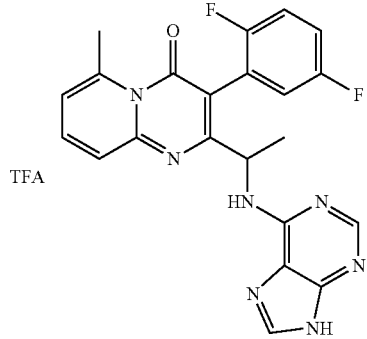 [SMILES: Cc1cccc2nc(C(C)Nc3ncnc4[nH]cnc34)c(-c3cc(F)ccc3F)c(=O)n12]

The desired compound was prepared according to the procedure of Example 49 using (2,5-difluorophenyl)boronic acid (instead of phenylboronic acid in step 4), [1,1'-bis(diphenylphosphino)ferrocene]dichloropalladium(II) complex with dichloromethane (1:1) (instead of dichloro(bis{di-tert-butyl[4-(dimethylamino)phenyl]phosphoranyl})palladium in step 4), and potassium carbonate (instead of sodium carbonate in step 4). LCMS for $C_{22}H_{18}F_2N_7O$ $(M+H)^+$: m/z=434.1.

Example 68. 3-(3,4-Difluorophenyl)-6-methyl-2-[1-(9H-purin-6-ylamino)ethyl]-4H-pyrido[1,2-a]pyrimidin-4-one trifluoroacetic acid salt

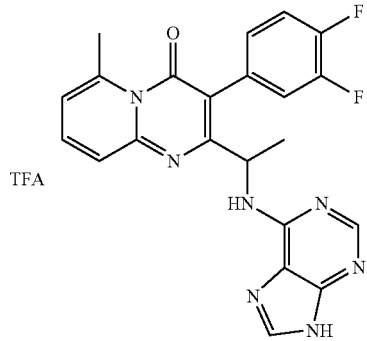 [SMILES: Cc1cccc2nc(C(C)Nc3ncnc4[nH]cnc34)c(-c3ccc(F)c(F)c3)c(=O)n12]

The desired compound was prepared according to the procedure of Example 49 using (3,4-difluorophenyl)boronic acid (instead of phenylboronic acid in step 4), [1,1'-bis(diphenylphosphino)ferrocene]dichloropalladium(II) complex with dichloromethane (1:1) (instead of dichloro(bis{di-tert-butyl[4-(dimethylamino)phenyl]phosphoranyl})palladium in step 4), and potassium carbonate (instead of sodium carbonate in step 4). LCMS for $C_{22}H_{18}F_2N_7O$ $(M+H)^+$: m/z=434.0.

Example 69. 3-(3,5-Difluorophenyl)-6-methyl-2-[1-(9H-purin-6-ylamino)ethyl]-4H-pyrido[1,2-a]pyrimidin-4-one trifluoroacetic acid salt

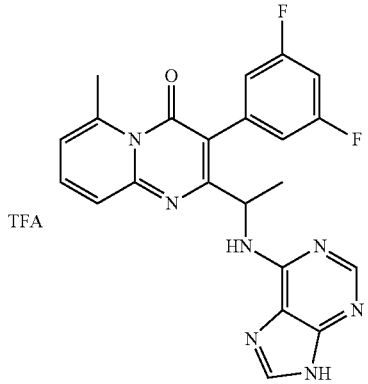 [SMILES: Cc1cccc2nc(C(C)Nc3ncnc4[nH]cnc34)c(-c3cc(F)cc(F)c3)c(=O)n12]

The desired compound was prepared according to the procedure of Example 49 using (3,5-difluorophenyl)boronic acid (instead of phenylboronic acid in step 4) and tetrakis(triphenylphosphine)palladium(0) (instead of dichloro(bis{di-tert-butyl[4-(dimethylamino)phenyl]phosphoranyl})palladium in step 4). LCMS for $C_{22}H_{18}F_2N_7O$ $(M+H)^+$: m/z=434.0. $^1$H NMR (300 MHz, DMSO-$d_6$): δ 8.80 (br s, 1H), 8.48 (s, 2H), 7.71 (dd, J=7.9, 7.6 Hz, 1H), 7.45 (d, J=8.2 Hz, 1H), 7.24 (d, J=9.7, 9.1 Hz, 1H), 7.18-7.11 (m, 3H), 6.97 (d, J=6.7 Hz, 1H), 5.29-5.20 (m, 1H), 2.89 (s, 3H), 1.46 (d, J=6.7 Hz, 3H).

Example 70. 3-(3-Fluorophenyl)-6-methyl-2-[1-(9H-purin-6-ylamino)ethyl]-4H-pyrido[1,2-a]pyrimidin-4-one trifluoroacetic acid salt

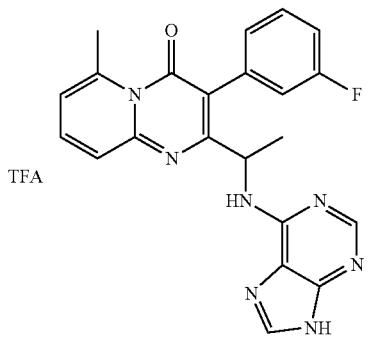 [SMILES: Cc1cccc2nc(C(C)Nc3ncnc4[nH]cnc34)c(-c3cccc(F)c3)c(=O)n12]

The desired compound was prepared according to the procedure of Example 49 using (3-fluorophenyl)boronic acid (instead of phenylboronic acid in step 4) and tetrakis(triphenylphosphine)palladium(0) (instead of dichloro(bis{di-tert-butyl[4-(dimethylamino)phenyl]phosphoranyl})palladium in step 4). LCMS for $C_{22}H_{19}FN_7O$ $(M+H)^+$: m/z=416.1. $^1$H NMR (300 MHz, DMSO-$d_6$): δ 8.85 (br s, 1H), 8.50 (s, 2H), 7.70 (dd, J=7.9, 7.6 Hz, 1H), 7.51-7.40 (m, 2H), 7.27-7.16 (m, 3H), 6.96 (d, J=6.7 Hz, 1H), 5.31-5.20 (m, 1H), 2.88 (s, 3H), 1.44 (d, J=6.7 Hz, 3H).

Example 71 and Example 72. Single enantiomers of 3-(3-Fluorophenyl)-6-methyl-2-[1-(9H-purin-6-ylamino)ethyl]-4H-pyrido[1,2-a]pyrimidin-4-one trifluoroacetic acid salt

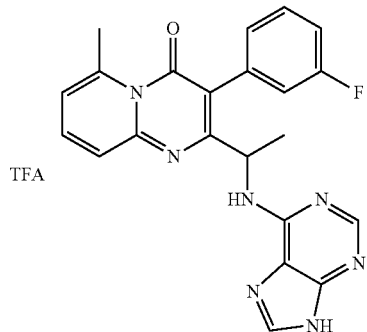 [SMILES: Cc1cccc2nc(C(C)Nc3ncnc4[nH]cnc34)c(-c3cccc(F)c3)c(=O)n12]

Step 1. Chiral separation of 2-(1-Azidoethyl)-3-iodo-6-methyl-4H-pyrido[1,2-a]pyrimidin-4-one

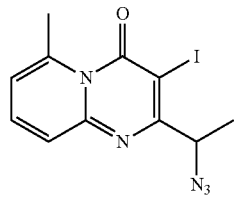 [SMILES: Cc1cccc2nc(C(C)N=[N+]=[N-])c(I)c(=O)n12]

The racemic mixture of 2-(1-azidoethyl)-3-iodo-6-methyl-4H-pyrido[1,2-a]pyrimidin-4-one was separated by HPLC (Chiracel OJ-H, eluting with 30% ethanol/70% hexanes, at flow rate of 20 mL/min) to give the two individual enantiomers (retention times=21.6 min, 27.2 min). Both peaks were advanced to the next step.

Step 2. Single enantiomers of 2-(1-azidoethyl)-3-(3-fluorophenyl)-6-methyl-4H-pyrido[1,2-a]pyrimidin-4-one trifluoroacetic acid salt

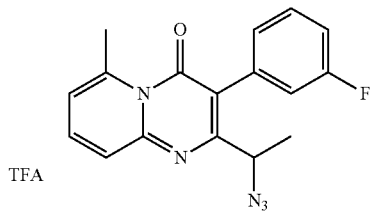 [SMILES: Cc1cccc2nc(C(C)N=[N+]=[N-])c(-c3cccc(F)c3)c(=O)n12]

The desired compounds were prepared according to the procedure of Example 49, step 4, using peak 1 and peak 2 of 2-(1-azidoethyl)-3-iodo-6-methyl-4H-pyrido[1,2-a]pyrimidin-4-one and (3-fluorophenyl)boronic acid as the starting materials after purification by RP-HPLC (XBridge C18 column, eluting with a gradient of acetonitrile/water containing 0.05% TFA, at flow rate of 60 mL/min). From peak 1: LCMS for $C_{17}H_{15}FN_5O$ (M+H)$^+$: m/z=324.1. From peak 2: LCMS for $C_{17}H_{15}FN_5O$ (M+H)$^+$: m/z=323.9.

Step 3. Single enantiomers of 3-(3-Fluorophenyl)-6-methyl-2-[1-(9H-purin-6-ylamino)ethyl]-4H-pyrido[1,2-a]pyrimidin-4-one trifluoroacetic acid salt The desired compounds were prepared according to the procedure of Example 49, step 5, using the single enantiomers of 2-(1-azidoethyl)-3-(3-fluorophenyl)-6-methyl-4H-pyrido[1,2-a]pyrimidin-4-one trifluoroacetic acid salt and (3-fluorophenyl)boronic acid as the starting materials. Example 71 (from peak 1): LCMS for $C_{22}H_{19}FN_7O$ (M+H)$^+$: m/z=415.9; $^1$H NMR (400 MHz, DMSO-d$_6$): δ 8.78 (br s, 1H), 8.48 (s, 2H), 7.70 (dd, J=7.8, 7.7 Hz, 1H), 7.50-7.41 (m, 2H), 7.28-7.17 (m, 3H), 6.96 (d, J=7.0 Hz, 1H), 5.30-5.21 (m, 1H), 2.88 (s, 3H), 1.44 (d, J=6.7 Hz, 3H). Example 72 (from peak 2): LCMS for $C_{22}H_{19}FN_7O$ (M+H)$^+$: m/z=416.1; $^1$H NMR (400 MHz, DMSO-d$_6$): δ 8.78 (br s, 1H), 8.48 (s, 2H), 7.70 (dd, J=8.1, 7.5 Hz, 1H), 7.50-7.42 (m, 2H), 7.27-7.18 (m, 3H), 6.96 (d, J=6.8 Hz, 1H), 5.30-5.21 (m, 1H), 2.88 (s, 3H), 1.44 (d, J=6.7 Hz, 3H).

Example 73. 2-{1-[(2-Amino-9H-purin-6-yl)amino]ethyl}-3-(3-fluorophenyl)-6-methyl-4H-pyrido[1,2-a]pyrimidin-4-one trifluoroacetic acid salt

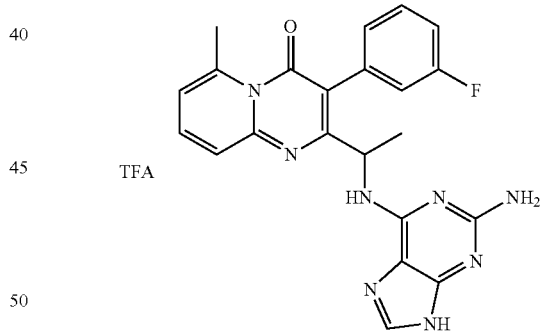

The desired compound was prepared according to the procedure of Example 49 using (3-fluorophenyl)boronic acid (instead of phenylboronic acid in step 4), tetrakis(triphenylphosphine)palladium(0) (instead of dichloro(bis{di-tert-butyl[4-(dimethylamino)phenyl]phosphoranyl})palladium in step 4), and 2-amino-6-bromopurine (instead of 6-bromo-9H-purine in step 5). LCMS for $C_{22}H_{20}FN_8O$ (M+H)$^+$: m/z=431.2. $^1$H NMR (300 MHz, DMSO-d$_6$): δ 8.72 (d, J=7.3 Hz, 1H), 8.17 (s, 1H), 7.74-7.68 (m, 1H), 7.50-7.41 (m, 2H), 7.29-7.14 (m, 5H), 6.98 (d, J=6.4 Hz, 1H), 5.26-5.17 (m, 1H), 2.89 (s, 3H), 1.37 (d, J=6.7 Hz, 3H).

Example 74 and Example 75. Single enantiomers of 2-{1-[(2-Amino-9H-purin-6-yl)amino]ethyl}-3-(3-fluorophenyl)-6-methyl-4H-pyrido[1,2-a]pyrimidin-4-one trifluoroacetic acid salt

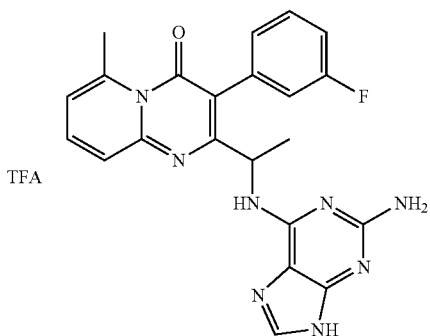 [SMILES: Cc1cccc2nc(C(C)Nc3nc(N)nc4[nH]cnc34)c(-c3cccc(F)c3)c(=O)n12]

The desired compounds were prepared according to the procedure of Example 71 and 72. 2-amino-6-bromopurine (instead of 6-bromo-9H-purine in step 5). Example 74 (from peak 1): $C_{22}H_{20}FN_8O$ (M+H)$^+$: m/z=431.0; $^1$H NMR (400 MHz, DMSO-d$_6$): δ 8.72 (d, J=7.3 Hz, 1H), 8.17 (s, 1H), 7.72 (dd, J=8.8, 7.1 Hz, 1H), 7.48-7.40 (m, 2H), 7.27-7.13 (m, 5H), 6.98 (d, J=6.8 Hz, 1H), 5.25-5.18 (m, 1H), 2.89 (s, 3H), 1.37 (d, J=6.7 Hz, 3H). Example 75 (from peak 2): $C_{22}H_{20}FN_8O$ (M+H)$^+$: m/z=431.1; $^1$H NMR (400 MHz, DMSO-d$_6$): δ 8.72 (d, J=7.1 Hz, 1H), 8.17 (s, 1H), 7.71 (dd, J=8.9, 7.1 Hz, 1H), 7.49-7.42 (m, 2H), 7.28-7.15 (m, 5H), 6.98 (d, J=6.8 Hz, 1H), 5.25-5.18 (m, 1H), 2.89 (s, 3H), 1.37 (d, J=6.8 Hz, 3H).

Example 76. 3-(3,5-Difluorophenyl)-6-ethyl-2-[1-(9H-purin-6-ylamino)ethyl]-4H-pyrido[1,2-a]pyrimidin-4-one trifluoroacetic acid salt

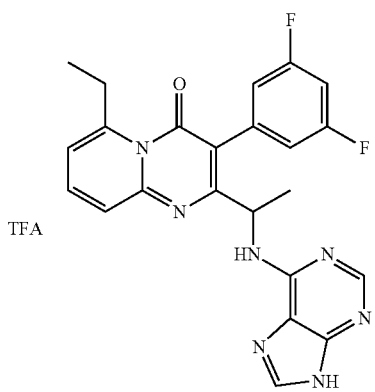 [SMILES: CCc1cccc2nc(C(C)Nc3ncnc4[nH]cnc34)c(-c3cc(F)cc(F)c3)c(=O)n12]

The desired compound was prepared according to the procedure of Example 49 using 6-ethylpyridin-2-amine (instead of 6-methyl-2-pyridinamine in step 1), A-bromosuccinimide (instead of N-iodosuccinimide in step 2), (3,5-difluorophenyl)boronic acid (instead of phenylboronic acid in step 4), and tetrakis(triphenylphosphine)palladium(0) (instead of dichloro(bis{di-tert-butyl[4-(dimethylamino)phenyl]phosphoranyl})palladium in step 4). LCMS for $C_{23}H_{20}F_2N_7O$ (M+H)$^+$: m/z=448.2. $^1$H NMR (300 MHz, DMSO-d$_6$): δ 8.57-8.44 (m, 1H), 8.40 (s, 2H), 7.75 (dd, J=8.2, 7.9 Hz, 1H), 7.48 (d, J=8.8 Hz, 1H), 7.29-7.12 (m, 3H), 7.04 (d, J=6.1 Hz, 1H), 5.30-5.17 (m, 1H), 3.33 (q, J=7.0 Hz, 2H), 1.45 (d, J=6.7 Hz, 3H), 1.14 (t, J=7.0 Hz, 3H).

Example 77. 2-{1-[(2-Amino-9#-purin-6-yl)amino]ethyl}-3-(3,5-difluorophenyl)-6-ethyl-4H-pyrido[1,2-a]pyrimidin-4-one trifluoroacetic acid salt

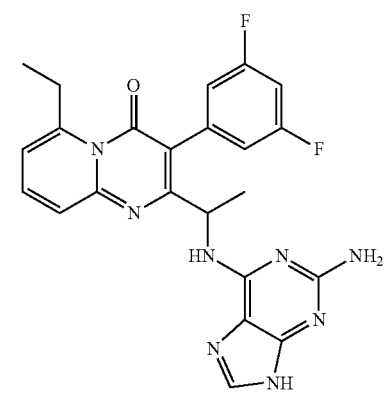

The desired compound was prepared according to the procedure of Example 49 using 6-ethylpyridin-2-amine (instead of 6-methyl-2-pyridinamine in step 1), N-bromosuccinimide (instead of N-iodosuccinimide in step 2), (3,5-difluorophenyl)boronic acid (instead of phenylboronic acid in step 4), tetrakis(triphenylphosphine)palladium(0) (instead of dichloro(bis{di-tert-butyl[4-(dimethylamino)phenyl]phosphoranyl})palladium in step 4) and 2-amino-6-bromopurine (instead of 6-bromo-9H-purine in step 5). LCMS for $C_{23}H_{21}F_2N_8O$ (M+H)$^+$: m/z=463.2. $^1$H NMR (300 MHz, DMSO-d$_6$): δ 8.74-8.69 (m, 1H), 8.17 (s, 1H), 7.78 (dd, J=8.8, 7.0 Hz, 1H), 7.50 (d, J=8.5 Hz, 1H), 7.32-7.16 (m, 3H), 7.14-7.04 (m, 2H), 5.26-5.16 (m, 1H), 3.35 (q, J=7.3 Hz, 2H), 1.41 (d, J=6.7 Hz, 3H), 1.15 (t, J=7.3 Hz, 3H).

Example 78. 6-Ethyl-3-(4-fluorophenyl)-2-[1-(9H-purin-6-ylamino)ethyl]-4H-pyrido[1,2-a]pyrimidin-4-one trifluoroacetic acid salt

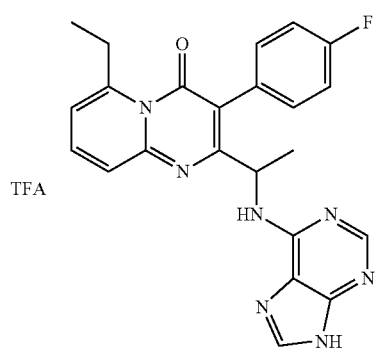 [SMILES: CCc1cccc2nc(C(C)Nc3ncnc4[nH]cnc34)c(-c3ccc(F)cc3)c(=O)n12]

The desired compound was prepared according to the procedure of Example 49 using 6-ethylpyridin-2-amine (instead of 6-methyl-2-pyridinamine in step 1), N-bromosuccinimide (instead of N-iodosuccinimide in step 2), (4-fluorophenyl)boronic acid (instead of phenylboronic acid in step 4), and tetrakis(triphenylphosphine)palladium(0) (instead of dichloro(bis{di-tert-butyl[4-(dimethylamino)phenyl]phosphoranyl})palladium in step 4). LCMS for $C_{23}H_{21}FN_7O$ (M+H)$^+$: m/z=430.2.

Example 79. 3-(3,5-Difluorophenyl)-2-[1-(9H-purin-6-ylamino)ethyl]-4H-pyrido[1,2-a]pyrimidin-4-one trifluoroacetic acid salt

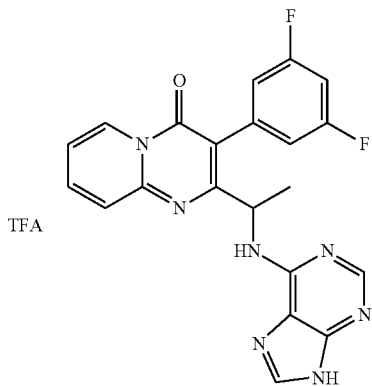 [SMILES: CC(Nc1ncnc2[nH]cnc12)c1nc2ccccn2c(=O)c1-c1cc(F)cc(F)c1]

The desired compound was prepared according to the procedure of Example 49 using 2-pyridinamine (instead of 6-methyl-2-pyridinamine in step 1), N-bromosuccinimide (instead of N-iodosuccinimide in step 2), (3,5-difluorophenyl)boronic acid (instead of phenylboronic acid in step 4), and tetrakis(triphenylphosphine)palladium(0) (instead of dichloro(bis{di-tert-butyl[4-(dimethylamino)phenyl]phosphoranyl})palladium in step 4). LCMS for $C_{21}H_{16}F_2N_7O$ (M+H)$^+$: m/z=420.0. $^1$H NMR (300 MHz, DMSO-d$_6$): δ 8.96 (d, J=7.3 Hz, 1H), 8.36 (s, 2H), 8.01 (dd, J=8.2, 7.3 Hz, 1H), 7.74 (d, J=8.8 Hz, 1H), 7.40 (dd, J=6.7, 6.4 Hz, 1H), 7.32-7.16 (m, 3H), 5.37-5.26 (m, 1H), 1.46 (d, J=6.7 Hz, 3H).

Example 80. 2-{1-[(2-Amino-9H-purin-6-yl)amino]ethyl}-3-(3,5-difluorophenyl)-4H-pyrido[1,2-a]pyrimidin-4-one trifluoroacetic acid salt

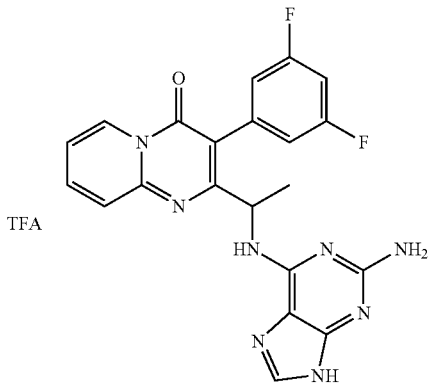 [SMILES: CC(Nc1nc(N)nc2[nH]cnc12)c1nc2ccccn2c(=O)c1-c1cc(F)cc(F)c1]

The desired compound was prepared according to the procedure of Example 49 using 2-pyridinamine (instead of 6-methyl-2-pyridinamine in step 1), N-bromosuccinimide (instead of N-iodosuccinimide in step 2), (3,5-difluorophenyl)boronic acid (instead of phenylboronic acid in step 4), tetrakis(triphenylphosphine)palladium(0) (instead of dichloro(bis{di-tert-butyl[4-(dimethylamino)phenyl]phosphoranyl})palladium in step 4) and 2-amino-6-bromopurine (instead of 6-bromo-9#-purine in step 5). LCMS for $C_{21}H_{17}F_2N_8O$ (M+H)$^+$: m/z=435.0. $^1$H NMR (300 MHz, DMSO-d$_6$): δ 8.98 (d, J=7.0 Hz, 1H), 8.82-8.72 (br s, 1H), 8.17 (s, 1H), 8.06-8.00 (m, 1H), 7.76 (d, J=9.1 Hz, 1H), 7.43 (dd, J=7.0, 5.6 Hz, 1H), 7.30-7.07 (m, 5H), 5.32-5.22 (m, 1H), 1.42 (d, J=6.7 Hz, 3H).

Example 81. 3-(6-Chloro-5-methylpyridin-3-yl)-6-methyl-2-[1-(9H-purin-6-ylamino)ethyl]-4H-pyrido[1,2-a]pyrimidin-4-one trifluoroacetic acid salt

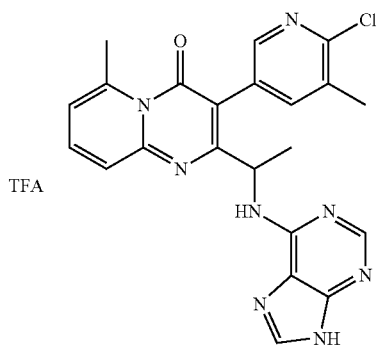 [SMILES: Cc1cc(-c2c(C(C)Nc3ncnc4[nH]cnc34)nc3cccc(C)n3c2=O)cnc1Cl]

The desired compound was prepared according to the procedure of Example 49 using N-bromosuccinimide (instead of N-iodosuccinimide in step 2), (6-chloro-5-methylpyridin-3-yl)boronic acid (instead of phenylboronic acid in step 4), and tetrakis(triphenylphosphine)palladium(0) (instead of dichloro(bis{di-tert-butyl[4-(dimethylamino)phenyl]phosphoranyl})palladium in step 4). LCMS for $C_{22}H_{20}ClN_8O$ (M+H)$^+$: m/z=446.9. $^1$H NMR (300 MHz, DMSO-d$_6$): δ 8.37 (br s, 2H), 8.26 (s, 1H), 7.82 (s, 1H), 7.71 (dd, J=9.1, 7.0 Hz, 1H), 7.45 (d, J=8.8 Hz, 1H), 6.97 (d, J=6.2 Hz, 1H), 5.21-5.10 (m, 1H), 2.88 (s, 3H), 2.33 (s, 3H), 1.45 (d, J=6.7 Hz, 3H).

Example 82. 2-{1-[(2-Amino-9H-purin-6-yl)amino]ethyl}-3-(6-chloro-5-methylpyridin-3-yl)-6-methyl-4H-pyrido[1,2-a]pyrimidin-4-one trifluoroacetic acid salt

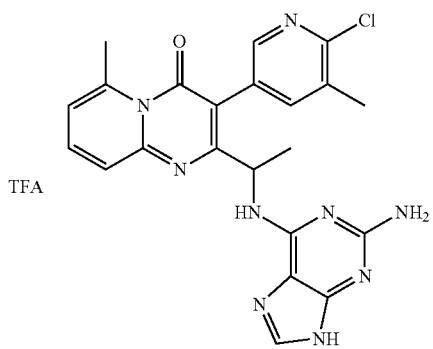 [SMILES: Cc1cc(-c2c(C(C)Nc3nc(N)nc4[nH]cnc34)nc3cccc(C)n3c2=O)cnc1Cl]

The desired compound was prepared according to the procedure of Example 49 using N-bromosuccinimide (instead of N-iodosuccinimide in step 2), (6-chloro-5-methyl-pyridin-3-yl)boronic acid (instead of phenylboronic acid in step 4), tetrakis(triphenylphosphine)palladium(0) (instead of dichloro(bis{di-tert-butyl[4-(dimethylamino)phenyl]phosphoranyl})palladium in step 4), and 2-amino-6-bromopurine (instead of 6-bromo-9H-purine in step 5). LCMS for $C_{22}H_{21}ClN_9O$ (M+H)$^+$: m/z=462.0. $^1$H NMR (500 MHz, DMSO-d$_6$): δ 8.74 (br s, 1H), 8.24 (s, 1H), 8.18 (s, 1H), 7.79-7.71 (m, 2H), 7.50 (d, J=8.8 Hz, 1H), 7.29-7.14 (m, 2H), 7.03 (d, J=6.9 Hz, 1H), 5.23-5.16 (m, 1H), 2.92 (s, 3H), 2.31 (s, 3H), 1.43 (d, J=6.7 Hz, 3H).

Example 83. 3-{6-Methyl-4-oxo-2-[1-(9H-purin-6-ylamino)ethyl]-4H-pyrido[1,2-a]pyrimidin-3-yl}benzonitrile trifluoroacetic acid salt

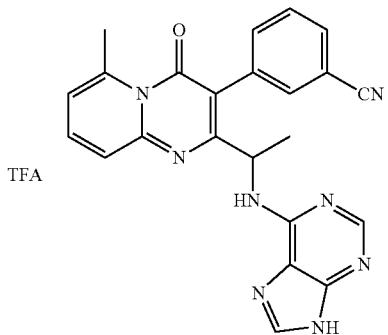 [SMILES: Cc1cccc2nc(C(C)Nc3ncnc4[nH]cnc34)c(-c3cccc(C#N)c3)c(=O)n12]

The desired compound was prepared according to the procedure of Example 49 using N-bromosuccinimide (instead of N-iodosuccinimide in step 2), (3-cyanophenyl)boronic acid (instead of phenylboronic acid in step 4), and tetrakis(triphenylphosphine)palladium(0) (instead of dichloro(bis{di-tert-butyl[4-(dimethylamino)phenyl]phosphoranyl})palladium in step 4). LCMS for $C_{23}H_{19}N_8O$ (M+H)$^+$: m/z=422.9. $^1$H NMR (500 MHz, DMSO-d$_6$): δ 8.46 (br s, 1H), 8.40 (s, 2H), 7.91-7.83 (m, 2H), 7.81-7.76 (m, 1H), 7.75-7.69 (m, 1H), 7.69-7.63 (m, 1H), 7.48 (d, J=8.7 Hz, 1H), 6.98 (d, J=6.7 Hz, 1H), 5.24-5.15 (br s, 1H), 2.91 (s, 3H), 1.46 (d, J=6.6 Hz, 3H).

Example 84. 3-(2-{1-[(2-Amino-9H-purin-6-yl)amino]ethyl}-6-methyl-4-oxo-4H-pyrido[1,2-a]pyrimidin-3-yl)benzonitrile trifluoroacetic acid salt

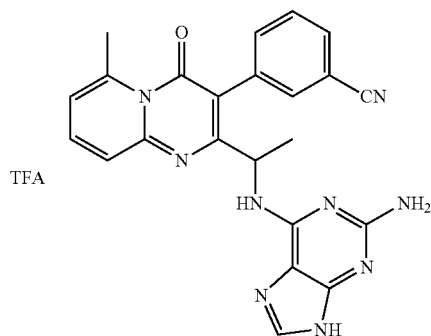 [SMILES: Cc1cccc2nc(C(C)Nc3nc(N)nc4[nH]cnc34)c(-c3cccc(C#N)c3)c(=O)n12]

The desired compound was prepared according to the procedure of Example 49 using N-bromosuccinimide (instead of N-iodosuccinimide in step 2), (3-cyanophenyl)boronic acid (instead of phenylboronic acid in step 4), tetrakis(triphenylphosphine)palladium(0) (instead of dichloro(bis{di-tert-butyl[4-(dimethylamino)phenyl]phosphoranyl})palladium in step 4), and 2-amino-6-bromopurine (instead of 6-bromo-9H-purine in step 5). LCMS for $C_{23}H_{20}N_9O$ (M+H)$^+$: m/z=438.0. $^1$H NMR (500 MHz, DMSO-d$_6$): δ 8.73 (br s, 1H), 8.18 (s, 1H), 7.84-7.80 (m, 2H), 7.78-7.71 (m, 2H), 7.64 (dd, J=8.2, 8.0 Hz, 1H), 7.49 (d, J=8.7 Hz, 1H), 7.24 (br s, 2H), 7.01 (d, J=6.9 Hz, 1H), 5.21-5.15 (m, 1H), 2.92 (s, 3H), 1.40 (d, J=6.7 Hz, 3H).

Example A1: PI3K Enzyme Assay

PI3-Kinase luminescent assay kit including lipid kinase substrate, D-myo-phosphatidylinositol 4,5-bisphosphate (PtdIns(4,5)P2)D (+)-sn-1,2-di-O-octanoylglyceryl, 3-O-phospho linked (PIP2), biotinylated I(1,3,4,5)P4, PI(3,4,5)P3 Detector Protein, was purchased from Echelon Biosciences (Salt Lake City, Utah). AlphaScreen™ GST Detection Kit including donor and acceptor beads was purchased from PerkinElmer Life Sciences (Waltham, Mass.). PI3Kδ (p110δ/p85α) was purchased from Millipore (Bedford, Mass.). ATP, MgCb, DTT, EDTA, HEPES and CHAPS were purchased from Sigma-Aldrich (St. Louis, Mo.).

AlphaScreen™ Assay for PI3Kδ

The kinase reaction was conducted in 384-well REMP plate from Thermo Fisher Scientific in a final volume of 40 μL. Inhibitors were first diluted serially in DMSO and added to the plate wells before the addition of other reaction components. The final concentration of DMSO in the assay was 2%. The PI3K assays were carried out at room temperature in 50 mM HEPES, pH 7.4, 5 mM MgCl$_2$, 50 mM NaCl, 5 mM DTT and CHAPS 0.04%. Reactions were initiated by the addition of ATP, the final reaction mixture consisted of 20 μM PIP2, 20 μM ATP, 1.2 nM PI3Kδ were incubated for 20 min. 10 μL of reaction mixture was then transferred to 5 μL 50 nM biotinylated I(1,3,4,5)P4 in quench buffer: 50 mM HEPES pH 7.4, 150 mM NaCl, 10 mM EDTA, 5 mM DTT, 0.1% Tween-20, followed with the addition of 10 μL AlphaScreen™ donor and acceptor beads suspended in quench buffer containing 25 nM PI(3,4,5)P3 detector protein. The final concentration of both donor and acceptor beads is 20 mg/ml. After plate sealing, the plate was incubated in a dark location at room temperature for 2 hours. The activity of the product was determined on Fusion-alpha microplate reader (Perkin-Elmer). IC$_{50}$ determination was performed by fitting the curve of percent control activity versus the log of the inhibitor concentration using the GraphPad Prism 3.0 software.

Example A2: PI3K Enzyme Assay

Materials: Lipid kinase substrate, phosphoinositol-4,5-bisphosphate (PIP2), was purchased from Echelon Biosciences (Salt Lake City, Utah). PI3K isoforms α, β, δ and γ were purchased from Millipore (Bedford, Mass.). ATP, MgCh, DTT, EDTA, MOPS and CHAPS were purchased from Sigma-Aldrich (St. Louis, Mo.).

The kinase reaction was conducted in clear-bottom 96-well plate from Thermo Fisher Scientific in a final volume of 24 μL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl$_2$, 5 mM DTT and CHAPS 0.03%. The reaction mixture was prepared containing 50 µM PIP2, kinase and varying concentration of inhibitors. Reactions were initiated by the addition of ATP containing 2.2 µCi [γ-$^{33}$P]ATP to a final concentration of 1000 µM. The final concentration of PI3K isoforms α, β, δ and γ in the assay were 1.3, 9.4, 2.9 and 10.8 nM respectively. Reactions were incubated for 180 min and terminated by the addition of 100 µL of 1 M potassium phosphate pH 8.0, 30 mM EDTA quench buffer. A 100 µL aliquot of the reaction solution was then transferred to 96-well Millipore MultiScreen IP 0.45 µm PVDF filter plate (The filter plate was prewetted with 200 µL 100% ethanol, distilled water, and 1 M potassium phosphate pH 8.0, respectively). The filter plate was aspirated on a Millipore Manifold under vacuum and washed with 18×200 µL wash buffer containing 1 M potassium phosphate pH 8.0 and 1 mM ATP. After drying by aspiration and blotting, the plate was air dried in an incubator at 37° C. overnight. Packard TopCount adapter (Millipore) was then attached to the plate followed with addition of 120 µL Microscint 20 scintillation cocktail (Perkin Elmer) in each well. After the plate sealing, the radioactivity of the product was determined by scintillation counting on Topcount (Perkin-Elmer). IC$_{50}$ determination was performed by fitting the curve of percent control activity versus the log of the inhibitor concentration using the GraphPad Prism 3.0 software. Compounds having and IC$_{50}$ value of 10 µM or less are considered active. See Table 1 for data related to compounds of the invention.

Example A3: PI3Kδ Scintillation Proximity Assay

Materials

[γ-$^{33}$P]ATP (10 mCi/mL) was purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) was purchased from Millipore (Bedford, Mass.). ATP, MgCl$_2$, DTT, EDTA, MOPS and CHAPS were purchased from Sigma-Aldrich (St. Louis, Mo.). Wheat Germ Agglutinin (WGA) YSi SPA Scintillation Beads was purchased from GE healthcare life sciences (Piscataway, N.J.).

The kinase reaction was conducted in polystyrene 384-well matrix white plate from Thermo Fisher Scientific in a final volume of 25 µL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 µM PIP2, 20 µM ATP, 0.2 µCi [γ-$^{33}$P] ATP, 4 nM PI3Kδ. Reactions were incubated for 210 min and terminated by the addition of 40 µL SPA beads suspended in quench buffer: 150 mM potassium phosphate pH 8.0, 20% glycerol, 25 mM EDTA, 400 µM ATP. The final concentration of SPA beads was 1.0 mg/mL. After the plate sealing, plates were shaken overnight at room temperature and centrifuged at 1800 rpm for 10 minutes, the radioactivity of the product was determined by scintillation counting on Topcount (Perkin-Elmer). IC$_{50}$ determination was performed by fitting the curve of percent control activity versus the log of the inhibitor concentration using the GraphPad Prism 3.0 software.

TABLE 1

| | IC$_{50}$ data for PI3Kδ enzyme assays A1, A2, or A3* | | | | |
|---|---|---|---|---|---|
| Example | PI3Kδ$^a$ IC$_{50}$ (nM) | PI3Kδ$^b$ IC$_{50}$ (nM) | PI3Kα$^c$ IC$_{50}$ (nM) | PI3Kβ$^c$ IC$_{50}$ (nM) | PI3Kγ$^c$ IC$_{50}$ (nM) |
| 1 | +++ | +++ | | | |
| 2 | ++ | + | | | |
| 3 | +++ | +++ | | | |
| 4 | +++ | ++ | | | |
| 5 | +++ | ++ | | | |
| 6 | +++ | +++ | | | |
| 7 | +++ | ++ | | | |
| 8 | ++ | + | | | |
| 9 | + | + | ++++ | ++++ | ++ |
| 10 | + | + | ++++ | ++++ | ++++ |
| 11 | + | + | ++++ | ++++ | +++ |
| 12 | + | + | | | |
| 13 | + | + | ++++ | ++++ | +++ |
| 14 | ++ | ++ | | | |
| 15 | + | + | ++++ | ++++ | ++++ |
| 17 | | +++ | | | |
| 18 | | +++ | | | |
| 19 | | +++ | | | |
| 20 | | + | | | |
| 21 | | + | | | |
| 22 | | ++ | | | |
| 23 | | + | | | ++++ |
| 24 | | ++++ | | | |
| 25 | | ++++ | | | |
| 26 | | +++ | | | |
| 27 | | +++ | | | |
| 28 | | ++++ | | | |
| 29 | | ++++ | | | |
| 30 | + | + | ++++ | ++++ | ++++ |
| 31 | | +++ | | | |
| 32 | | ++ | | | |
| 33 | | + | | | |
| 34 | | + | | | |
| 35 | | ++ | | | |
| 36 | | +++ | | | |
| 37 | | +++ | | | |
| 38 | | ++ | | | |
| 39 | | 1$^{st}$ peak: +++ 2$^{nd}$ peak: + | | | |
| 40 | | + | | | |
| 41 | | ++ | | | |
| 42 | | +++ | | | |
| 43 | | 1$^{st}$ peak: +++ 2$^{nd}$ peak: + | | | |
| 44 | + | + | ++++ | ++++ | ++++ |
| 45 | | + | | | |
| 46 | | + | | | |
| 47 | | +++ | | | |
| 48 | | ++ | | | |
| 49 | | + | | | |
| 50 | | + | | | |
| 51 | | +++ | | | |
| 52 | | + | | | |
| 53 | | +++ | | | |
| 54 | | + | | | |
| 55 | | ++++ | | | |
| 56 | | ++++ | | | |
| 57 | | + | | | |
| 58 | | + | | | |
| 59 | | + | | | |
| 60 | | + | | | |
| 61 | | ++++ | | | |
| 62 | | +++ | | | |
| 63 | | +++ | | | |
| 64 | | + | | | |
| 65 | | + | | | |
| 66 | | + | | | |
| 67 | | + | | | |
| 68 | | +++ | | | |
| 69 | | +++ | | | |
| 70 | | ++ | | | |
| 71 | | + | | | ++++ |
| 72 | | ++++ | | | |
| 73 | | + | | | |
| 74 | | + | | | |

TABLE 1-continued

IC$_{50}$ data for PI3Kδ enzyme assays A1, A2, or A3*

| Example | PI3Kδ[a] IC$_{50}$ (nM) | PI3Kδ[b] IC$_{50}$ (nM) | PI3Kα[c] IC$_{50}$ (nM) | PI3Kβ[c] IC$_{50}$ (nM) | PI3Kγ[c] IC$_{50}$ (nM) |
|---|---|---|---|---|---|
| 75 | | ++++ | | | |
| 76 | | +++ | | | |
| 77 | | ++ | | | |
| 78 | | + | | | |
| 79 | | ++++ | | | |
| 80 | | +++ | | | |
| 81 | | ++++ | | | |
| 82 | | ++++ | | | |
| 83 | | +++ | | | |
| 84 | | ++ | | | |

*"+" = <50 nM; "++" = 50-100 nM; "+++" = 100-500 nM; "++++" = >500 nM.
[a]Results in this column were obtained by Assay A1, except for Examples 15, 30 and 44 which used Assay A2.
[b]Results in this column were obtained by Assay A3.
[c]Results in this column were obtained by Assay A2.

Example B1: B Cell Proliferation Assay

To acquire B cells, human PBMC were isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells were then purified by positive immunosorting using an autoMacs (Miltenyi Biotech) according to the manufacturer's instruction.

The purified B cells (2×10$^5$/well/200 μL) were cultured in 96-well ultra-low binding plates (Corning, Corning, N.Y.) in RPMI1640, 10% FBS and goat F(ab')2 anti-human IgM (10 μg/ml) (Invitrogen, Carlsbad, Calif.), in the presence of different amount of test compounds, for three days. [$^3$H]-thymidine (1 μCi/well) (PerkinElmer, Boston, Mass.) in PBS was then added to the B cell cultures for an additional 12 hrs before the incorporated radioactivity was separated by filtration with water through GF/B filters (Packard Bioscience, Meriden, Conn.) and measured by liquid scintillation counting with a TopCount (Packard Bioscience). Compounds having and IC$^{50}$ value of 10 μM or less are considered active. See Table 2 for data related to compounds of the invention.

TABLE 2

IC$_{50}$ data for B cell proliferation assay*

| Example | B cell IC$_{50}$ (nM) |
|---|---|
| 1 | + |
| 2 | +++ |
| 3 | + |
| 4 | + |
| 5 | + |
| 6 | ++ |
| 7 | ++++ |
| 8 | + |
| 9 | + |
| 10 | + |
| 11 | + |
| 12 | + |
| 13 | + |
| 15 | + |
| 30 | + |
| 44 | + |
| 71 | + |

*"+" = <50 nM; "++" = 50-100 nM; "+++" = 100-500 nM; "++++" = >500 nM.

Example B2: Pfeiffer Cell Proliferation Assay

Pfeiffer cell line (diffuse large B cell lymphoma) was purchased from ATCC (Manassas, Va.) and maintained in the culture medium recommended (RPMI and 10% FBS). To measure the anti-proliferation activity of the PI3Kδ submittals, the Pfeiffer cells were plated with the culture medium (2×10$^3$ cells/well/per 200 μl) into 96-well ultra-low binding plates (Corning, Corning, N.Y.), in the presence or absence of a concentration range of test compounds. After 3-4 days, [$^3$H]-thymidine (1 μCi/well) (PerkinElmer, Boston, Mass.) in PBS was then added to the cell culture for an additional 12 hrs before the incorporated radioactivity was separated by filtration with water through GF/B filters (Packard Bioscience, Meriden, Conn.) and measured by liquid scintillation counting with a TopCount (Packard Bioscience). See Table 3 for data related to compounds of the invention.

TABLE 3

IC$_{50}$ data for Pfeiffer cell proliferation assay*

| Example | IC$_{50}$ (nM) |
|---|---|
| 1 | +++ |
| 2 | + |
| 3 | +++ |
| 4 | +++ |
| 5 | ++ |
| 6 | +++ |
| 7 | ++++ |
| 8 | + |
| 9 | + |
| 10 | + |
| 11 | + |
| 12 | +++ |
| 13 | + |
| 14 | +++++ |
| 15 | + |
| 17 | +++ |
| 18 | ++ |
| 19 | +++++ |
| 20 | ++ |
| 21 | ++ |
| 22 | +++ |
| 23 | + |
| 24 | +++ |
| 25 | ++++ |
| 27 | +++ |
| 30 | + |
| 31 | +++ |
| 32 | + |
| 33 | + |
| 34 | + |
| 35 | + |
| 36 | ++ |
| 37 | ++ |
| 38 | ++ |
| 39 | First peak: +++ Second peak: + |
| 40 | ++ |
| 41 | ++ |
| 42 | +++ |
| 43 | First peak: +++ Second peak: + |
| 44 | + |
| 45 | ++ |
| 46 | + |
| 48 | ++ |
| 49 | ++ |
| 50 | + |
| 51 | +++ |
| 52 | ++ |
| 53 | ++ |
| 54 | ++ |
| 57 | ++ |
| 58 | + |

TABLE 3-continued

IC$_{50}$ data for Pfeiffer cell proliferation assay*

| Example | IC$_{50}$ (nM) |
|---|---|
| 59 | +++ |
| 60 | ++ |
| 62 | ++++ |
| 63 | +++ |
| 64 | ++ |
| 65 | ++ |
| 66 | +++ |
| 67 | ++ |
| 68 | ++++ |
| 69 | ++ |
| 70 | + |
| 71 | + |
| 72 | ++++ |
| 73 | + |
| 74 | + |
| 75 | ++++ |
| 76 | +++ |
| 77 | + |
| 78 | +++ |
| 80 | +++ |
| 83 | +++ |
| 84 | +++ |

*"+" = <50 nM; "++" = 50-100 nM; "+++" = 100-500 nM; "++++" = 500-1000 nM; "+++++" = >1000 nM.

Example C: Akt Phosphorylation Assay

Ramos cells (B lymphocyte from Burkitts lymphoma) were obtained from ATCC (Manassas, Va.) and maintained in RPMI1640 and 10% FBS. The cells (3×10$^7$ cells/tube/3 mL in RPMI) were incubated with different amounts of test compounds for 2 hrs at 37° C. and then stimulated with goat F(ab')2 anti-human IgM (5 μg/mL) (Invitrogen) for 17 min. in a 37° C. water bath. The stimulated cells were spun down at 4° C. with centrifugation and whole cell extracts prepared using 300 μL lysis buffer (Cell Signaling Technology, Danvers, Mass.). The resulting lysates were sonicated and supernatants were collected. The phosphorylation level of Akt in the supernatants were analyzed by using PathScan phospho-Akt1 (Ser473) sandwich ELISA kits (Cell Signaling Technology) according to the manufacturer's instruction.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula IId:

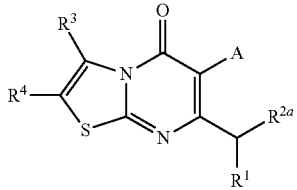

IId or a pharmaceutically acceptable salt thereof, wherein:

A is aryl, heteroaryl, cycloalkyl, or heterocycloalkyl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

R$^1$ is NR$^A$R$^B$;

R$^{2a}$ is H, halo, OH, CN, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^e$)NR$^{c2}$R$^{d2}$, NR$^{c2}$C(=NR$^e$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

R$^3$ and R$^4$ are independently selected from H, halo, CN, NO$_2$, OR$^{a3}$, SR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$S(O)$_2$R$^{b3}$, NR$^{c3}$S(O)$_2$NR$^{c3}$R$^{d3}$, S(O)$_2$NR$^{c3}$R$^{d3}$, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^e$)NR$^{c3}$R$^{d3}$, NR$^{c3}$C(=NR$^e$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

R$^A$ is heteroaryl, heterocycloalkyl, heteroarylalkyl, or heterocycloalkylalkyl, each optionally substituted with 1, 2, 3, 4, or 5 substituents independently selected from —($C_{1-4}$ alkyl)$_r$-Cy$^1$, halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^e$)NR$^{c1}$R$^{d1}$, NR$^{c1}$C(=NR$^e$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^B$ is selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$Cy^1$ is aryl, heteroaryl, cycloalkyl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^a$, $R^b$, $R^c$, and $R^d$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or $R^c$ and $R^d$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$R^{a1}$, $R^{b1}$, $R^{c1}$, and $R^{d1}$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or $R^{c1}$ and $R^{d1}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$R^{a2}$, $R^{b2}$, $R^{c2}$, and $R^{d2}$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or $R^{c2}$ and $R^{d2}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$R^{a3}$, $R^{b3}$, $R^{c3}$, and $R^{d3}$ are independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or $R^{c3}$ and $R^{d3}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, halo, $C_{1-6}$ haloalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

$R^e$ and $R^f$ are independently selected from H, CN, $NO_2$, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

$R^{a5}$, $R^{b5}$, $R^{c5}$, and $R^{d5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$ haloalkoxy;

or $R^{c5}$ and $R^{d5}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$ haloalkoxy; and r is 0 or 1.

2. The compound of claim 1, or a pharmaceutically acceptable salt thereof, wherein A is cycloalkyl or heterocycloalkyl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

3. The compound of claim 1, or a pharmaceutically acceptable salt thereof, wherein A is aryl or heteroaryl, each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$S(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

4. The compound of claim 1, or a pharmaceutically acceptable salt thereof, wherein A is aryl optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, C(=NR$^e$)NR$^c$R$^d$, NR$^c$C(=NR$^e$)NR$^c$R$^d$, NR$^c$R$^d$, NR$_c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

5. The compound of claim 1, or a pharmaceutically acceptable salt thereof, wherein A is phenyl optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O) NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

6. The compound of claim 1, or a pharmaceutically acceptable salt thereof, wherein A is phenyl optionally substituted with 1, 2, 3, 4, or 5 substituents independently selected from halo, $C_{1-6}$ alkyl, or $C_{1-6}$ haloalkyl.

7. The compound of claim 1, or a pharmaceutically acceptable salt thereof, wherein A is phenyl.

8. The compound of claim 1, or a pharmaceutically acceptable salt thereof, wherein A is heteroaryl optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O) NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

9. The compound of claim 1, or a pharmaceutically acceptable salt thereof, wherein A is 6-membered heteroaryl optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

10. The compound of claim 1, or a pharmaceutically acceptable salt thereof, wherein A is pyridyl optionally substituted with 1, 2, or 3 substituents independently selected from halo, $C_{1-6}$ alkyl, or $C_{1-6}$ haloalkyl.

11. The compound of claim 1, or a pharmaceutically acceptable salt thereof, wherein A is 5-membered heteroaryl optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, aryl, cycloalkyl, heteroaryl, or heterocycloalkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

12. The compound of claim 1, or a pharmaceutically acceptable salt thereof, wherein A is pyrazolyl optionally substituted with 1 or 2 substituents independently selected from halo, $C_{1-6}$ alkyl, or $C_{1-6}$ haloalkyl.

13. The compound of claim 1, or a pharmaceutically acceptable salt thereof, wherein $R^A$ is heteroaryl optionally substituted with 1, 2, 3, 4, or 5 substituents independently selected from $-(C_{1-4}\ alkyl)_r-Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

14. The compound of claim 1, or a pharmaceutically acceptable salt thereof, wherein $R^A$ is bicyclic heteroaryl optionally substituted with 1, 2, 3, 4, or 5 substituents independently selected from $-(C_{1-4}\ alkyl)_r-Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

15. The compound of claim 1, or a pharmaceutically acceptable salt thereof, wherein $R^A$ is purinyl optionally substituted with 1 or 2 substituents independently selected from $-(C_{1-4}\ alkyl)_r-Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)$ $NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

16. The compound of claim 1, or a pharmaceutically acceptable salt thereof, wherein $R^A$ is purinyl optionally substituted with 1 or 2 substituents independently selected from $C_{1-6}$ alkyl, $C_{1-6}$ haloalkyl, $NR^{c5}R^{d5}$, $NR^{c5}C(O)R^{b5}$, $NR^{c5}C(O)NR^{c5}R^{d5}$, $NR^{c5}C(O)OR^{a5}$, $NR^{c5}C(=NR^f)NR^{c5}R^{d5}$, $NR^{c5}S(O)_2R^{b5}$, $NR^{c5}S(O)_2NR^{c5}R^{d5}$, and $S(O)_2NR^{c5}R^{d5}$.

17. The compound of claim 1, or a pharmaceutically acceptable salt thereof, wherein $R^A$ is:

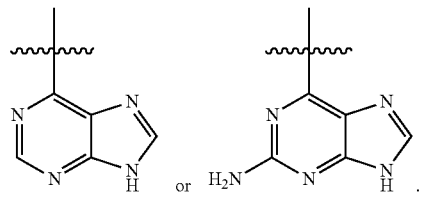 [SMILES: *c1ncnc2[nH]cnc12 ; *c1nc(N)nc2[nH]cnc12]

18. The compound of claim 1, or a pharmaceutically acceptable salt thereof, wherein $R^B$ is selected from H and $C_{1-6}$ alkyl.

19. The compound of claim 1, or a pharmaceutically acceptable salt thereof, wherein $R^B$ is H.

20. The compound of claim 1, or a pharmaceutically acceptable salt thereof, wherein $R^{2a}$ is H, halo, OH, CN, $C_{1-6}$ alkyl, $C_{1-6}$ haloalkyl, $C_{2-6}$ alkenyl, or $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^e)NR^{c2}R^{d2}$, $NR^{c2}C(=NR^e)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

21. The compound of claim 1, or a pharmaceutically acceptable salt thereof, wherein $R^{2a}$ is halo, OH, CN, $C_{1-6}$ alkyl, $C_{1-6}$ haloalkyl, $C_{2-6}$ alkenyl, or $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^e)NR^{c2}R^{d2}$, $NR^{c2}C(=NR^e)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

22. The compound of claim 1, or a pharmaceutically acceptable salt thereof, wherein $R^{2a}$ is H, halo, OH, CN, $C_{1-6}$ alkyl, $C_{1-6}$ haloalkyl, $C_{2-6}$ alkenyl, or $C_{2-6}$ alkynyl.

23. The compound of claim 1, or a pharmaceutically acceptable salt thereof, wherein $R^{2a}$ is methyl or ethyl.

24. The compound of claim 1, or a pharmaceutically acceptable salt thereof, wherein $R^3$ is halo, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}S(O)_2R^{b3}$, $NR^{c3}S(O)_2NR^{c3}R^{d3}$, $S(O)_2NR^{c3}R^{d3}$, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^e)NR^{c3}R^{d3}$, $NR^{c3}C(=NR^e)NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$.

25. The compound of claim 1, or a pharmaceutically acceptable salt thereof, wherein $R^3$ is H, halo, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}S(O)_2R^{b3}$, $S(O)_2NR^{c3}R^{d3}$, or $C_{1-6}$ alkyl, wherein said $C_{1-6}$ alkyl, is optionally substituted with 1, 2, 3, 4, or 5 substituents independently selected from halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^e)NR^{c3}R^{d3}$, $NR^{c3}C(=NR^e)NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$.

26. The compound of claim 1, or a pharmaceutically acceptable salt thereof, wherein $R^3$ is H or $C_{1-6}$ alkyl.

27. The compound of claim 1, or a pharmaceutically acceptable salt thereof, wherein $R^3$ is $C_{1-6}$ alkyl.

28. The compound of claim 1, or a pharmaceutically acceptable salt thereof, wherein $R^3$ is methyl.

29. The compound of claim 1, or a pharmaceutically acceptable salt thereof, wherein $R^4$ is selected from H, halo, $C_{1-6}$ alkyl, or $C_{1-6}$ haloalkyl.

30. The compound of claim 1, or a pharmaceutically acceptable salt thereof, wherein $R^4$ is H.

31. The compound of claim 1, or a pharmaceutically acceptable salt thereof, having Formula IIg:

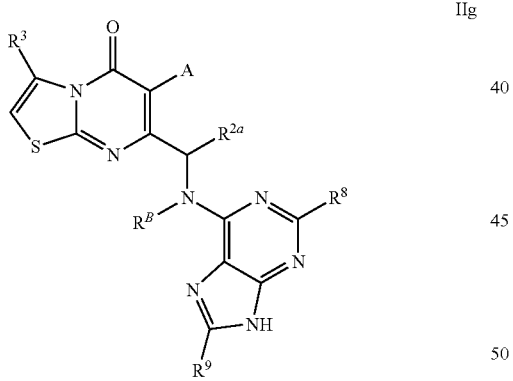

IIg wherein $R^8$ and $R^9$ are independently selected from H, $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$.

32. The compound of claim 1, or a pharmaceutically acceptable salt thereof; wherein:
A is aryl or heteroaryl, each optionally substituted with 1, 2, or 3 substituents independently selected from halo, $C_{1-6}$ alkyl, $C_{1-6}$ haloalkyl, CN, and $OR^a$;
$R^1$ is $NR^AR^B$
$R^{2a}$ is $C_{1-6}$ alkyl;

$R^3$ and $R^4$ are independently selected from H, halo, CN, $NO_2$, $OR^{a3}$, and $C_{1-6}$ alkyl; wherein said $C_{1-6}$ alkyl is optionally substituted with 1, 2, 3, 4, or 5 substituents independently selected from halo;
$R^A$ is heteroaryl, which is optionally substituted with 1, 2, 3, 4, or 5 substituents independently selected from halo, $C_{1-6}$ alkyl, CN, $OR^{a1}$, and $NR^{c1}R^{d1}$;
$R^B$ is H;
each $R^a$ is independently selected from H and $C_{1-6}$ alkyl;
each $R^{a1}$, $R^{c1}$, and $R^{d1}$ is independently selected from H and $C_{1-6}$ alkyl, wherein said $C_{1-6}$ alkyl is optionally substituted with 1, 2, 3, 4, or 5 substituents independently selected from halo; and
each $R^{a3}$ is independently selected from H and $C_{1-6}$ alkyl, wherein said $C_{1-6}$ alkyl is optionally substituted with 1, 2, 3, 4, or 5 substituents independently selected from halo.

33. The compound of claim 32, or a pharmaceutically acceptable salt thereof, wherein:
A is phenyl, 5-membered heteroaryl or 6-membered heteroaryl, each optionally substituted with 1, 2, or 3 substituents independently selected from halo, $C_{1-6}$ alkyl, $C_{1-6}$ haloalkyl, CN, and $OR^a$;
$R^1$ is $NR^AR^B$;
$R^{2a}$ is $C_{1-6}$ alkyl;
$R^3$ and $R^4$ are independently selected from H, halo, CN, $NO_2$, $OR^{a3}$, and $C_{1-6}$ alkyl; wherein said $C_{1-6}$ alkyl is optionally substituted with 1, 2, 3, 4, or 5 substituents independently selected from halo;
$R^A$ is selected from:

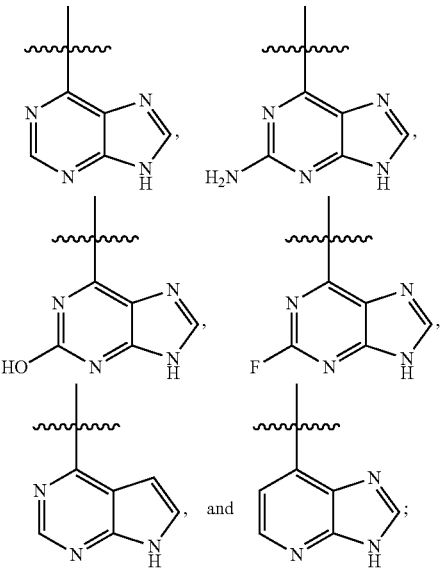 [SMILES: *c1ncnc2[nH]cnc12 ; *c1nc(N)nc2[nH]cnc12 ; *c1nc(O)nc2[nH]cnc12 ; *c1nc(F)nc2[nH]cnc12 ; *c1ncnc2[nH]ccc12 ; *c1ccnc2[nH]cnc12]

$R^B$ is H;
each $R^a$ is independently selected from H and $C_{1-6}$ alkyl; and
each $R^{a3}$ is independently selected from H and $C_{1-6}$ alkyl, wherein said $C_{1-6}$ alkyl is optionally substituted with 1, 2, 3, 4, or 5 substituents independently selected from halo.

34. The compound of claim 1, selected from:
3-methyl-6-phenyl-7-[1-(9H-purin-6-ylamino)ethyl]-5H-[1,3]thiazolo[3,2-a]pyrimidin-5-one;
7-{1-[(2-amino-9H-purin-6-yl)amino]ethyl}-3-methyl-6-phenyl-5H-[1,3]thiazolo[3,2-a]pyrimidin-5-one;

6-(3-fluorophenyl)-3-methyl-7-[1-(9H-purin-6-ylamino)
ethyl]-5H-[1,3]thiazolo[3,2-a]pyrimidin-5-one;
7-{1-[(2-amino-9H-purin-6-yl)amino]ethyl}-6-(3-fluoro-
phenyl)-3-methyl-5H-[1,3]thiazolo[3,2-a]pyrimidin-5-
one;
6-(3,5-difluorophenyl)-3-methyl-7-[1-(9H-purin-6-
ylamino)ethyl]-5H-[1,3]thiazolo[3,2-a]pyrimidin-5-
one;
7-{1-[(2-amino-9H-purin-6-yl)amino]ethyl}-6-(3,5-dif-
luorophenyl)-3-methyl-5H-[1,3]thiazolo[3,2-a]pyrimi-
din-5-one; and
3-methyl-7-[1-(9H-purin-6-ylamino)ethyl]-6-pyridin-2-
yl-5H-[1,3]thiazolo[3,2-a]pyrimidin-5-one, or a phar-
maceutically acceptable salt of any of the aforemen-
tioned.

35. The compound of claim 1, selected from:
6-(3,5-difluorophenyl)-3-methyl-7-[1-(7H-pyrrolo[2,3-d]
pyrimidin-4-ylamino)ethyl]-5H-[1,3]thiazolo[3,2-a]
pyrimidin-5-one;
6-(3,5-difluorophenyl)-7-{1-[(2-fluoro-9H-purin-6-yl)
amino]ethyl}-3-methyl-5H-[1,3]thiazolo[3,2-a]pyrimi-
din-5-one;
3-methyl-7-[1-(9H-purin-6-ylamino)ethyl]-6-pyridin-4-
yl-5H-[1,3]thiazolo[3,2-a]pyrimidin-5-one;
3-methyl-7-[1-(9H-purin-6-ylamino)ethyl]-6-(1,3-thi-
azol-2-yl)-5H-[1,3]thiazolo[3,2-a]pyrimidin-5-one;
3-methyl-7-[1-(9H-purin-6-ylamino)ethyl]-6-(1,3-thi-
azol-4-yl)-5H-[1,3]thiazolo[3,2-a]pyrimidin-5-one;
6-(4-fluorophenyl)-3-methyl-7-[1-(9H-purin-6-ylamino)
ethyl]-5H-[1,3]thiazolo[3,2-a]pyrimidin-5-one;
7-{1-[(2-amino-9H-purin-6-yl)amino]ethyl}-6-(3,5-dif-
luorophenyl)-5H-[1,3]thiazolo[3,2-a]pyrimidin-5-one;
6-(3,5-difluorophenyl)-7-[1-(9H-purin-6-ylamino)ethyl]-
5H-[1,3]thiazolo[3,2-a]pyrimidin-5-one;
7-{1-[(2-amino-9H-purin-6-yl)amino]ethyl}-6-(3-fluoro-
phenyl)-5H-[1,3]thiazolo[3,2-a]pyrimidin-5-one;
7-{1-[(2-amino-9H-purin-6-yl)amino]ethyl}-6-phenyl-
5H-[1,3]thiazolo[3,2-a]pyrimidin-5-one;
6-(3-fluorophenyl)-7-[1-(9H-purin-6-ylamino)ethyl]-5H-
[1,3]thiazolo[3,2-a]pyrimidin-5-one;
6-phenyl-7-[1-(9H-purin-6-ylamino)ethyl]-5H-[1,3]thi-
azolo[3,2-a]pyrimidin-5-one;
3-methyl-6-(4-methylphenyl)-7-[1-(9H-purin-6-ylamino)
ethyl]-5H-[1,3]thiazolo[3,2-a]pyrimidin-5-one;
7-{1-[(2-amino-9H-purin-6-yl)amino]ethyl}-6-(3-chloro-
phenyl)-3-methyl-5H-[1,3]thiazolo[3,2-a]pyrimidin-5-
one;
7-{1-[(2-amino-9H-purin-6-yl)amino]ethyl}-6-(2-fluoro-
phenyl)-3-methyl-5H-[1,3]thiazolo[3,2-a]pyrimidin-5-
one;
7-{1-[(2-amino-9H-purin-6-yl)amino]ethyl}-6-(2,3-dif-
luorophenyl)-3-methyl-5H-[1,3]thiazolo[3,2-a]pyrimi-
din-5-one;
7-{1-[(2-amino-9H-purin-6-yl)amino]ethyl}-6-(3-chloro-
5-fluorophenyl)-3-methyl-5H-[1,3]thiazolo[3,2-a]py-
rimidin-5-one;
6-(3-chlorophenyl)-3-methyl-7-[1-(9H-purin-6-ylamino)
ethyl]-5H-[1,3]thiazolo[3,2-a]pyrimidin-5-one;
6-(3-chloro-5-fluorophenyl)-3-methyl-7-[1-(9H-purin-6-
ylamino)ethyl]-5H-[1,3]thiazolo[3,2-a]pyrimidin-5-
one;
7-{1-[(2-amino-9H-purin-6-yl)amino]ethyl}-6-(5-fluoro-
pyridin-3-yl)-3-methyl-5H-[1,3]thiazolo[3,2-a]pyrimi-
din-5-one;
7-{1-[(2-amino-9H-purin-6-yl)amino]ethyl}-6-(2-chloro-
phenyl)-3-methyl-5H-[1,3]thiazolo[3,2-a]pyrimidin-5-
one;
6-(2-fluorophenyl)-3-methyl-7-[1-(9H-purin-6-ylamino)
ethyl]-5H-[1,3]thiazolo[3,2-a]pyrimidin-5-one;
6-(2,3-difluorophenyl)-3-methyl-7-[1-(9H-purin-6-
ylamino)ethyl]-5H-[1,3]thiazolo[3,2-a]pyrimidin-5-
one;
6-(5-fluoropyridin-3-yl)-3-methyl-7-[1-(9H-purin-6-
ylamino)ethyl]-5H-[1,3]thiazolo[3,2-a]pyrimidin-5-
one;
6-(2-chlorophenyl)-3-methyl-7-[1-(9H-purin-6-ylamino)
ethyl]-5H-[1,3]thiazolo[3,2-a]pyrimidin-5-one;
6-(2,5-difluorophenyl)-3-methyl-7-[1-(9H-purin-6-
ylamino)ethyl]-5H-[1,3]thiazolo[3,2-a]pyrimidin-5-
one;
6-(3-Fluorophenyl)-7-[(1S)-1-(3H-imidazo[4,5-b]pyri-
din-7-ylamino)ethyl]-3-methyl-5H-[1,3]thiazolo[3,2-
a]pyrimidin-5-one;
6-(3-Fluorophenyl)-7-{(1S)-1-[(2-hydroxy-9H-purin-6-
yl)amino]ethyl}-3-methyl-5H-[1,3]thiazolo[3,2-a]py-
rimidin-5-one; and
6-(3-Fluorophenyl)-7-[1-(9H-purin-6-ylamino)ethyl]-3-
(trifluoromethyl)-5H-[1,3]thiazolo[3,2-a]pyrimidin-5-
one;
or a pharmaceutically acceptable salt of any of the afore-
mentioned.

36. The compound of claim 1, wherein the compound is (S)-7-(1-(9H-purin-6-ylamino)ethyl)-6-(3-fluorophenyl)-3-methyl-5H-thiazolo[3,2-a]pyrimidin-5-one or 7-(1-(9H-purin-6-ylamino)ethyl)-6-(3-fluorophenyl)-3-methyl-5H-thiazolo[3,2-a]pyrimidin-5-one; or a pharmaceutically acceptable salt thereof.

37. A composition comprising a compound according to claim 1, or a pharmaceutically acceptable salt thereof, and at least one pharmaceutically acceptable carrier.

38. A method of inhibiting an activity of PI3Kδ comprising contacting said PI3Kδ with a compound of claim 1, or a pharmaceutically acceptable salt thereof.

39. The method of claim 38, wherein said compound is a selective inhibitor for PI3Kδ over one or more of PI3Kα, PI3Kβ, and PI3Kγ.

40. A method of treating a disease selected from B cell lymphoma, rheumatoid arthritis, myasthenia gravis, Sjöegren's syndrome, multiple sclerosis, glomerulonephritis, lupus, and inflammation related to rheumatoid arthritis, glomerulonephritis, or lupus, in a patient, comprising administering to said patient a therapeutically effective amount of a compound of claim 1, or a pharmaceutically acceptable salt thereof.

41. The method of claim 40, wherein the disease is rheumatoid arthritis.

42. The method of claim 40, wherein the disease is B cell lymphoma.

43. The method of claim 42, wherein the B cell lymphoma is diffuse large B cell lymphoma.

44. The method of claim 40, wherein the disease is myasthenia gravis.

45. The method of claim 40, wherein the disease is Sjöegren's syndrome.

46. The method of claim 40, wherein the disease is multiple sclerosis.

47. The method of claim 40, wherein the disease is glomerulonephritis.

48. The method of claim 40, wherein the disease is lupus.

49. The method of claim 40, wherein the disease is inflammation related to rheumatoid arthritis.

50. The method of claim 40, wherein the disease is inflammation related to glomerulonephritis.

51. The method of claim 40, wherein the disease is inflammation related to lupus.

\* \* \* \* \*